US012492337B2

(12) United States Patent
Zhu et al.

(10) Patent No.: US 12,492,337 B2
(45) **Date of Patent: *Dec. 9, 2025**

(54) FLUORESCENT PROBE, PREPARATION METHOD THEREFOR AND USE THEREOF

(71) Applicant: FLUORESCENCE DIAGNOSIS (SHANGHAI) BIOTECH COMPANY, Shanghai (CN)

(72) Inventors: Linyong Zhu, Shanghai (CN); Yi Yang, Shanghai (CN); Bingkun Bao, Shanghai (CN); Chenxia Zhang, Shanghai (CN); Dasheng Zhang, Shanghai (CN); Chunyan Bao, Shanghai (CN); Qiuning Lin, Shanghai (CN); Ningfeng Li, Shanghai (CN); Xin Hua, Shanghai (CN); Yongliang Zhao, Shanghai (CN); Renmei Liu, Shanghai (CN); Zhengda Chen, Shanghai (CN); Yuying Sun, Shanghai (CN)

(73) Assignee: FLUORESCENCE DIAGNOSIS (SHANGHAI) BIOTECH COMPANY, Shanghai (CN)

( * ) Notice: Subject to any disclaimer, the term of this patent is extended or adjusted under 35 U.S.C. 154(b) by 970 days.

This patent is subject to a terminal disclaimer.

(21) Appl. No.: 16/652,208

(22) PCT Filed: Sep. 29, 2018

(86) PCT No.: PCT/CN2018/108519

§ 371 (c)(1),
(2) Date: Mar. 30, 2020

(87) PCT Pub. No.: WO2019/062876

PCT Pub. Date: Apr. 4, 2019

(65) Prior Publication Data

US 2020/0248069 A1 Aug. 6, 2020

(30) Foreign Application Priority Data

Sep. 29, 2017 (CN) ........................ 201710909828.2

(51) Int. Cl.

| | |
|---|---|
| ***C07C 255/23*** | (2006.01) |
| ***C07D 215/38*** | (2006.01) |
| ***C07D 233/96*** | (2006.01) |
| ***C07D 263/54*** | (2006.01) |
| ***C07D 277/64*** | (2006.01) |
| ***C07D 307/68*** | (2006.01) |
| ***C07D 333/60*** | (2006.01) |
| ***C07D 401/06*** | (2006.01) |
| ***C07D 409/06*** | (2006.01) |
| ***C07D 413/06*** | (2006.01) |
| ***C07D 417/06*** | (2006.01) |
| ***C07D 495/04*** | (2006.01) |
| ***C07D 495/14*** | (2006.01) |
| ***C09K 11/07*** | (2006.01) |
| ***G01N 33/58*** | (2006.01) |
| ***G01N 33/68*** | (2006.01) |

(52) U.S. Cl.

CPC ............ *C09K 11/07* (2013.01); *C07C 255/23* (2013.01); *C07D 215/38* (2013.01); *C07D 233/96* (2013.01); *C07D 263/54* (2013.01); *C07D 277/64* (2013.01); *C07D 307/68* (2013.01); *C07D 333/60* (2013.01); *C07D 401/06* (2013.01); *C07D 409/06* (2013.01); *C07D 413/06* (2013.01); *C07D 417/06* (2013.01); *C07D 495/04* (2013.01); *C07D 495/14* (2013.01); *G01N 33/582* (2013.01); *G01N 33/6803* (2013.01); *C09K 2211/1007* (2013.01); *C09K 2211/1011* (2013.01); *C09K 2211/1018* (2013.01); *G01N 2458/00* (2013.01)

(58) Field of Classification Search

CPC .............. C07C 255/23; A61K 49/0021; A61K 49/0052; C09K 11/07; G01N 33/582; G01N 2458/00; C07D 233/96

See application file for complete search history.

(56) References Cited

U.S. PATENT DOCUMENTS 2,776,310 A * 1/1957 Straley .................... C09B 23/04 558/403
2019/0187144 A1* 6/2019 Zhu ....................... C07F 7/0816

FOREIGN PATENT DOCUMENTS

| | | | |
|---|---|---|---|
| CN | 102127059 | A | 7/2011 |
| CN | 103666456 | A | 3/2014 |
| CN | 104745177 | A | 7/2015 |
| CN | 107641121 | A | 1/2018 |
| CN | 107663384 | A | 2/2018 |
| EP | 3489324 | A1 | 5/2019 |

(Continued)

OTHER PUBLICATIONS

J. Grimm, et.al. 1663, Methods in Molecular Biology (Clifton, N.J.), 179-188 (Jan. 1, 2017) (Year: 2017).*

(Continued)

*Primary Examiner* — Alexander R Pagano
*Assistant Examiner* — Frank S. Hou
(74) *Attorney, Agent, or Firm* — XSENSUS LLP

(57) ABSTRACT

Provided are a fluorescent probe, a preparation method therefor and a use thereof. The fluorescent probe responds to viscosity sensitively and specifically, can be used for the specific fluorescence labeling of proteins and can also be used in the quantification, detection or kinetic study of proteins and the imaging of cells, tissues and living bodies.

6 Claims, 5 Drawing Sheets

(56) References Cited

FOREIGN PATENT DOCUMENTS

| | | | |
|---|---|---|---|
| WO | 2004031405 A1 | | 4/2004 |
| WO | 2004072232 A2 | | 8/2004 |
| WO | 2007041241 A2 | | 4/2007 |
| WO | WO2007078926 | * | 7/2007 |
| WO | 2008012296 A1 | | 1/2008 |

OTHER PUBLICATIONS

CAS Abstract of RN 325475-51-2 (Year: 2001).*
The First Office Action mailed Nov. 9, 2020, in Chinese Application No. 201710909828.2, 12 pages including English translation.
The Second Office Action Sep. 1, 2021, in Chinese Application No. 201710909828.2, 10 pages including English translation.
Supplementary European Search Report mailed May 27, 2021, in European Application No. 18861947.2, 7 pages.
European Office Communication mailed Mar. 12, 2025, in European Application No. 18861947.2, 3 pages.
Spencer A. Clark et al., "Light-Up "Channel Dyes" for Haloalkane-Based Protein Labeling in Vitro and in Bacterial Cells", Bioconjugate Chemistry, vol. 27, No. 12, published on Nov. 21, 2016, pp. 2839-2843, total 5 pages.
Tao-Kai Liu et al., "A Rapid SNAP-Tag Fluorogenic Probe Based on an Environment-Sensitive Fluorophore for No-Wash Live Cell Imaging", ACS Chemical Biology, published on Aug. 8, 2014, pp. 2359-2365, total 7 pages.
Toru Komatsu et al., "Real-Time Measurements of Protein Dynamics Using Fluorescence Activation-Coupled Protein Labeling Method", Journal of The American Chemical Society, published on Apr. 7, 2011, pp. 6745-6751, total 7 pages.
Wang-Ting Yu et al., "Protein sensing in living cells by molecular rotor-based fluorescence-switchable chemical probes", Chemical Science, published on Oct. 1, 2015, pp. 301-307, total 7 pages.
Shunsuke Sasaki et al., "Design of donor-acceptor geometry for tuning excited-state polarization: fluorescence solvatochromism of push-pull biphenyls with various torsional restrictions on their aryl-aryl bonds", Tetrahedron, Elsevier, available online Aug. 16, 2014, pp. 7551-7559, total 9 pages.
Jagattaran Das et al., "Effects of positional and geometrical isomerism on the biological activity of some novel oxazolidinones", Bioorganic & Medicinal Chemistry Letters (2005), Elsevier, accepted on Oct. 25, 2004, pp. 337-343, total 7 pages.
Jing Jing et al., "Rational design of ZnSalen as a single and two photon activatable fluorophore in living cells", Chemical Science, published on Aug. 24, 2012, pp. 3315-3320, total 6 pages.
Kaijun Tian et al., "Multiple fluorescence ΔCIE and ΔRGB codes for sensing volatile organic compounds with a wide range of responses", Chem.Commun., published on Aug. 9, 2011, pp. 10052-10054, total 3 pages.
Ruikui Chen et al., "Effect of Tetrahydroquinoline Dyes Structure on the Performance of Organic Dye-Sensitized Solar Cells", Chem. Mater, published on Web Jul. 11, 2007, pp. 4007-4015, total 9 pages.
Chun-Guey Wu et al., "Molecular engineering of cyclopentadithiophene-containing organic dyes for dye-sensitized solar cell: Experimental results vs theoretical calculation", Dyes and Pigments, Elsevier, available online on Aug. 30, 2013, pp. 1091-1100, total 10 pages.
Liangxing Wu et al., "Syntheses of Highly Fluorescent GFP-Chromophore Analogues", JACS Articles, published on Web on Mar. 6, 2008, pp. 4089-4096, total 8 pages.
Sangwon Ko et al., "Silole-spaced triarylamine derivatives as highly efficient organic sensitizers in dye-sensitized solar cells (DSSCs)", Journal of Materials Chemistry, published on Feb. 10, 2010, pp. 2391-2399, total 9 pages.
M.Klikar et al., "Multipodal arrangement of push-pull chromophores: a fundamental parameter affecting their electronic and optical properties", NewJ.Chem., published on Dec. 13, 2016, pp. 1459-1472, total 14 pages.
Shengbo Zhu et al., "Cyclic thiourea functionalized dyes with binary π-linkers: Influence of different π-conjugation segments on the performance of dye-sensitized solar cells", Dyes and Pigments, Elsevier, available online Feb. 4, 2015, pp. 146-154, total 9 pages.
Hui Wang et al., "Modifications of DCDHF single molecule fluorophores to impart water solubility", Tetrahedron Letters, Elsevier, available online Mar. 12, 2007, pp. 3471-3474, total 4 pages.
Xiaohu Dong et al., "Quinoline-Based Two-Photon Fluorescent Probe for Nitric Oxide in Live Cells and Tissues", Analytical Chemistry, published on Dec. 16, 2013, pp. 308-311, total 4 pages.
Andrea Ojeda-Porras et al., "Transamidation of thioacetamide catalyzed by SbCl3", Tetrahedron Letters, Elsevier, available online May 21, 2015, pp. 4308-4311, total 4 pages.
Andrew J.Hallett et al., "Luminescent, water-soluble gold nanoparticles functionalised with 3MLCT emitting rhenium complexes", Chem. Commun., published on Jun. 8, 2009, pp. 4278-4280, total 3 pages.
Kimin Lim et al., "Enhancing the Performance of Organic Dye-Sensitized Solar Cells via a Slight Structure Modification", The Journal of Physical Chemistry C, published on Oct. 7, 2011, pp. 22640-22646, total 7 pages.

* cited by examiner

FLUORESCENT PROBE, PREPARATION METHOD THEREFOR AND USE THEREOF

TECHNICAL FIELD

The present invention relates to a fluorescent probe and a preparation method and use thereof.

BACKGROUND ART

Fluorescence specific labeling is a powerful tool for studying protein function and quantification. Contrast to other study methods, fluorescent labels have the irreplaceable advantages, such as being sensitive, in situ, instant, and visual. Currently, the most often used method of fluorescent labeling proteins is expressing the fluorescent protein in situ on the target protein by gene fusion technology, thereby realizing specific illumination of the target protein and making it possible to perform tracking studies of the target protein in cells or tissues under a fluorescence microscope. Fluorescent protein technology has been developed for a long time, and this technology is relatively mature. However, there are a few shortcomings. For example, fluorescent proteins matures and folds slowly and requires participation of oxygen, and tendency to aggregate. Once the fluorescent protein is expressed, it is difficult to carry out post-modification. In addition, most fluorescent proteins still have a shortcoming such as less photostability, etc. These shortcomings limit the application of fluorescent proteins in some extent.

In fact, the chromophores structure of fluorescent protein is relatively simple, which makes it very difficult to construct different types or functionalized fluorescent proteins. Furthermore, there is little guideline to follow, and sea screen can only be carried out by means of random mutation. In contrast, organic small molecule fluorescent dyes are rich in molecular structure, but small molecule fluorescent probes still have many defects in protein-specific labeling. Recently, the emergence of chemical tag technology has effectively solved this problem. With chemical tags, the target protein is tagged with a polypeptide or a protein tag with specific recognition function, and small-molecule fluorescent probe-specific protein labeling is achieved by the highly specific binding of the tag to the substrate. Thus, chemistry tags combine the advantage of specificity through genetic encoding with a modular organic fluorophore which inherits all aspects of organic dye probes compared to fluorescent proteins. Currently SNAP-tag (K. Johnsson et. al. WO 2004031405.), CLIP-tag (K. Johnmsson et. al. WO 2008012296.), Halo-tag (Wood, Keith V et. al. WO 2004072232), have been commercialized.

Although chemical tag such as SNAP-tag and Halo-tag are capable of specifically labeling their protein of interest during the labeling process, no matter free probes or labeled probes in the system all emit fluorescent. That is, the probes emits fluorescence within the system, no matter the probe binds to the target or not. This non-characteristic fluorescence emission is clearly a serious problem in current chemical labeling technology. Therefore, in a strict sense, this method still cannot achieve the same specificity as fluorescent protein. The only effective way to solve this problem is washing out the unlabeled probe. Apparently, the application of this technology will be severely limited in situations where it is needed quickly or the probe cannot be washed.

If a method for fluorescent-activated protein-specific labeling for Halo tag is designed, which remains dark or emits very weak fluorescence before labeling, and the fluorescence of the dye is sharply enhanced once it is bind to the protein. Undoubtedly, this kinds of probes will be able to achieve the same specificity as fluorescent proteins, which will not only eliminate the washing out procedure of free probes, but also greatly reduce the background interference of free probes, furthermore will widen the application of HaloTag technology. A method for designing a fluorescently activated protein-specific label suitable for this technique must consider a suitable fluorescence ON/OFF switching mechanism. The FRET mechanism is first applied to this design, which additionally adds the ligand with a fluorescence quenching group. Normally, the small molecule fluorescence is quenched by the quenching group; once the ligand binds to the chemical tag, the quenching group is released, to achieve fluorescence activation (T. Komatsu. et. al. J. Am. Chem. Soc. 2011, 133, 6745-6751.). However, the introduction of the quenching group greatly increases the molecular volume of the probe, which greatly reduces the labeling speed, and severely limits the real-time tracking and detection of proteins in cells and tissues by the probe. Furthermore, there must be a good energy level match between the fluorescent probe and the quenching group, which makes the FRET design of long wavelength fluorescent probes become very difficult, for example, the red light emitting dye. In addition, some dyes that are extremely sensitive to fluorescence have also been used to design fluorescent probes (T K Liu. et. al. ACS Chem. Biol. 2014, 9, 2359-2365.). These probes exhibit no fluorescence or weak fluorescence when the dyes are in polar fluids, such as cell fluid. When the ligand binds to the protein, the probe is placed in the non-polar pocket of the protein, result the probe emits stronger fluorescence. However, on the one hand, due to the presence of a more polar hydration layer on the surface of the protein, the fluorescence enhancement of the probe is limited; on the other hand, the cell or tissue itself is a very complex system, and the polarity of each organelle changes very much greatly, which can lead to polar-sensitive probes with a high background in cell or tissue imaging. Recently, the literature (T Y Wang et. al. Chem Sci. 2016, 7, 301-307.) reported a molecular rotor fluorescent probe with viscosity sensitivity, which is sterically hindered after protein ligands are covalently bound to proteins. The action reduces the molecular rotor's degree of freedom, thereby allowing fluorescent of the probe to be activated. However, in this literature, the fluorescence intensity of the probe after fluorescence activation is dim, and the fluorescence quantum yield is very low. Therefore, the method reported in this literature cannot be used as qualified fluorescent protein tags for labeling, tracking, localization and quantification of target proteins.

SUMMARY OF THE INVENTION

The inventors have discovered that by linking a ligand moiety to a part of a viscosity-responsive fluorescent dye, a significant increase in fluorescent intensity is achieved after the ligand is bound to a tag protein, thereby obtaining a novel structured fluorescent probe, which is viscosity-responsive and can be used for specific labeling of proteins, which can be effectively used for labeling, tracking, localization and/or quantification of target proteins.

A fluorescent probe is provided, which comprises a ligand moiety A, an optional linker moiety B, and a fluorescent dye moiety C. The fluorescent dye moiety C is a viscosity-responsive fluorescent dye which comprises an electron donor portion D, a conjugated system E and an electron acceptor moiety. The ligand moiety A is a group capable of specifically identifying and labeling a target protein of a protein tag or a fusion protein tag, and optionally, the ligand moiety A is capable of identifying and covalently labeling a target protein of a protein tag or a fusion protein tag.

Optionally, the above-mentioned fluorescent probe is a compound having a structure represented by formula (I), or a salt thereof,

A-B-C (I)

wherein, the linker moiety B is an optionally existing group independently selected from an alkylene group and a modified alkylene group;

the fluorescent dye moiety C in the formula (I) is a structural moiety represented by a formula (I-R), (I-R)

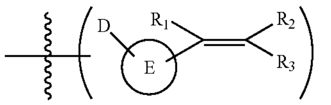

wherein, in the formula (I-R), the hydrogen at the position connected to the linker moiety B or the ligand moiety A is replaced by the linker moiety B or the ligand moiety A;

the electron donor moiety -D is —$NX_1$—$X_2$, $X_1$ is independently selected from hydrogen, an alkyl group, or a modified alkyl group, $X_2$ is independently selected from hydrogen, an alkyl group, or a modified alkyl group, and $X_1$, $X_2$ are optionally connected to each other to form an aliphatic heterocycle with the N atom;

the conjugated system E is a group formed by conjugated connection of at least one of a double bond, a triple bond, an aromatic ring, and an aromatic heterocyclic, and has a structure represented by the following formula (I-1), wherein each hydrogen contained therein is optionally independently substituted with a substituent selected from a halogen atom, a nitro group, a hydrophilic group, an alkyl group, and a modified alkyl group, and the substituents are optionally connected to each other to form an aliphatic ring or an aliphatic heterocycle;

(I-1)

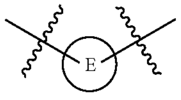

optionally, the structure of formula (I-1) is connected to $X_1$ and $X_2$ to form an aliphatic heterocycle;

the electron acceptor moiety has a structure represented by the following formula (I-2), (I-2)

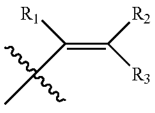

wherein, $R_1$ is selected from hydrogen, a halogen atom, a nitro group, an alkyl group, an aryl group, a heteroaryl group, a hydrophilic group or a modified alkyl;

$R_2$ is selected from hydrogen, a cyano group, a carboxyl group, a keto group, an ester group, an amide group, a thioamino group, a thioester group, a phosphite group, a phosphate group, a sulfonic acid group, a sulfonate group, a sulfone group, a sulfoxide group, an aryl group, a heteroaryl group, an alkyl group or a modified alkyl group;

$R_3$ is a cyano group;

the electron acceptor moiety optionally forms a ring structure of the following formulae (I-2-a), (I-2-b), and (I-2-c):

(I-2-a)

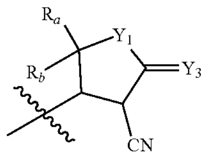

(I-2-b)

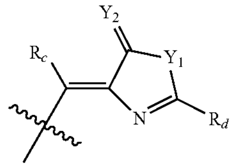

(I-2-c)

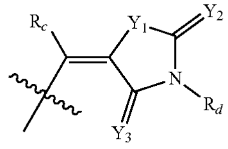

wherein $R_a$ and $R_b$ are independently selected from hydrogen, a hydrophilic group, an alkyl group, and a modified alkyl group, and $R_a$ and $R_b$ are optionally connected to each other to form an aliphatic ring or an aliphatic heterocycle;

each $R_c$ is independently selected from hydrogen, a halogen atom, a nitro group, an alkyl group, an aryl group, a heteroaryl group, a hydrophilic group or a modified alkyl group; each $R_d$ is independently selected from hydrogen, a halogen atom, a nitro group, an alkyl group, an aryl group, a heteroaryl group, a hydrophilic group or a modified alkyl group or a group formed by conjugate connection of a double bond with at least one of an aromatic ring and an aromatic heterocyclic ring;

each $Y_1$ is independently selected from —O—, —S—, —(SO)—, and —($NR_i$)—, wherein $R_i$ is independently selected from hydrogen, an alkyl group, or a modified alkyl group;

each $Y_2$ is independently selected from =O, =S, =S, =O, and =NR, wherein R is independently selected from hydrogen, an alkyl group, or a modified alkyl group;

each $Y_3$ is independently selected from =O, =S, =S=O, and =NR, wherein $R_i$ is independently selected from hydrogen, an alkyl group, or a modified alkyl group;

or, each $Y_3$ is independently =C($R_e$)(CN);

$R_e$ is selected from a cyano group, a carboxyl group, a keto group, an ester group, an amide group, a phosphite group, a phosphate group, a sulfonic acid group, a sulfonate group, a sulfone group, a sulfoxide group, an aryl group, a heteroaryl group, an alkyl group or a modified alkyl group;

when $R_2$ or $R_e$ is an aryl group or a heteroaryl group, the hydrogen atom on the ring is optionally independently substituted by a substituent selected from a halogen atom, a cyano group, a nitro group, a hydrophilic group, an alkyl group, or a modified alkyl group; optionally, the substituents are connected to each other to form a saturated or unsaturated aliphatic ring or aliphatic heterocycle;

wherein, the "alkyl group" is a $C_1$-$C_{10}$ linear or branched alkyl; optionally, a $C_1$-$C_{10}$ linear or branched alkyl; optionally, a $C_1$-$C_7$ linear or branched alkyl; optionally, $C_1$-$C_5$ linear or branched alkyl; optionally, selected from methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl or 2,2,3-trimethylbutyl;

the "alkylene group" is a $C_1$-$C_{30}$ linear or branched alkylene; optionally, a $C_1$-$C_7$ linear or branched alkylene; optionally, a $C_1$-$C_5$ linear or branched alkylene; the "modified alkyl group" is a group obtained by replacement of any carbon atom of an alkyl group with at least one group selected from a halogen atom, —O—, —OH, —CO—, —CS—, —$NO_2$, —CN, —S—, —$SO_2$—, —(S═O)—,

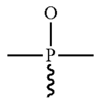
, a phenyl group, a phenylene group, a primary amino group, a secondary amino group, a tertiary amino group, a quaternary ammonium group, a saturated or unsaturated monocyclic or bicyclic cycloalkylene group, a biaryl heterocyclic group, and a bridged aliphatic heterocyclic group, the modified alkyl group having 1 to 30 carbon atoms, and the carbon-carbon single bond is optionally independently replaced by a carbon-carbon double bond or a carbon-carbon triple bond.

the "modified alkylene" is a group obtained by replacement of any carbon atom of an alkylene group with at least one group selected from a halogen atom, —O—, —OH, —CO—, —$NO_2$, —CN, —S—, —CS—, —$SO_2$—, —(S═O)—,

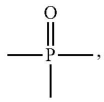
, a phenyl group, a phenylene group, a primary amino group, a secondary amino group, a tertiary amino group, a quaternary ammonium group, a saturated or unsaturated monocyclic or bicyclic cycloalkylene group, a biaryl heterocyclic group, and a bridged aliphatic heterocyclic group, the modified alkylene group has 1 to 30 carbon atoms, and the carbon-carbon single bond is optionally independently replaced by a carbon-carbon double bond or a carbon-carbon triple bond;

the replacement of the carbon atom means that the carbon atom or the carbon atom and the hydrogen atom thereon together are replaced by a corresponding group;

the "aliphatic ring" is a saturated or unsaturated 4- to 10-membered monocyclic or polycyclic aliphatic ring, the "aliphatic heterocycle" is a saturated or unsaturated 4- to 10-membered monocyclic or polycyclic aliphatic heterocycle containing at least one heteroatom selected from N, O, S, or Si; when the aliphatic heterocycle contains an S atom, the S is in the form of —S—, —SO—, or —$SO_2$—; the aliphatic heterocycle is optionally substituted with a halogen atom, a nitro group, an alkyl group, an aryl group, a hydrophilic group, and a modified alkyl group;

the "aryl or aromatic ring" is a 5- to 10-membered monocyclic or fused bicyclic aromatic group;

the "heteroaryl or aromatic heterocyclic ring" is a 5- to 10-membered monocyclic or fused bicyclic heteroaromatic group containing at least one heteroatom selected from N, O, S or Si on the ring;

optionally, the "heteroaryl or aromatic heterocyclic ring" is an 11- to 14-membered fused tricyclic heteroaromatic group containing at least one heteroatom selected from N, O, S, or Si on the ring;

the "halogen atom" is independently selected from F, Cl, Br, I;

the "hydrophilic group" is a hydroxyl group, a sulfonic acid group, a carboxyl group, a phosphite group, a primary amino group, a secondary amino group, or a tertiary amino group;

the "monocyclic cycloalkylene group" is a 4- to 7-membered cycloalkylene group;

the "bicyclic cycloalkylene group" is a 5- to 7-membered bicyclic cycloalkylene group;

the "bridged aliphatic heterocycle" is a 5- to 20-membered bridged aliphatic heterocycle containing at least one hetero atom selected from N, O, or S on the ring;

the "keto group" is an R—(C═O)R' group;

the "ester group" is an R(C═O)OR' group;

the "amide group" is a RCONR' group;

the "thioamide group" is an R(C═S)NR' group;

the "thioester group" is an R(C═S)OR' group;

the "phosphite group" is an RP(—O)$(OH)_2$ group;

the "phosphate group" is a ROP(═O)$(OH)_2$ group;

the "sulfonic group" is an $RSO_3H$ group;

the "sulfonate group" is an $RSO_2OR'$ group;

the "sulfone group" is an $RSO_2R'$ group;

the "sulfoxide" RSOR' group;

the "primary amino group" is a $RNH_2$ group;

the "secondary amino group" is a RNHR' group;

the "tertiary amino group" is an RNR'R" group;

the "quaternary ammonium salt" $RR'R''R'''N^+$ group;

each R, R', R", R'" is independently a single bond, an alkyl group, an alkylene group, a modified alkyl group, or a modified alkylene group, and the modified alkyl group or modified alkylene group is a group obtained by replacement of any carbon atom of $C_1$-$C_{10}$ (preferably $C_1$-$C_6$) alkyl or alkylene group with a group selected from —O—, —OH, —CO—, —CS—, —(S═O)—;

optionally, the modified alkyl group or modified alkylene group each is independently a group containing at least one group selected from —OH, —O—, an ethylene glycol unit (—$(CH_2CH_2O)_n$—), a $C_1$-$C_8$ alkyl group, and a $C_1$-$C_8$ alkoxy group, a $C_1$-$C_8$ acyloxy group, a $C_1$-$C_8$ haloalkyl group, a monosaccharide group, a disaccharide group, a polysaccharide group, —O—CO—, —NH—CO—, —(—NH—CHR''''—CO—)—, —$SO_2$—O—, —SO—, —$SO_2$—NH—, —S—S—, —CH═CH—, —C≡C—, a halogen atom, a cyano group, a nitro group, an o-nitrophenyl group, a benzoylmethyl group, and a phosphate group, wherein n is 1 to 100, optionally 1 to 50, optionally 1 to 30, optionally 1 to 10; R'''' is H or a residue of a amino acid; the “phosphate group” has the definition as described above;

the “monosaccharide unit” is a saccharide unit that can no longer be simply hydrolyzed into smaller sugar molecules;

the “disaccharide unit” is a saccharide unit formed by dehydration of two monosaccharides;

the “polysaccharide unit” is a saccharide unit formed by dehydration of 10 or more monosaccharides;

optionally, the $C_1$-$C_8$ alkyl group is methyl, ethyl, propyl, or isopropyl, and the $C_1$-$C_8$ alkoxy group is methoxy, ethoxy, propoxy, or isopropoxy, the $C_1$-$C_8$ acyloxy is acetoxy, ethyl, propyl, isopropyl, and the $C_1$-$C_8$ haloalkyl is trifluoromethyl, chloromethyl, bromomethyl;

optionally, the aliphatic heterocycle is selected from azetidine, pyrrolidine, piperidine, tetrahydrofuran, tetrahydropyran, morpholine, and thiomorpholine;

optionally, the heteroaryl ring is selected from thiophene, furan, and pyrrole.

Optionally, the above-mentioned fluorescent probe is a compound having a structure represented by (I-a) or (I-b), or a salt thereof:

(I-a)

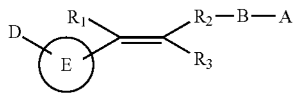

(I-b)

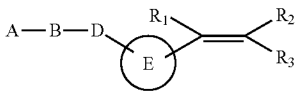

The electron acceptor moiety has a structure represented by the following formulae (I-2) and (I-2-i), (I-2)

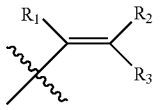

(I-2-i)

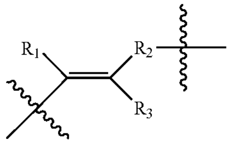

Optionally, the above-mentioned fluorescent probe is characterized in that:

the protein tag is a purified product, an unpurified product, or an in situ state existing in a cell or a tissue;

optionally, the protein tag is selected from a dehalogenase;

optionally, the protein tag is a haloalkane dehalogenase (HaloTag) or a mutant thereof;

optionally, the ligand moiety A is derived from a halogenated hydrocarbon compound;

optionally, the ligand moiety A suitable for HaloTag is derived from a dehalogenase substrate;

optionally, the ligand moiety A is a haloalkane group; optionally a haloethyl group, optionally a structure of the following formula:

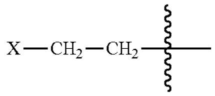

wherein,

X is halogen, optionally chlorine;

optionally, the linker moiety B is selected from a saturated linear or branched alkyl group having 1 to 30 carbon atoms, one or more carbon atoms on the alkyl chain being replaced with one or more —O—; said replacement of carbon atom with —O— means that a carbon atom or a carbon atom and the hydrogen atom thereon together are replaced with —O—;

optionally, $X_1$ is a $C_{1-30}$ linear or branched alkyl group optionally substituted with one or more groups selected from a hydroxyl group, a cyano group, a halogen atom, a carboxyl group, and a quaternary ammonium group, and $X_2$ is an $C_{1-30}$ linear or branched chain alkyl or alkylene group optionally substituted one or more groups selected from a hydroxyl group, a cyano group, a halogen atom, a carboxyl group, and a quaternary ammonium group; optionally, $X_1$ and $X_2$ are each independently selected from $C_{1-30}$ ether chain group which contains 1 to 10 oxygen atoms and is optionally substituted with one or more groups selected from a sulfonic acid group and a carboxyl group;

optionally, $X_1$ and $X_2$ are each independently a $C_{4-30}$ alkyl or alkylene group which is modified with —HN(C═O)—O—, and is optionally substituted with one or more groups selected from a sulfonic acid group and a carboxyl group, optionally, —$NX_1$—$X_2$ forms any group selected from the following formulae (I-i-1), (I-i-2)

(I-i-1)

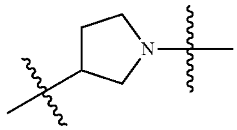

(I-i-2)

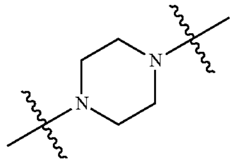

optionally, $X_1$ is a $C_{1-10}$ linear or branched alkyl group optionally substituted with one or more groups selected from a hydroxyl group, a cyano group, a halogen atom, a carboxyl group, and a quaternary ammonium group, and $X_2$ is a $C_{1-10}$ linear or branched chain alkyl or alkylene group independently substituted with one or more groups selected from a hydroxyl group, a cyano group, a halogen atom, a carboxyl group, and a quaternary ammonium group;

optionally, two adjacent substituents in the conjugated system E are connected to each other to form a saturated or unsaturated aliphatic ring or aliphatic heterocycle;

optionally, H on CH in the conjugated system E is substituted with a halogen atom, a nitro group, a hydrophilic group, an alkyl group, or a modified alkyl group;

optionally, the conjugated system E contains NH; optionally, H on the NH is substituted with an alkyl group or a modified alkyl group;

optionally, the conjugated system E is selected from the structures of the following formulae (I-1-1) to (I-1-38):

(I-1-1)

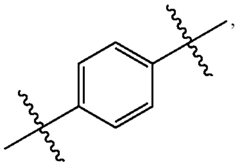

(I-1-2)

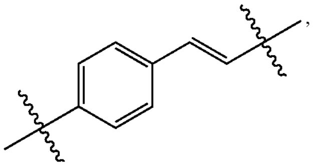

(I-1-3)

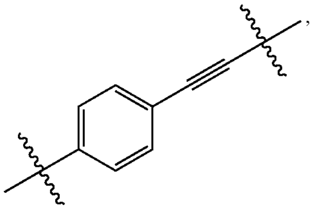

(I-1-4)

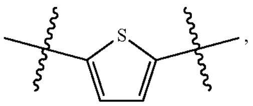

(I-1-5)

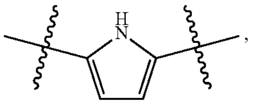

(I-1-6)

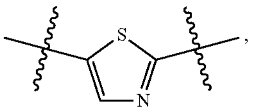

(I-1-7)

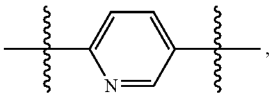

-continued (I-1-8)

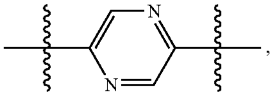

(I-1-9)

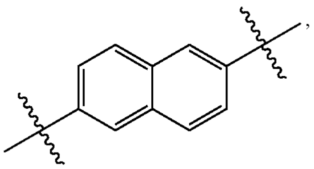

(I-1-10)

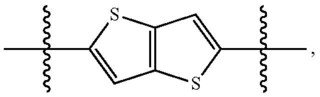

(I-1-11)

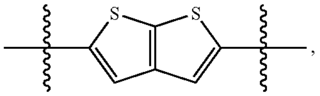

(I-1-12)

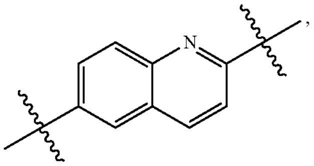

(I-1-13)

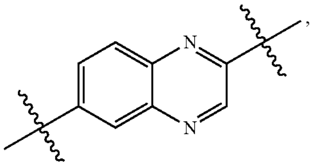

(I-1-14)

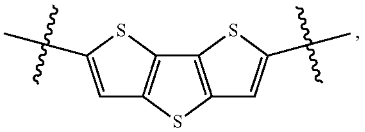

(I-1-15)

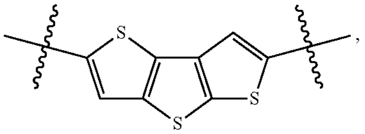

(I-1-16)

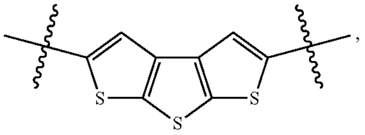

(I-1-17)

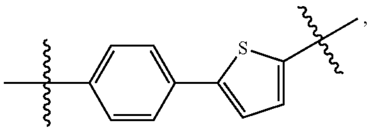

(I-1-18)

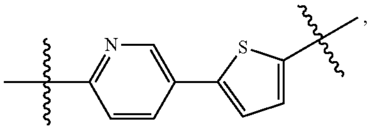

-continued
(I-1-19)
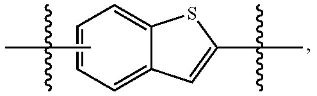
(I-1-20)
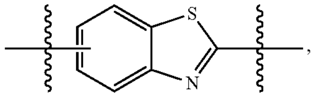
(I-1-21)
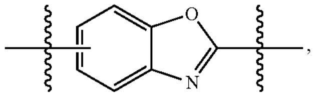
(I-1-22)
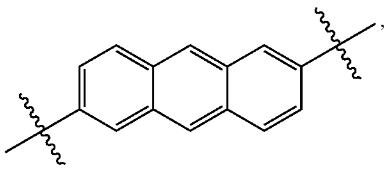
(I-1-23)
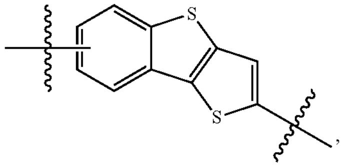
(I-1-24)
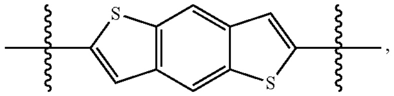
(I-1-25)
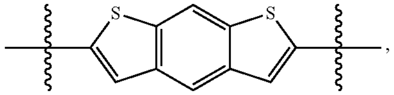
(I-1-26)
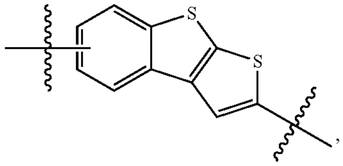
(I-1-27)
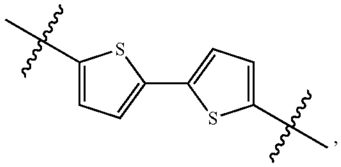
(I-1-28)
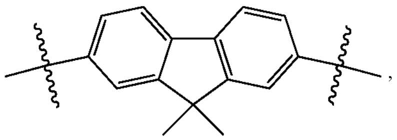
(I-1-29)
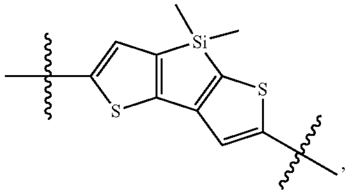
-continued
(I-1-30)
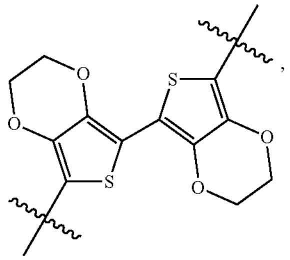
(I-1-31)
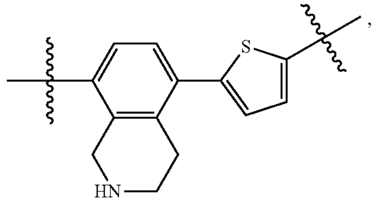
(I-1-32)
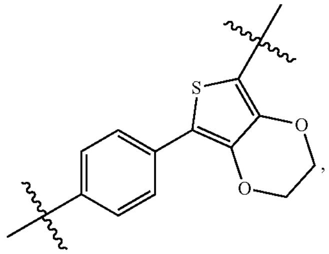
(I-1-33)
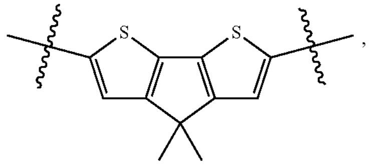
(I-1-34)
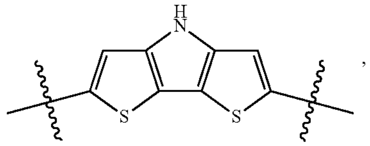
(I-1-35)
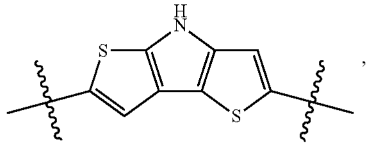
(I-1-36)
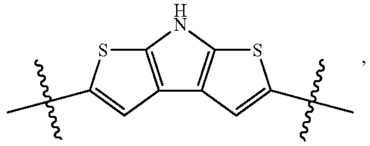
(I-1-37)
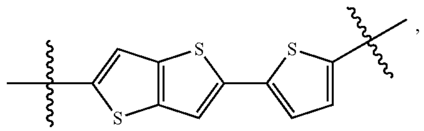

-continued (I-1-38)

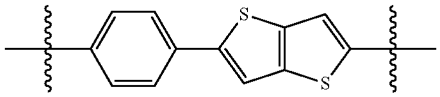
, (I-1-39)

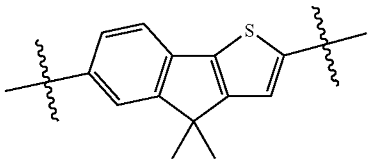
;

Optionally, the conjugated system E and —$NX_1$—$X_2$ form an aliphatic heterocycle as shown in (I-i-3) to (I-i-7):

(I-i-3)

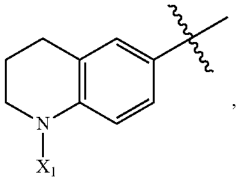
, (I-i-4)

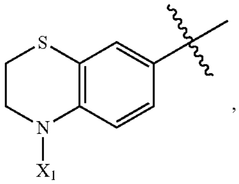
, (I-i-5)

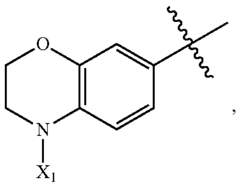
, (I-i-6)

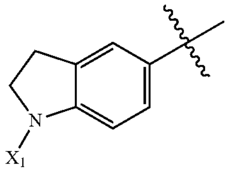
, (I-i-7)

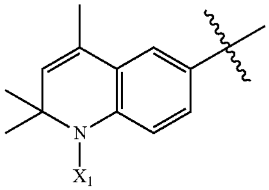

Alternatively, the conjugated system E and —$NX_1$—$X_2$ form the structure shown in (I-i-8) as follows:

(I-i-8)

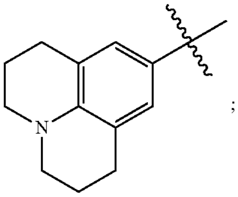
;

optionally, $R_2$ and $R_e$ are independently a group selected from the following structures, or a bicyclic or polycyclic fused aromatic ring or fused aromatic heterocyclic ring formed by fusion of the following structure itself or with each other; optionally is a bicyclic or tricyclic fused aromatic ring or fused aromatic heterocyclic ring;

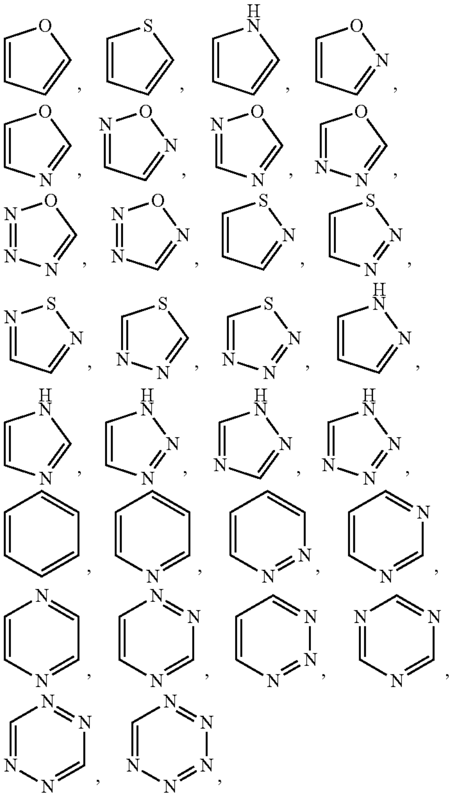

optionally, H on CH in the above structures of $R_2$ or $R_e$ is substituted with a halogen atom, a cyano group, a nitro group, a hydrophilic group, an alkyl group, or a modified alkyl group; optionally, $R_2$ or $R_e$ is a NH-containing group selected from the above structures, and optionally, H on the NH is substituted with an alkyl group or a modified alkyl group;

alternatively, the $R_2$ is selected from hydrogen, a cyano group, a carboxyl group, a keto group, an ester group, an amide group, a thioamino group, a thioester group, and when $R_2$ is selected from a keto group, an ester group, or an amide group, the carbonyl group in the keto group, the ester group or the amide group is connected to the alkenyl carbon of the formula (I-2) or (I-2-i); when $R_2$ is selected from a thioamino group and a thioester group, the thiocarbonyl group in the thioamino group or the thioester group is connected to the alkenyl carbon of the formula (I-2) and the formula (I-2-i); R is selected from a cyano group, a keto group, an ester group, and an amide group; when R is selected from a keto group, an ester group, or an amide group, the carbonyl group in the keto group, the ester group, or the amide group is connected to the alkenyl carbon of the formula (I-2-a), the formula (I-2-b), or the formula (I-2-c); optionally, the electron acceptor moiety is one selected from the following formulae (I-2-1) to (I-2-38):

(I-2-1)

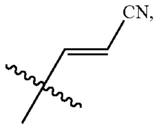

(I-2-2)

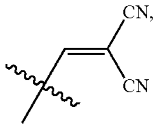

(I-2-3)

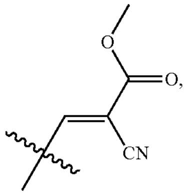

(I-2-4)

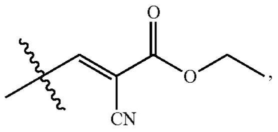

(I-2-5)

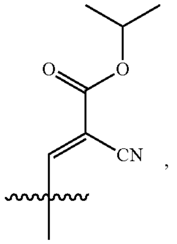

(I-2-6)

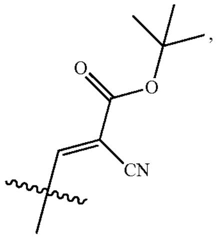

-continued (I-2-7)

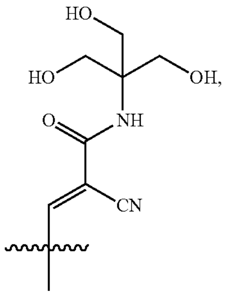

(I-2-8)

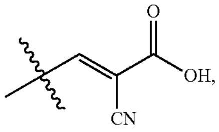

(I-2-9)

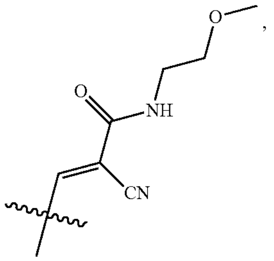

(I-2-10)

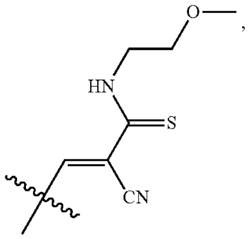

(I-2-11)

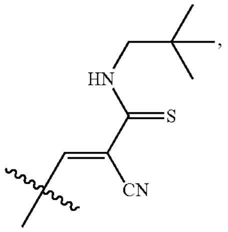

(I-2-12)

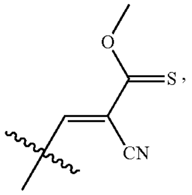

-continued
(I-2-13)
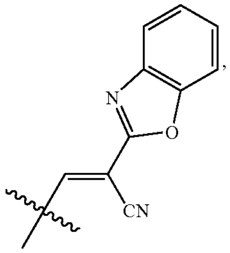
(I-2-14)
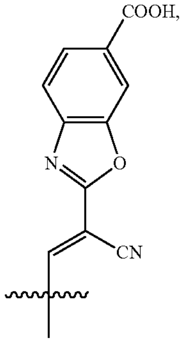
(I-2-15)
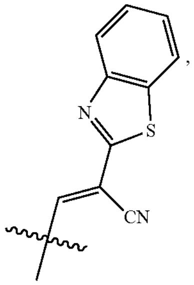
(I-2-16)
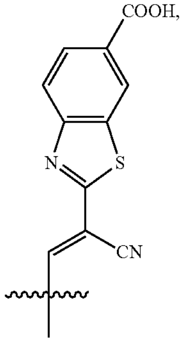
(I-2-17)
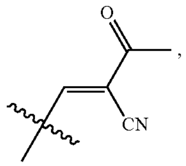
(I-2-18)
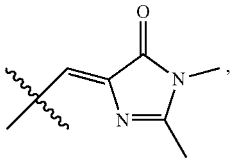
-continued
(I-2-19)
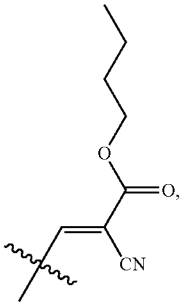
(I-2-20)
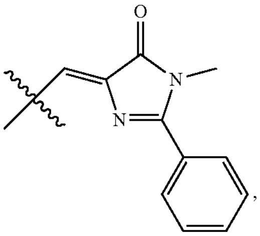
(I-2-21)
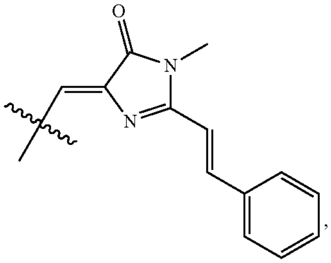
(I-2-22)
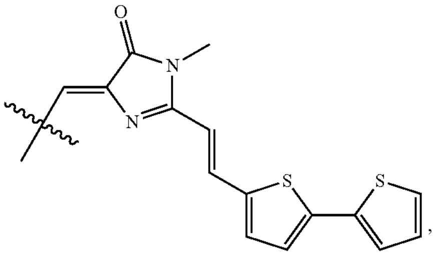
(I-2-23)
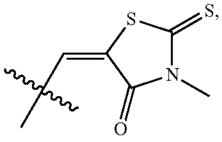
(I-2-24)
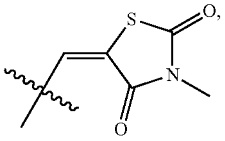
(I-2-25)
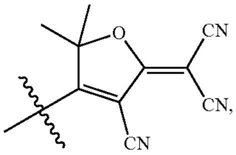

-continued
(I-2-26)
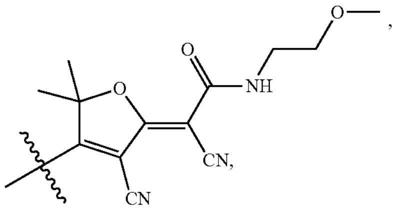
(I-2-27)
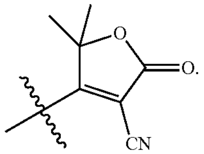
(I-2-28)
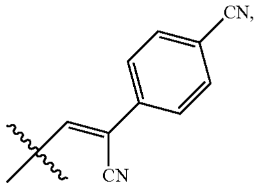
(I-2-29)
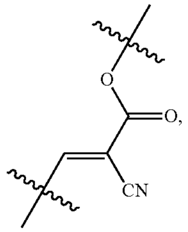
(I-2-30)
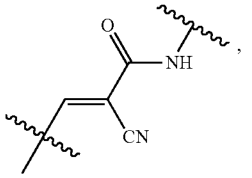
(I-2-31)
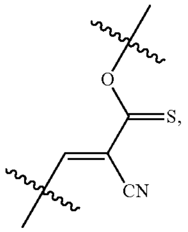
(I-2-32)
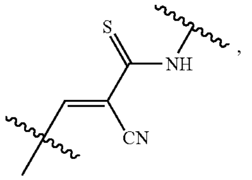
-continued
(I-2-33)
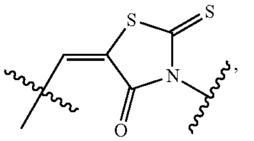
(I-2-34)
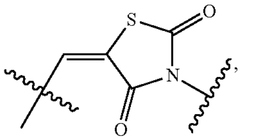
(I-2-35)
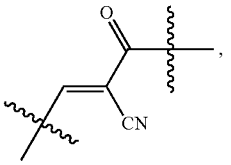
(I-2-36)
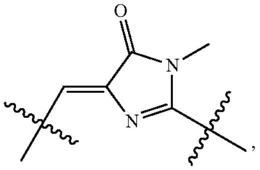
(I-2-37)
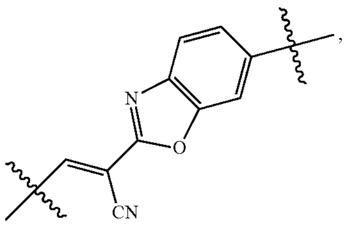
(I-2-38)
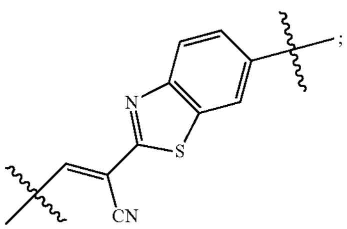
Optionally, the above-mentioned fluorescent probe is characterized in that the fluorescent probe is selected from compounds of the following formulae or salts thereof:

Probe 1
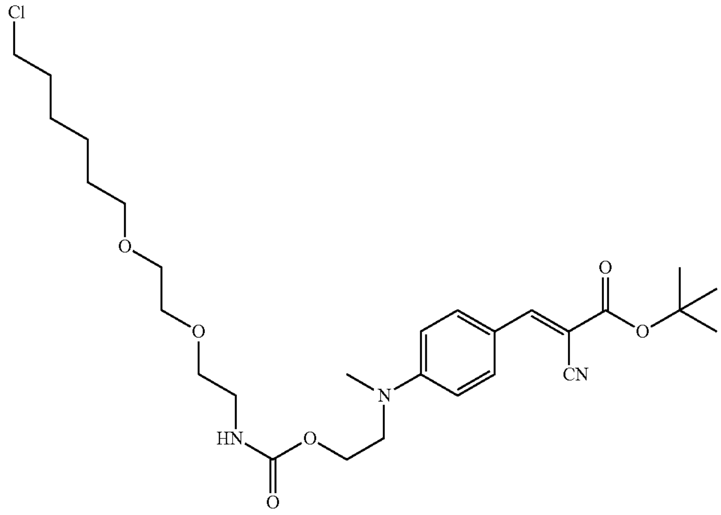
Probe 2
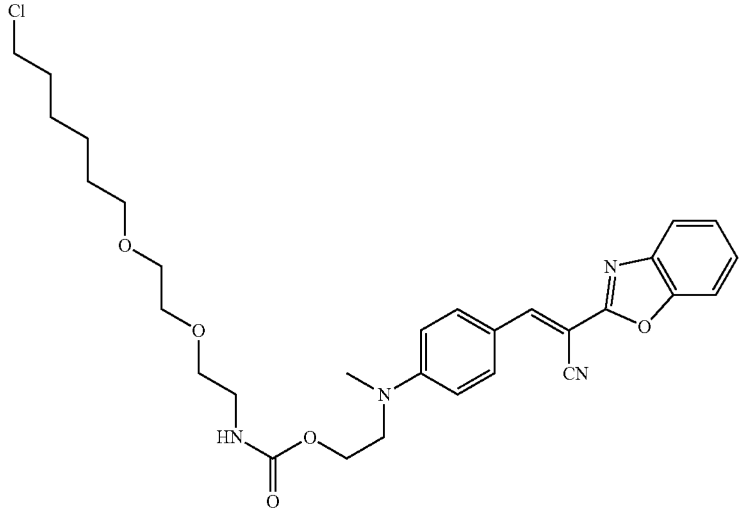
Probe 3
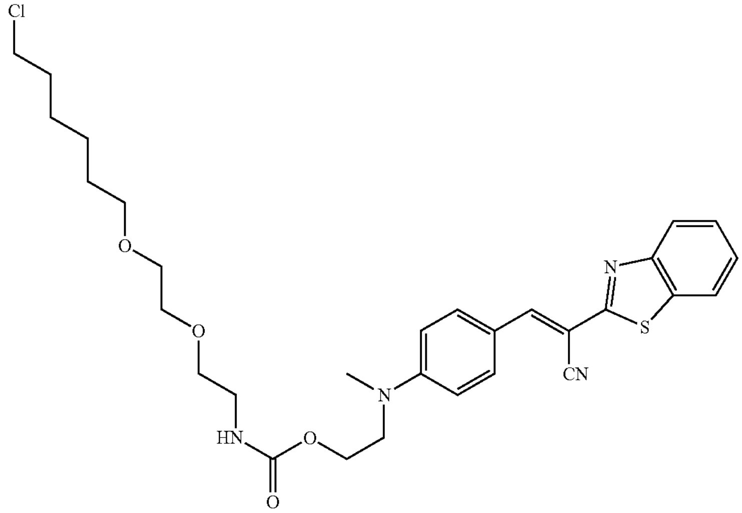

-continued
Probe 4
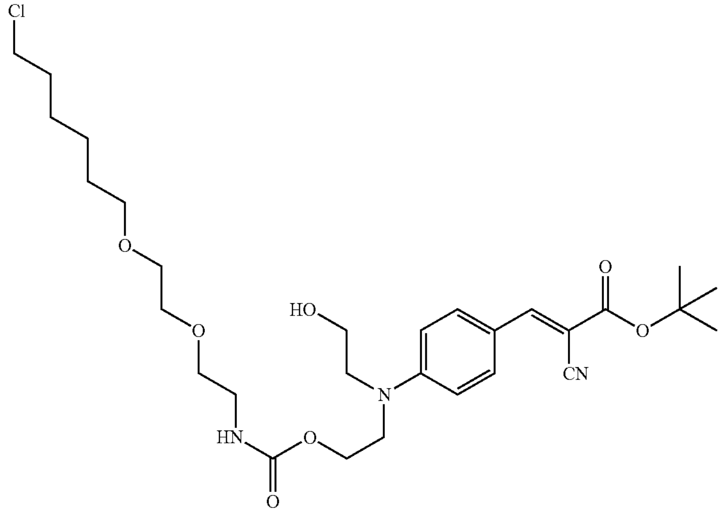
Probe 5
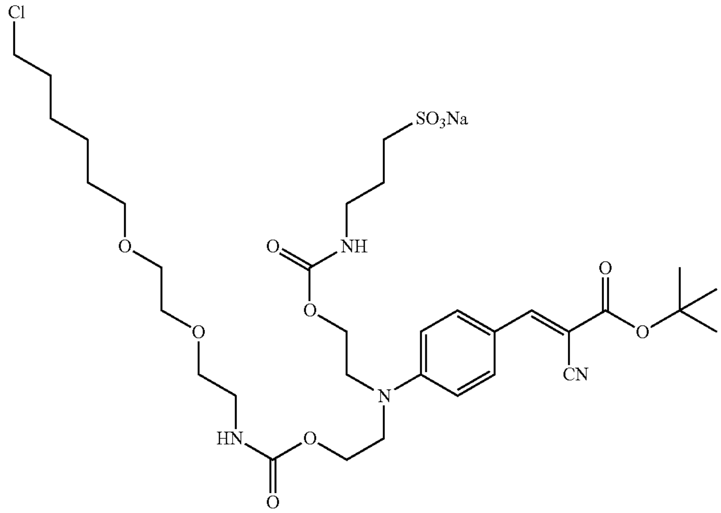
Probe 6
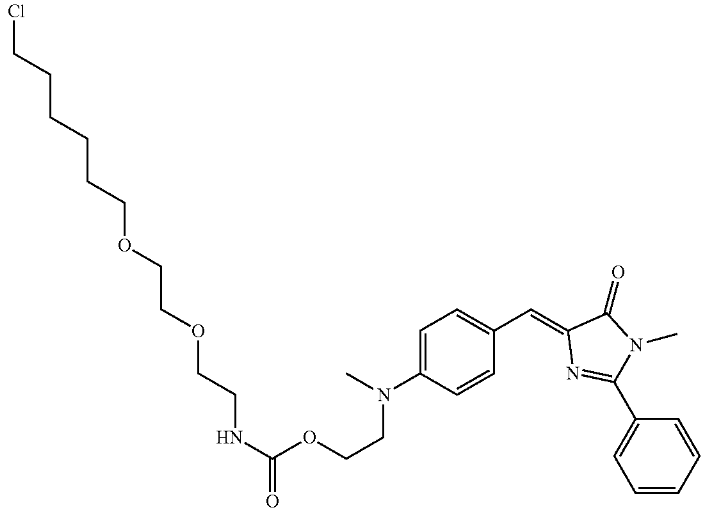

-continued
Probe 7
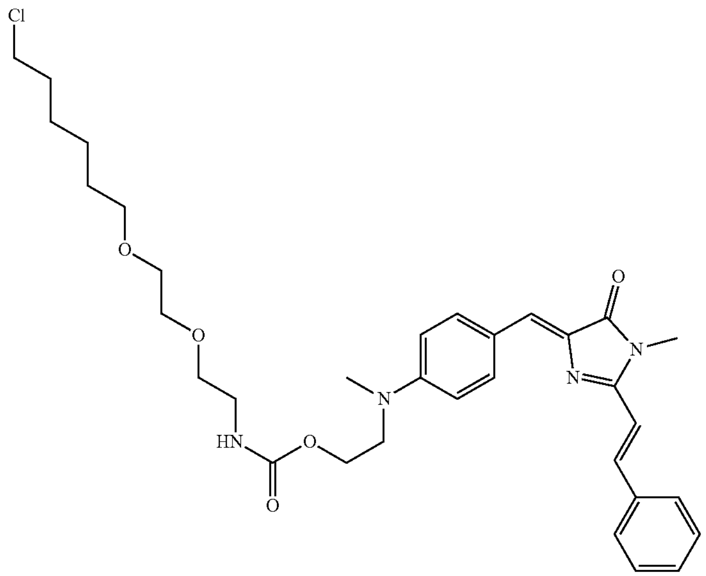
Probe 8
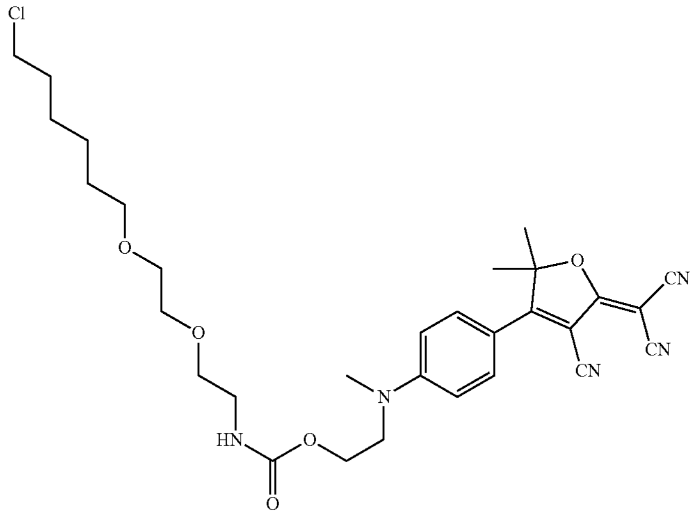
Probe 9
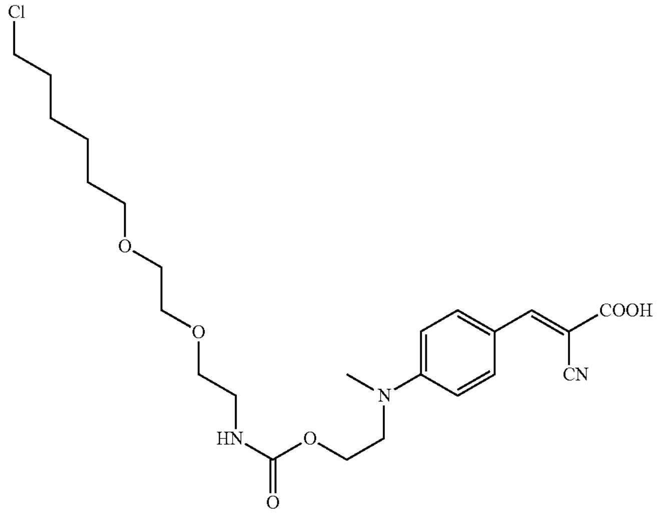

-continued
Probe 10
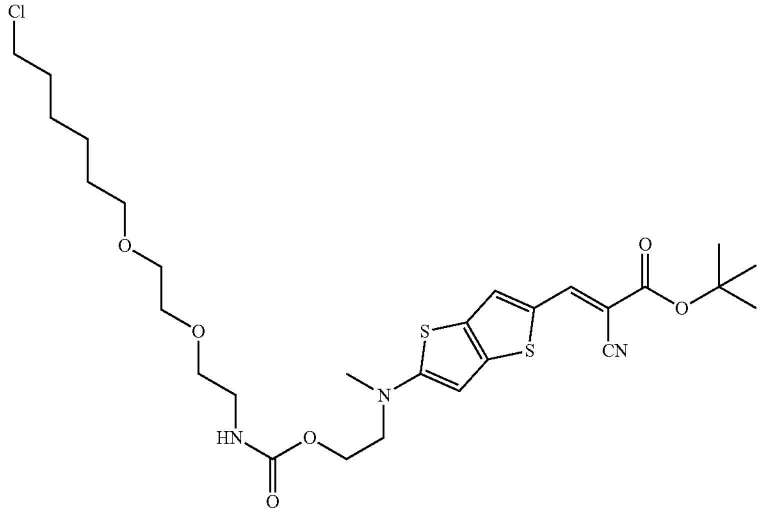
Probe 11
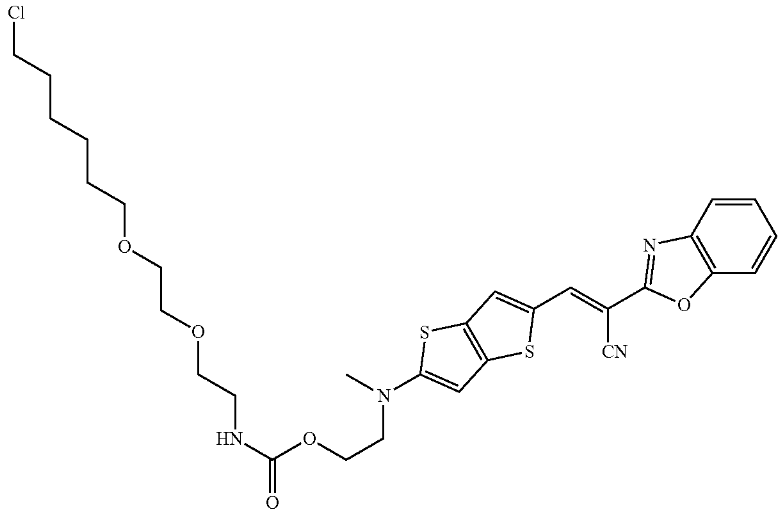
Probe 12
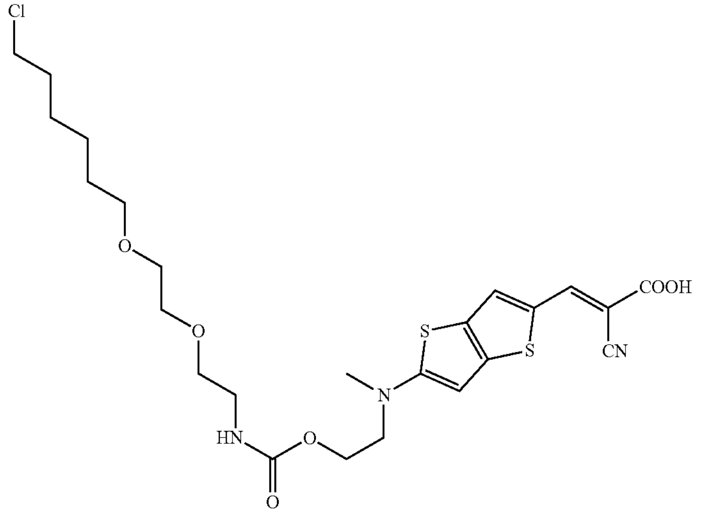

-continued
Probe 13
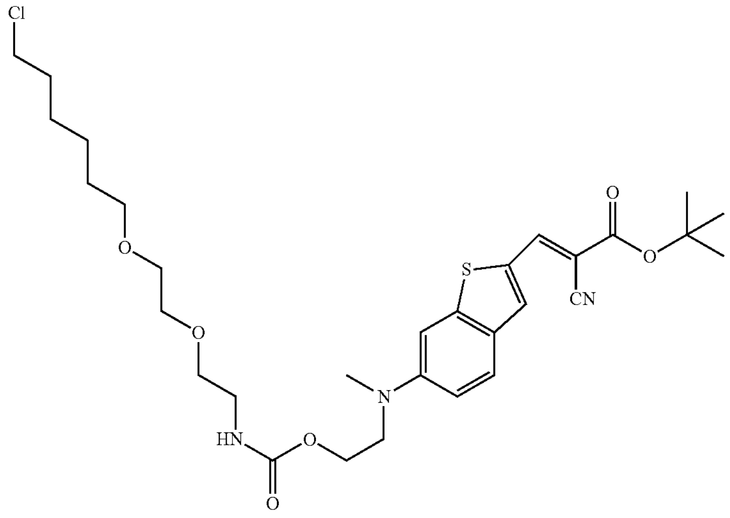
Probe 14
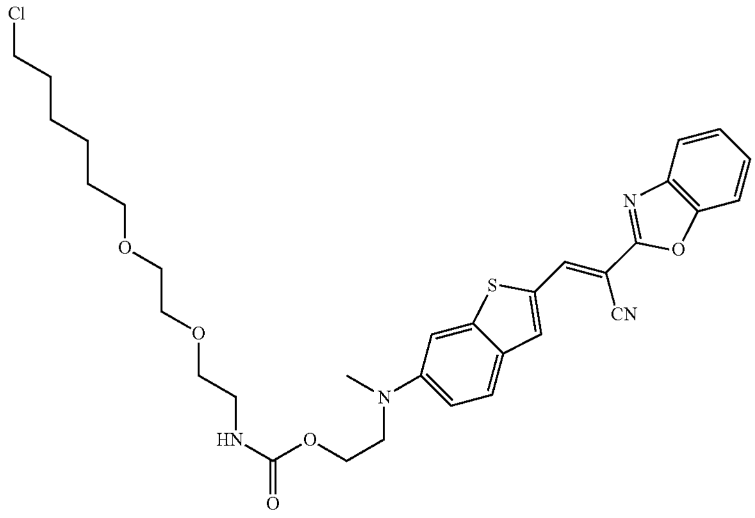
Probe 15
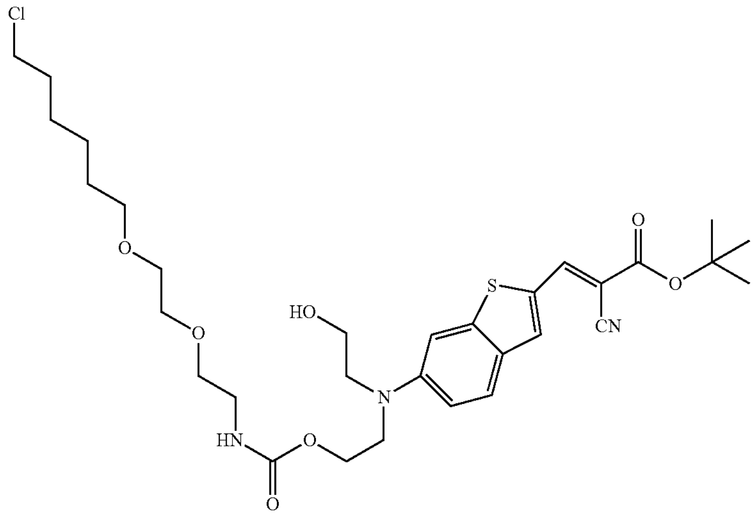

-continued
Probe 16
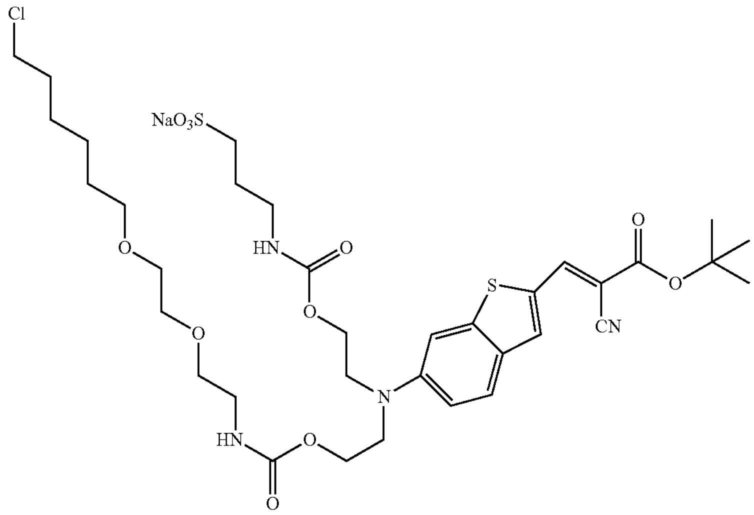
Probe 17
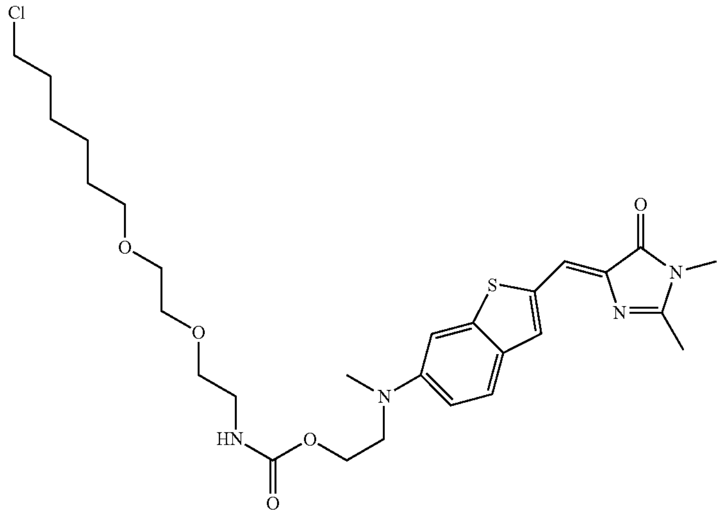
Probe 18
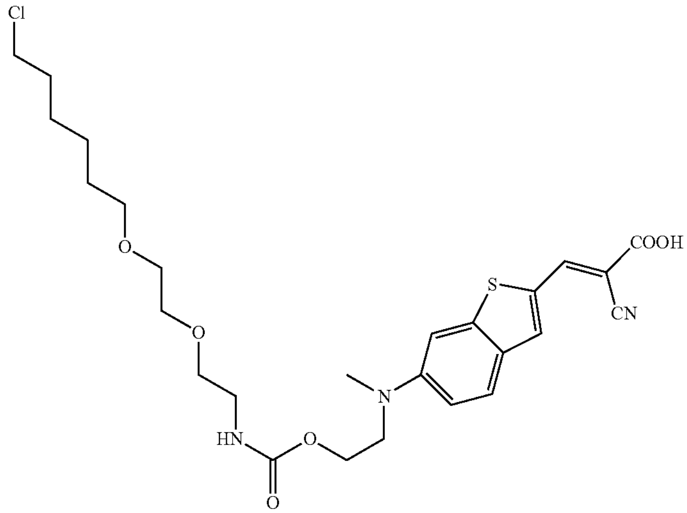

-continued
Probe 19
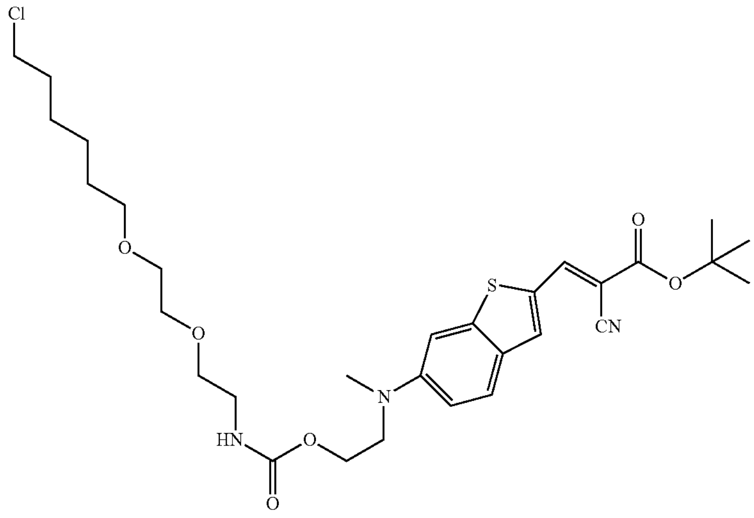
Probe 20
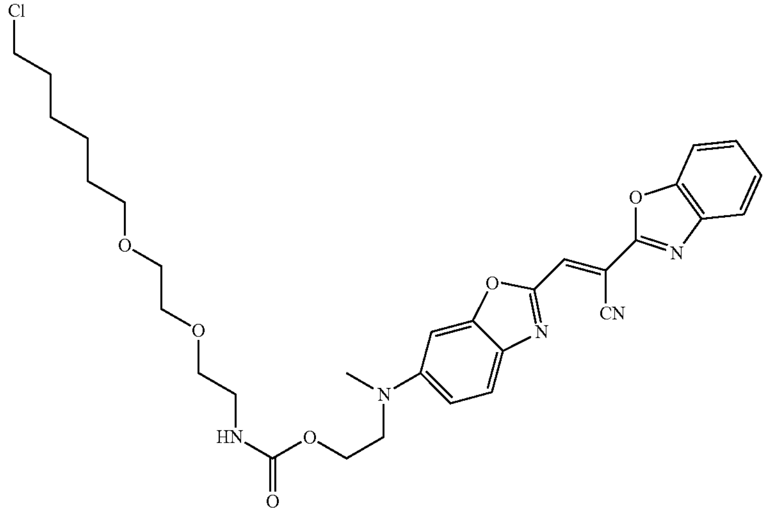
Probe 21
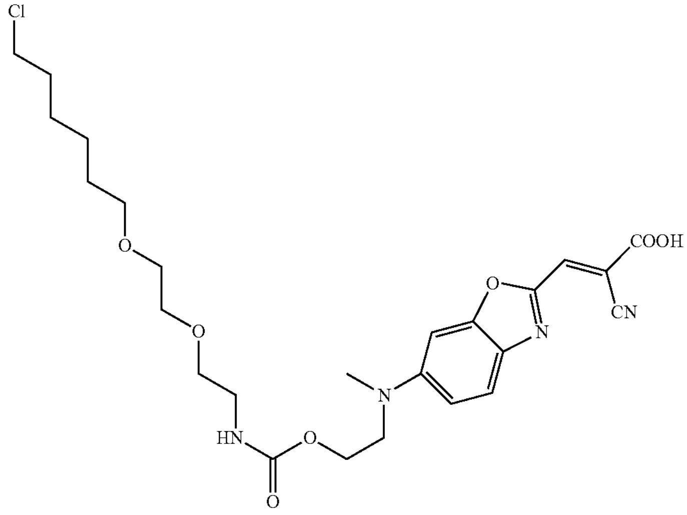

-continued
Probe 22
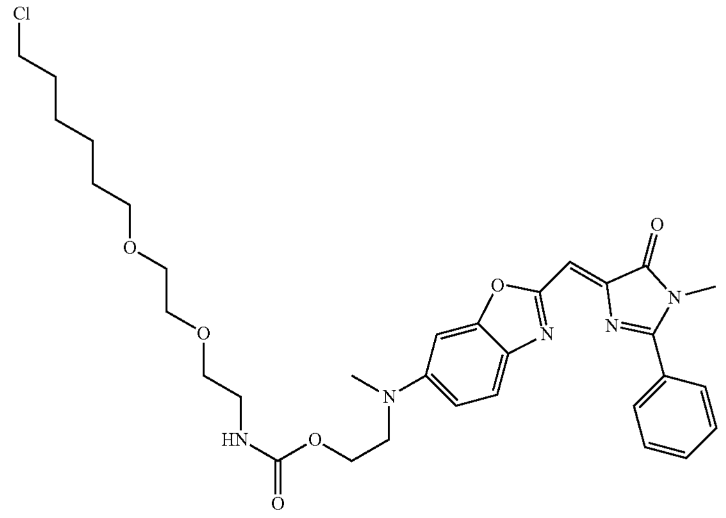
Probe 23
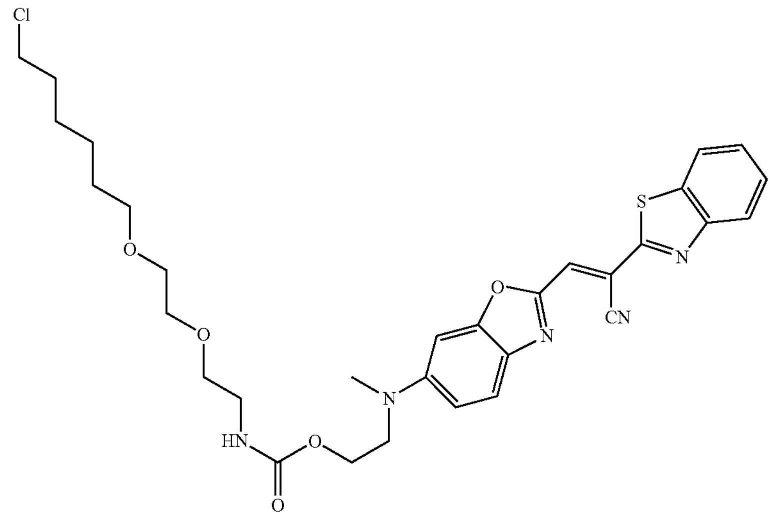
Probe 24
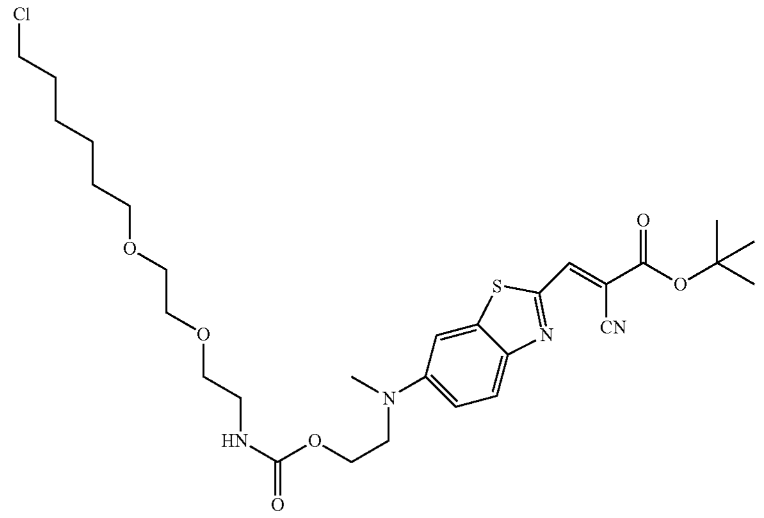

-continued
Probe 25
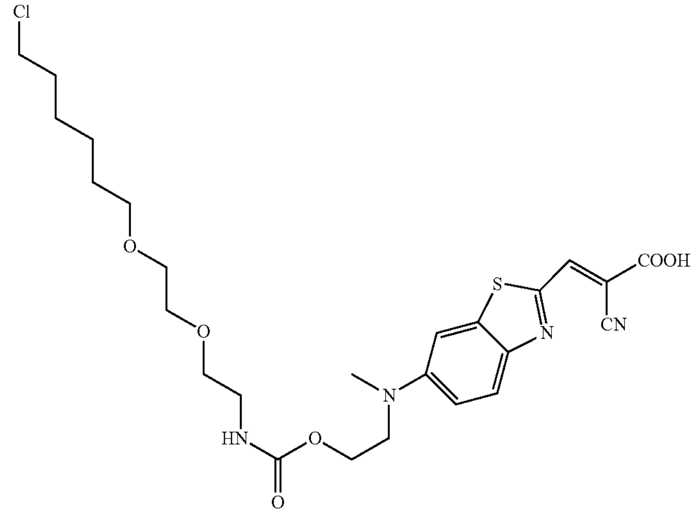
Probe 26
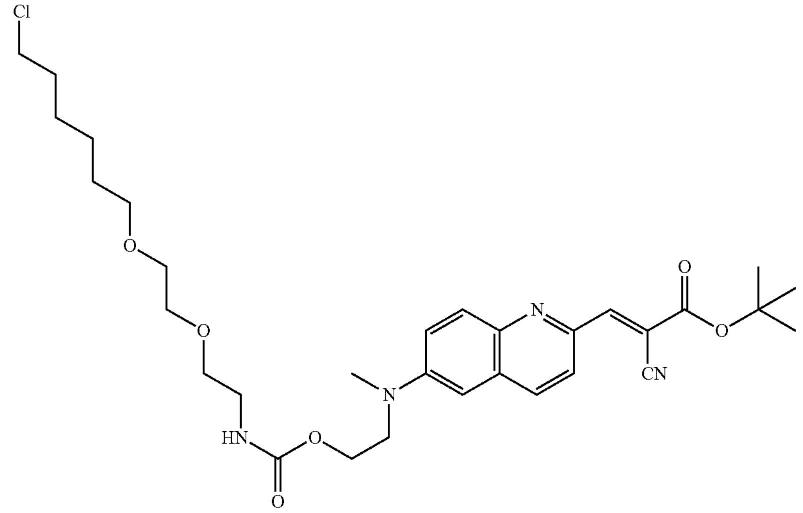
Probe 27
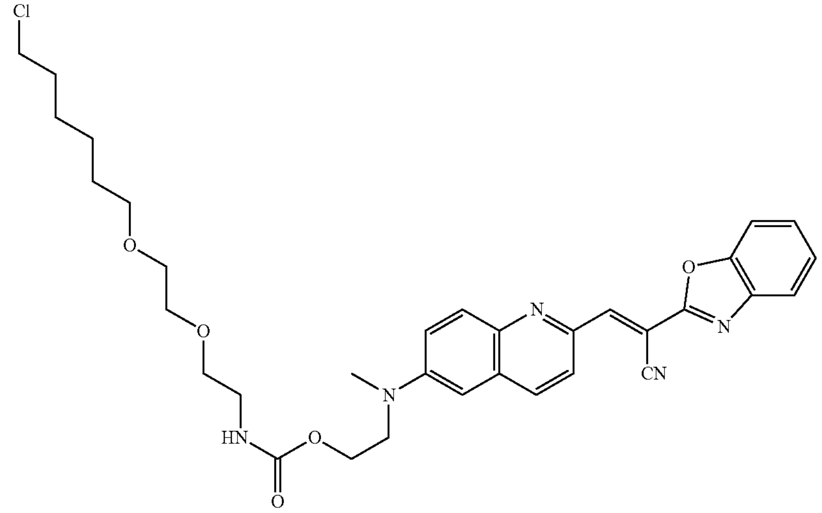

-continued
Probe 28
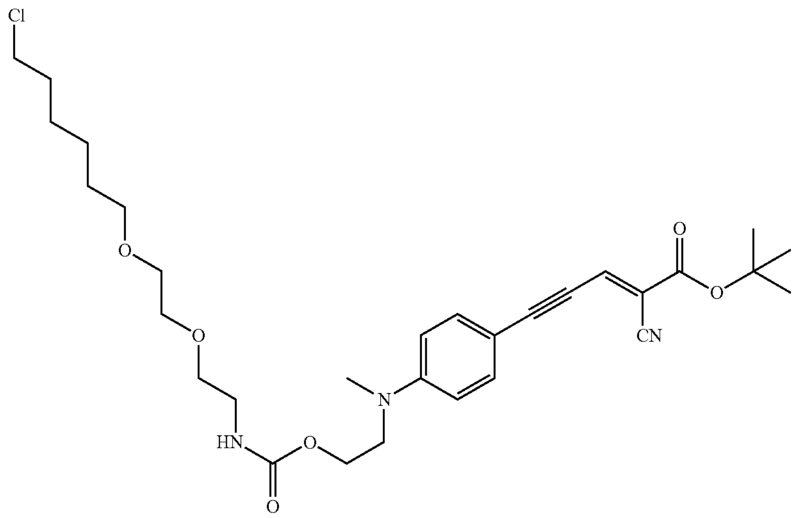
Probe 29
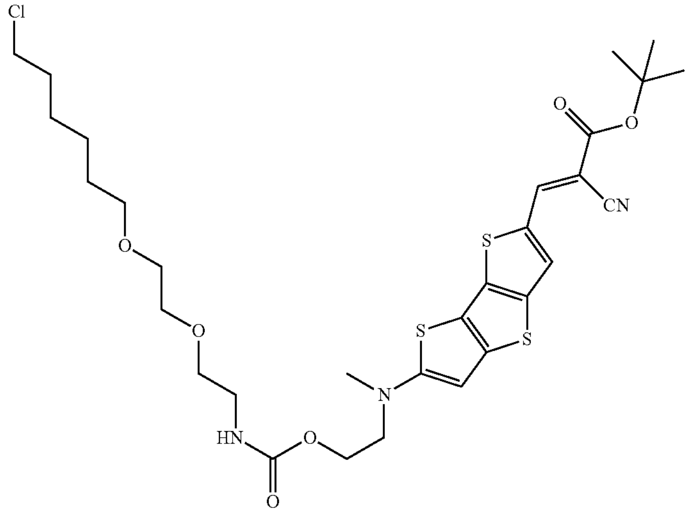
Probe 30
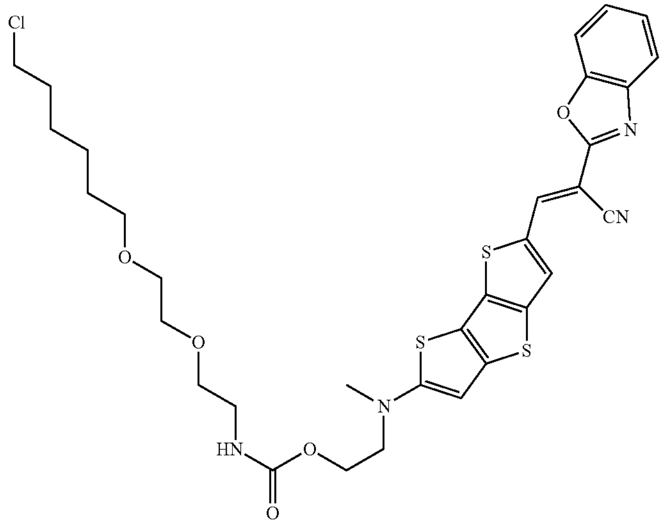

-continued
Probe 31
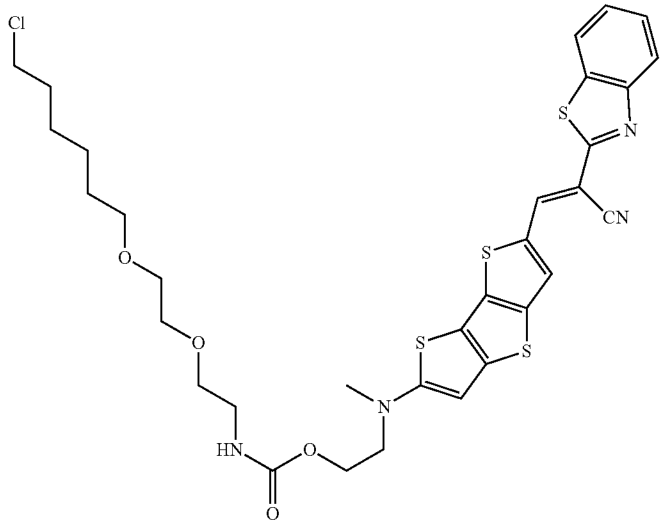
Probe 32
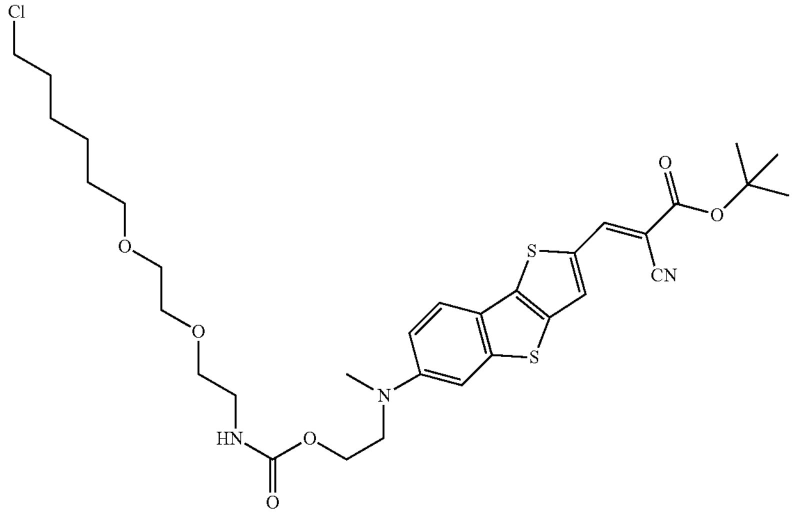
Probe 33
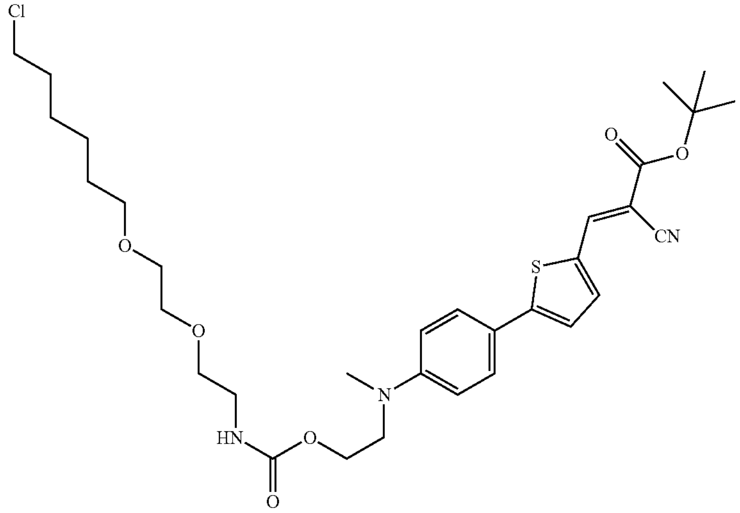

-continued
Probe 34
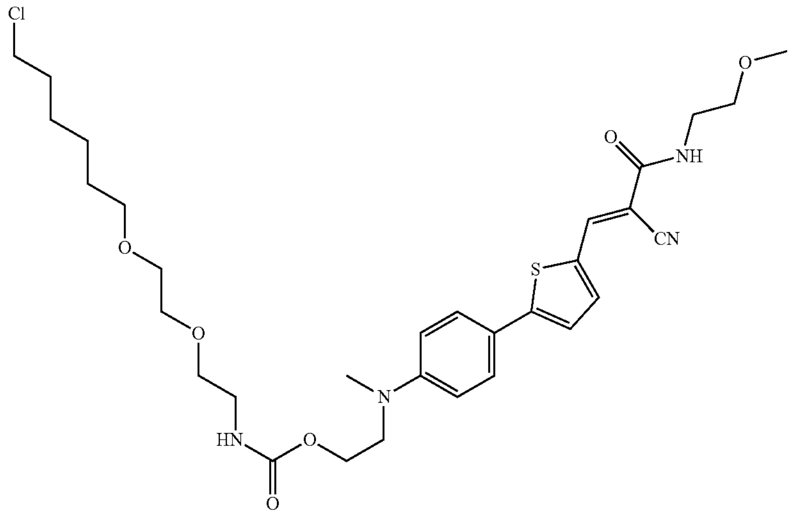
Probe 35
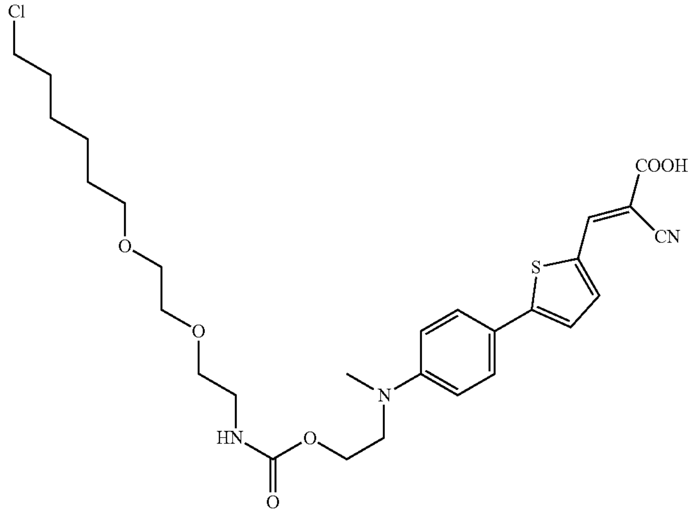
Probe 36
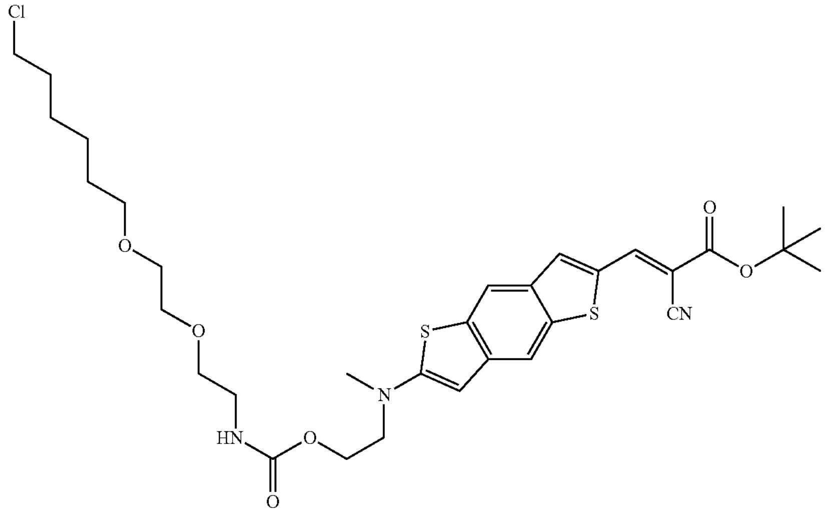

-continued
Probe 37
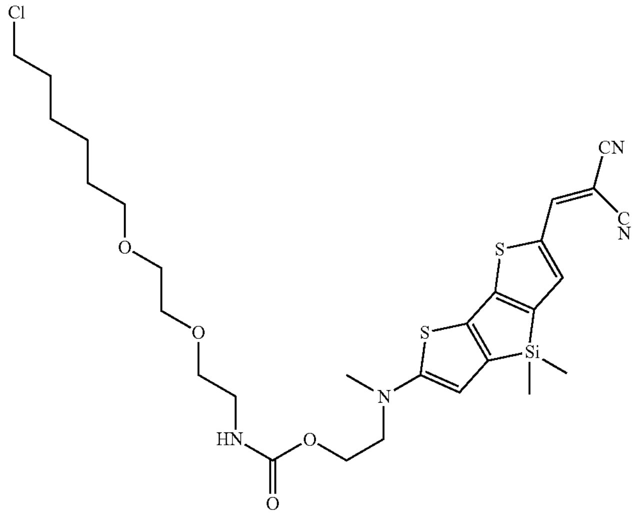
Probe 38
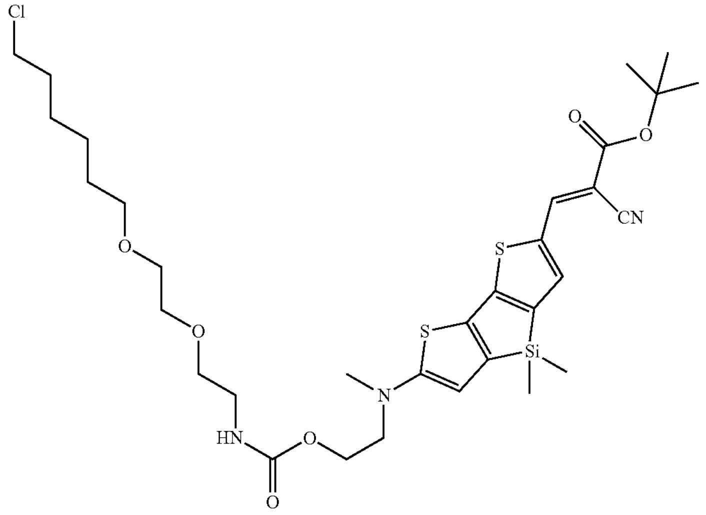
Probe 39
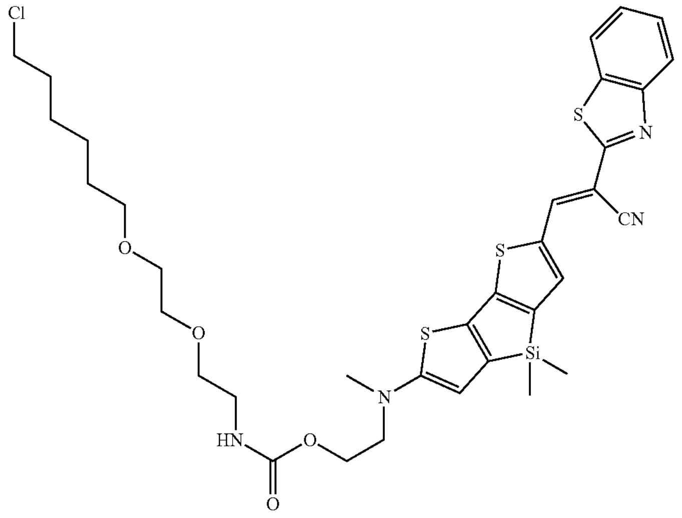

-continued
Probe 40
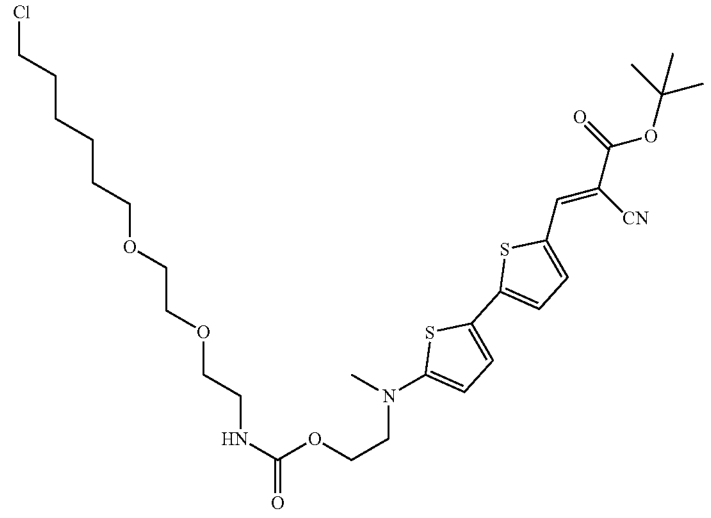
Probe 41
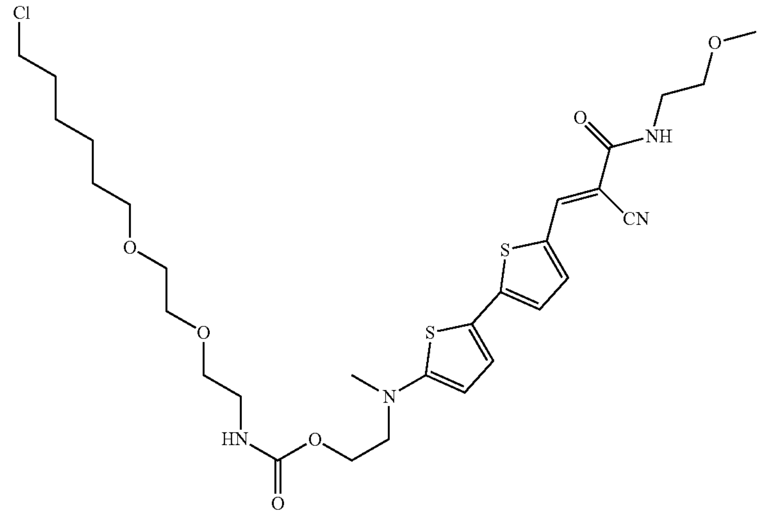
Probe 42
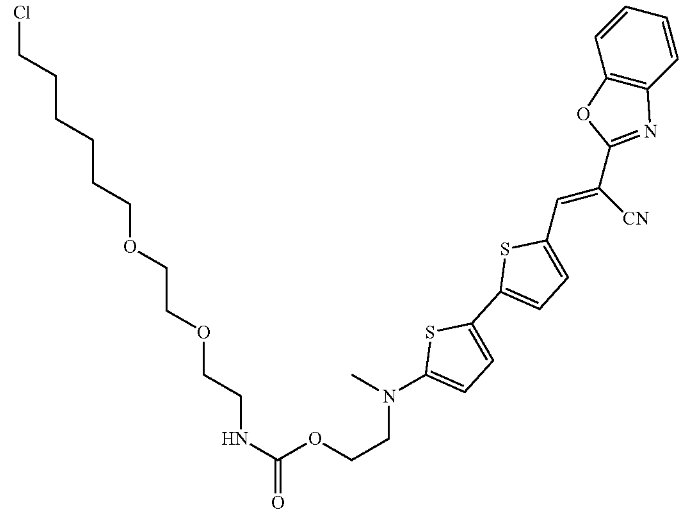

-continued
Probe 43
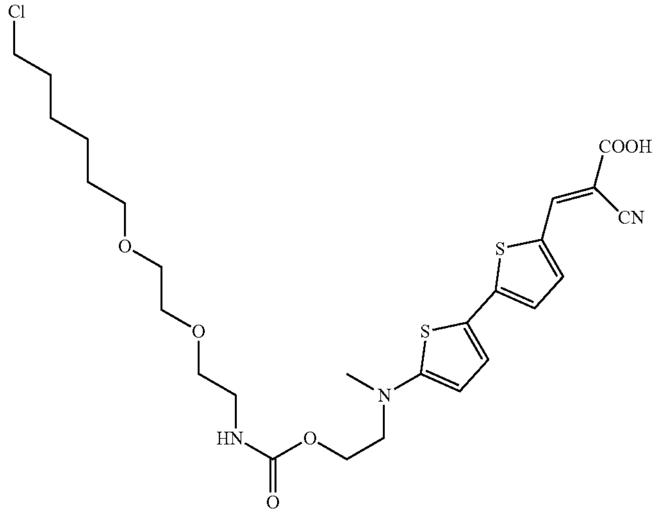
Probe 44
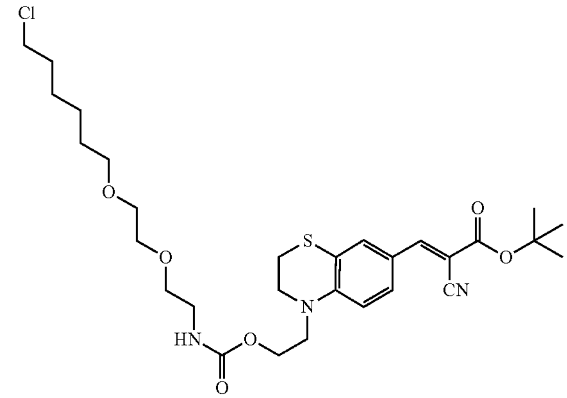
Probe 45
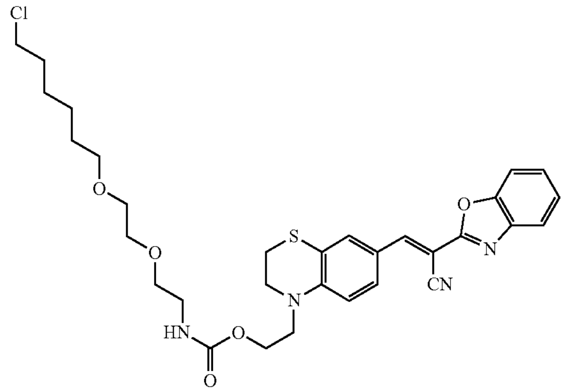
Probe 46
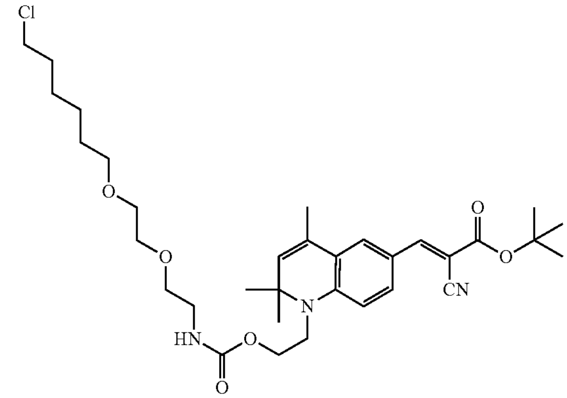
Probe 47
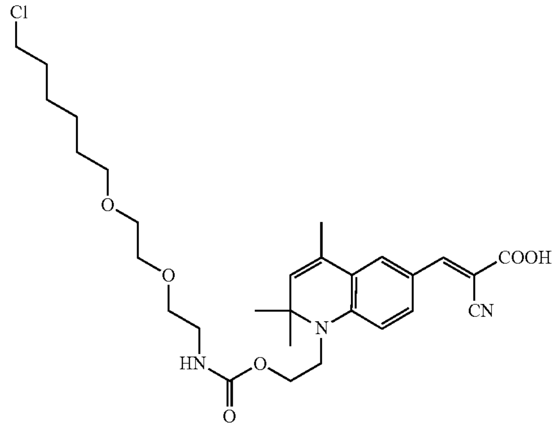

-continued
Probe 48
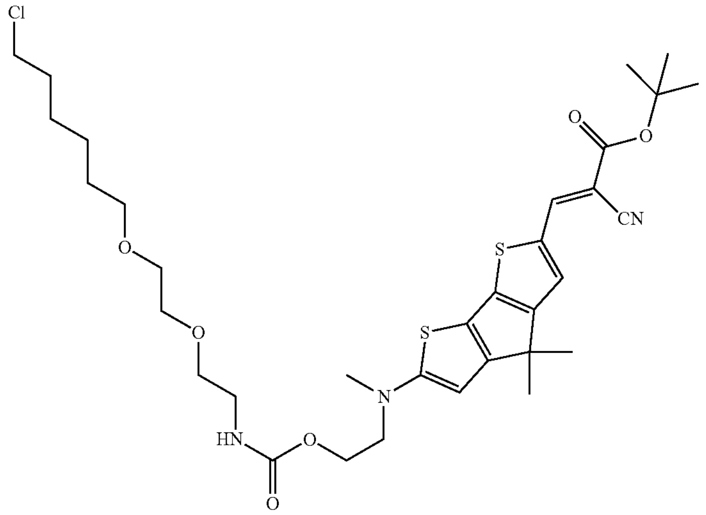
Probe 49
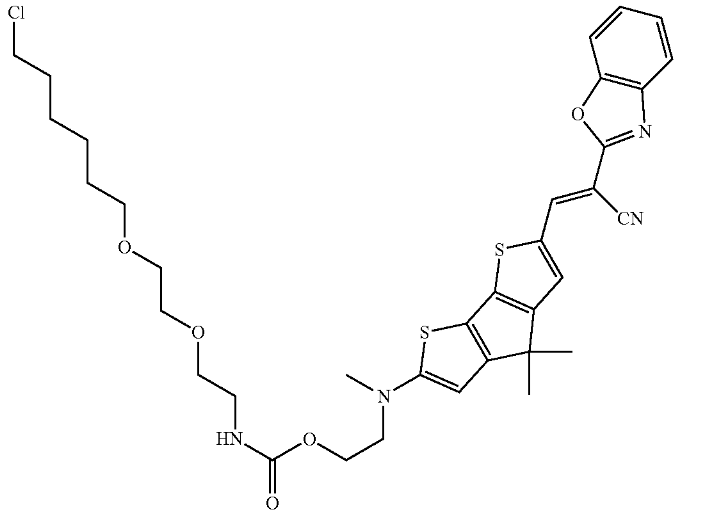
Probe 50
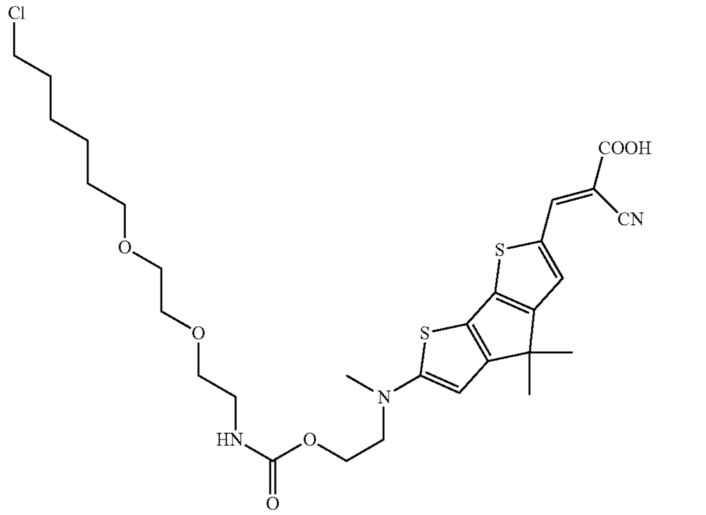

-continued
Probe 51
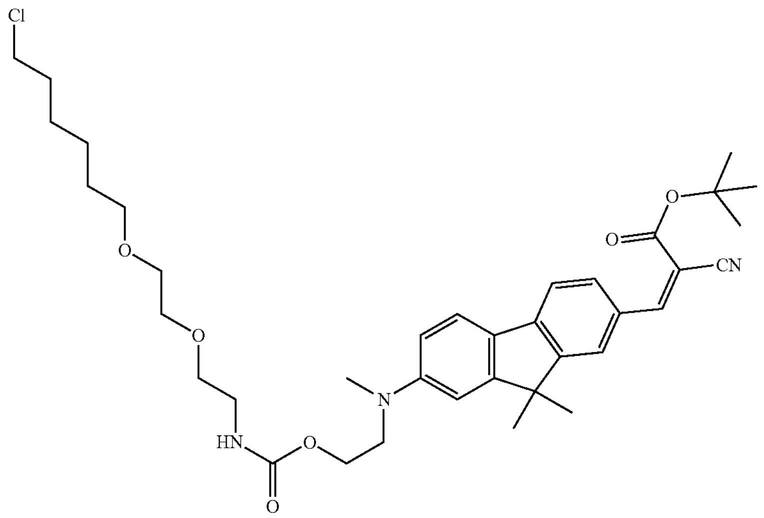
Probe 52
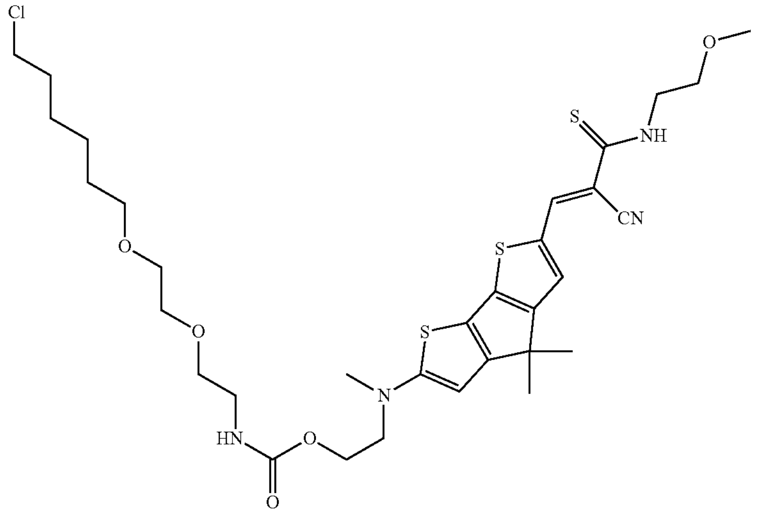
Probe 53
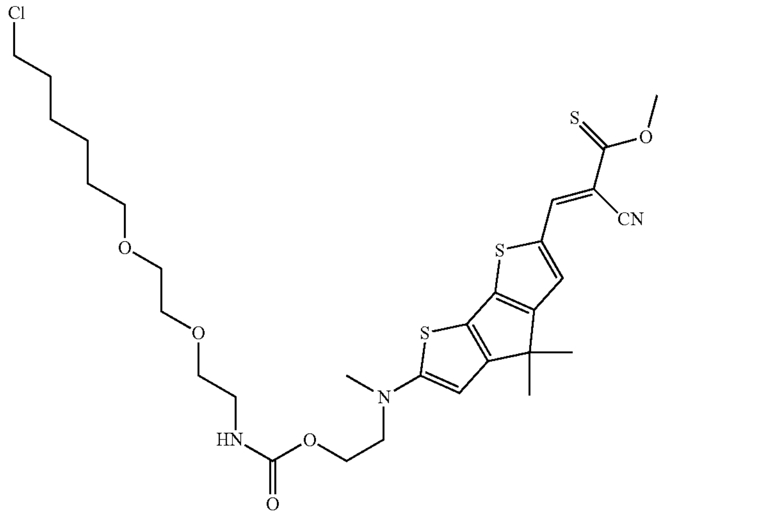

-continued
Probe 54
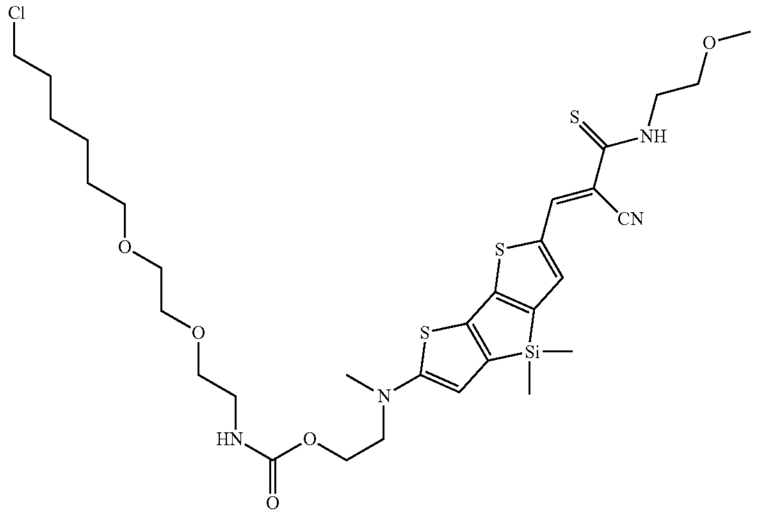
Probe 55
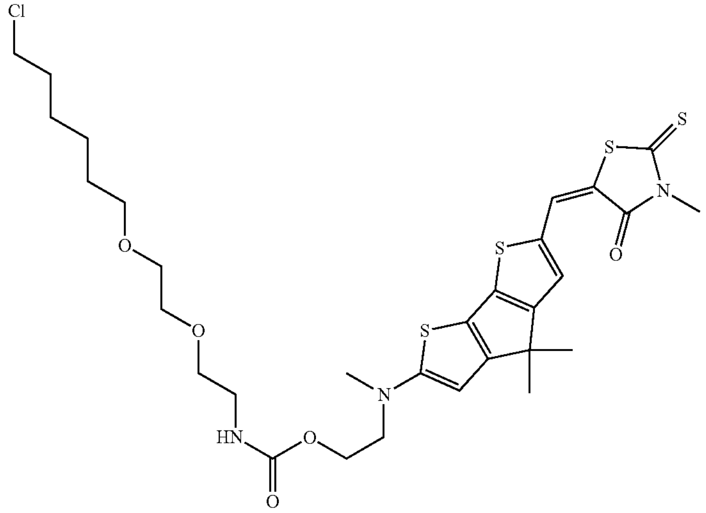
Probe 56
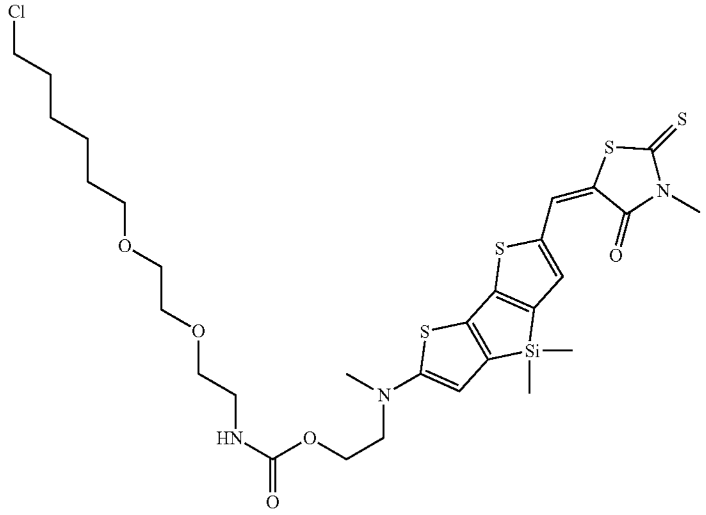

-continued
Probe 57
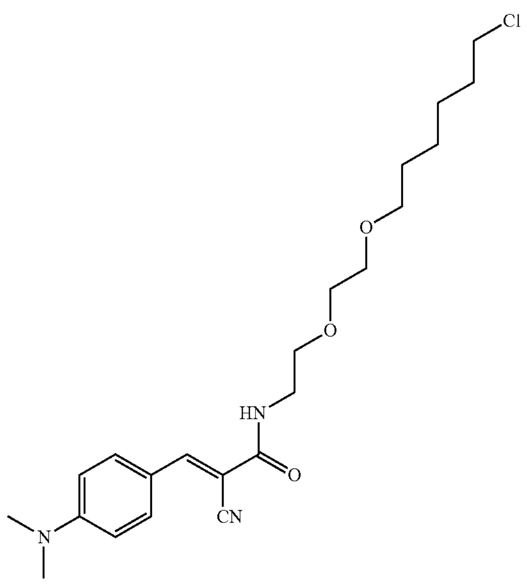
Probe 58
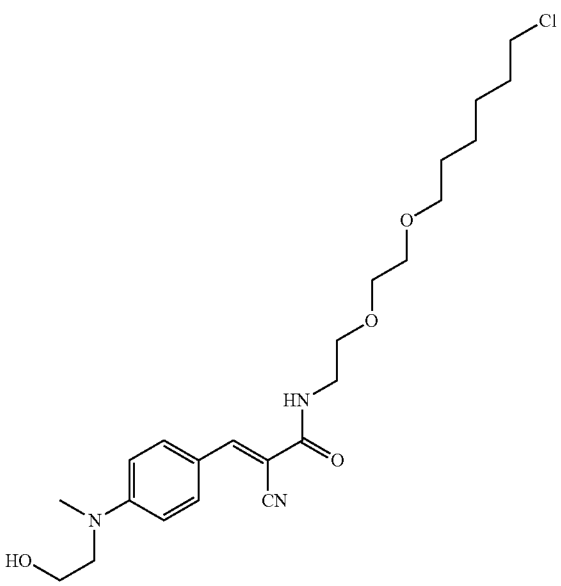
Probe 59
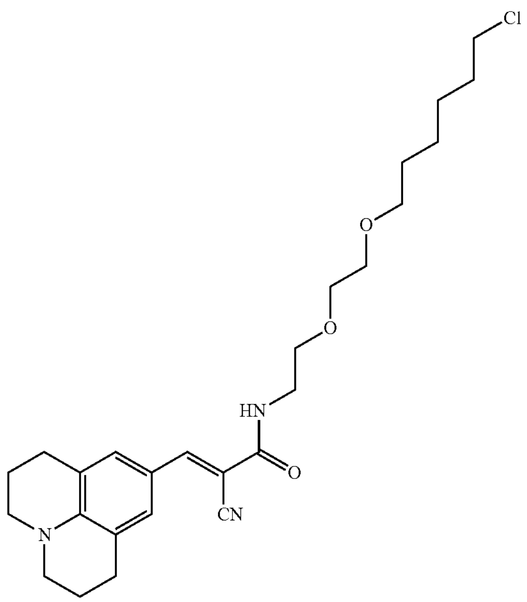
Probe 60
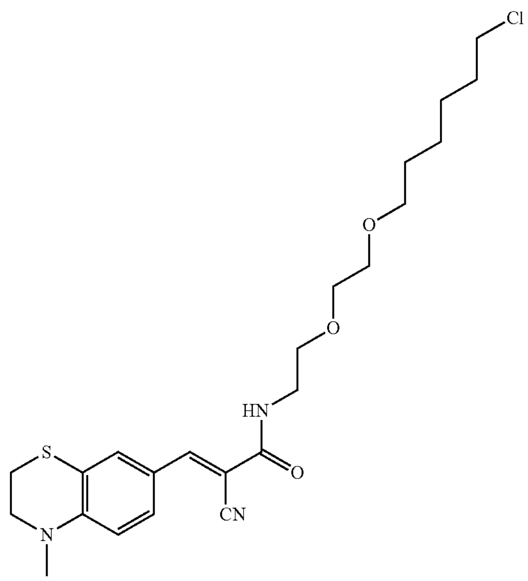

-continued
Probe 61
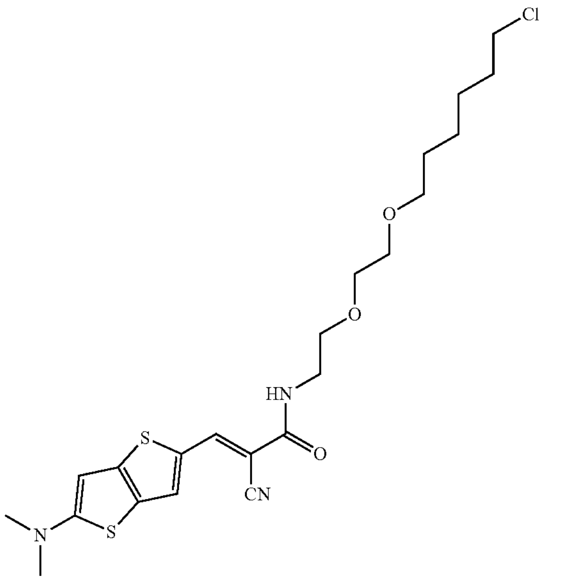
Probe 62
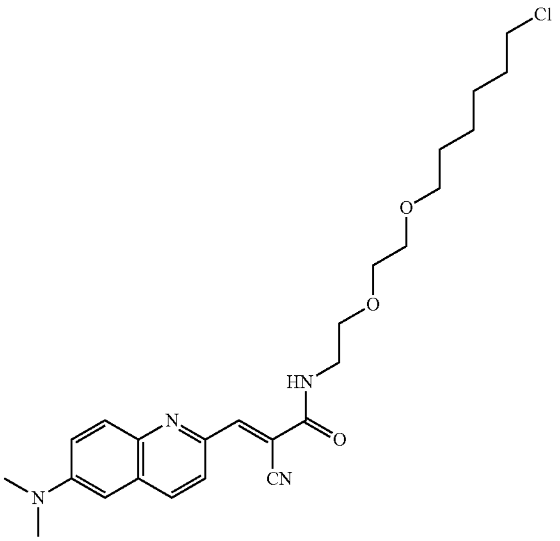
Probe 63
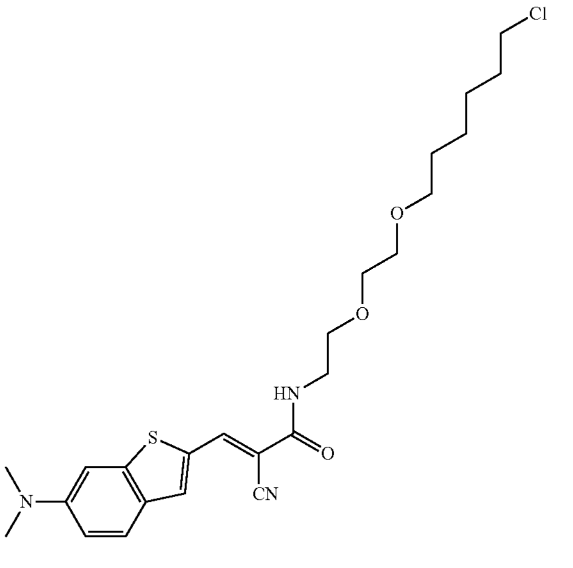
Probe 64
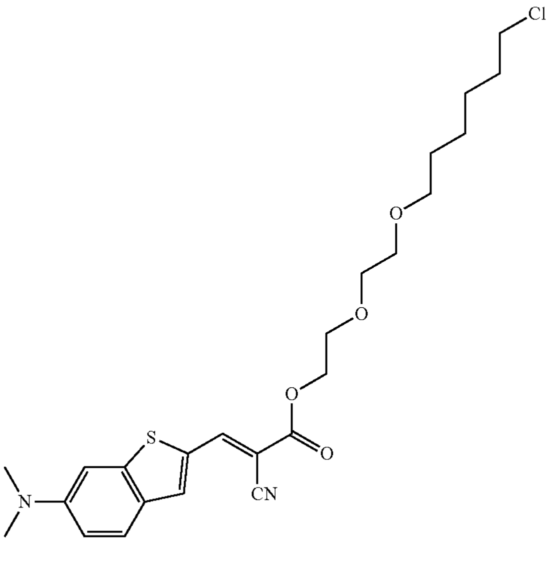

-continued
Probe 65
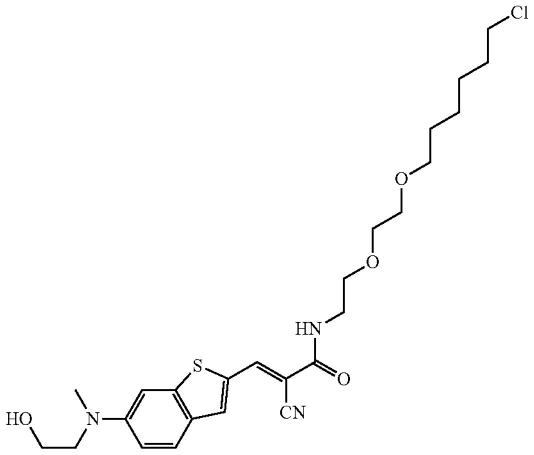
Probe 66
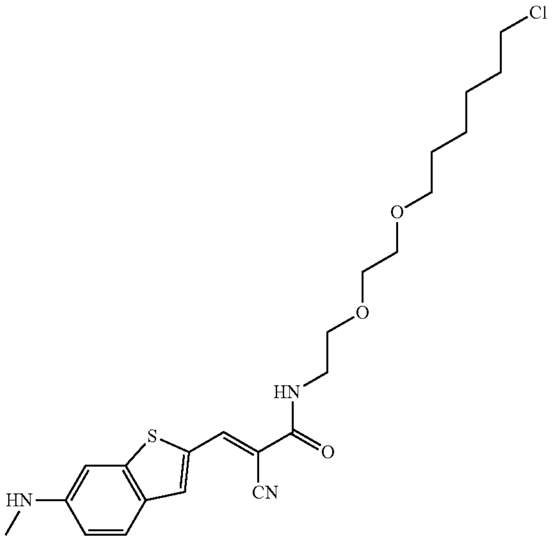
Probe 67
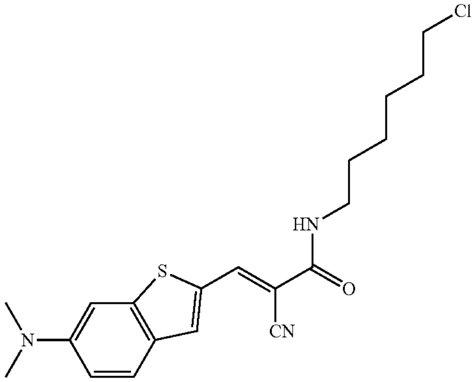
Probe 68
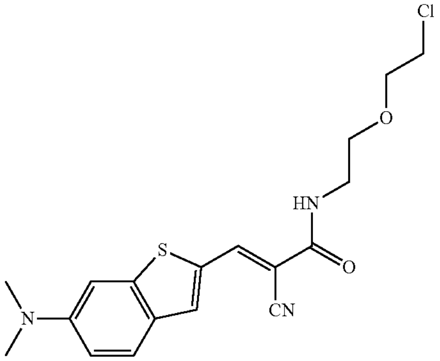
Probe 69
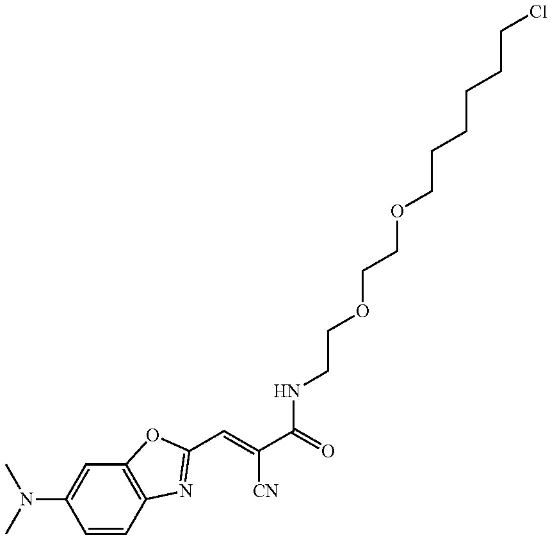
Probe 70
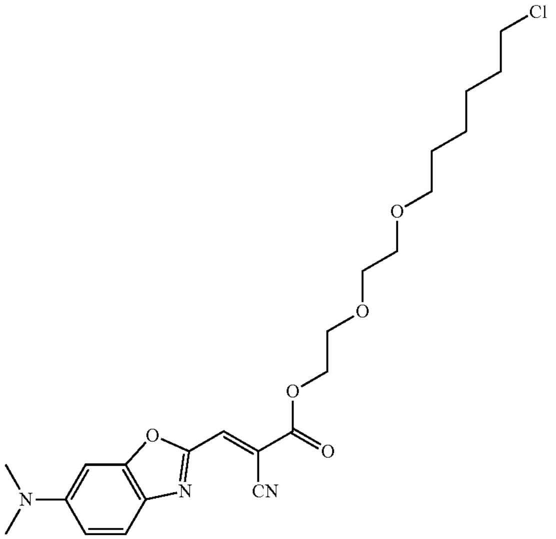

-continued
Probe 71
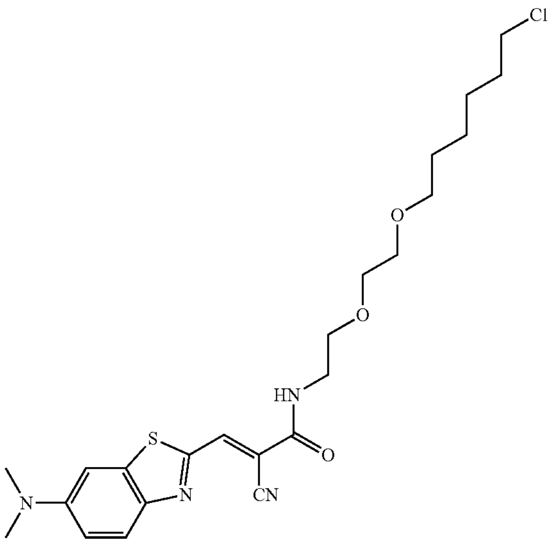
Probe 72
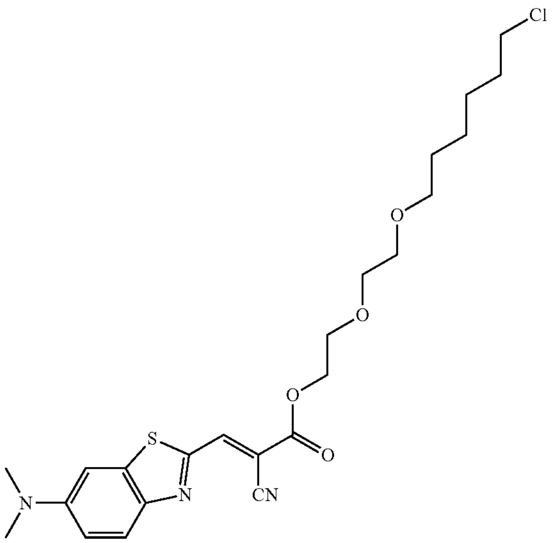
Probe 73
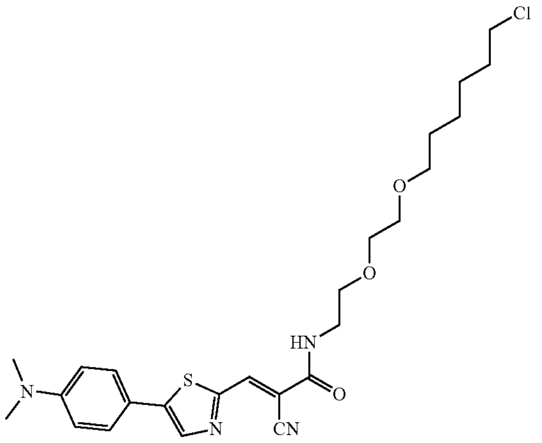
Probe 74
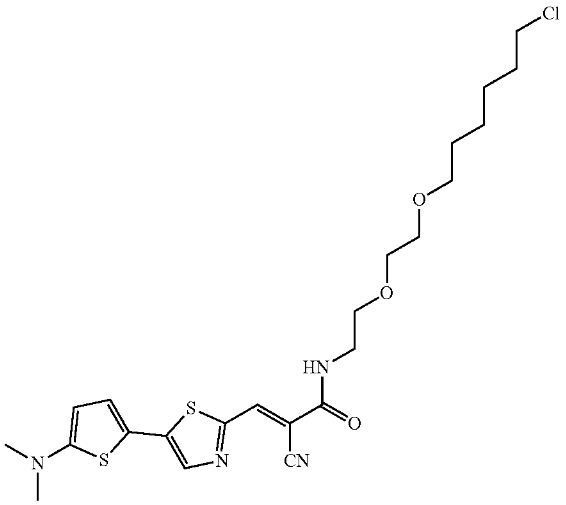
Probe 75
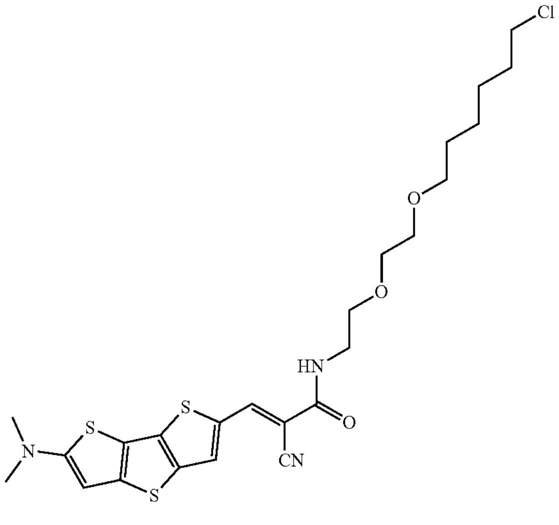
Probe 76
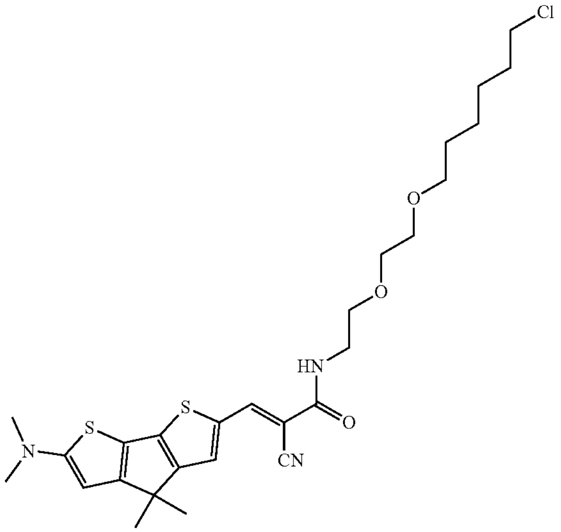

-continued
Probe 77
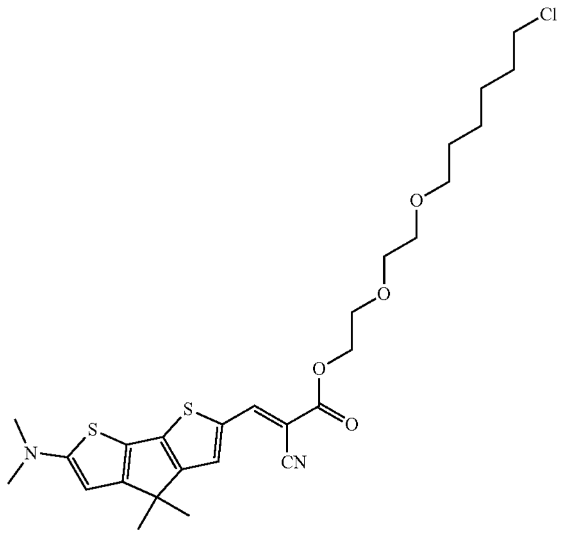
Probe 78
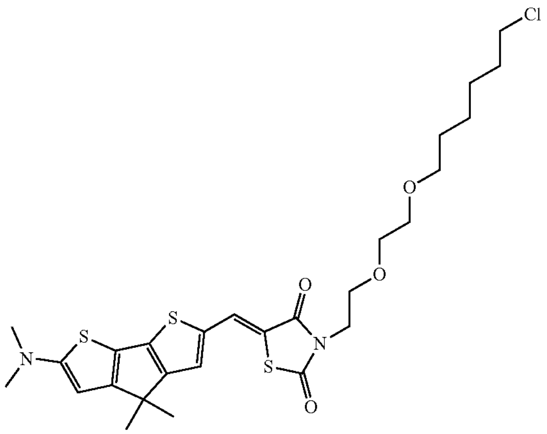
Probe 79
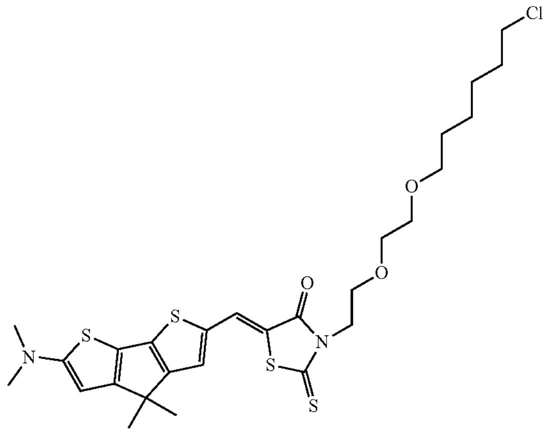
Probe 80
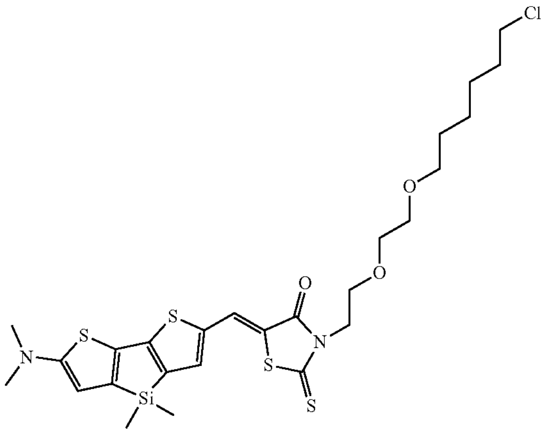
Probe 81
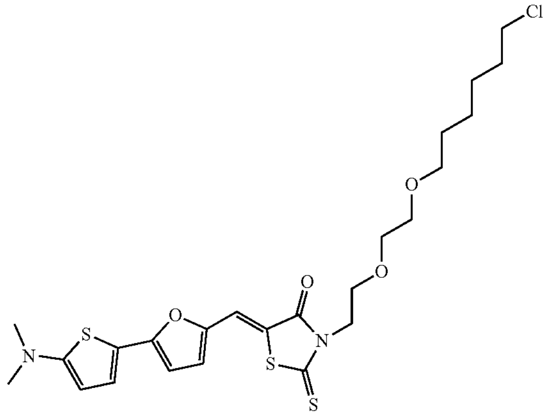
Probe 82
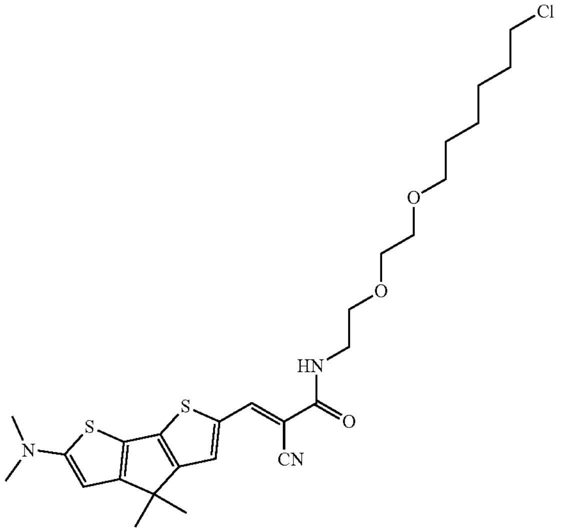

-continued

Probe 83

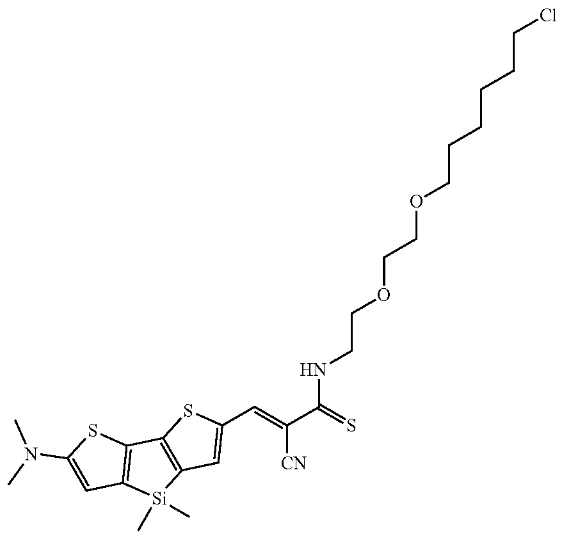

Probe 84

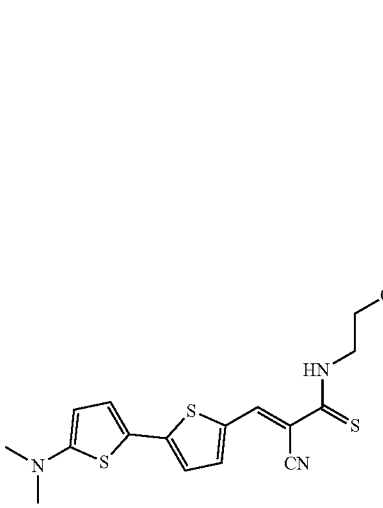

Probe 86

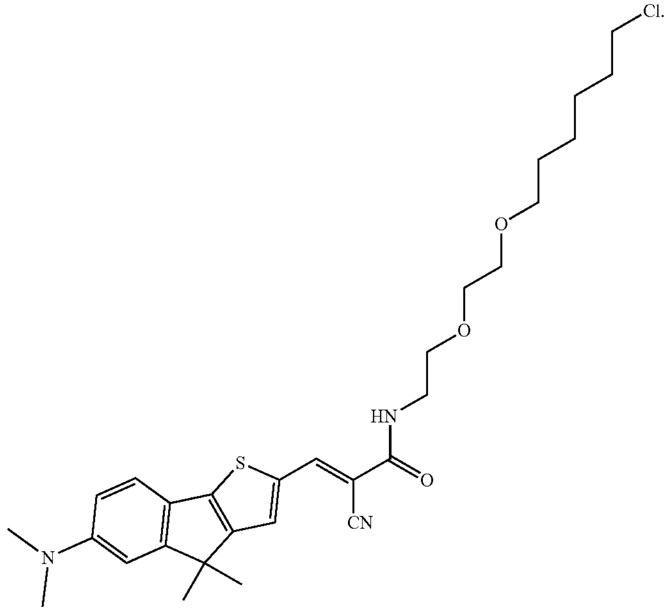

The salts of the above compounds may be an alkali metal salt, an alkaline earth metal salt, an anion salt, and optionally a sodium salt, a potassium salt, a calcium salt, a hydrochloride, a sulfate, a sulfonate, a carboxylate, and the like.

In another aspect, a method for preparing the above-mentioned fluorescent probe is also provided, which comprises a step of reacting the fluorescent dye represented by formula (II) with a ligand and an optional linker:

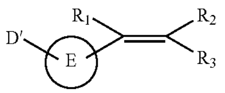

(II)

Wherein, after reaction D-group is formed from D' and is bound to a linking group or a ligand; or after reaction $R_2$-group is formed from $R_2$' and is bound to the linking group or the ligand.

In another aspect, there is provided a fluorescent activated protein specific labeling method, comprising steps of contacting the above-mentioned fluorescent probe with a target protein of a protein tag or a fusion protein tag; performing labeling reaction between the ligand moiety of the fluorescent probe and the protein tag to label the protein tag with the fluorescent probe; optionally, the labeling of the protein tag with the fluorescent probe is covalently labeling;

optionally, a reaction medium of the labeling reaction is selected from a pure protein solution, a cell lysate or an in situ medium in which the target protein of a protein tag or a fusion protein tag is located, optionally, the in situ medium is intracellular media, organelle media, living tissue media, blood or body fluids.

In another aspect, there is provided use of the above-mentioned fluorescent probe for fluorescent labeling, quantification, detection or kinetic studies of proteins, and for imaging of cells, tissues, and living bodies.

In another aspect, there is further provided a probe kit comprising the aforesaid fluorescent probe.

Optionally, the probe kit further comprises a biocompatible medium; optionally, the biocompatible medium is at least one selected from dimethyl sulfoxide, a buffer, and physiological saline; optionally, the buffer includes phosphate buffer.

The above-mentioned target protein of a protein tag or a fusion protein tag can be prepared by the existing genetic engineering techniques.

The above-mentioned viscosity-responsive fluorescent dye means that the fluorescence intensity of the dye responds to the viscosity of the solution. As the viscosity of the solution increases, the fluorescence intensity increases. Optionally, the viscosity-responsive fluorescent dye is an organic dye molecule which, under the same concentration and excitation wavelength, at 25° C. has a ratio of the maximum fluorescence emission intensity of the dye in glycerol to the fluorescence intensity in methanol of greater than 2, optionally greater than 5, optionally greater than 10. The concentration of the viscosity-responsive dye ranges from $1\times10^{-7}$ M to $1\times10^{-5}$ M.

Depending on the specific situation, the person skilled in the art can select the corresponding tags and ligands as needed.

Those skilled in the art can track and monitor the target protein of a protein tag or a fusion protein tag with equipment with corresponding configuration. The equipment used, as needed, includes equipment and facilities capable of testing or displaying fluorescence, such as fluorescence spectrometers, fluorescence Microscopes, confocal fluorescence microscopes, microplate readers, flow cytometers, and in vivo imagers.

Depending on the needs, the operator can choose different types of dyes with different emission/excitation wavelengths.

According to an embodiment of one aspect, the fluorescent probe has a wide range of fluorescence emission wavelengths.

According to an embodiment of one aspect, the fluorescence intensity of the fluorescent probe increases as the environmental viscosity increases, is sensitive to viscosity and has viscosity responsiveness.

According to an embodiment of one aspect, the fluorescent probe can be used for specific labeling of a protein tag of a protein tag or a fusion protein tag. After the fluorescent probe is bound to the protein tag, fluorescence can be activated, the fluorescent probe has good fluorescent molecular switching properties, and the fluorescence activation multiple is high, and the fluorescence activation brightness is high.

According to an embodiment of one aspect, the fluorescent probe has a very fast speed of labeling the protein.

According to an embodiment of one aspect, the fluorescent probe has a good linear relationship between the fluorescence intensity and the protein tag concentration and can be used for the quantitative detection of a target protein.

According to an embodiment of one aspect, the fluorescent probe can achieve specific labeling of intracellular protein tags, and achieve fluorescence-specific lighting, and at the same time, the probe fluorescence is not affected by the intracellular environment.

According to an embodiment of one aspect, a fluorescent probe can be used as a powerful tool for labeling cell subcellular organelle, such as labeling nucleus, mitochondria, Golgi apparatus, endoplasmic reticulum, whole cells, cytoskeleton, extracellular membrane, lysosome, intracellular membrane, or the like.

According to an embodiment of one aspect, the spectra of fluorophores of different fluorescent probes do not interfere with each other, and fluorescent probes of different colors can be used for multi-color labeling of samples, and can simultaneously perform orthogonal label imaging.

According to an embodiment of one aspect, the fluorescence of the fluorescent probe is not affected by the internal environment of the animal, and can be applied to a living animal, for example, to specifically label a Halo-Tag protein tag expressed in the liver and generate a strong fluorescent signal.

According to an embodiment of one aspect, a fluorescent probe can be used to track and monitor the degradation process of a target protein.

According to an embodiment of one aspect, the fluorescent probe monitors the assembly and degradation process of biological macromolecules in mammalian cells in real time.

According to an embodiment of one aspect, the fluorescent probe can perform rapid contrast imaging on a tissue that is not suitable for washing, such as tissues, living bodies, and the like.

According to an embodiment of one aspect, the fluorescent probe does not exhibit any detection signal when the fluorescent probe does not label the target protein of the protein tag or the fusion protein tag, and does not interfere with the detection of the sample, and can realize rapid quantitative detection of target protein in complex samples, and can also track the dynamics of the labeling reaction process.

DETAILED DESCRIPTION

Figure 1:
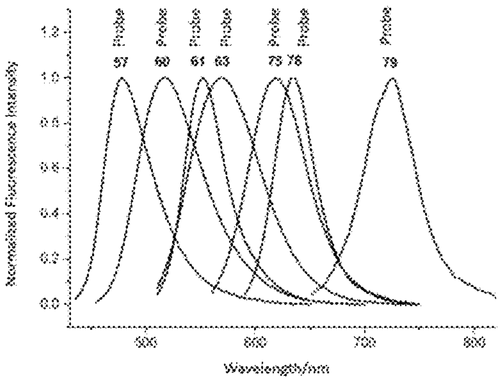
FIG. 1 is a fluorescence emission diagram in which different wavelengths of fluorescence are activated after different probes are bound to a protein tag.

Specific embodiments of the present invention will be described in detail below. It should be understood that the specific embodiments described herein are only used to illustrate the present invention by way of examples, and are not intended to limit the present invention.

Example 1

Molecular rotors were used as viscosity responsive fluorescent dyes to construct a fluorescent-activated covalently labeled probe 1 for HaloTag labeling:

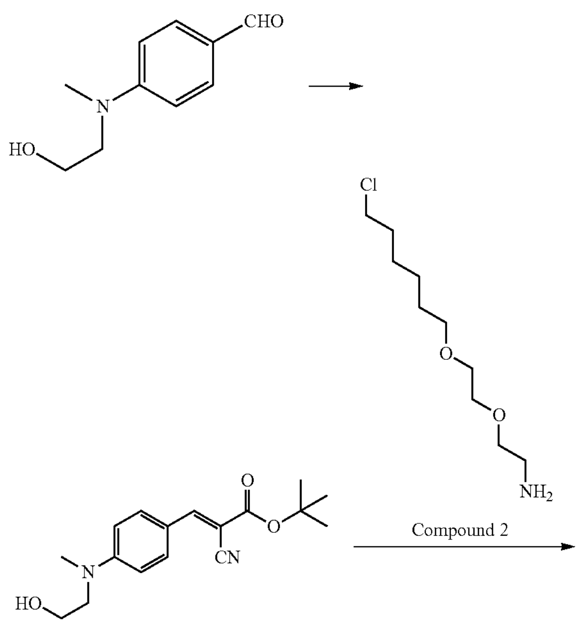

Compound 2

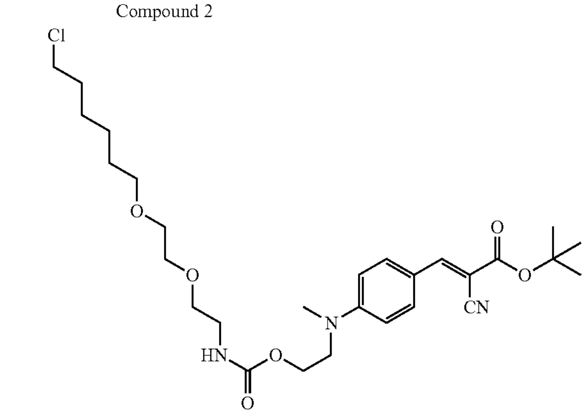

Probe 1

Compound 1:

N-methyl-N-(2-hydroxyethyl)-4-aminobenzaldehyde (0.358 g, 2 mmol) and tert-butyl cyanoacetate (0.338 g, 2.4 mmol) were dissolved in 50 ml of absolute ethanol. Then add a catalytic amount of anhydrous zinc chloride, and heat it in an oil bath for 5 hours under Ar protection. After the reaction, the reaction solution was cooled to room temperature, and a part of the solvent was removed by rotary evaporation. A large amount of solid precipitated in the system, and filtered. The filter cake was washed twice with cold ethanol and dried under vacuum to obtain yellow compound 1 (0.49 g, 81%). $^1$H-NMR (400 MHz, DMSO-$d_6$): δ=8.01 (s, 1H), 7.97 (d, 2H, J=9.2 Hz), 6.85 (d, 2H, J=9.2 Hz), 4.79 (bt, 1H), 3.59-3.55 (m, 4H), 3.08 (s, 3H), 1.50 (s, 9H).

Compound 2:

The synthesis method was performed according to the method disclosed in the document (Craig M. Crews et. al. Nature Chemical Biology. 2011, 7, 538-543.). $^1$H-NMR (400 MHz, $CDCl_3$) δ=6.47 (brs, 1H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 1.79-1.71 (m, 2H), 1.60-1.53 (m, 2H), 1.46-1.39 (m, 2H), 1.36-1.28 (m, 2H).

Probe 1:

Compound 1 (0.302 g, 1.0 mmol) and 4-dimethylaminopyridine (0.146 g, 1.2 mmol) were dissolved in 20 ml of anhydrous dichloromethane. Under the protection of argon, the above solution was slowly added dropwise to phenyl p-nitrochloroformate (0.242 g, 1.2 mmol) dissolved in 10 ml of anhydrous dichloromethane solution. After the dropwise addition was completed, the mixture was stirred at room temperature for 1 h. After the reaction, the solvent was evaporated to dryness, and the residue was dissolved in 10 ml of anhydrous N, N-dimethylformamide. Compound 2 (0.269 g, 1.2 mmol) and anhydrous triethylamine (0.16 ml, 1.2 mmol) were added and stirred for 30 min at room temperature under Ar protection. After the reaction was completed, the solvent was rotated to dryness, and the residue was separated through a column to obtain 0.42 g of the probe 1 with a yield of 70%. $^1$H-NMR (400 MHz, DMSO-$d_6$): δ=8.18 (t, 1H), 8.01 (s, 1H), 7.97 (d, 2H, J=9.2 Hz), 6.85 (d, 2H, J=9.2 Hz), 3.69 (t, J=4.9 Hz, 2H), 3.63-3.60 (m, 2H), 3.56-3.53 (m, 2H), 3.59-3.55 (m, 4H), 3.52 (t, J=6.6 Hz, 2H), 3.44 (t, J=6.8 Hz, 2H), 3.12 (t, J=4.9 Hz, 2H), 3.08 (s, 3H), 1.79-1.71 (m, 2H), 1.60-1.53 (m, 2H), 1.50 (s, 9H), 1.46-1.39 (m, 2H), 1.36-1.28 (m, 2H).

Example 2

Molecular rotors were used as viscosity responsive fluorescent dyes to construct a fluorescent-activated covalently labeled probe 2 for HaloTag protein tags:

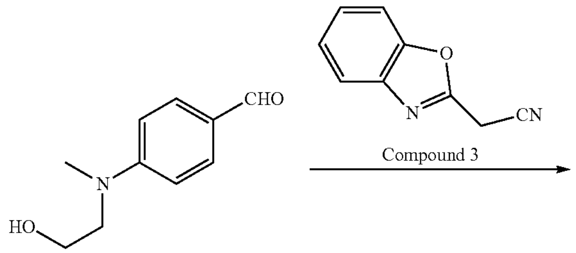
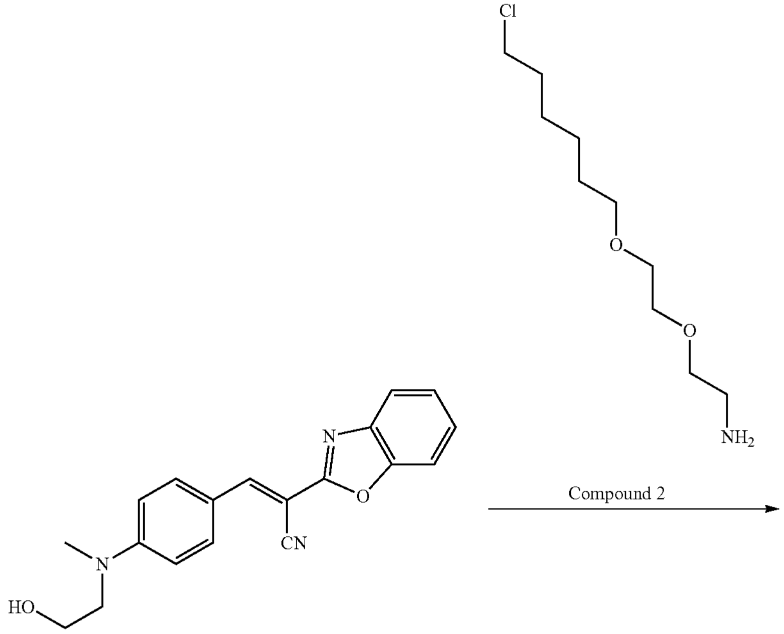
Compound 4
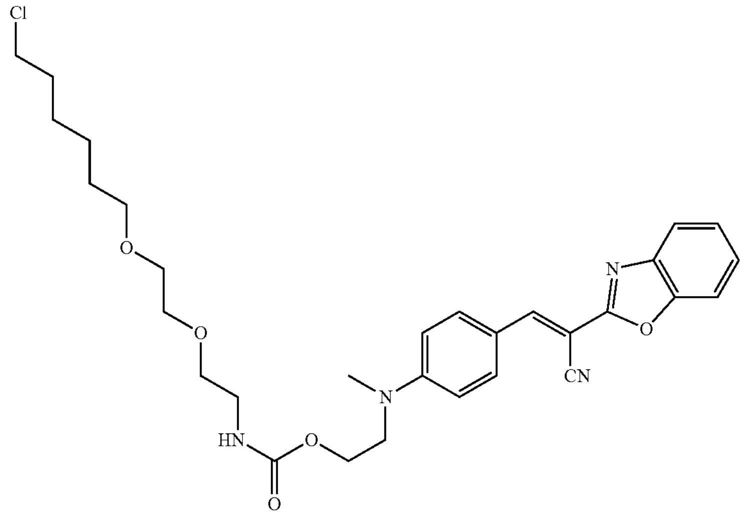
Probe 2

Compound 3:

The synthesis method was performed according to the method disclosed in the document (J. Das et. al. Bioorg. Med. Chem. Lett. 2005, 15, 337-343.). $^1$H-NMR (400 MHz, $CDCl_3$): δ=7.74 (d, 1H, J=4.0 Hz), 7.55 (d, 1H, J=4.0 Hz), 7.36-7.42 (m, 2H), 4.12 (s, 2H).

Compound 4:

With reference to the synthetic method of compound 1. $^1$H-NMR (400 MHz, DMSO-$d_6$): δ=8.11-8.07 (m, 2H), 8.01-7.97 (m, 3H), 7.70 (d, 1H, J=8.8 Hz), 7.46-7.43 (m, 1H), 6.27 (dd, 1H, J=9.2, 1.6 Hz), 6.02 (s, 1H), 3.88 (t, 2H, J=5.6 Hz), 3.64 (t, 2H, J=5.6 Hz), 3.15 (s, 3H).

Probe 2:

With reference to the synthetic method of probe 1, the yield was 75%. $^1$H-NMR (400 MHz, DMSO-$d_6$): δ=8.18 (t, 1H), 8.11-8.07 (m, 2H), 8.01-7.97 (m, 2H), 7.70 (d, 1H, J=8.8 Hz), 7.46-7.43 (m, 1H), 6.27 (dd, 1H, J=9.2, 1.6 Hz), 6.02 (s, 1H), 3.88 (t, 2H, J=5.6 Hz), 3.69 (t, J=4.9 Hz, 2H), 3.64 (t, 2H, J=5.6 Hz), 3.63-3.60 (m, 2H), 3.56-3.53 (m, 2H), 3.52 (t, J=6.6 Hz, 2H), 3.44 (t, J=6.8 Hz, 2H), 3.15 (s, 3H), 3.12 (t, J=4.9 Hz, 2H), 1.79-1.71 (m, 2H), 1.60-1.53 (m, 2H), 1.46-1.39 (m, 2H), 1.36-1.28 (m, 2H).

Example 3

Molecular rotors were used as viscosity responsive fluorescent dyes to construct a fluorescent-activated covalently labeled probe 3 for HaloTag protein tags:

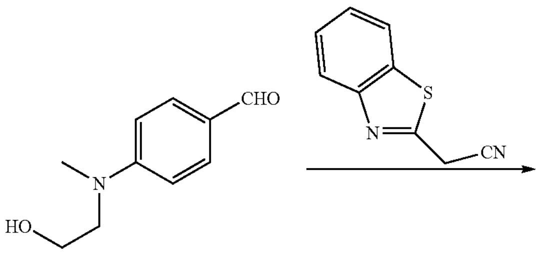

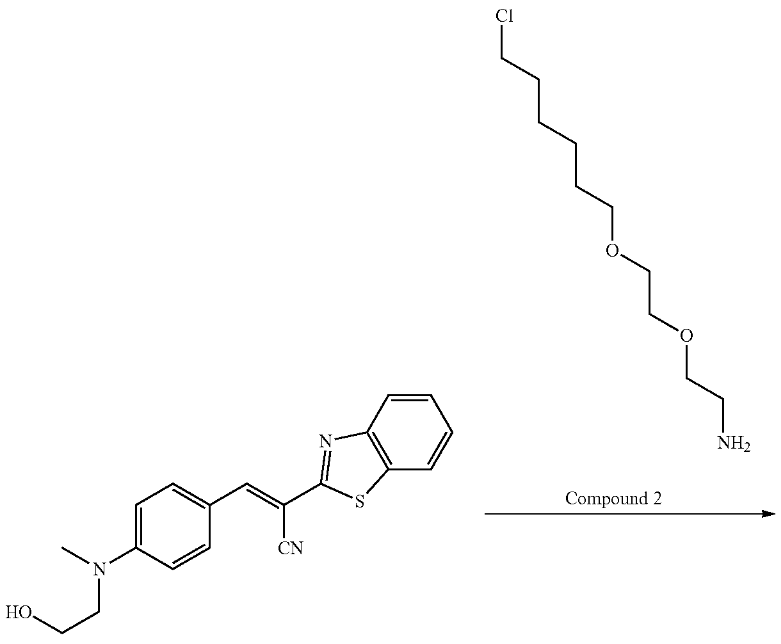

Compound 5

-continued

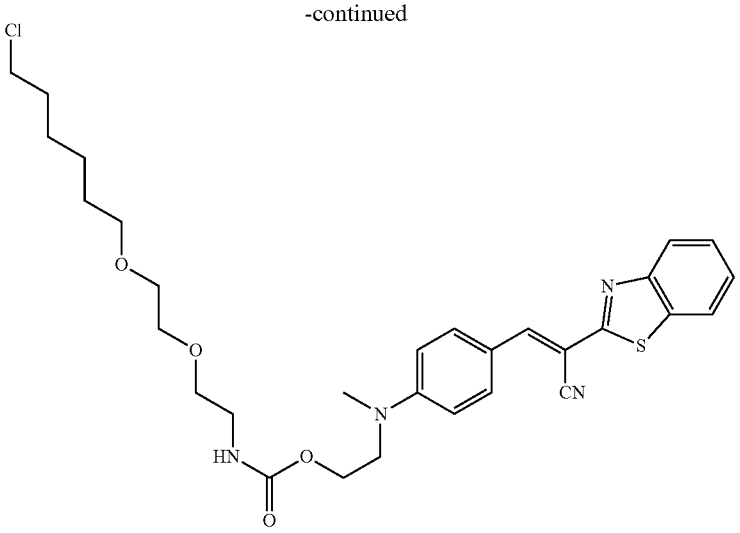

Probe 3

Compound 5:

With reference to the synthetic method of compound 1, the yield was 95%. $^1$H-NMR (400 MHz, $CDCl_3$): δ=8.09 (s, 1H), 8.02 (d, 1H, J=8.0 Hz), 7.98 (d, 2H, J=9.2 Hz), 7.86 (d, 1H, J=8.4 Hz), 7.48 (t, 1H, J=7.8 Hz), 7.36 (t, 1H, J=7.36 Hz), 6.73 (d, 2H, J=9.2 Hz), 3.88 (t, 2H, J=5.6 Hz), 3.64 (t, 2H, J=5.6 Hz), 3.15 (s, 3H).

Probe 3:

With reference to the synthetic method of probe 1, the yield was 65%. $^1$H-NMR (400 MHz, DMSO-$d_6$): δ=8.18 (t, 1H), 8.02 (d, 1H, J=8.0 Hz), 7.98 (d, 2H J=9.2 Hz), 7.86 (d, 1H, J=8.4 Hz), 7.48 (t, 1H, J=7.8 Hz), 7.36 (t, 1H, J=7.36 Hz), 6.73 (d, 2H, J=9.2 Hz), 3.88 (t, 2H, J=5.6 Hz), 3.69 (t, J=4.9 Hz, 2H), 3.64 (t, 2H, J=5.6 Hz), 3.63-3.60 (m, 2H), 3.56-3.53 (m, 2H), 3.52 (t, J=6.6 Hz, 2H), 3.44 (t, J=6.8 Hz, 2H), 3.15 (s, 3H), 3.12 (t, J=4.9 Hz, 2H), 1.79-1.71 (m, 2H), 1.60-1.53 (m, 2H), 1.46-1.39 (m, 2H), 1.36-1.28 (m, 2H).

Example 4

Molecular rotors were used as viscosity responsive fluorescent dyes to construct a fluorescent-activated covalently labeled probe 4 for HaloTag protein tags:

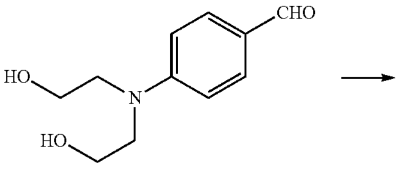

-continued

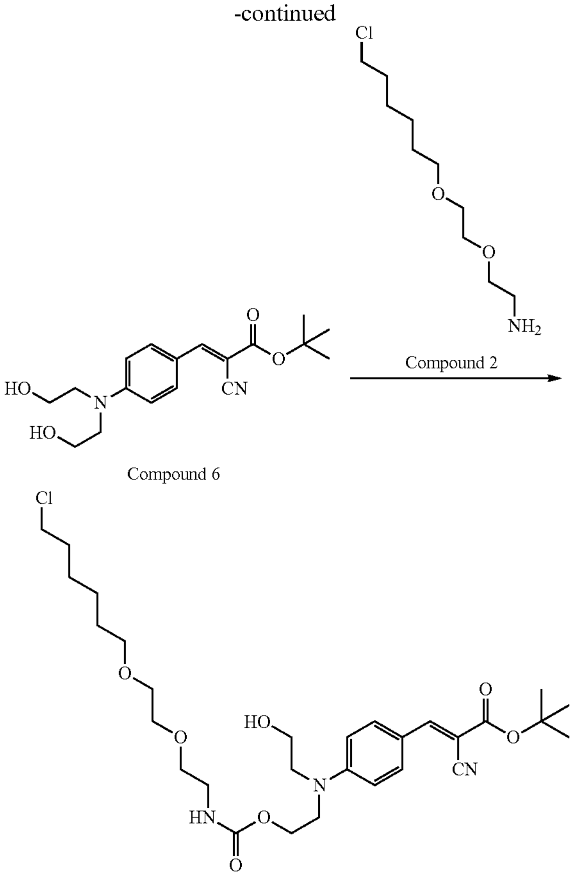

Compound 6

Probe 4

Compound 6:

With reference to the synthetic method of compound 1, the yield was 95%. $^1$H-NMR (400 MHz, DMSO-d6): δ=8.01 (s, 1H), 7.97 (d, 2H, J=9.2 Hz), 6.85 (d, 2H, J=9.2 Hz), 4.79 (bt, 2H), 3.85 (t, 4H, J=5.6 Hz), 3.60 (t, 4H, J=5.6 Hz), 1.50 (s, 9H).

Probe 4:

With reference to the synthetic method of probe 1, the yield was 35%. $^{1}$H-NMR (400 MHz, DMSO-$d_6$): δ=8.18 (t, 1H), 7.97 (d, 2H, J=9.2 Hz), 6.85 (d, 2H, J=9.2 Hz), 4.79 (bt, 1H), 3.85 (t, 4H, J=5.6 Hz), 3.69 (t, J=4.9 Hz, 2H), 3.63-3.60 (m, 2H), 3.60 (t, 4H, J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 1.79-1.71 (m, 2H), 1.60-1.53 (m, 2H), 1.50 (s, 9H), 1.46-1.39 (nm, 2H), 1.36-1.28 (m, 2H).

Example 5

Molecular rotors were used as viscosity responsive fluorescent dyes to construct a fluorescent-activated covalently labeled probe 5 for HaloTag protein tags:

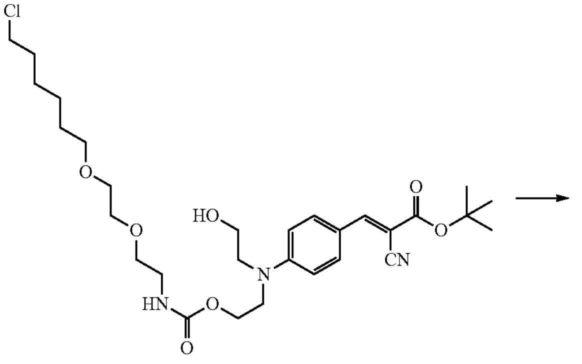

Probe 4

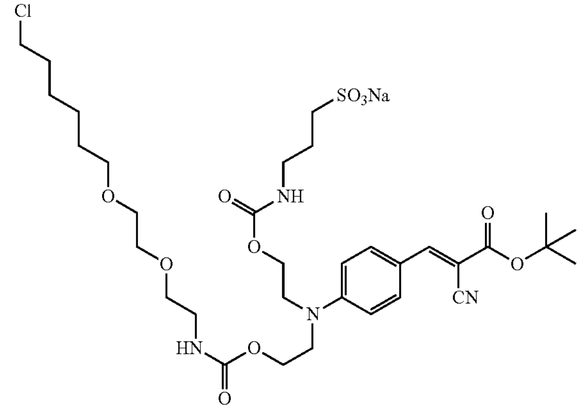

Probe 5

Probe 5:

Probe 4 (0.581 g, 1.0 mmol) and 4-dimethylaminopyridine (0.146 g, 1.2 mmol) were dissolved in 20 ml of anhydrous dimethylformamide. Under the protection of argon, the above solution was slowly added dropwise to phenyl p-nitrochloroformate (0.242 g, 1.2 mmol) dissolved in 10 ml of anhydrous dichloromethane solution. After the dropwise addition was completed, the mixture was stirred at room temperature for 1 h. After the reaction was completed, sodium 3-amino-propanesulfonate (0.168 g, 1.2 mmol) and anhydrous triethylamine (0.16 ml, 1.2 mmol) were added and stirred for 30 min at room temperature under Ar protection. After the reaction was completed, the solvent was rotated to dryness, and the residue was separated an a reversed-phase column to obtain 0.397 g of the probe with a yield of 50%. $^{1}$H-NMR (400 MHz, DMSO-$d_6$): δ=8.18 (t, 2H), 7.97 (d, 2H, J=9.2 Hz), 6.85 (d, 2H, J=9.2 Hz), 3.85 (t, 4H, J=5.6 Hz), 3.69 (t, J=4.9 Hz, 2H), 3.63-3.60 (m, 2H), 3.60 (t, 8H, J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 1.79-1.71 (m, 2H), 1.60-1.53 (m, 2H), 1.50 (s, 9H), 1.46-1.39 (m, 2H), 1.36-1.28 (m, 4H).

Example 6

Molecular rotors were used as viscosity responsive fluorescent dyes to construct a fluorescent-activated covalently labeled probe 6 for HaloTag protein tags:

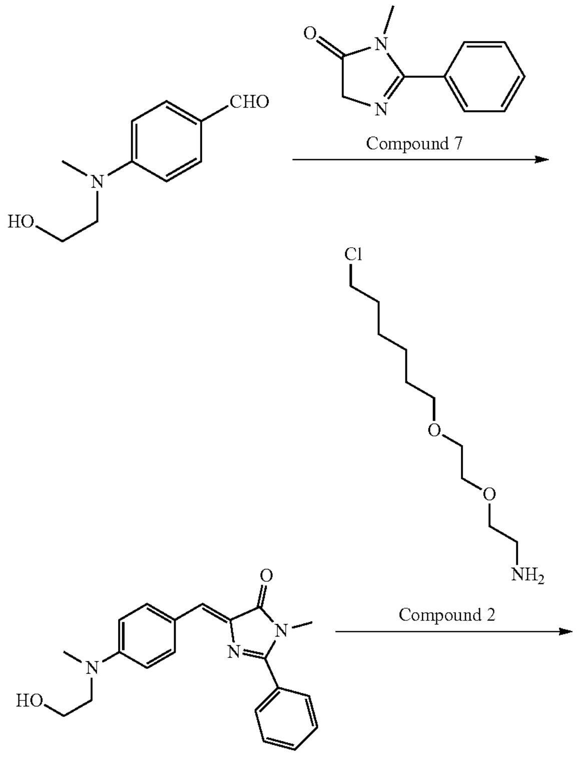

Compound 8

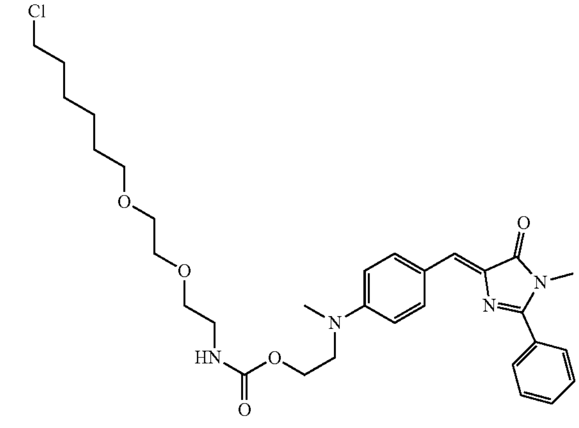

Probe 6

Compound 7:

The synthesis method was performed according to the method disclosed in the document (L. X. Wu, K. Buress, J. Am. Chem. Soc. 2008, 130, 4089-4096.). $^{1}$H-NMR (400 MHz. $CDCl_3$): δ=7.63-7.48 (m, 5H), 4.27 (s, 2H), 3.13 (s, 3H).

Compound 8:

With reference to the synthetic method of compound 1, the yield was 99%. $^1$H-NMR (400 MHz, $CDCl_3$): δ=8.03 (s, 1H), 7.97 (d, 2H, J=9.2 Hz), 6.85 (d, 2H, J=9.2 Hz), 4.27 (s, 2H), 3.55-3.59 (m, 4H), 3.08 (s, 3H), 3.13 (s, 3H).

Probe 6:

With reference to the synthetic method of probe 1, the yield was 70%. $^1$H-NMR (400 MHz, DMSO-$d_6$): δ=8.18 (t, 1H), 8.03 (s, 1H), 7.97 (d, 2H, J=9.2 Hz), 6.85 (d, 2H, J=9.2 Hz), 4.27 (s, 2H), 3.69 (t, J=4.9 Hz, 2H), 3.63-3.60 (m, 2H), 3.59-3.55 (m, 4H), 3.56-3.53 (m, 2H), 3.52 (t, J=6.6 Hz, 2H), 3.44 (t, J=6.8 Hz, 2H), 3.13 (s, 3H) 3.12 (t, J=4.9 Hz, 2H), 3.08 (s, 3H), 1.79-1.71 (m, 2H), 1.60-1.53 (m, 2H), 1.46-1.39 (m, 2H), 1.36-1.28 (m, 2H).

Example 7

Molecular rotors were used as viscosity responsive fluorescent dyes to construct a fluorescent-activated covalently labeled probe 7 for HaloTag protein tag:

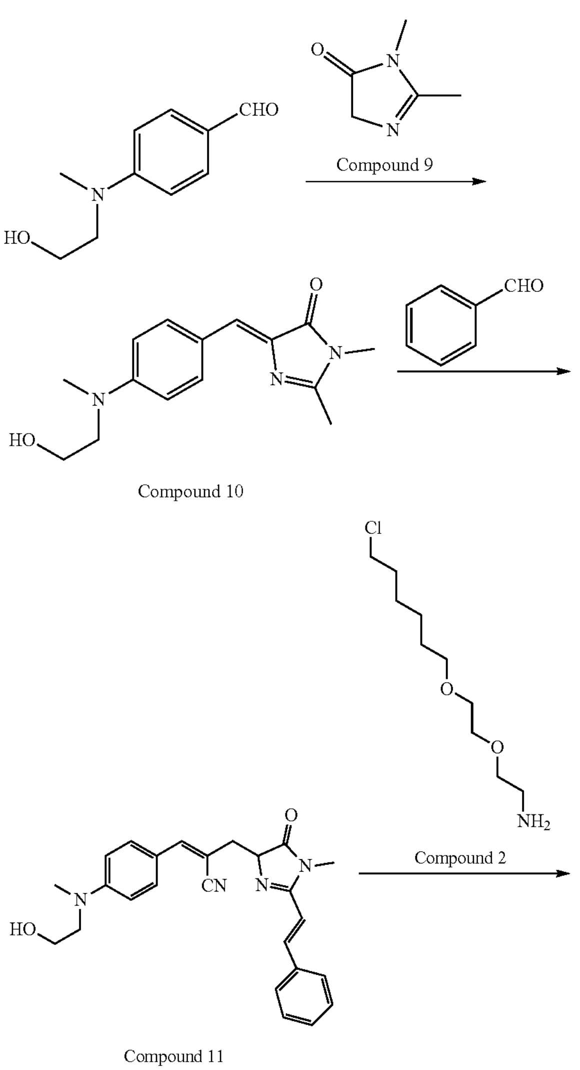

-continued

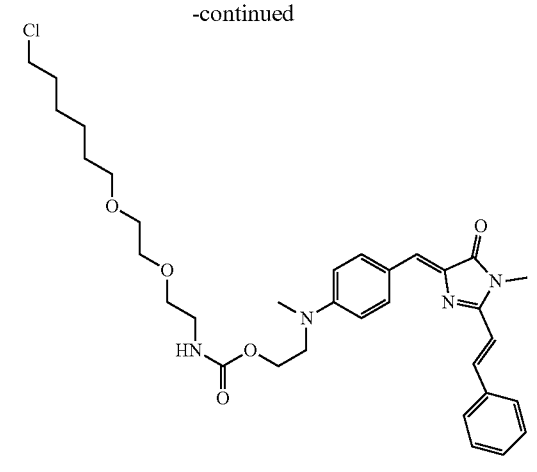

Probe 7

Compound 9:

The synthesis method was performed according to the method disclosed in the document (L. X. Wu, K. Burgess, J. Am. Chem. Soc. 2008, 130, 4089-4096.). $^1$H-NMR (400 MHz, $CDCl_3$): δ=3.98 (q, 2H, J=2.4 Hz), 3.01 (s, 3H), 2.15 (t, 3H, J=2.4 Hz).

Compound 10:

With reference to the synthetic method of compound 1, the yield was 97%. $^1$H-NMR (400 MHz, DMSO-$d_6$): δ=8.00 (s, 1H), 7.97 (d, 2H, J=9.2 Hz), 6.85 (d, 2H, J=9.2 Hz), 3.98 (q, 2H, J=2.4 Hz), 3.55-3.59 (m, 4H), 3.08 (s, 3H), 3.01 (s, 3H), 2.15 (t, 3H, J=2.4 Hz).

Compound 11:

Compound 10 (0.546 g, 2 mmol), benzaldehyde (0.530 g, 5 mmol) and anhydrous zinc chloride (0.545 g 4 mmol) were dissolved in 100 ml of anhydrous toluene. The oil bath was heated to reflux under Ar protection for 48 h. After the reaction is completed, the solvent was evaporated to dryness, the residue was dissolved in 100 ml of dichloromethane, washed three times with water, and the organic phase was dried over anhydrous sodium sulfate. The solvent was rotated to dryness, and the residue was separated by column chromatography to obtain 0.181 g of a red-brown solid with a yield of 25%. $^1$H-NMR (400 MHz, DMSO-ds): δ=8.21 (d, 2H, J=8.8 Hz), 8.00 (d, 1H, J=16 Hz), 7.85 (d, 2H, J=8.0 Hz), 7.45-7.38 (m, 3H), 7.24 (s, 1H), 7.01 (s, 1H), 6.92 (d, 2H, J=8.8 Hz), 3.85 (t, 2H, J=5.6 Hz), 3.60 (t, 2H, J=5.6 Hz), 3.10 (s, 3H).

Probe 7:

With reference to the synthetic method of probe 1, the yield was 66%. $^1$H-NMR (400 MHz, DMSO-d): 8.21 (d, 2H, J=8.8 Hz), δ=8.18 (t, 1H), 8.00 (d, 1H, J=16 Hz), 7.85 (d, 2H, J=8.0 Hz), 7.45-7.38 (m, 3H), 7.24 (s, 1H), 7.01 (s, 1H), 6.92 (d, 2H, J=8.8 Hz), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.46-1.39 (m, 2H), 1.36-1.28 (m, 2H).

Example 8

Molecular rotors were used as viscosity responsive fluorescent dyes to construct a fluorescent-activated covalently labeled probe 8 for HaloTag protein tag:

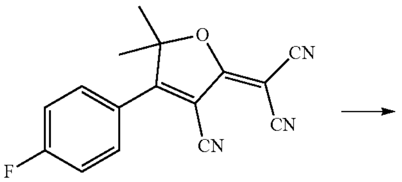

Compound 12

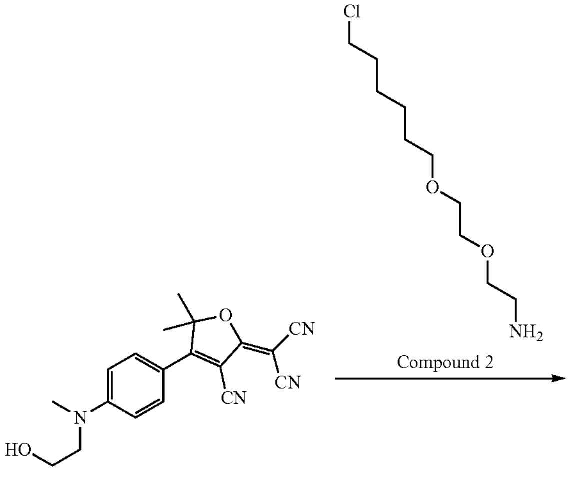

Compound 13

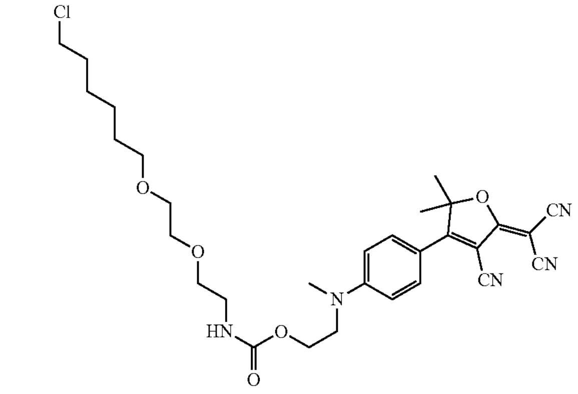

Probe 8

Compound 12:

The synthesis method was performed according to the method disclosed in the document (Wang H. et al. Tetra Let 2007, 48, 3471-3474.). $^1$H-NMR (400 MHz, DMSO-$d_6$): δ=8.05 (m, 2H), 7.01 (m, 2H), 1.83 (s, 6H).

Compound 13:

Compound 12 (0.279 g, 1 mmol) was dissolved in 20 ml of anhydrous pyridine, and 1 ml of N-methyl-N-hydroxyethyl was added. The mixture was heated in an oil bath at 40° C. overnight under Ar protection. After the reaction, the solvent was rotated to dryness, and the residue was separated by column chromatography to obtain 0.187 g of a red product with a yield of 56%. $^1$H-NMR (400 MHz, DMSO-d): δ=8.05 (m, 2H), 7.01 (m, 2H), 3.85 (t, 2H, J=5.6 Hz), 3.60 (t, 2H, J=5.6 Hz), 3.10 (s, 3H), 1.83 (s, 6H).

Probe 8:

With reference to the synthetic method of probe 1, the yield was 56%. $^1$H-NMR (400 MHz, DMSO-$d_6$): δ=8.18 (t, 1H), 8.05 (m, 2H), 7.01 (m, 2H), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.83 (s, 6H), 1.79-1.71 (m, 2H), 1.60-1.53 (m, 2H), 1.46-1.39 (m, 2H), 1.36-1.28 (m, 2H).

Example 9

Molecular rotors were used as viscosity responsive fluorescent dyes to construct a fluorescent-activated covalently labeled probe 9 for HaloTag protein tag:

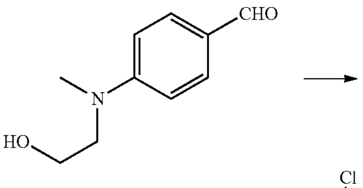

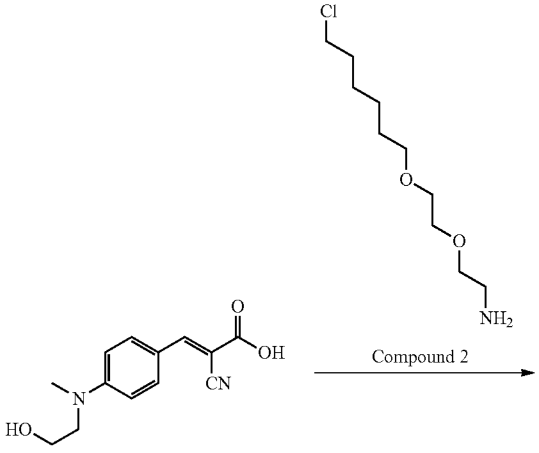

Compound 14

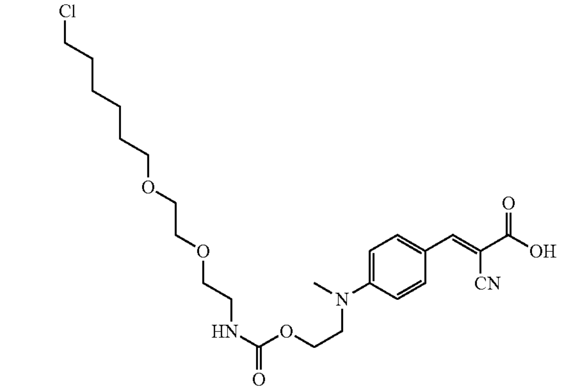

Probe 9

Compound 14:

With reference to the synthetic method of compound 1, the yield was 95%. $^1$H-NMR (400 MHz, DMSO-d6): δ=8.07 (s, 1H), 7.93 (d, 2H, J=9.2 Hz), 6.85 (d, 2H, J=9.2 Hz), 3.55-3.59 (m, 4H), 3.08 (s, 3H).

Probe 9:

With reference to the synthetic method of probe 1, the yield was 35%. $^1$H-NMR (400 MHz, DMSO-d6): δ=8.18 (t, 1H), 8.07 (s, 1H), 7.93 (d, 2H, J=9.2 Hz), 6.85 (d, 2H, J=9.2 Hz), 3.69 (t, J=4.9 Hz, 2H), 3.63-3.60 (m, 2H), 3.59-3.55 (m, 4H), 3.56-3.53 (m, 2H), 3.52 (t, J=6.6 Hz, 2H), 3.44 (t, J=6.8 Hz, 2H), 3.12 (t, J=4.9 Hz, 2H), 3.08 (s, 3H), 1.79-1.71 (m, 2H), 1.60-1.53 (m, 2H), 1.46-1.39 (m, 2H), 1.36-1.28 (m, 2H).

Example 10

Molecular rotors were used as viscosity responsive fluorescent dyes to construct a fluorescent-activated covalently labeled probe 10 for HaloTag protein tag:

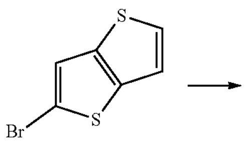

Compound 15

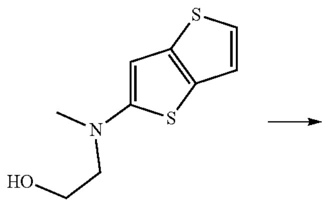

Compound 16

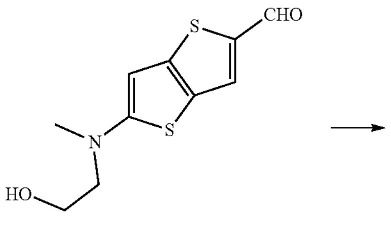

Compound 17

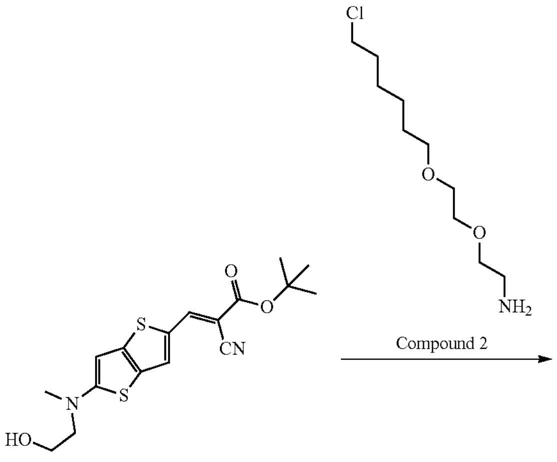

Compound 18

-continued

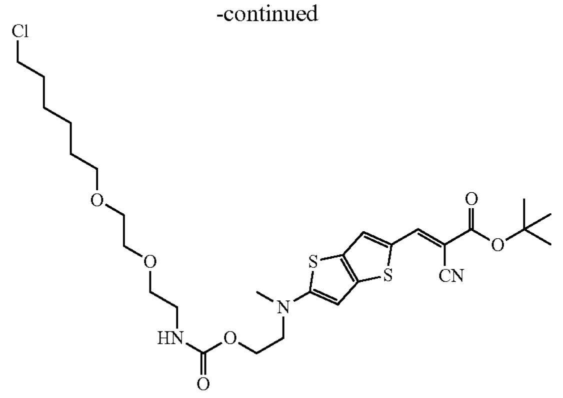

Probe 10

Compound 15:

The synthesis method was performed according to the method disclosed in the document (WO 2013142841 (A1), 2013.09.26.). $^{1}$H-NMR (400 MHz, $CDCl_3$): δ=7.92 (s, 1H), 7.63 (d, 1H, J=52 Hz), 7.31 (d, 1H, J=5.2 Hz).

Compound 16:

Compound 15 (0.438 g, 2 mmol) was dissolved in 15 mL of N-methyl-N-hydroxyethylamine, copper powder (6.4 mg, 0.01 mmol), cuprous iodide (19 mg, 0.01 mmol), and tripotassium phosphate (0.850 g, 4 mmol) were added to the above solution, and heated at 80° C. in an oil bath overnight under Ar protection. After the reaction was completed, the mixture was cooled to room temperature, and the system was poured into 50 mL of water and extracted three times with 50 mL of dichloromethane. The organic phases were combined, the solvent was evaporated to dryness, and 0.362 g of a yellow product was obtained by column chromatography with a yield of 85%. $^{1}$H-NMR (400 MHz, $CDCl_3$): δ=7.92 (s, 1H), 7.63 (d, 1H, J=5.2 Hz), 7.31 (d, 1H, J=5.2 Hz), 3.85 (t, 2H, J=5.6 Hz), 3.60 (t, 2H, J=5.6 Hz), 3.10 (s, 3H).

Compound 17:

Compound 16 (0.426 g, 2 mmol) was dissolved in 50 ml of anhydrous dichloromethane, 1 ml of triethylamine was added, and acetic anhydride (0.3 ml, 3 mmol) was slowly added dropwise under an ice bath. After the addition, the system was slowly warmed to room temperature and stirred for 3 h. After the reaction was completed, 100 ml of water was added to separate the organic phase. The aqueous phase was extracted twice with 50 ml of dichloromethane. The organic phases were combined, dried over anhydrous sodium sulfate, and the solvent was evaporated to dryness. The residue was used in the next step without further purification.

The above residue was dissolved in 50 ml of dichloromethane, 5 ml of dimethylformamide was added, 2 ml of phosphorus oxychloride was added under ice bath conditions, and the mixture was stirred for 0.5 h under the protection of Ar. The system was slowly warmed to room temperature and stirred for 5 h. After the reaction. Add saturated sodium carbonate solution to adjust pH=10.0, stir overnight at room temperature, separate the organic phase the next day, and extract the aqueous phase three times with 50 ml of dichloromethane. The organic phases were combined, washed twice with saturated brine, and the organic phases were dried over anhydrous sodium sulfate. The solvent was rotary evaporated to dryness, and the residue was subjected to column chromatography to obtain 0.285 g of a yellow solid with a yield of 59%. $^{1}$H-NMR (400 MHz, $CDCl_3$): δ=10.01 (s, 1H), 7.92 (s, 1H), 7.63 (s, 1H) 3.85 (t, 2H, J=5.6 Hz), 3.60 (t, 2H, J=5.6 Hz), 3.10 (s, 3H).

Compound 18:

With reference to the synthetic method of compound 1, the yield was 89%. $^1$H-NMR (400 MHz, DMSO-$d_6$): δ=8.22 (s, 1H), 8.02 (s, 1H), 6.43 (s, 1H), 3.85 (t, 2H, J=5.6 Hz), 3.60 (t, 2H, J=5.6 Hz), 3.10 (s, 3H), 1.49 (s, 9H).

Probe 10:

With reference to the synthetic method of probe 1, the yield was 65%. $^1$H-NMR (400 MHz, DMSO-$d_6$): δ=8.22 (s, 1H), 8.18 (t, 1H), 8.02 (s, 1H), 6.43 (s, 1H), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.49 (s, 9H), 1.46-1.39 (m, 2H), 1.36-1.28 (m, 2H).

Example 11

Molecular rotors were used as viscosity responsive fluorescent dyes to construct a fluorescent-activated covalently labeled probe 11 for HaloTag protein tag:

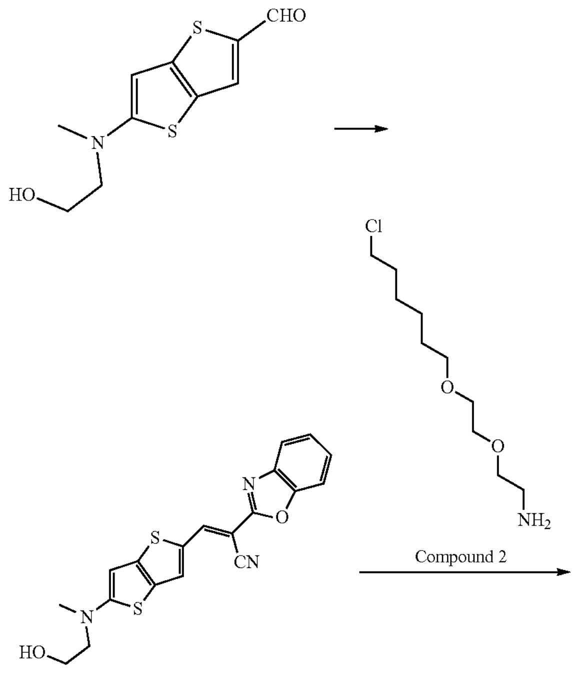

Compound 19

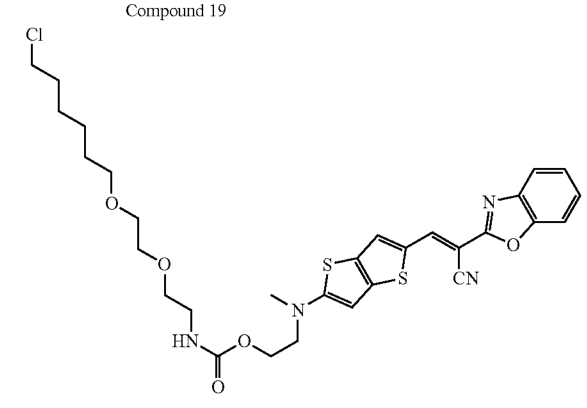

Probe 11

Compound 19:

With reference to the synthetic method of compound 1, the yield was 93%. $^1$H-NMR (400 MHz, $CDCl_3$): δ=8.22 (s, 1H), 8.02 (s, 1H), 7.74 (d, 1H, J=4.0 Hz), 7.55 (d, 1H, J=4.0 Hz), 7.36-7.42 (m, 2H), 6.43 (s, 1H), 3.75 (t, 2H, J=5.6 Hz), 3.55 (t, 2H, J=5.6 Hz), 3.10 (s, 3H).

Probe 11:

With reference to the synthetic method of probe 1, the yield was 66%. $^1$H-NMR (400 MHz, DMSO-$d_6$): δ=8.22 (s, 1H), 8.18 (t, 1H), 8.02 (s, 1H), 7.74 (d, 1H, J=4.0 Hz), 7.55 (d, 1H, J=4.0 Hz), 7.36-7.42 (m, 2H), 6.43 (s, 1H), 3.75 (t, 2H, J=5.6 Hz), 3.69 (t, J=4.9 Hz, 2H), 3.63-3.60 (m, 2H), 3.56-3.53 (m, 2H), 3.55 (t, 2H, J=5.6 Hz), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.46-1.39 (m, 2H), 1.36-1.28 (nm 2H).

Example 12

Molecular rotors were used as viscosity responsive fluorescent dyes to construct a fluorescent-activated covalently labeled probe 12 for HaloTag protein tag:

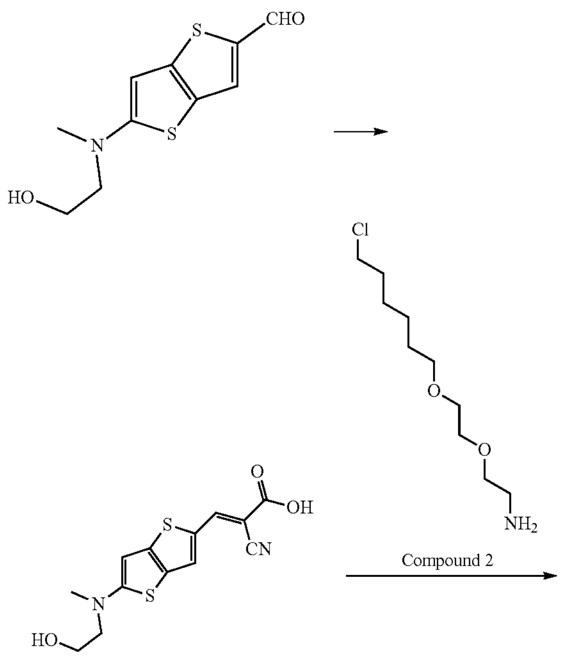

Compound 21

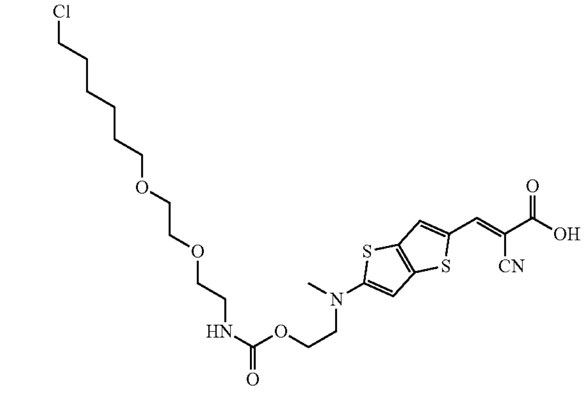

Probe 12

Compound 20:

With reference to the synthetic method of compound 1, the yield was 96%. $^1$H-NMR (400 MHz, DMSO-$d_6$): δ=8.22 (s, 1H), 8.02 (s, 1H), 6.43 (s, 1H), 3.85 (t, 2H, J=5.6 Hz), 3.60 (t, 2H, J=5.6 Hz), 3.10 (s, 3H).

Probe 12:

With reference to the synthetic method of probe 1, the yield was 39%. $^1$H-NMR (400 MHz, DMSO-$d_6$): δ=8.22 (s, 1H), 8.18 (t, 1H), 8.02 (s, 1H), 6.43 (s, 1H), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.46-1.39 (m, 2H), 1.36-1.28 (m, 2H).

Example 13

Molecular rotors were used as viscosity responsive fluorescent dyes to construct a fluorescent-activated covalently labeled probe 13 for HaloTag protein tag:

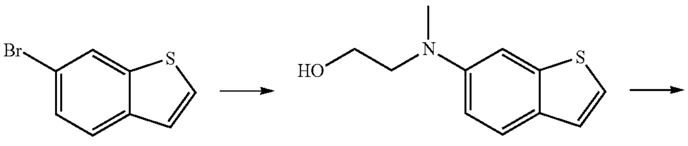

Compound 21

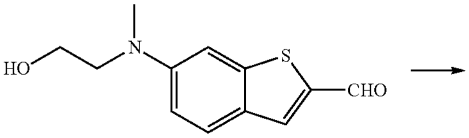

Compound 22

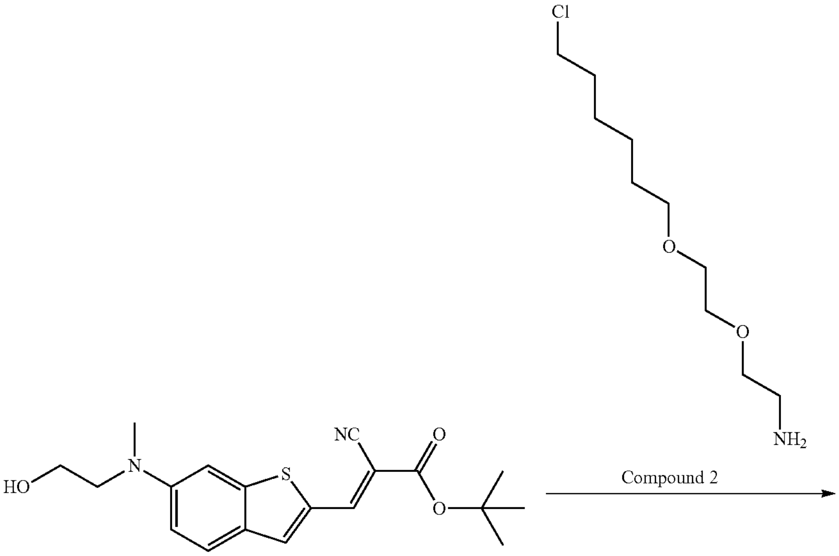

Compound 23

-continued

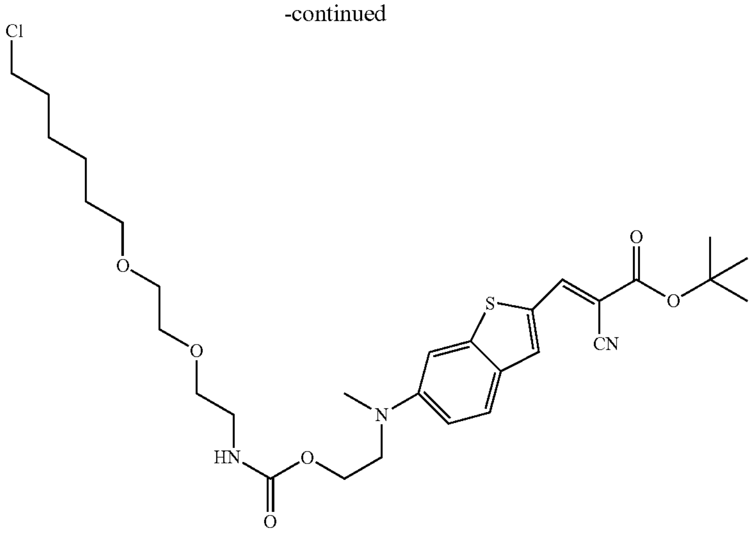

Probe 13

Compound 21:

With reference to the synthetic method of compound 16, the yield was 87%. $^1$H-NMR (400 MHz, $CDCl_3$): δ=8.02 (s, 1H), 7.66 (d, 1H, J=8.4 Hz), 7.44-7.48 (m, 1H), 7.41 (m, 1H), 7.29 (m, 1H), 3.60 (t, 2H, J=5.6 Hz), 3.34 (t, J=8.0 Hz, 3H), 3.10 (s, 3H).

Compound 22:

With reference to the synthetic method of compound 17, the yield was 56%. $^1$H-NMR (400 MHz, $CDCl_3$): δ=9.92 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.61 (t, J=8.0 Hz, 2H), 3.34 (t, J=8.0 Hz, 2H), 3.10 (s, 3H).

Compound 23:

With reference to the synthetic method of compound 1, the yield was 91%. $^1$H-NMR (400 MHz, $CDCl_3$): δ=8.02 (s, 1H), 7.81 (s, 1H), 7.68 (d, J=9.0 Hz, 1H), 6.92 (d, J=2.0 Hz, 1H), 6.82 (d, J=9.1, 2.3 Hz, 1H), 3.61 (t, J=8.0 Hz, 2H), 3.34 (t, J=8.0 Hz, 2H), 3.11 (s, 3H), 1.48 (s, 9H).

Probe 13:

With reference to the synthetic method of probe 1, the yield was 66%. $^1$H-NMR (400 MHz, $CDCl_3$): δ=8.18 (t, 1H), 8.02 (s, 1H), 7.81 (s, 1H), 7.68 (d, J=9.0 Hz, 1H), 6.92 (& J=2.0 Hz, 1H), 6.82 (d, J=9.1, 2.3 Hz, 1H), 3.69 (t, J=4.9 Hz, 2H), 3.63-3.60 (m, 2H), 3.61 (t, J=8.0 Hz, 2H), 3.56-3.53 (m, 2H), 3.52 (t, J=6.6 Hz, 2H), 3.44 (t, J=6.8 Hz, 2H), 3.34 (t, J=8.0 Hz, 2H), 3.12 (t, J=4.9 Hz, 2H), 3.11 (s, 3H), 1.48 (s, 9H), 1.79-1.71 (m, 2H), 1.60-1.53 (nm, 2H), 1.46-1.39 (m, 2H), 1.36-1.28 (m, 2H).

Example 14

Molecular rotors were used as viscosity responsive fluorescent dyes to construct a fluorescent-activated covalently labeled probe 14 for HaloTag protein tag:

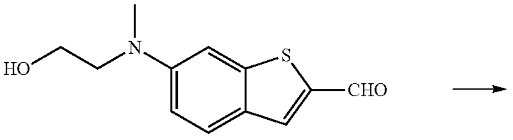

-continued

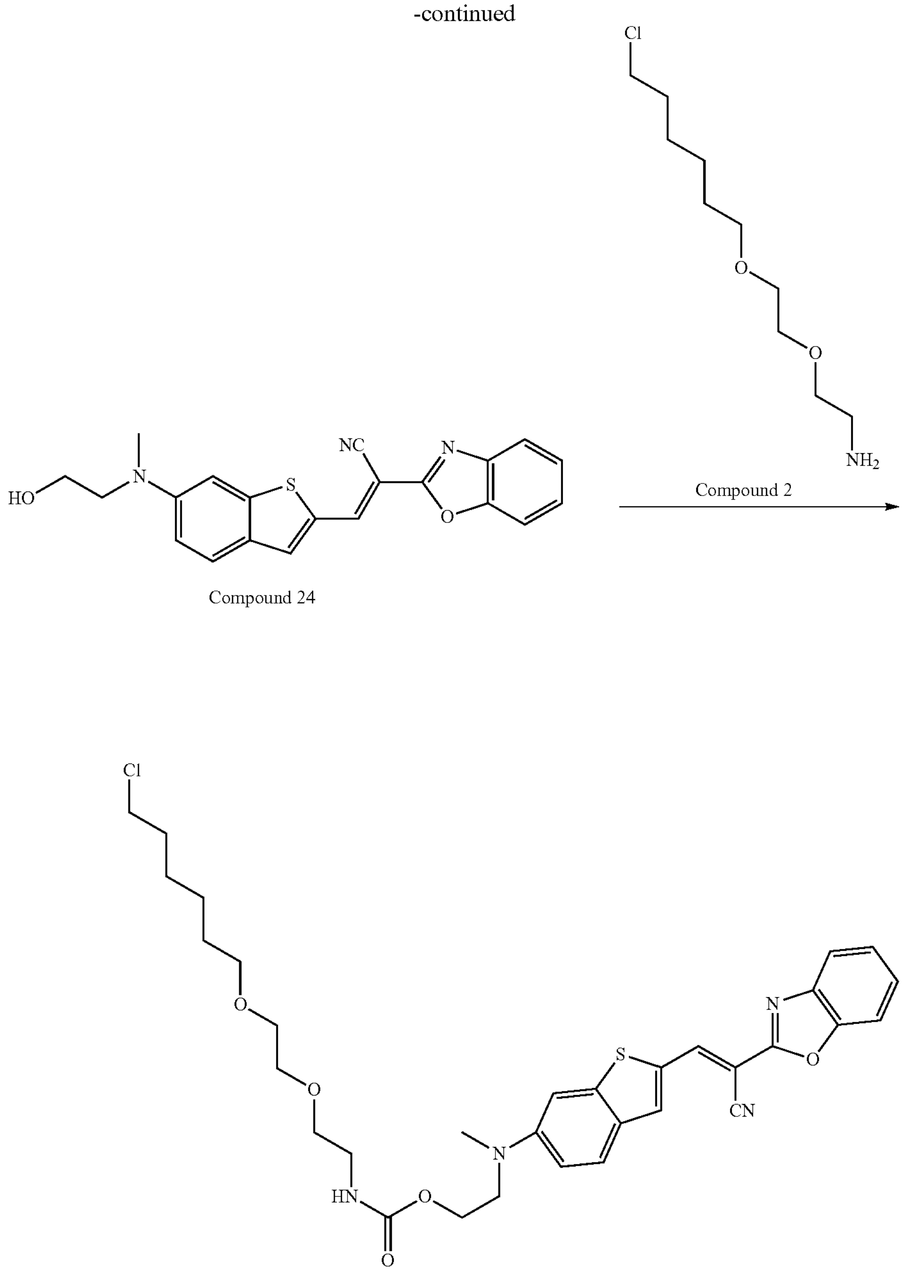

Compound 24

Probe 14

Compound 24:

With reference to the synthetic method of compound 4, the yield was 93%. ¹H-NMR (400 MHz, DMSO-$d_6$): δ=8.45 (s, 1H), 8.09 (d, J=8.00 Hz, 2H), 8.07 (s, 1H), 7.94 (d, J=8.00 Hz, 2H), 7.51 (m, 1H), 7.41 (m, 1H), 6.45 (s, 1H), 3.61 (t, J=8.0 Hz, 2H), 3.34 (t, J=8.0 Hz, 2H), 3.21 (s, 3H).

Probe 14:

With reference to the synthetic method of probe 1, the yield was 71%. ¹H-NMR (400 MHz, DMSO-$d_6$): δ=8.45 (s, 1H), 8.18 (t, 1H), 8.09 (d, J=8.00 Hz, 2H), 8.07 (s, 1H), 7.94 (d, J=8.00 Hz, 2H), 7.51 (m, 1H), 7.41 (m, 1H), 6.45 (s, 1H), 3.69 (t, J=4.9 Hz, 2H), 3.63-3.60 (m, 2H), 3.61 (t, J=8.0 Hz, 2H), 3.56-3.53 (m, 2H), 3.52 (t, J=6.6 Hz, 2H), 3.44 (t, J=6.8 Hz, 2H), 3.34 (t, J=8.0 Hz, 2H), 3.21 (s, 3H), 3.12 (t, J=4.9 Hz, 2H), 1.79-1.71 (m, 2H), 1.60-1.53 (m, 2H), 1.46-1.39 (m, 2H), 1.36-1.28 (m, 2H).

Example 15

Molecular rotors were used as viscosity responsive fluorescent dyes to construct a fluorescent-activated covalently labeled probe 15 for HaloTag protein tag:

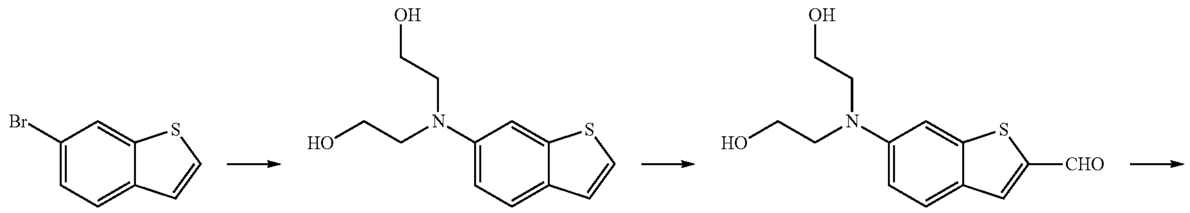
Compound 25
Compound 26
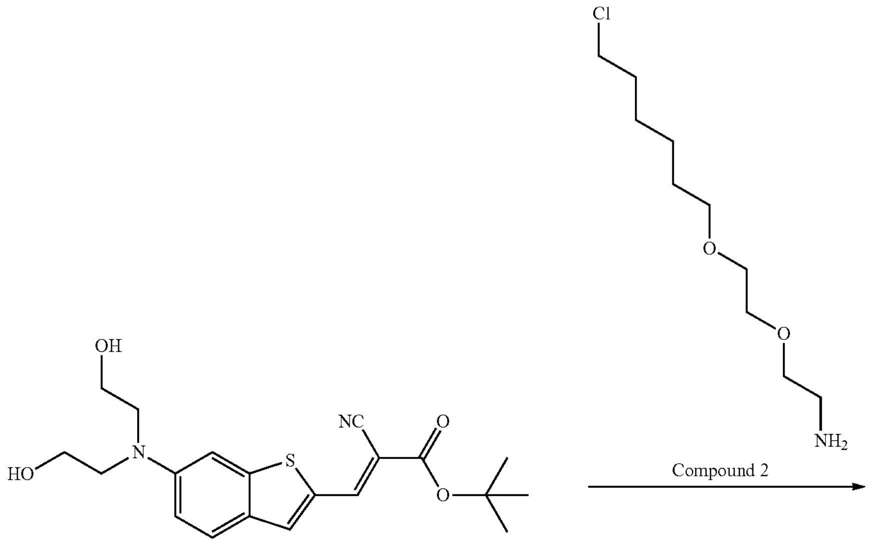
Compound 27
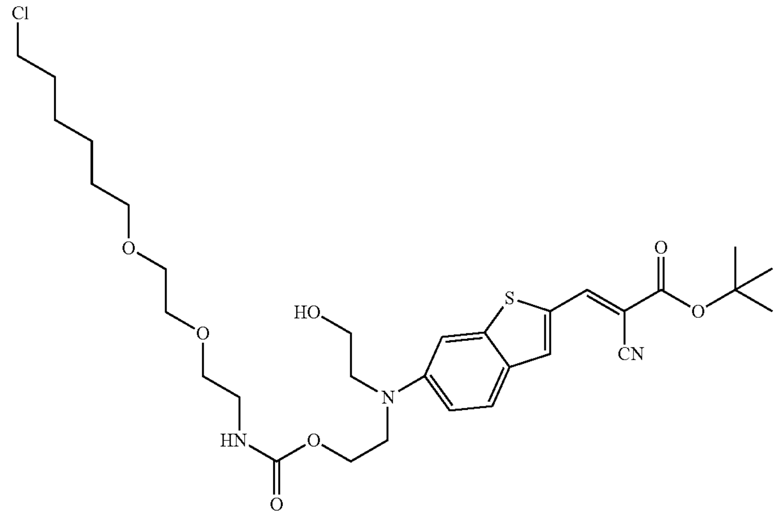
Probe 15

Compound 25:

With reference to the synthetic method of compound 16, the yield was 67%. $^1$H-NMR (400 MHz, $CDCl_3$): δ=7.62 (d, 1H, J=8.8 Hz), 7.15 (d, 1H, J=5.6 Hz), 7.08-7.01 (m, 2H), 6.81 (d, 1H, J=2.4 Hz), 3.62 (t, 4H, J=8.0 Hz), 3.35 (t, 4H, J=8.0 Hz).

Compound 26:

With reference to the synthetic method of compound 17, the yield was 67%. $^1$H-NMR (400 MHz, $CDCl_3$): δ=9.99 (s, 1H), 7.81 (s, 1H), 7.68 (d, 1H, J=9.0 Hz), 6.92 (d, 1H, J=2.0 Hz), 6.81 (m, 1H), 3.62 (t, 4H, J=8.0 Hz), 3.35 (t, 4H, J=8.0 Hz).

Compound 27:

With reference to the synthetic method of compound 1, the yield was 96%. $^1$H-NMR (400 MHz, $CDCl_3$): δ=8.00 (s, 1H), 7.83 (s, 1H), 7.69 (d, 1H, J=9.0 Hz), 6.92 (d, 1H, J=2.0 Hz), 6.81 (m, 1H), 3.62 (t, 4H, J=8.0 Hz), 3.35 (t, 4H, J=8.0 Hz), 1.49 (s, 9H).

Probe 15:

With reference to the synthetic method of probe 1, the yield was 44%. $^1$H-NMR (400 MHz, $CDCl_3$): δ=8.18 (t, 1H), 8.00 (s, 1H), 7.83 (s, 1H), 7.69 (d, 1H, J=9.0 Hz), 6.92 (d, 1H, J=2.0 Hz), 6.81 (m, 1H), 3.69 (t, J=4.9 Hz, 2H), 3.62 (t, 4H, J=8.0 Hz), 3.63-3.60 (m, 2H), 3.56-3.53 (m, 2H), 3.52 (t, J=6.6 Hz, 2H), 3.44 (t, J=6.8 Hz, 2H), 3.35 (t, 4H, J=8.0 Hz), 3.12 (t, J=4.9 Hz, 2H), 1.79-1.71 (m, 2H), 1.60-1.53 (m, 2H), 1.49 (s, 9H), 1.46-1.39 (m, 2H), 1.36-1.28 (m, 2H).

Example 16

Molecular rotors were used as viscosity responsive fluorescent dyes to construct a fluorescent-activated covalently labeled probe 16 for HaloTag protein tag:

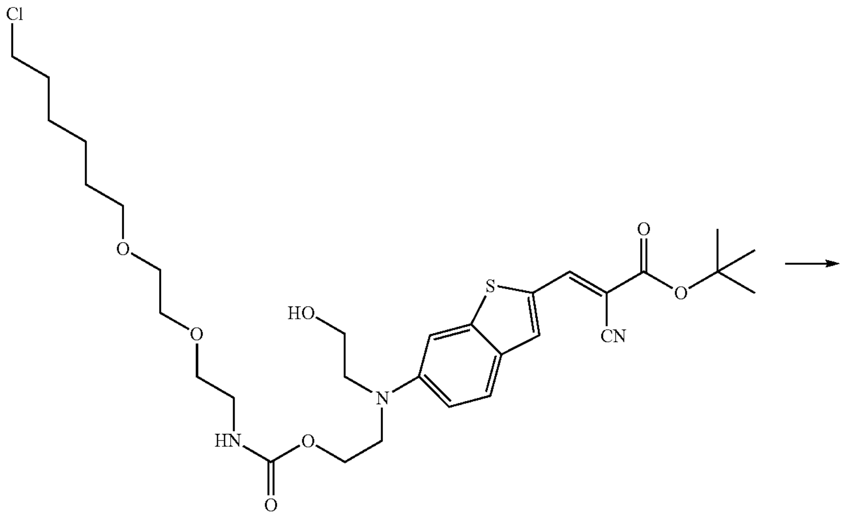

Probe 15

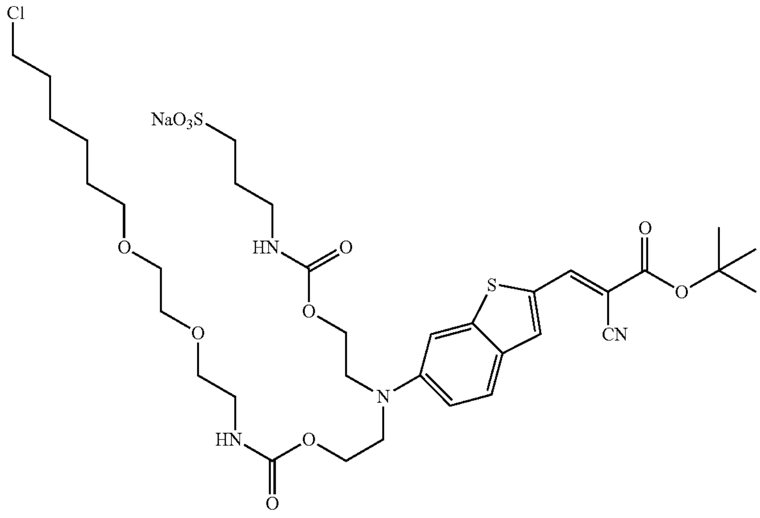

Probe 16

Probe 16:
With reference to the synthetic method of probe 5, the yield was 44%. $^{1}$H-NMR (400 MHz, $CDCl_3$): δ=8.18 (m, 2H), 8.00 (s, 1H), 7.83 (s, 1H), 7.69 (d, 1H, J=9.0 Hz), 6.92 (d, 1H, J=2.0 Hz), 6.81 (m, 1H), 3.69 (t, J=4.9 Hz, 2H), 3.62 (t, 4H, J=8.0 Hz), 3.63-3.60 (m, 6H), 3.56-3.53 (m, 2H), 3.52 (t, J=6.6 Hz, 2H), 3.44 (t, J=6.8 Hz, 2H), 3.35 (t, 4H, J=8.0 Hz), 3.12 (t, J=4.9 Hz, 2H), 1.79-1.71 (m, 2H),
1.60-1.53 (m, 2H), 1.49 (s, 9H), 1.46-1.39 (m, 4H), 1.36-1.28 (m, 2H).
Example 17
Molecular rotors were used as viscosity responsive fluorescent dyes to construct a fluorescent-activated covalently labeled probe 17 for HaloTag protein tag:
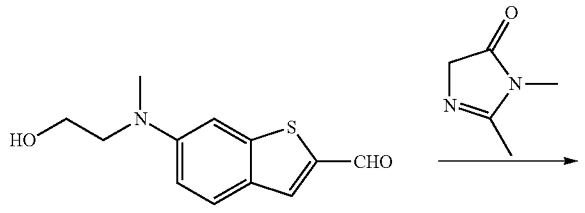
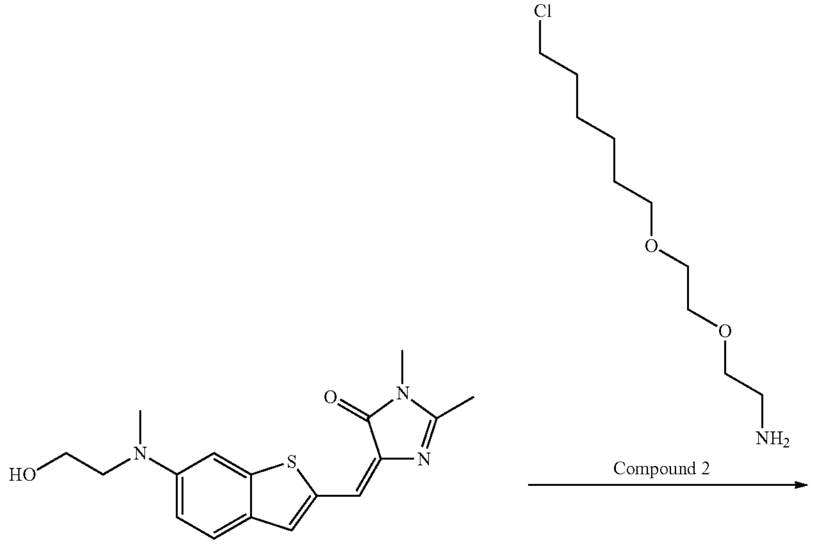
Compound 28
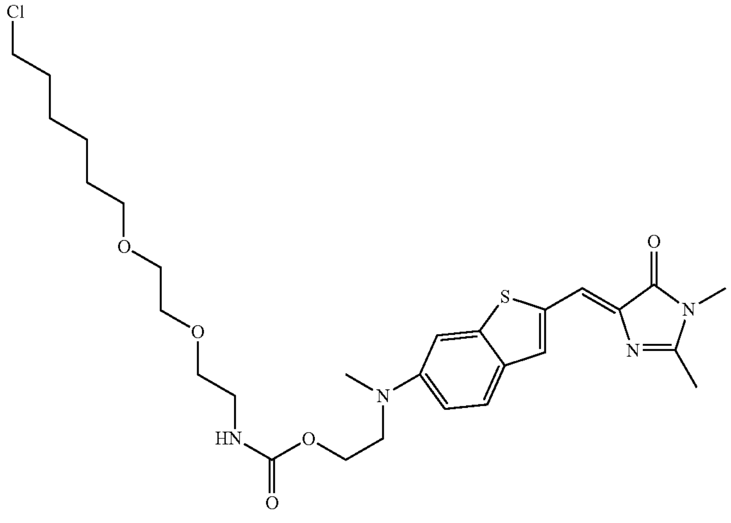
Probe 17

Compound 28:

With reference to the synthetic method of compound 10, the yield was 91%. $^1$H-NMR (400 MHz. $CDCl_3$): δ=8.22 (s, 1H), 8.02 (s, 1H), 6.43 (s, 1H), 3.61 (t, J=8.0 Hz, 3H), 3.34 (t, J=8.0 Hz, 3H), 3.11 (s, 3H), 3.00 (s, 3H), 2.15 (t, 3H, J=2.4 Hz), 1.48 (s, 9H).

Probe 17:

With reference to the synthetic method of probe 1, the yield was 55%. $^1$H-NMR (400 MHz, $CDCl_3$): δ=8.22 (s, 1H), 6=8.18 (t, 1H), 8.02 (s, 1H), 6.43 (s, 1H), 3.69 (t, J=4.9 Hz, 2H), 3.63-3.60 (m, 2H), 3.61 (t, J=8.0 Hz, 3H), 3.56-3.53 (m, 2H), 3.52 (t, J=6.6 Hz, 2H), 3.44 (t, J=6.8 Hz, 2H), 3.34 (t, J=8.0 Hz, 3H), 3.12 (t, J=4.9 Hz, 2H), 3.11 (s, 3H), 3.00 (s, 3H), 2.15 (t, 3H, J=2.4 Hz), 1.79-1.71 (m, 2H), 1.60-1.53 (m, 2H), 1.48 (s, 9H), 1.46-1.39 (m, 2H), 1.36-1.28 (m, 2H).

Example 18

Molecular rotors were used as viscosity responsive fluorescent dyes to construct a fluorescent-activated covalently labeled probe 18 for HaloTag protein tag:

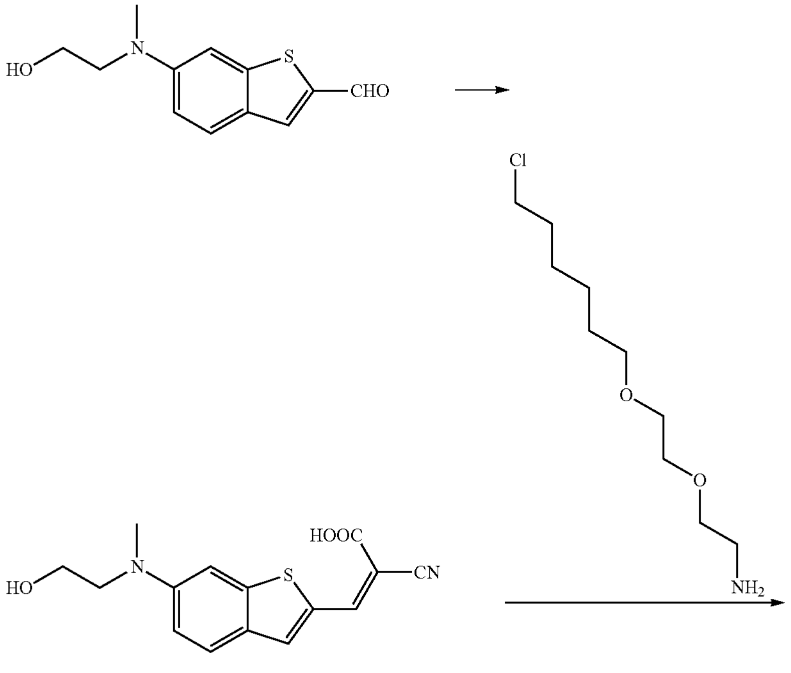

Compound 29

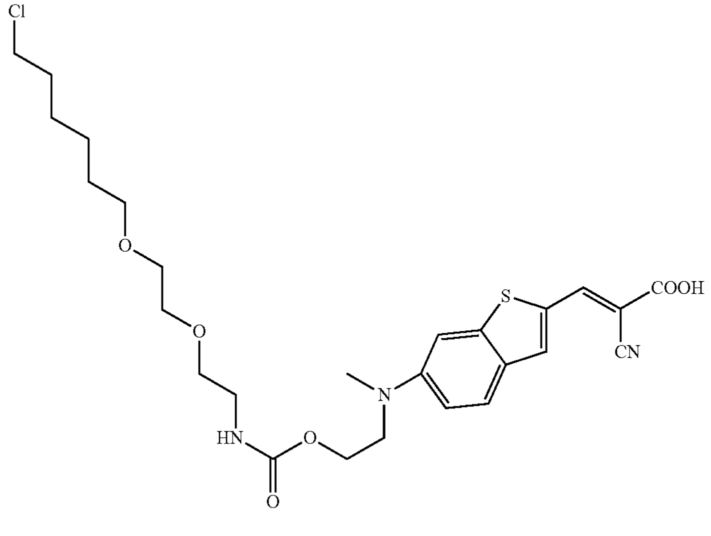

Probe 18

Compound 29:

With reference to the synthetic method of compound 14, the yield was 98%. $^1$H-NMR (400 MHz, $CDCl_3$): δ=7.95 (s, 1H), 7.81 (s, 1H), 7.68 (d, 1H, J=9.0 Hz), 6.92 (d, 1H, J=2.0), 6.82 (d, 1H, J=9.2 Hz), 3.85 (t, 2H, J=5.6 Hz), 3.60 (t, 2H, J=5.6 Hz), 3.10 (s, 3H).

Probe 18:

With reference to the synthetic method of probe 9, the yield was 91%. $^1$H-NMR (400 MHz, $CDCl_3$): δ=8.18 (t, 1H), 7.95 (s, 1H), 7.81 (s, 1H), 7.68 (d, 1H, J=9.0 Hz), 6.92 (d, 1H, J=2.0), 6.82 (d, 1H, J=9.2 Hz), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.46-1.39 (m, 2H), 1.36-1.28 (m, 2H).

Example 19

Molecular rotors were used as viscosity responsive fluorescent dyes to construct a fluorescent-activated covalently labeled probe 19 for HaloTag protein tag:

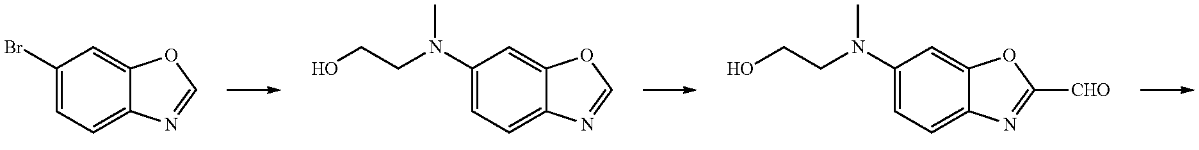

Compound 30 Compound 31

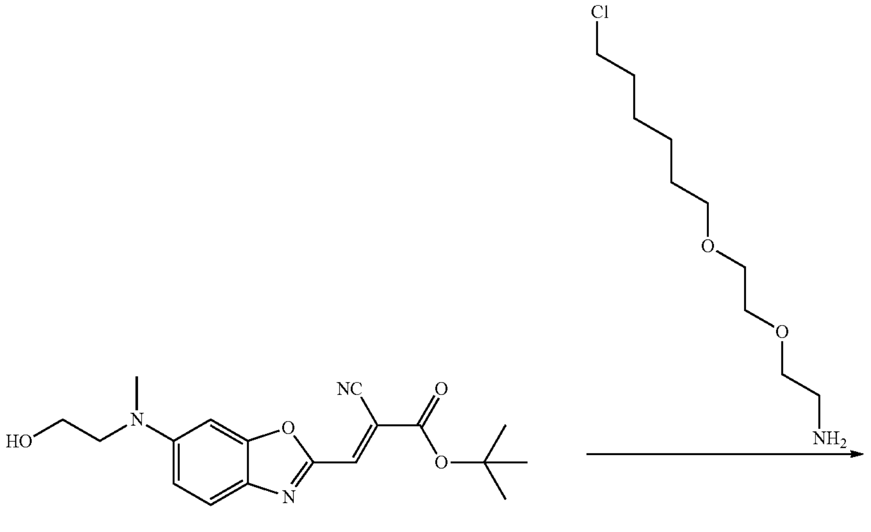

Compound 32

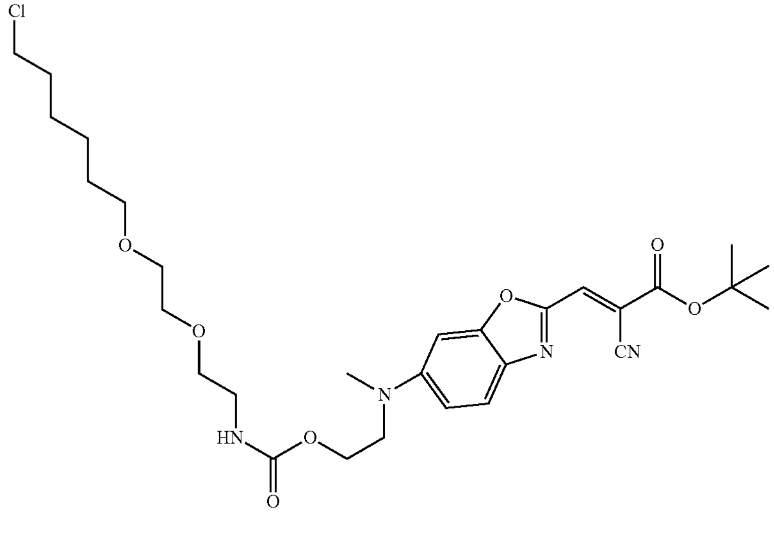

Probe 19

Compound 30:

With reference to the synthetic method of compound 16, the yield was 78%. $^1$H-NMR (400 MHz. $CDCl_3$): δ=8.07 (s, 1H), 7.77 (d, 1H, J=1.6 Hz), 7.66 (d, 1H, J=8.4 Hz), 7.50 (dd, 1H, J=8.4 Hz. J=1.6 Hz), 3.61 (t, 2H, J=8.0 Hz), 3.34 (t, 2H, J=8.0 Hz), 3.11 (s, 3H).

Compound 31:

With reference to the synthetic method of compound 17, the yield was 81%. $^1$H-NMR (400 MHz, $CDCl_3$): δ=9.99 (s, 1H), 7.61 (d, 1H, J=1.6 Hz), 7.49 (d, 1H, J=8.4 Hz), 7.40 (dd, 1H, $J_1$=8.4 Hz, $J_2$=1.6 Hz), 3.61 (t, 2H, J=8.0 Hz), 3.34 (t, 2H, J=8.0 Hz), 3.11 (s, 3H).

Compound 32:

With reference to the synthetic method of compound 1, the yield was 98%. $^1$H-NMR (400 MHz, $CDCl_3$): δ=8.01 (s, 1H), 7.61 (d, 1H, J=1.6 Hz), 7.49 (d, 1H, J=8.4 Hz), 7.40 (dd, 1H, $J_1$=8.4 Hz, $J_2$=1.6 Hz), 3.61 (t, 2H, J=8.0 Hz), 3.34 (t, 2H, J=8.0 Hz), 3.11 (s, 3H), 1.50 (s, 9H).

Probe 19:

With reference to the synthetic method of probe 1, the yield was 66%. $^1$H-NMR (400 MHz, $CDCl_3$): δ=8.18 (t, 1H), 8.01 (s, 1H), 7.61 (d, 1H, J=1.6 Hz), 7.49 (d, 1H, J=8.4 Hz), 7.40 (dd, 1H, $J_1$=8.4 Hz, $J_2$=1.6 Hz), 3.69 (t, J=4.9 Hz, 2H), 3.63-3.60 (m, 2H), 3.61 (t, 2H, J=8.0 Hz), 3.56-3.53 (m, 2H), 3.52 (t, J=6.6 Hz, 2H), 3.44 (t, J=6.8 Hz, 2H), 3.34 (t, 2H, J=8.0 Hz), 3.12 (t, J=4.9 Hz, 2H), 3.11 (s, 3H), 1.79-1.71 (m, 2H), 1.60-1.53 (m, 2H), 1.50 (s, 9H), 1.46-1.39 (m, 2H), 1.36-1.28 (m, 2H).

Example 20

Molecular rotors were used as viscosity responsive fluorescent dyes to construct a fluorescent-activated covalently labeled probe 20 for HaloTag protein tag:

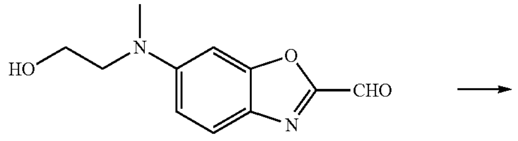

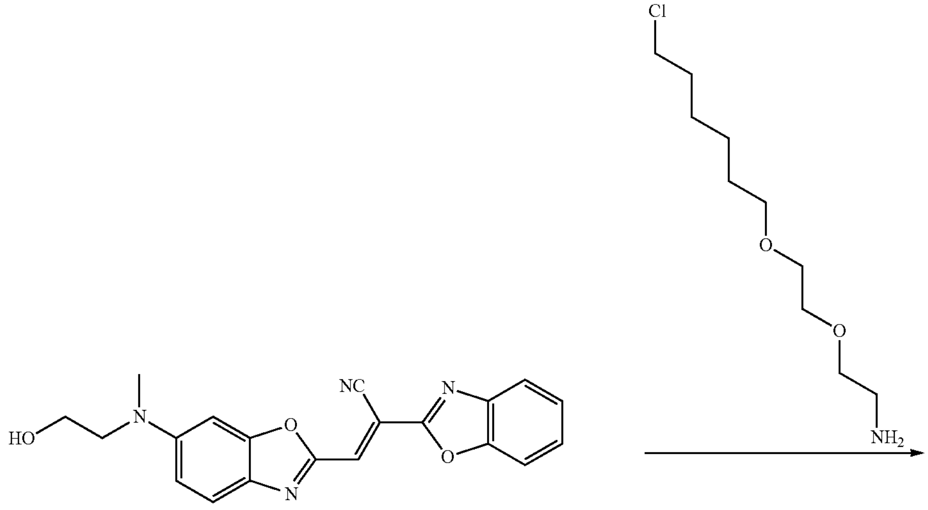

Compound 33

-continued

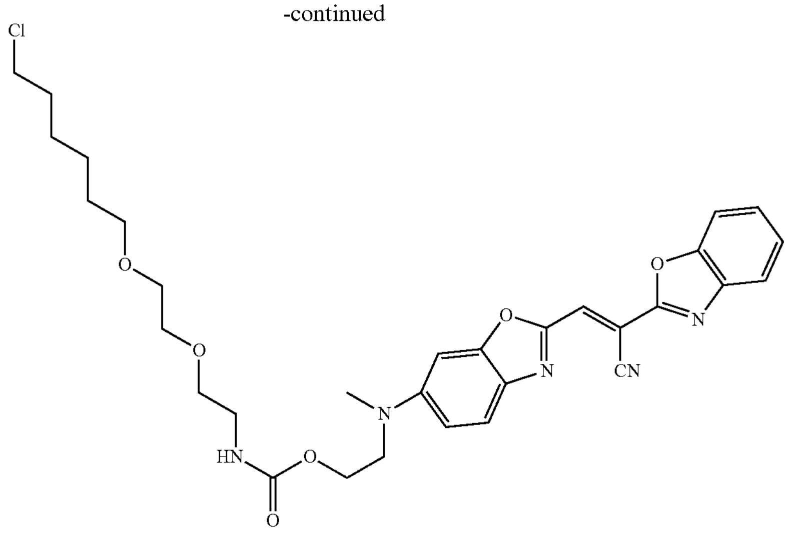

Probe 20

Compound 33:

With reference to the synthetic method of compound 1, the yield was 97%. $^1$H-NMR (400 MHz, $CDCl_3$): δ=7.99 (s, 1H), 7.61 (d, 1H, J=1.6 Hz), 7.74 (d, 1H, J=4.0 Hz), 7.55 (d, 1H, J=4.0 Hz), 7.49 (d, 1H, J=8.4 Hz), 7.36-7.42 (m, 3H), 3.61 (t, 2H, J=8.0 Hz), 3.34 (t, 2H, J=8.0 Hz), 3.11 (s, 3H).

Probe 20:

With reference to the synthetic method of probe 1, the yield was 65%. $^1$H-NMR (400 MHz, $CDCl_3$): δ=8.18 (t, 1H), 7.99 (s, 1H), 7.61 (d, 1H, J=1.6 Hz), 7.74 (d, 1H, J=4.0 Hz), 7.55 (d, 1H, J=4.0 Hz), 7.49 (d, 1H, J=8.4 Hz), 7.36-7.42 (m, 3H), 3.69 (t, J=4.9 Hz, 2H), 3.63-3.60 (m, 2H), 3.61 (t, 2H, J=8.0 Hz), 3.56-3.53 (m, 2H), 3.52 (t, J=6.6 Hz, 2H), 3.44 (t, J=6.8 Hz, 2H), 3.34 (t, 2H, J=8.0 Hz), 3.12 (t, J=4.9 Hz, 2H), 3.11 (s, 3H), 1.79-1.71 (m, 2H), 1.60-1.53 (m, 2H), 1.46-1.39 (m, 2H), 1.36-1.28 (m, 2H).

Example 21

Molecular rotors were used as viscosity responsive fluorescent dyes to construct a fluorescent-activated covalently labeled probe 21 for HaloTag protein tag:

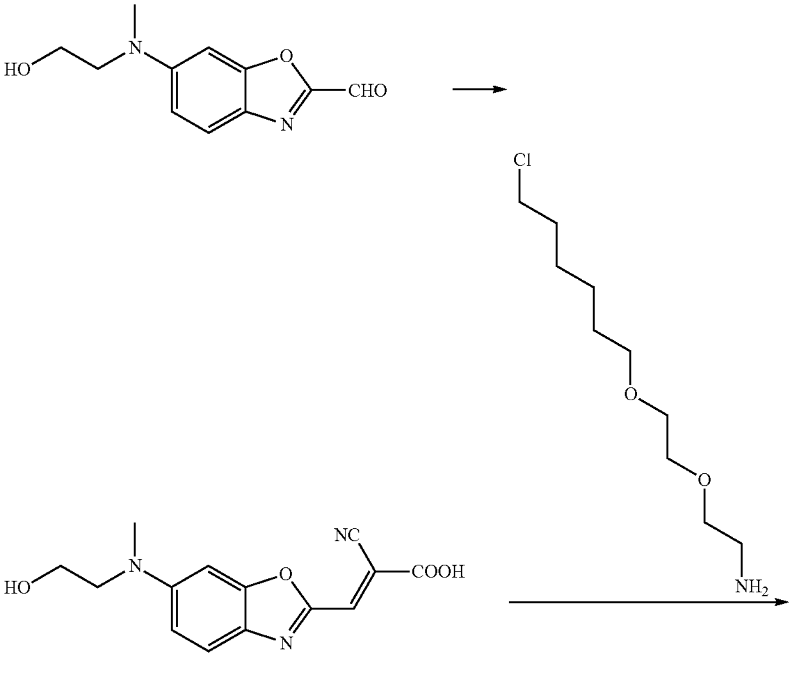

Compound 34

-continued

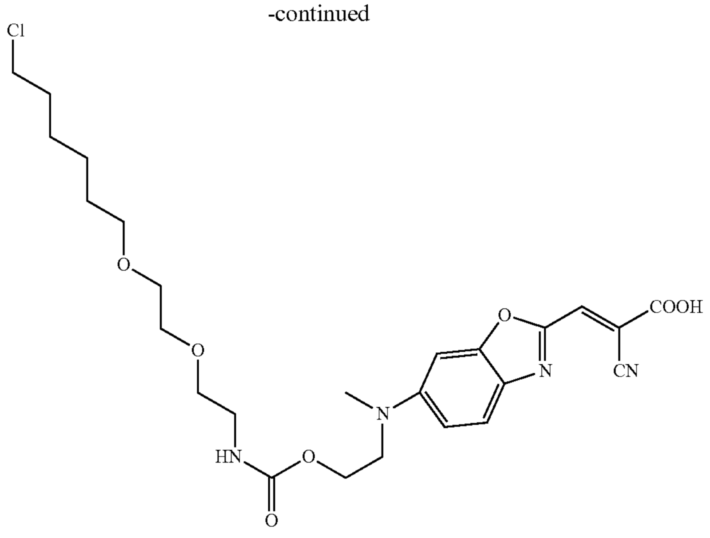

Probe 21

Compound 34:

With reference to the synthetic method of compound 1, the yield was 87%. $^1$H-NMR (400 MHz, $CDCl_3$): δ=7.99 (s, 1H), 7.61 (d, 1H, J=1.6 Hz), 7.49 (d, 1H, J=8.4 Hz), 7.40 (dd, 1H, $J_1$=8.4 Hz, $J_2$=1.6 Hz), 3.61 (t, 2H, J=8.0 Hz), 3.34 (t, 2H, J=8.0 Hz), 3.11 (s, 3H).

Probe 21:

With reference to the synthetic method of probe 1, the yield was 31%. $^1$H-NMR (400 MHz, DMSO-$d_6$): δ=8.18 (t, 1H), 7.99 (s, 1H), 7.61 (d, 1H, J=1.6 Hz), 7.49 (d, 1H, J=8.4 Hz), 7.40 (dd, 1H, $J_1$=8.4 Hz, $J_2$=1.6 Hz), 3.69 (t, J=4.9 Hz, 2H), 3.63-3.60 (m, 2H), 3.61 (t, 2H, J=8.0 Hz), 3.56-3.53 (m, 2H), 3.52 (t, J=6.6 Hz, 2H), 3.44 (t, J=6.8 Hz, 2H), 3.34 (t, 2H, J=8.0 Hz), 3.12 (t, J=4.9 Hz, 2H), 3.11 (s, 3H), 1.79-1.71 (m, 2H), 1.60-1.53 (m, 2H), 1.46-1.39 (m, 2H), 1.36-1.28 (m, 2H).

Example 22

Molecular rotors were used as viscosity responsive fluorescent dyes to construct a fluorescent-activated covalently labeled probe 22 for HaloTag protein tag:

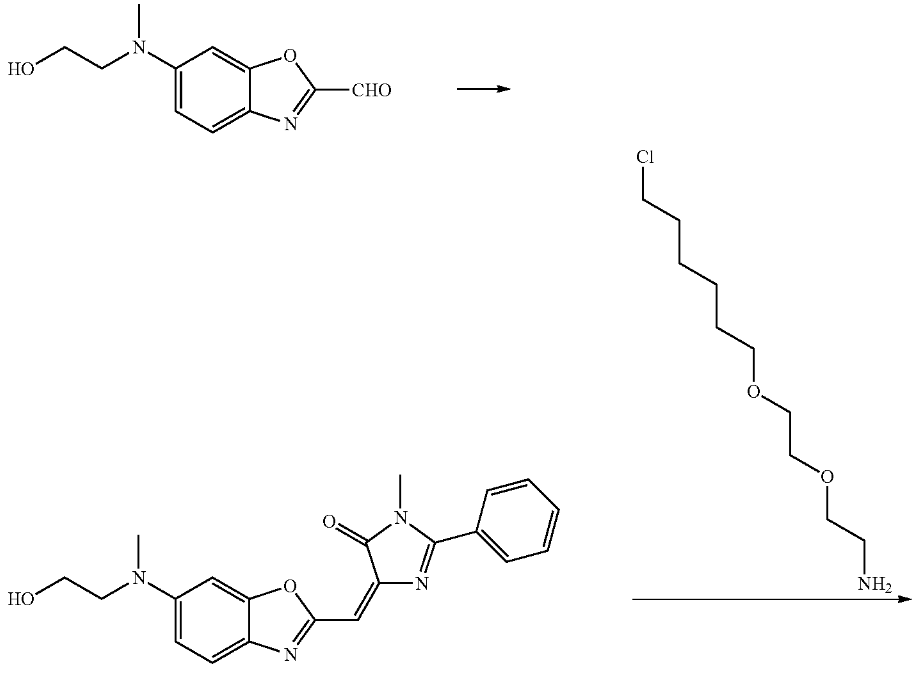

Compound 35

-continued

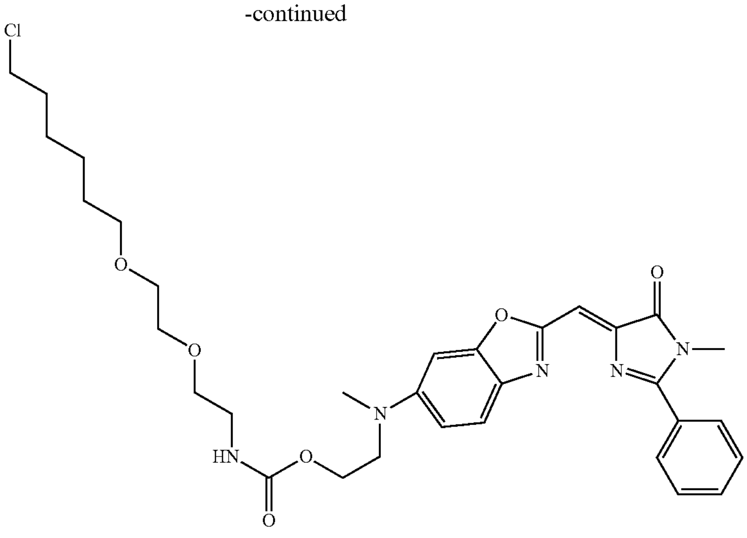

Probe 22

Compound 35:

With reference to the synthetic method of compound 1, the yield was 91%. $^1$H-NMR (400 MHz, $CDCl_3$): δ=7.98 (s, 1H), 7.64-7.48 (m, 7H), 7.40 (dd, 1H, $J_1$=8.4 Hz, $J_2$=1.6 Hz), 3.61 (t, 2H, J=8.0 Hz), 3.34 (t, 2H, J=8.0 Hz), 3.13 (s, 3H), 3.11 (s, 3H).

Probe 22:

With reference to the synthetic method of probe 1, the yield was 67%. $^1$H-NMR (400 MHz, $CDCl_3$): δ=8.18 (t, 1H), 7.98 (s, 1H), 7.64-7.48 (m, 7H), 7.40 (dd, 1H, $J_1$=8.4 Hz, $J_2$=1.6 Hz), 3.69 (t, J=4.9 Hz, 2H), 3.63-3.60 (m, 2H), 3.61 (t, 2H, J=8.0 Hz), 3.56-3.53 (m, 2H), 3.52 (t, J=6.6 Hz, 2H), 3.44 (t, J=6.8 Hz, 2H), 3.34 (t, 2H, J=8.0 Hz), 3.13 (s, 3H), 3.12 (t, J=4.9 Hz, 2H), 3.11 (s, 3H), 1.79-1.71 (m, 2H), 1.60-1.53 (m, 2H), 1.46-1.39 (m, 2H), 1.36-1.28 (m, 2H).

Example 23

Molecular rotors were used as viscosity responsive fluorescent dyes to construct a fluorescent-activated covalently labeled probe 23 for HaloTag protein tag:

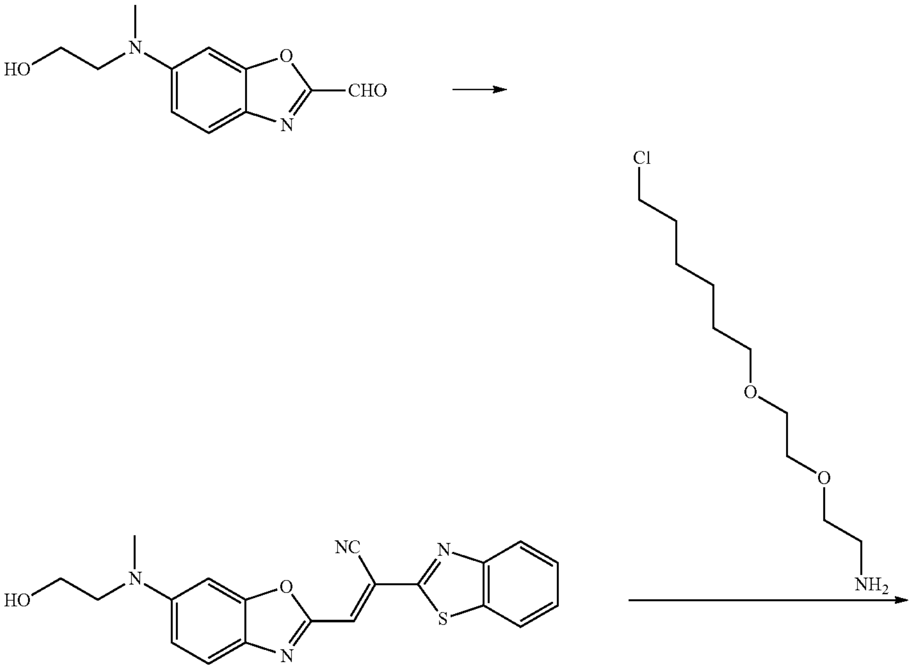

Compound 36

-continued

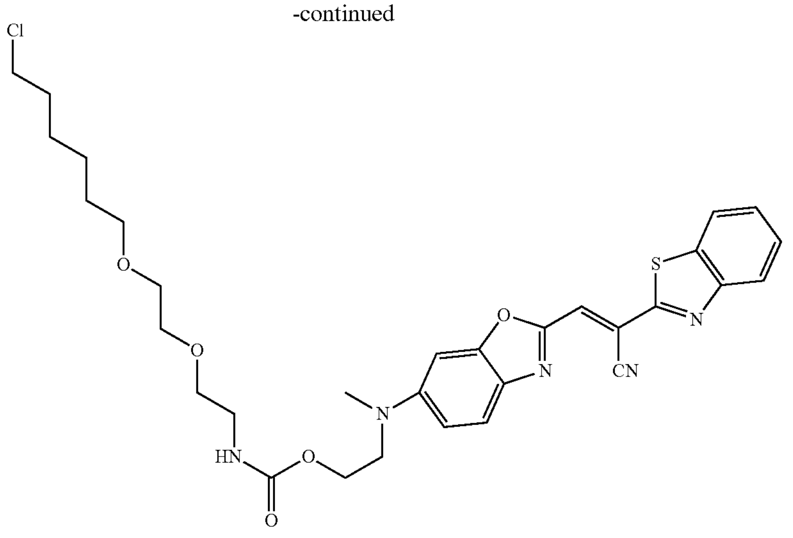

Probe 23

Compound 36:

With reference to the synthetic method of compound 1, the yield was 97%. $^1$H-NMR (400 MHz, $CDCl_3$): δ=8.04 (d, 1H, J=8.0 Hz), 7.90 (d, 1H, J=8.0 Hz), 7.99 (s, 1H), 7.61 (d, 1H, J=1.6 Hz), 7.53 (t, 1H, J=8.0 Hz), 7.49 (d, 1H, J=8.4 Hz), 7.45 (t, 1H, J=8.0 Hz), 7.40 (dd, 1H, $J_1$=8.4 Hz, $J_2$=1.6 Hz), 3.61 (t, 2H, J=8.0 Hz), 3.34 (t, 2H, J=8.0 Hz), 3.11 (s, 3H).

Probe 23:

With reference to the synthetic method of probe 1, the yield was 61%. $^1$H-NMR (400 MHz, $CDCl_3$): δ=8.18 (t, 1H), 8.04 (d, 1H, J=8.0 Hz), 7.90 (d, 1H, J=8.0 Hz), 7.99 (s, 1H), 7.61 (d, 1H, J=1.6 Hz), 7.53 (t, 1H, J=8.0 Hz), 7.49 (d, 1H, J=8.4 Hz), 7.45 (t, 1H, J=8.0 Hz), 7.40 (dd, 1H, $J_1$=8.4 Hz, $J_2$=1.6 Hz), 3.69 (t, J=4.9 Hz, 2H), 3.63-3.60 (m, 2H), 3.61 (t, 2H, J=8.0 Hz), 3.56-3.53 (m, 2H), 3.52 (t, J=6.6 Hz, 2H), 3.44 (t, J=6.8 Hz, 2H), 3.34 (t, 2H, J=8.0 Hz), 3.12 (t, J=4.9 Hz, 2H), 3.11 (s, 3H), 1.79-1.71 (m, 2H), 1.60-1.53 (m, 2H), 1.46-1.39 (m, 2H), 1.36-1.28 (m, 2H).

Example 24

Molecular rotors were used as viscosity responsive fluorescent dyes to construct a fluorescent-activated covalently labeled probe 24 for HaloTag protein tag:

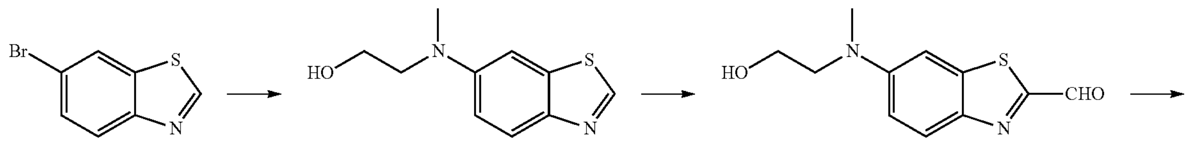

Compound 37 Compound 38

-continued

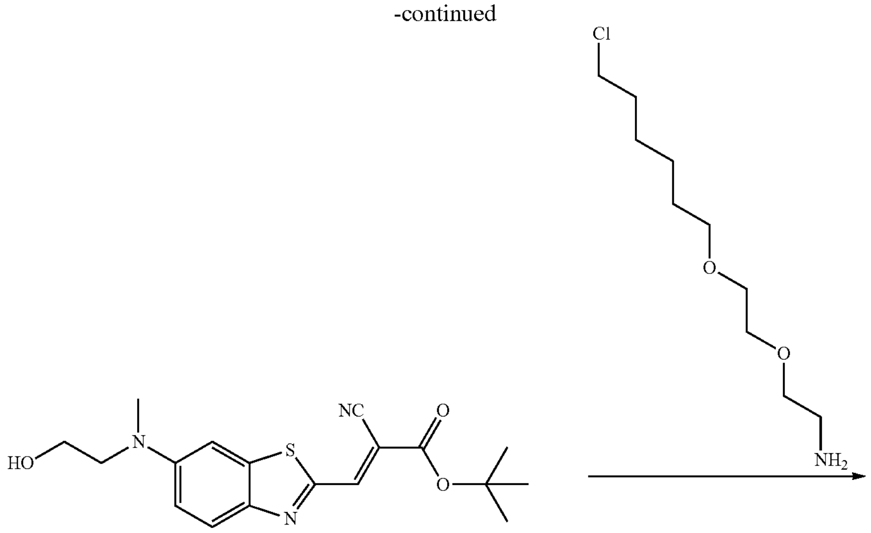

Compound 39

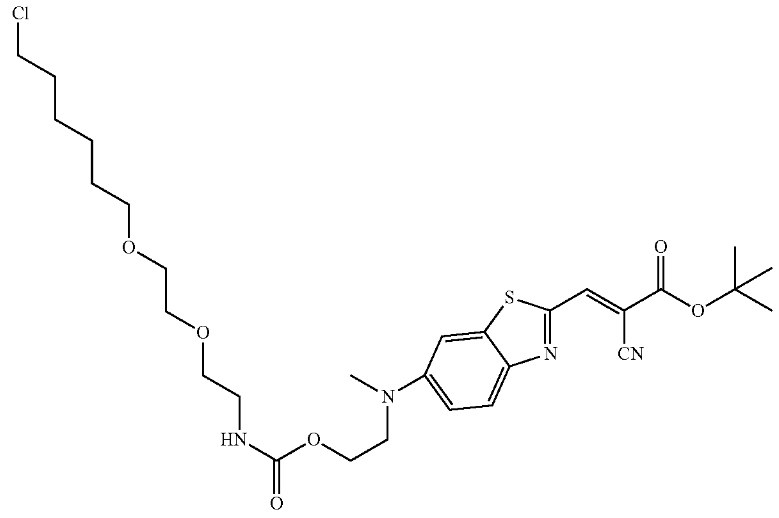

Probe 24

Compound 37:

With reference to the synthetic method of compound 16, the yield was 81%. $^1$H-NMR (400 MHz, $CDCl_3$): δ=8.67 (s, 1H), 7.95 (d, 1H, J=10.0 Hz), 7.15 (d, 1H, J=2.4 Hz), 7.00 (dd, 1H, $J_1$=8.8 Hz, $J_2$=2.4 Hz), 3.61 (t, 2H, J=8.0 Hz), 3.34 (t, 2H, J=8.0 Hz), 3.10 (s, 3H).

Compound 38:

With reference to the synthetic method of compound 17, the yield was 56%. $^1$H-NMR (400 MHz, $CDCl_3$): δ=10.06 (s, 1H), 8.03 (d, 1H, J=10.0 Hz), 7.07-7.04 (m, 2H), 3.61 (t, 2H, J=8.0 Hz), 3.34 (t, 2H, J=8.0 Hz), 3.10 (s, 3H).

Compound 39:

With reference to the synthetic method of compound 1, the yield was 96%. $^1$H-NMR (400 MHz, $CDCl_3$): δ=8.03 (d, 1H, J=10.0 Hz), 7.95 (s, 1H), 7.07-7.04 (m, 2H), 3.61 (t, 2H, J=8.0 Hz), 3.34 (t, 2H, J=8.0 Hz), 3.10 (s, 3H), 1.50 (s, 9H).

Probe 24:

With reference to the synthetic method of probe 1, the yield was 61%. $^1$H-NMR (400 MHz, DMSO-$d_6$): δ=8.18 (t, 1H), 8.03 (d, 1H, J=10.0 Hz), 7.95 (s, 1H), 7.07-7.04 (m, 2H), 3.69 (t, J=4.9 Hz, 2H), 3.63-3.60 (m, 2H), 3.61 (t, 2H, J=8.0 Hz), 3.56-3.53 (m, 2H), 3.52 (t, J=6.6 Hz, 2H), 3.44 (t, J=6.8 Hz, 2H), 3.34 (t, 2H, J=8.0 Hz), 3.12 (t, J=4.9 Hz, 2H), 3.10 (s, 3H), 1.79-1.71 (m, 2H), 1.60-1.53 (m, 2H), 1.50 (s, 9H), 1.46-1.39 (m, 2H), 1.36-1.28 (m, 2H).

Example 25

Molecular rotors were used as viscosity responsive fluorescent dyes to construct a fluorescent-activated covalently labeled probe 25 for HaloTag protein tag:

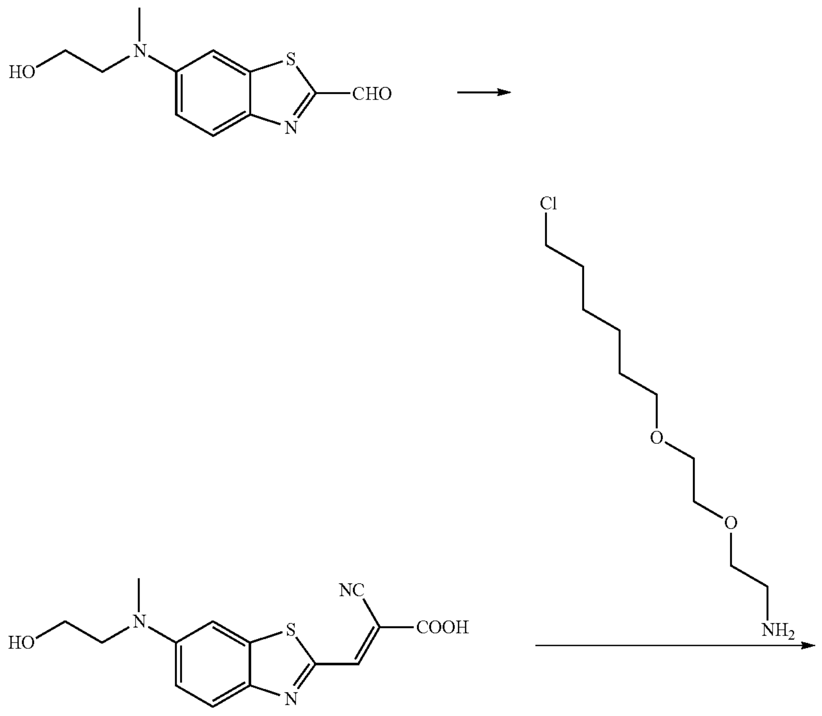

Compound 40

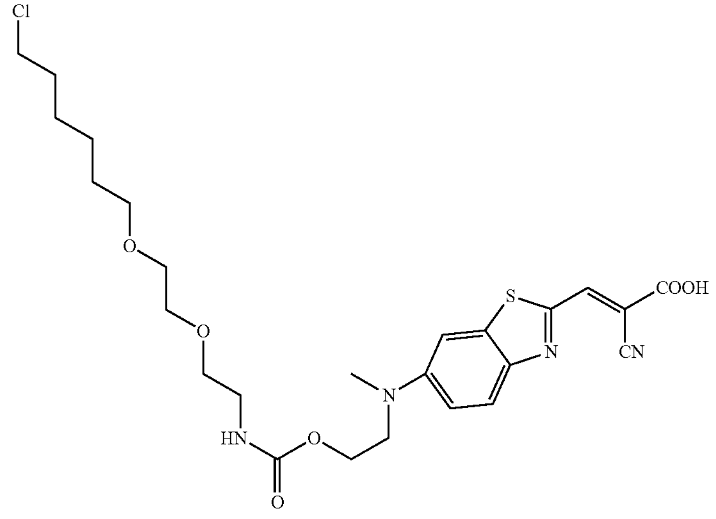

Probe 25

Compound 40:

With reference to the synthetic method of compound 1, the yield was 96%. $^{1}$H-NMR (400 MHz, $CDCl_3$): δ=8.06 (s, 1H), 8.03 (d, 1H, J=10.0 Hz), 7.07-7.04 (m, 2H), 3.85 (t, 2H, J=5.6 Hz), 3.60 (t, 2H, J=5.6 Hz), 3.10 (s, 3H).

Probe 25:

With reference to the synthetic method of probe 1, the yield was 89%. $^{1}$H-NMR (400 MHz, DMSO-ds): δ=8.18 (t, 1H), 8.06 (s, 1H), 8.03 (d, 1H, J=10.0 Hz), 7.07-7.04 (m, 2H), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.46-1.39 (m, 2H), 1.36-1.28 (m, 2H).

Example 26

Molecular rotors were used as viscosity responsive fluorescent dyes to construct a fluorescent-activated covalently labeled probe 26 for HaloTag protein tag:

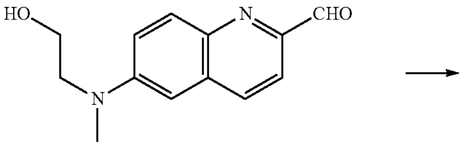

Compound 41

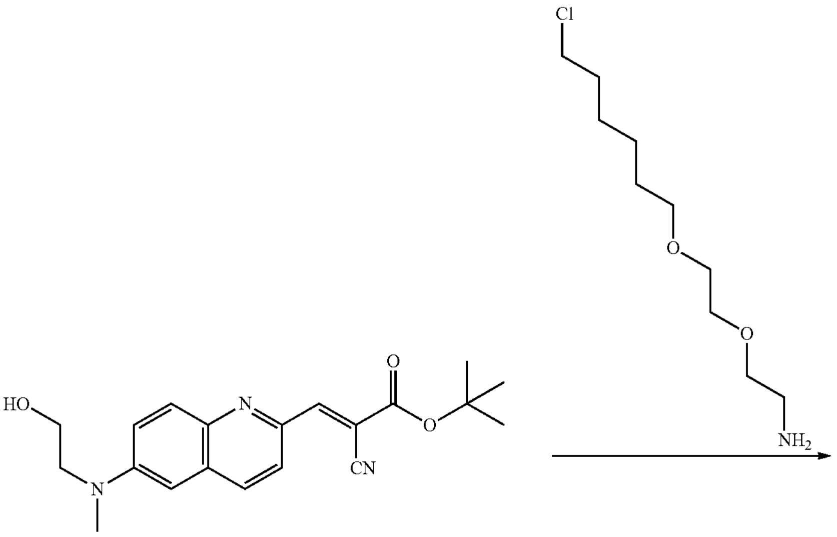

Compound 42

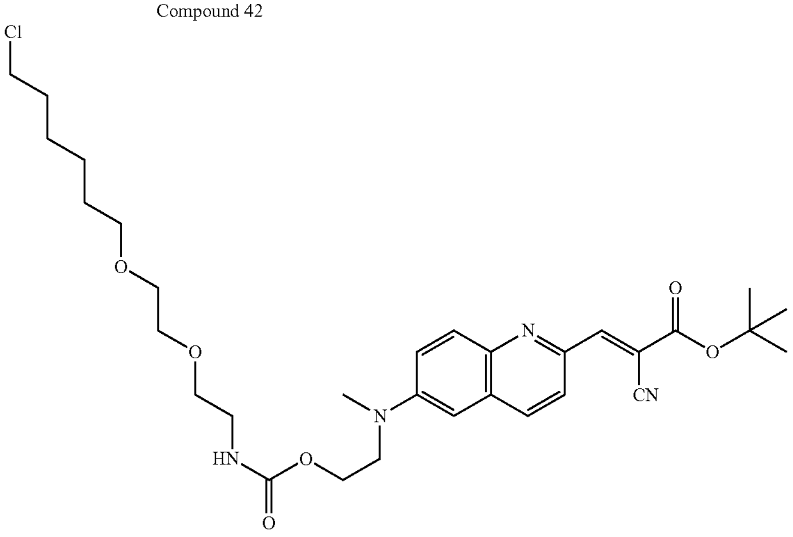

Probe 26

Compound 41:

The synthesis method was performed according to the method disclosed in the document (Hwan Myung Kim et al. ANAL CHEM. 2014, 86, 308-311.). $^1$H-NMR (400 MHz, $CDCl_3$): δ=10.13 (s, 1H), 7.83-7.89 (m, 2H), 7.25-7.34 (m, 1H), 7.13 (d, 1H), 6.73 (d, 1H), 3.68 (t, 2H, J=5.6 Hz), 3.53 (t, 2H, J=5.6 Hz), 3.08 (s, 3H).

Compound 42:

With reference to the synthetic method of probe 1, the yield was 82%. $^1$H-NMR (400 MHz, $CDCl_3$): δ=8.07 (s, 1H), 7.83-7.89 (m, 2H), 7.25-7.34 (m, 1H), 7.13 (d, 1H), 6.73 (d, 1H), 3.68 (t, 2H, J=5.6 Hz), 3.53 (t, 2H, J=5.6 Hz), 3.08 (s, 3H), 1.52 (s, 9H).

Probe 26:

With reference to the synthetic method of probe 1, the yield was 82%. $^1$H-NMR (400 MHz, DMSO-$d_6$): δ=8.18 (t, 1H), 8.07 (s, 1H), 7.83-7.89 (m, 2H), 7.25-7.34 (m, 1H), 7.13 (d, 1H), 6.73 (d, 1H), 3.69 (t, J=4.9 Hz, 2H), 3.68 (t, 2H, J=5.6 Hz), 3.63-3.60 (m, 2H), 3.56-3.53 (m, 2H), 3.53 (t, 2H, J=5.6 Hz), 3.52 (t, J=6.6 Hz, 2H), 3.44 (t, J=6.8 Hz, 2H), 3.12 (t, J=4.9 Hz, 2H), 3.08 (s, 3H), 1.79-1.71 (m, 2H), 1.60-1.53 (m, 2H), 1.52 (s, 9H), 1.46-1.39 (m, 2H), 1.36-1.28 (m, 2H).

Example 27

Molecular rotors were used as viscosity responsive fluorescent dyes to construct a fluorescent-activated covalently labeled probe 27 for HaloTag protein tag:

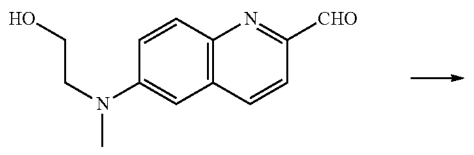

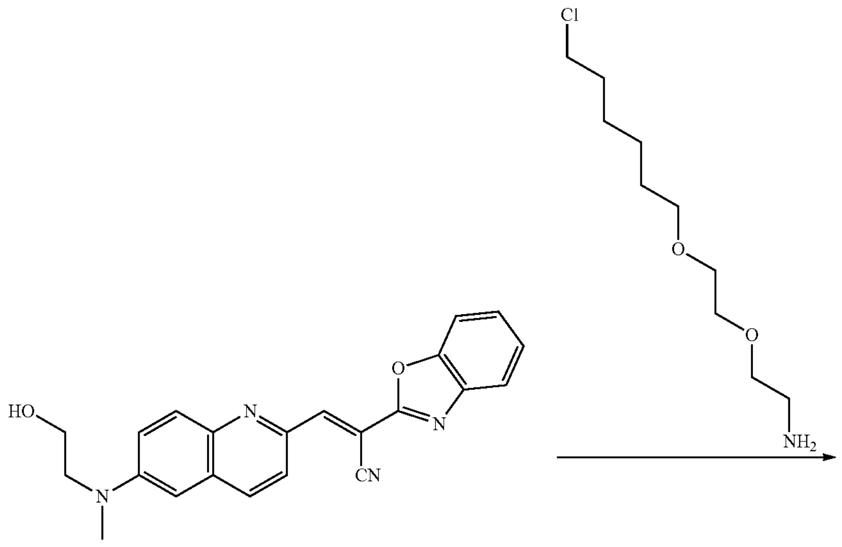

Compound 43

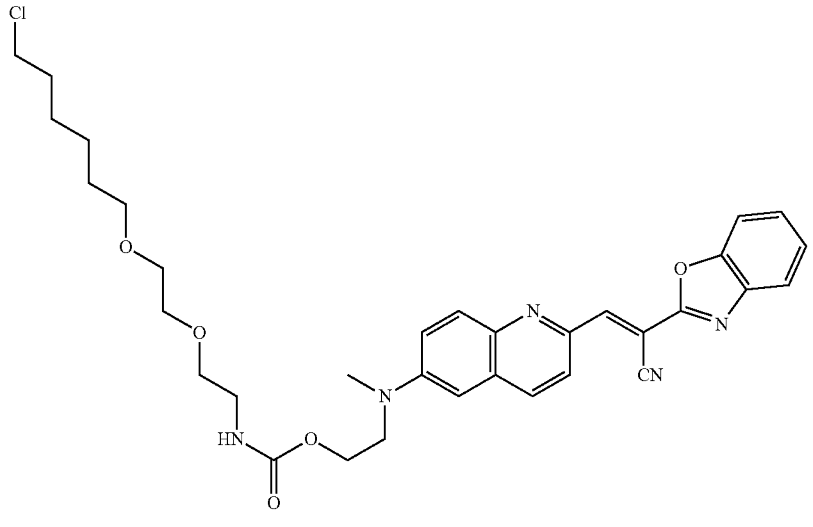

Probe 27

Compound 43:

With reference to the synthetic method of probe 1, the yield was 86%. $^1$H-NMR (400 MHz, $CDCl_3$): δ=8.08 (s, 1H), 7.83-7.89 (m, 2H), 7.49 (d, 1H, J=8.4 Hz), 7.36-7.42 (m, 3H), 7.25-7.34 (m, 1H), 7.13 (d, 1H), 6.73 (d, 1H), 3.61 (t, 2H J=8.0 Hz), 3.34 (t, 2H, J=8.0 Hz), 3.11 (s, 3H).

Probe 27:

With reference to the synthetic method of probe 1, the yield was 88%. $^1$H-NMR (400 MHz, DMSO-$d_6$): δ=8.18 (t, 1H), 8.08 (s, 1H), 7.83-7.89 (m, 2H), 7.49 (d, 1H, J=8.4 Hz), 7.36-7.42 (m, 3H), 7.25-7.34 (m, 1H), 7.13 (d, 1H), 6.73 (d, 1H), 3.69 (t, J=4.9 Hz, 2H), 3.63-3.60 (m, 2H), 3.61 (t, 2H, J=8.0 Hz), 3.56-3.53 (m 2H), 3.52 (t, J=6.6 Hz, 2H), 3.44 (t, J=6.8 Hz, 2H), 3.34 (t, 2H, J=8.0 Hz), 3.12 (t, J=4.9 Hz, 2H), 3.11 (s, 3H), 1.79-1.71 (m, 2H), 1.60-1.53 (m, 2H), 1.46-1.39 (m, 2H), 1.36-1.28 (m, 2H).

Example 28

Molecular rotors were used as viscosity responsive fluorescent dyes to construct a fluorescent-activated covalently labeled probe 28 for HaloTag protein tag:

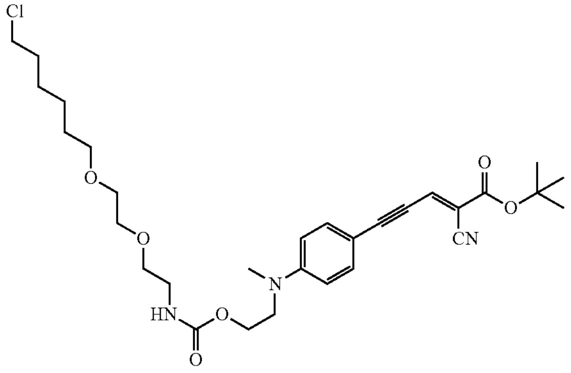

Probe 28

The synthesis method was performed according to the method disclosed in the document (M. Klikar et. al. New. J. Chem. 2017, 41, 1459-1472). (The preparation of intermediates that are actually probes refers to the preparation methods in this document. Same as below.). $^{1}$H-NMR (400 MHz, DMSO-$d_6$): δ=8.18 (t, 1H), 8.01 (s, 1H), 7.47 (d, 2H, J=8.8 Hz), 6.76 (d, 2H, J=8.8 Hz), 3.78 (t, 2H, J=4.80 Hz), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.32 (t, 2H, J=4.80 Hz), 3.12 (t, J=4.9 Hz, 2H), 3.02 (s, 3H), 1.79-1.71 (m, 2H), 1.60-1.53 (m, 2H), 1.50 (s, 9H), 1.46-1.39 (m, 2H), 1.36-1.28 (n, 2H).

Example 29

Molecular rotors were used as viscosity responsive fluorescent dyes to construct a fluorescent-activated covalently labeled probe 29 for HaloTag protein tag:

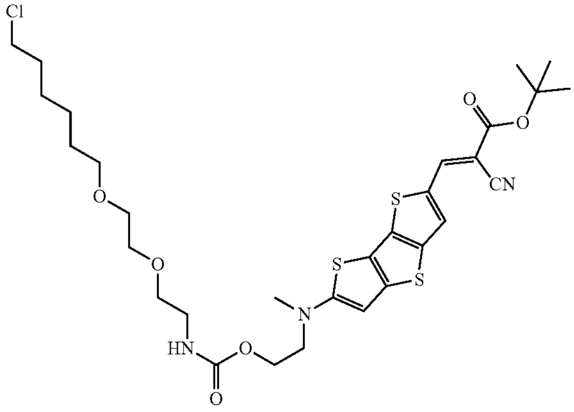

Probe 29

The synthesis method was performed according to the method disclosed in the document (Ruikui Chen et. al. Chem. Mater. 2007, 19, 4007-4015.) and probe 10. $^{1}$H-NMR (400 MHz, DMSO-d): δ=8.18 (t, 1H), 8.01 (s, 11H), 7.84 (s, 1H), 7.24 (s, 1H), 3.78 (t, 2H, J=4.80 Hz), 3.69 (t, J=4.9 Hz, 2H), 3.63-3.60 (m, 2H), 3.56-3.53 (m, 2H), 3.52 (t, J=6.6 Hz, 2H), 3.44 (m, 4H), 3.12 (t, J=4.9 Hz, 2H), 3.02 (s, 3H), 1.79-1.71 (m, 2H), 1.60-1.53 (m, 2H), 1.50 (s, 9H), 1.46-1.39 (m, 2H), 1.36-1.28 (m, 2H).

Example 30

Molecular rotors were used as viscosity responsive fluorescent dyes to construct a fluorescent-activated covalently labeled probe 30 for HaloTag protein tag:

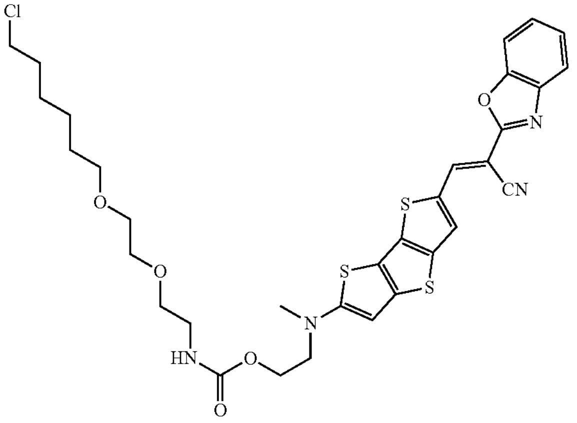

Probe 30

With reference to the synthetic method of probe 29. $^{1}$H-NMR (400 MHz, DMSO-$d_6$): δ=8.18 (t, 1H), 8.07 (H, d, J=8.0 Hz), 8.01 (s, 1H), 7.90 (1H, d, J=8.0 Hz), 7.84 (s, 1H), 7.53 (1H, t. J=8.0 Hz), 7.45 (1H, t, J=8.0 Hz), 7.24 (s, 1H), 3.78 (t, 2H, J=4.80 Hz), 3.69 (t, J=4.9 Hz, 2H), 3.63-3.60 (m, 2H), 3.56-3.53 (m, 2H), 3.52 (t, J=6.6 Hz, 2H), 3.44 (m, 4H), 3.12 (t, J=4.9 Hz, 2H), 3.02 (s, 3H), 1.79-1.71 (m, 2H), 1.60-1.53 (m, 2H), 1.46-1.39 (m, 2H), 1.36-1.28 (m, 2H).

Example 31

Molecular rotors were used as viscosity responsive fluorescent dyes to construct a fluorescent-activated covalently labeled fluorescent probe 31 for HaloTag:

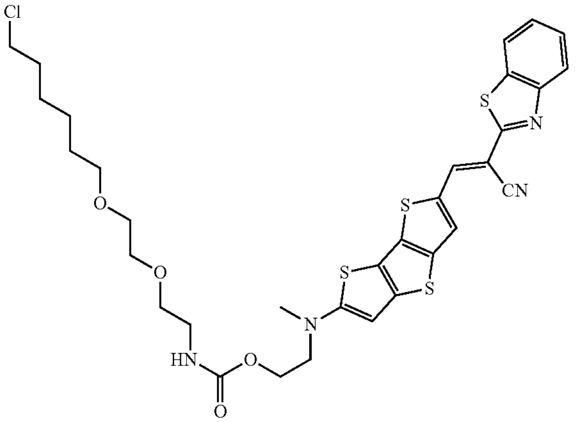

Probe31

Refer to the method of probe 29 for synthesis. 1H-NMR (400 MHz, DMSO-d6): δ=8.18 (t, 1H), 8.07 (1H, d, J=8.0 Hz), 8.01 (s, 1H), 7.90 (1H, d, J=8.0 Hz), 7.84 (s, 1H), 7.53 (1H, t, J=8.0 Hz), 7.45 (1H, t, J=8.0 Hz), 7.24 (s, 1H), 3.78 (t, 211 J=4.80 Hz), 3.69 (t, J=4.9 Hz, 2H), 3.63-3.60 (m, 2H), 3.56-3.53 (m, 2H), 3.52 (t, J=6.6 Hz, 2H), 3.44 (m, 4H), 3.12 (t, J=4.9 Hz, 2H), 3.02 (s, 3H), 1.79-1.71 (m, 2H), 1.60-1.53 (m, 2H), 1.46-1.39 (m, 2H), 1.36-1.28 (m, 2H).

Example 32

Molecular rotors were used as viscosity responsive fluorescent dyes to construct a fluorescent-activated covalently labeled fluorescent probe 32 for HaloTag:

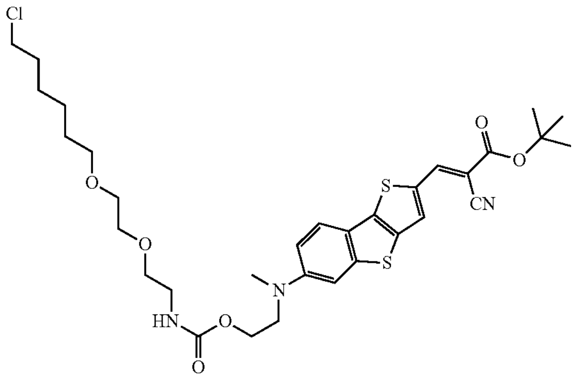

Probe32

Refer to the method of probe 29 for synthesis. 1H-NMR (400 MHz, DMSO-d6): δ=8.18 (t, 1H), 8.01 (s, 1H), 7.87 (m, 1H), 7.71 (m, 1H), 7.51 (d, J=5.4 Hz, 1H), 7.32 (d, J=5.4 Hz, 1H), 3.78 (t, 2H, J=4.80 Hz), 3.69 (t, J=4.9 Hz, 2H), 3.63-3.60 (m, 2H), 3.56-3.53 (m, 2H), 3.52 (t, J=6.6 Hz, 2H), 3.44 (m, 4H), 3.12 (t, J=4.9 Hz, 2H), 3.02 (s, 3H), 1.79-1.71 (n, 2H), 1.60-1.53 (m, 2H), 1.49 (s, 9H), 1.46-1.39 (m, 2H), 1.36-1.28 (m, 2H).

Example 33

Molecular rotors were used as viscosity responsive fluorescent dyes to construct a fluorescent-activated covalently labeled fluorescent probe 33 for HaloTag

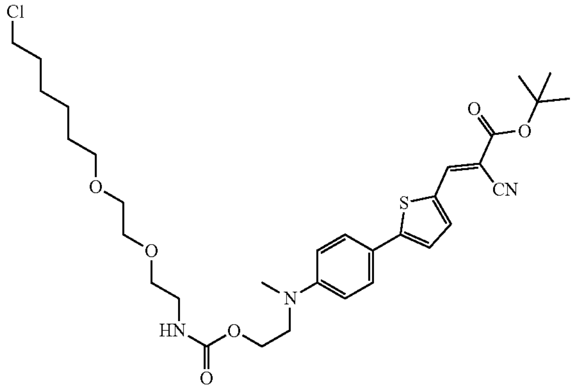

Probe33

With reference to the literature (ShengboZhu et. al. 2015, 16, 146-154) and the method of probe 10 for synthesis. 1H-NMR (400 MHz, DMSO-d6): δ=8.18 (t, 1H), 8.01 (s, 1H), 7.68 (s, 1H), 7.55 (d, 1H, J=8.00 Hz), 7.25 (d, 2H, J=8.00 Hz), 6.78 (d, 2H, J=8.00 Hz), 3.86 (t, 2H, J=4.80 Hz), 3.69 (t, J=4.9 Hz, 2H), 3.63-3.60 (m, 2H), 3.56 (t, 2H, J=4.80 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.06 (s, 3H), 1.79-1.71 (m, 2H), 1.60-1.53 (m, 2H), 1.50 (s, 9H), 1.46-1.39 (m, 2H), 1.36-1.28 (m, 2H)

Example 34

Molecular rotors were used as viscosity responsive fluorescent dyes to construct a fluorescent-activated covalently labeled fluorescent probe 34 for HaloTag:

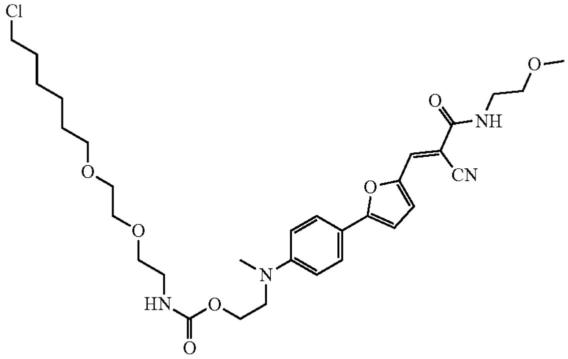

Probe34

Refer to the method of probe 33 for synthesis. 1H-NMR (400 MHz, DMSO-d6): δ=8.31 (s, 1H), 8.22 (bt, 1H), 8.18 (t, 1H), 7.82 (d, 1H, J=4.00 Hz), 7.58 (d, 2H, J=8.80 Hz), 7.50 (d, 2H, J=4.00 Hz), 6.77 (d, 2H, J=8.80 Hz), 4.74 (bt, 1H), 3.69 (t, J=4.9 Hz, 2H), 3.63-3.60 (m, 2H), 3.57 (t, 2H, J=5.20 Hz), 3.56-3.53 (m, 2H), 3.52 (t, J=6.6 Hz, 2H), 3.48-3.41 (m, 6H), 3.38 (t, 2H, J=5.20 Hz), 3.27 (s, 3H), 3.12 (t, J=4.9 Hz, 2H), 3.01 (s, 3H), 1.79-1.71 (m, 2H), 1.60-1.53 (m, 2H), 1.46-1.39 (m, 2H), 1.36-1.28 (m, 2H)

Example 35

Molecular rotors were used as viscosity responsive fluorescent dyes to construct a fluorescent-activated covalently labeled fluorescent probe 35 for HaloTag:

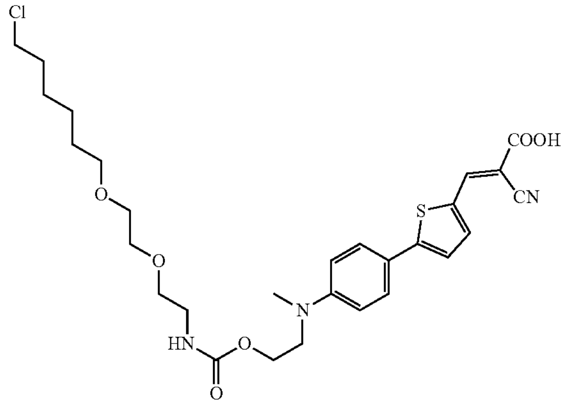

Probe35

Refer to the method of probe 33 for synthesis. 1H-NMR (400 MHz, DMSO-d6): δ=8.18 (t, 1H), 8.00 (s, 1H), 7.68 (d, 1H, J=4.0 Hz), 7.56 (d, 2H, J=9.0 Hz), 7.24 (d, 1H, J=4.0

Hz), 6.72 (d, 2H, J=9.0 Hz), 3.85 (t, 2H, J=5.6 Hz), 3.69 (t, J=4.9 Hz, 2H), 3.63-3.60 (m, 2H), 3.60 (t, 2H J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.46-1.39 (m, 2H), 1.36-1.28 (m, 2H)

Example 36

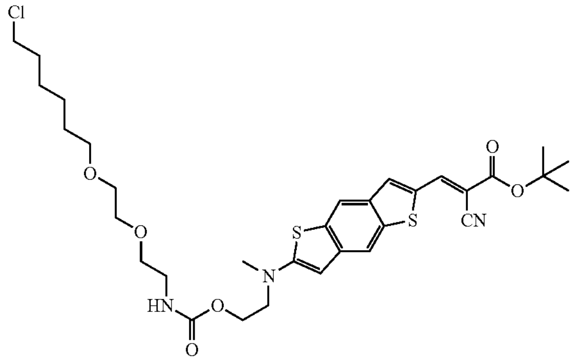

Probe36

Refer to the method of probe 29 for synthesis. 1H-NMR (400 MHz, DMSO-d6): δ=8.18 (t, 1H), 7.89 (s, 2H), 7.59 (s, 1H), 7.27 (s, 1H), 7.05 (s, 1H), 3.86 (t, 2H, J=4.80 Hz), 3.69 (t, J=4.9 Hz, 2H), 3.63-3.60 (m, 2H), 3.56 (t, 2H, J=4.80 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.06 (s, 3H), 1.79-1.71 (m, 2H), 1.60-1.53 (m, 2H), 1.46-1.39 (m, 2H), 1.36-1.28 (m, 2H)

Example 37

Molecular rotors were used as viscosity responsive fluorescent dyes to construct a fluorescent-activated covalently labeled fluorescent probe 37 for HaloTag:

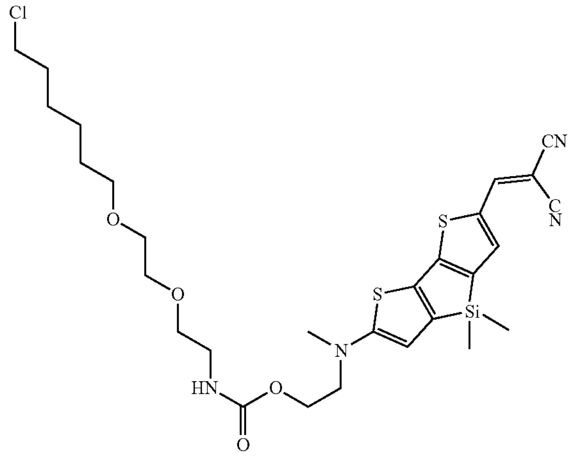

Probe37

With reference to the literature (Sangwon Ko et. al. J. Mater. Chem. 2010, 20, 2391-2399) and the method of probe 10 for synthesis. 1H-NMR (400 MHz, DMSO-d6): δ=8.18 (t, 1H), 7.83 (s, 1H), 7.11 (s, 1H), 3.85 (t, 2H, J=4.80 Hz), 3.69 (t, J=4.9 Hz, 2H), 3.63-3.60 (m, 2H), 3.56-3.53 (m, 2H), 3.52 (t, J=6.6 Hz, 2H), 3.46 (t, 2H, J=4.80 Hz), 3.44 (t, J=6.8 Hz, 2H), 3.12 (t, J=4.9 Hz, 2H), 3.06 (s, 3H), 1.79-1.71 (m, 2H), 1.60-1.53 (m, 2H), 1.46-1.39 (m, 2H), 1.36-1.28 (m, 2H), 0.46 (s, 6H)

Example 38

Molecular rotors were used as viscosity responsive fluorescent dyes to construct a fluorescent-activated covalently labeled fluorescent probe 38 for HaloTag:

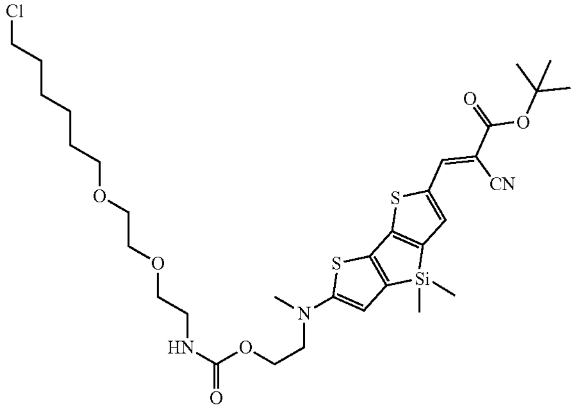

Probe38

Refer to the method of probe 37 for synthesis. $^{1}$H-NMR (400 MHz, DMSO-$d_6$): δ=8.18 (t, 1H), 7.83 (s, 1H), 7.11 (s, 1H), 3.85 (t, 2H, J=4.80 Hz), 3.69 (t, J=4.9 Hz, 2H), 3.63-3.60 (m, 2H), 3.56-3.53 (m, 2H), 3.52 (t, J=6.6 Hz, 2H), 3.46 (t, 2H, J=4.80 Hz), 3.44 (t, J=6.8 Hz, 2H), 3.12 (t, J=4.9 Hz, 2H), 3.06 (s, 3H), 1.79-1.71 (m, 2H), 1.60-1.53 (m, 2H), 1.50 (s, 9H), 1.46-1.39 (m, 2H), 1.36-1.28 (m, 2H), 6=0.42 (s, 6H)

Example 39

Molecular rotors were used as viscosity responsive fluorescent dyes to construct a fluorescent-activated covalently labeled fluorescent probe 39 for HaloTag:

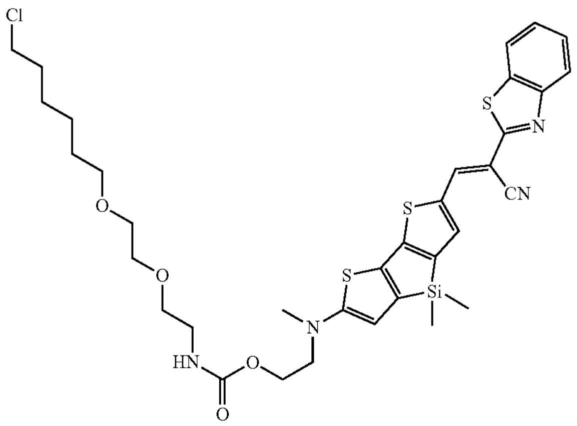

Probe39

Refer to the method of probe 37 for synthesis. $^{1}$H-NMR (400 MHz, DMSO-$d_6$): δ=8.18 (t, 1H), 7.99 (s, 1H), 7.11 (s, 1H), 6.50 (s, 1H), 3.85 (t, 2H, J=4.80 Hz), 3.69 (t, J=4.9 Hz, 2H), 3.63-3.60 (m, 2H), 3.56-3.53 (m, 2H), 3.52 (t, J=6.6 Hz, 2H), 3.46 (t, 2H, J=4.80 Hz), 3.44 (t, J=6.8 Hz, 2H), 3.12 (t, J=4.9 Hz, 2H), 3.06 (s, 3H), 1.79-1.71 (m, 2H), 1.60-1.53 (m, 2H), 1.46-1.39 (m, 2H), 1.36-1.28 (m, 2H), 0.46 (s, 6H)

Example 40

Molecular rotors were used as viscosity responsive fluorescent dyes to construct a fluorescent-activated covalently labeled fluorescent probe 40 for HaloTag:

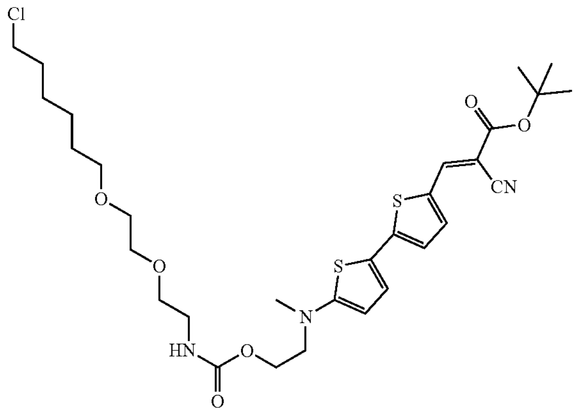

Probe40

With reference to the literature (Kassem Amro et. al. 2014. 70. 1903-1909) and the method of probe 10 for synthesis. $^1$H-NMR (400 MHz, DMSO-$d_6$): δ=8.18 (t, 1H), 8.00 (s, 1H), 7.57 (d, 1H, J=4.00 Hz), 7.13 (d, 1H, J=4.00 Hz), 6.95 (d, 1H, J=4.00 Hz), 5.81 (d, 1H, J=4.00 Hz), 3.69 (t, J=4.9 Hz, 2H), 3.67 (t, 2H, J=5.60 Hz), 3.63-3.60 (m, 2H), 3.56-3.53 (m, 2H), 3.52 (t, J=6.6 Hz, 2H), 3.44 (t, J=6.8 Hz, 2H), 3.35 (t, 2H, J=5.60 Hz), 3.12 (t, J=4.9 Hz, 2H), 3.13 (s, 3H), 1.79-1.71 (m, 2H), 1.60-1.53 (m, 2H), 1.50 (s, 9H), 1.46-1.39 (m, 2H), 1.36-1.28 (m, 2H)

Example 41

Molecular rotors were used as viscosity responsive fluorescent dyes to construct a fluorescent-activated covalently labeled fluorescent probe 41 for HaloTag:

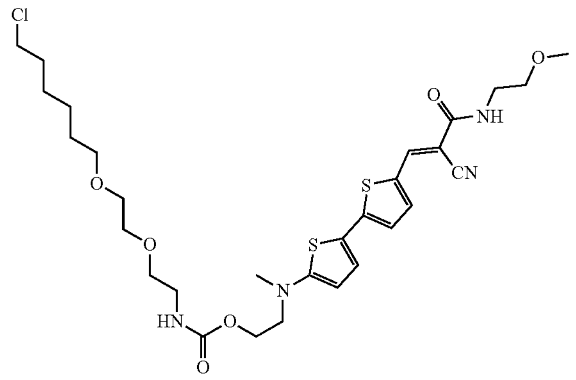

Probe41

Refer to the method of probe 40 for synthesis. H-NMR (400 MHz, DMSO-$d_6$): δ=12.42 (s, 1H), 10.01 (s, 1H), 8.18 (t, 1H), 8.00 (s, 1H), 7.81 (s, 1H), 7.57 (d, 1H, J=4.00 Hz), 7.40 (m, 4H), 7.13 (d, 1H, J=4.00 Hz), 6.95 (d, 1H, J=4.00 Hz), 6.29 (s, 2H), 5.81 (d, 1H, J=4.00 Hz), 5.46 (s, 2H), 4.40 (d, 2H, J=4.8 Hz), 3.69 (t, J=4.9 Hz, 2H), 3.67 (t, 2H, J=5.60 Hz), 3.63-3.60 (m, 2H), 3.56-3.53 (m, 2H), 3.48-3.52 (m, 6H), 3.44 (t, J=6.8 Hz, 2H), 3.38 (s, 3H), 3.35 (t, 2H, J=5.60 Hz), 3.13 (s, 3H), 3.12 (t J=4.9 Hz, 2H), 1.79-1.71 (m, 2H), 1.60-1.53 (m, 2H), 1.46-1.39 (m, 2H), 1.36-1.28 (in, 2H)

Example 42

Molecular rotors were used as viscosity responsive fluorescent dyes to construct a fluorescent-activated covalently labeled fluorescent probe 42 for HaloTag:

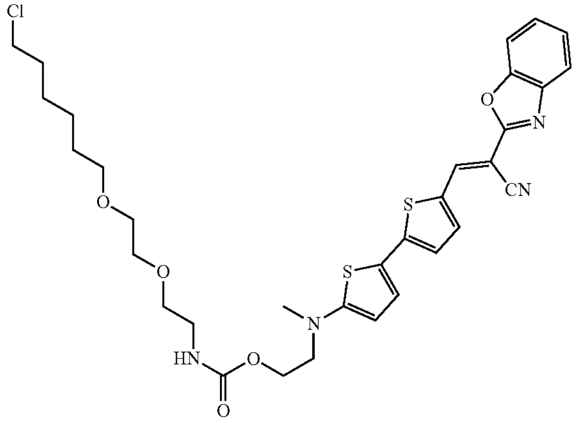

Probe42

Refer to the method of probe 40 for synthesis. $^1$H-NMR (400 MHz, DMSO-$d_6$): δ=8.18 (t, 1H), 8.00 (s, 1H), 7.74 (d, 1H, J=4.0 Hz), 7.57 (d, 1H, J=4.00 Hz), 7.51 (d, 1H, J=4.0 Hz), 7.36-7.42 (m, 2H), 7.13 (d, 1H, J=4.00 Hz), 6.95 (d, 1H, J=4.00 Hz), 5.81 (d, 1H, J=4.00 Hz), 3.69 (t, J=4.9 Hz, 2H), 3.67 (t, 2H, J=5.60 Hz), 3.63-3.60 (m, 2H), 3.56-3.53 (m, 2H), 3.52 (t, J=6.6 Hz, 2H), 3.44 (t, J=6.8 Hz, 2H), 3.35 (t, 2H, J=5.60 Hz), 3.13 (s, 3H), 3.12 (t, J=4.9 Hz, 2H), 1.79-1.71 (m, 2H), 1.60-1.53 (m, 2H), 1.46-1.39 (m, 2H), 1.36-1.28 (m, 2H)

Example 43

Molecular rotors were used as viscosity responsive fluorescent dyes to construct a fluorescent-activated covalently labeled fluorescent probe 43 for HaloTag:

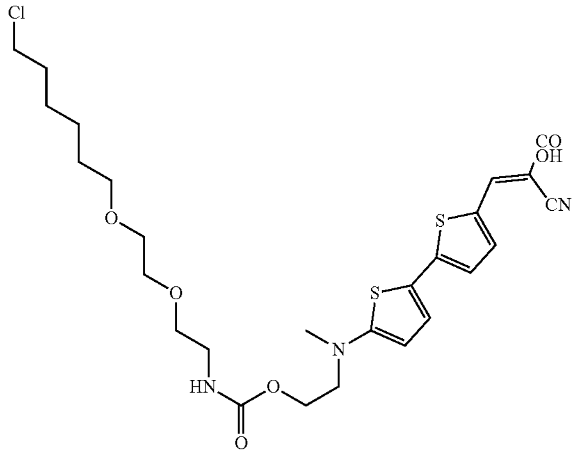

Probe43

Refer to the method of probe 40 for synthesis. $^1$H-NMR (400 MHz, DMSO-$d_6$): δ=8.18 (t, 1H), 7.99 (s, 1H), 7.57 (d, 1H, J=4.0 Hz), 7.13 (d, 1H, J=4.0 Hz), 6.95 (d, 1H, J=4.0 Hz), 5.81 (d, 1H, J=4.0 Hz), 3.85 (t, 2H, J=5.6 Hz), 3.69 (t, J=4.9 Hz, 2H), 3.60 (t, 2H, J=5.6 Hz), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.46-1.39 (m, 2H), 1.36-1.28 (m, 2H)

Example 44

Molecular rotors were used as viscosity responsive fluorescent dyes to construct a fluorescent-activated covalently labeled fluorescent probe 44 for HaloTag:

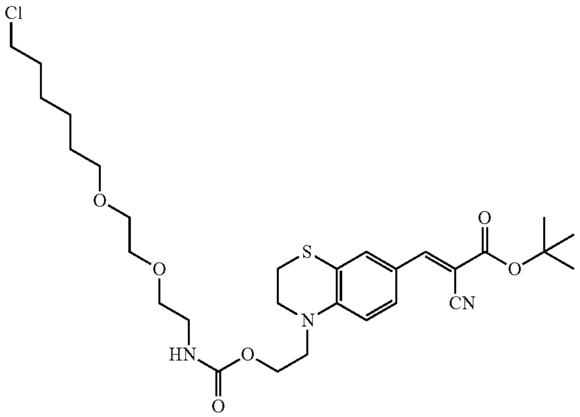

Probe44

With reference to the literature (Jing Jing et al. Chem. Sci. 2012. 3. 3315-3320) and the method of probe 10 for synthesis. $^1$H-NMR (400 MHz, DMSO-$d_6$): δ=8.18 (t, 1H), 7.99 (s, 1H), 7.21 (s, 1H), 6.71 (d, 1H, J=8.0 Hz), 6.50 (m, 1H) 4.71 (t, 1H, J=5.6 Hz), 3.69 (t, J=4.9 Hz, 2H), 3.62 (m, 2H), 3.63-3.60 (m, 2H), 3.56 (m, 2H), 3.56-3.53 (m, 2H), 3.52 (t, J=6.6 Hz, 2H), 3.44 (t, J=6.8 Hz, 2H), 3.35 (m, 2H), 3.12 (t, J=4.9 Hz, 2H), 3.00 (m, 2H), 1.79-1.71 (m, 2H), 1.60-1.53 (m, 2H), 1.49 (s, 9H), 1.46-1.39 (m, 2H), 1.36-1.28 (m, 2H)

Example 45

Molecular rotors were used as viscosity responsive fluorescent dyes to construct a fluorescent-activated covalently labeled fluorescent probe 45 for HaloTag:

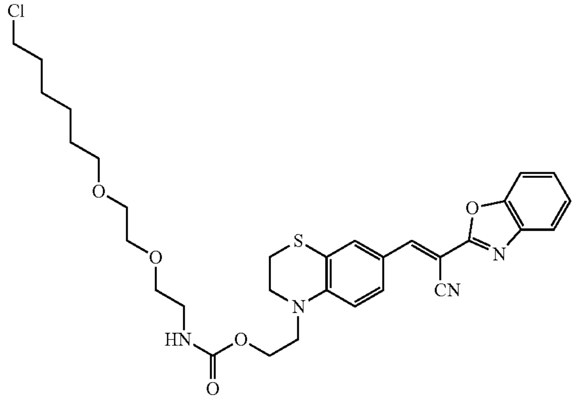

Probe45

Refer to the method of probe 44 for synthesis. H-NMR (400 MHz, DMSO-$d_6$): δ=8.18 (t, 1H), 7.99 (s, 1H), 7.74 (d, 1H, J=4.0 Hz), 7.55 (d, 1H, J=4.0 Hz), 7.36-7.42 (m, 2H), 7.21 (s, 1H), 6.71 (d, 1H, J=8.0 Hz), 6.50 (m, 1H) 4.71 (t, 1H, J=5.6 Hz), 3.69 (t, J=4.9 Hz, 2H), 3.63-3.60 (m, 2H), 3.62 (m, 2H), 3.56-3.53 (m, 2H), 3.56 (m, 2H), 3.52 (t, J=6.6 Hz, 2H), 3.44 (t, J=6.8 Hz, 2H), 3.35 (m, 2H), 3.12 (t, J=4.9 Hz, 2H), 3.00 (m, 2H), 1.79-1.71 (m, 2H), 1.60-1.53 (m, 2H), 1.46-1.39 (m, 2H), 1.36-1.28 (m, 2H)

Example 46

Molecular rotors were used as viscosity responsive fluorescent dyes to construct a fluorescent-activated covalently labeled fluorescent probe 46 for HaloTag:

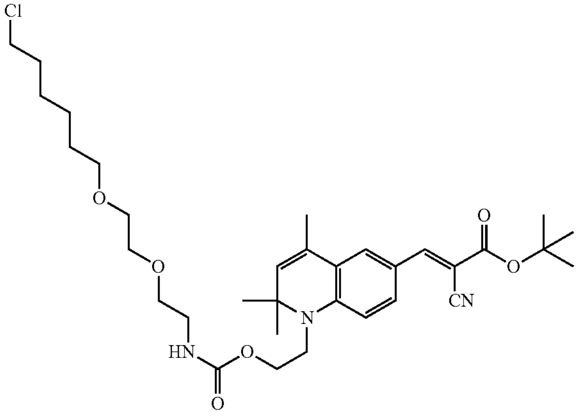

Probe46

With reference to the literature (Kaijun Tian et. al. Chem. Commun. 2011. 47. 10052-10054) and the method of probe 10 for synthesis. $^1$H-NMR (400 MHz, DMSO-$d_6$): δ=8.18 (t, 1H), 8.03 (s, 1H), 7.36 (d, 1H, J=7.6 Hz), 6.78 (t, 1H, J=7.2 Hz), 6.49 (d, 1H, 7.8 Hz), 3.69 (t, J=4.9 Hz, 2H), 3.63-3.60 (m, 2H), 3.56-3.53 (m, 2H), 3.52 (t, J=6.6 Hz, 2H), 3.46 (m, 4H), 3.44 (t, J=6.8 Hz, 2H), 2.35 (s, 3H), 3.12 (t, J=4.9 Hz, 2H), 1.79-1.71 (m, 2H), 1.60-1.53 (m, 2H), 1.50 (s, 9H), 1.46-1.39 (m, 2H), 1.36 (s, 6H), 1.36-1.28 (m, 2H)

Example 47

Molecular rotors were used as viscosity responsive fluorescent dyes to construct a fluorescent-activated covalently labeled fluorescent probe 47 for HaloTag:

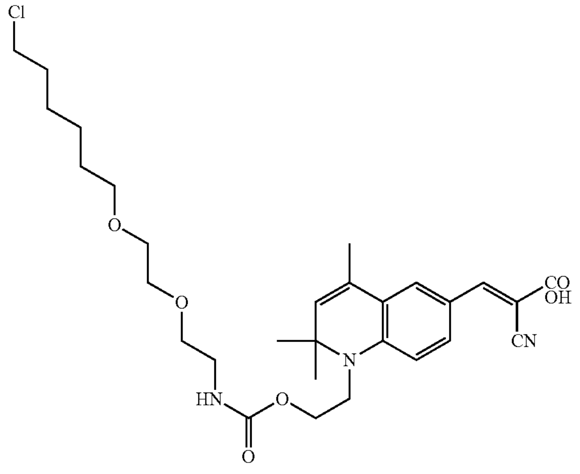

Probe47

Refer to the method of probe 46 for synthesis. $^1$H-NMR (400 MHz, DMSO-$d_6$): δ=8.18 (t, 1H), 8.03 (s, 1H), 7.36 (d, 1H, J=7.6 Hz), 6.78 (t, 1H, J=7.2 Hz), 6.49 (d, 1H, 7.8 Hz), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.11 (m, 4H), 2.35 (s, 3H), 1.79-1.71 (m, 2H), 1.60-1.53 (m, 2H), 1.46-1.39 (m, 2H), 1.36 (s, 6H), 1.36-1.28 (m, 2H)

Example 48

Molecular rotors were used as viscosity responsive fluorescent dyes to construct a fluorescent-activated covalently labeled fluorescent probe 48 for HaloTag:

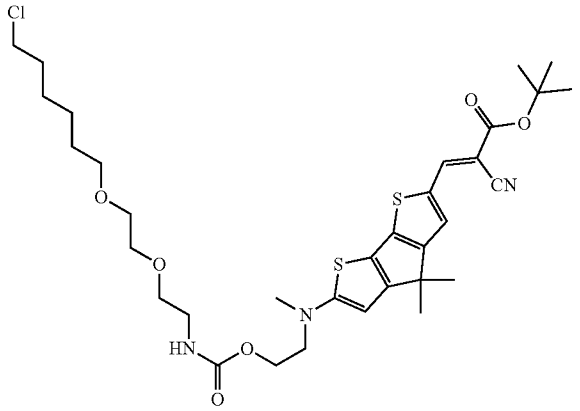

Probe48

With reference to the literature (Chun-GueyWu et. al. 2013. 99. 1091-1100) and the method of probe 10 for synthesis. $^1$H-NMR (400 MHz, DMSO-$d_6$): δ=8.18 (t, 1H), 7.89 (s, 1H), 7.18 (s, 1H), 6.96 (d, 1H), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.50 (m, 15H), 1.46-1.39 (m, 2H), 1.36-1.28 (m, 2H)

Example 49

Molecular rotors were used as viscosity responsive fluorescent dyes to construct a fluorescent-activated covalently labeled fluorescent probe 49 for HaloTag:

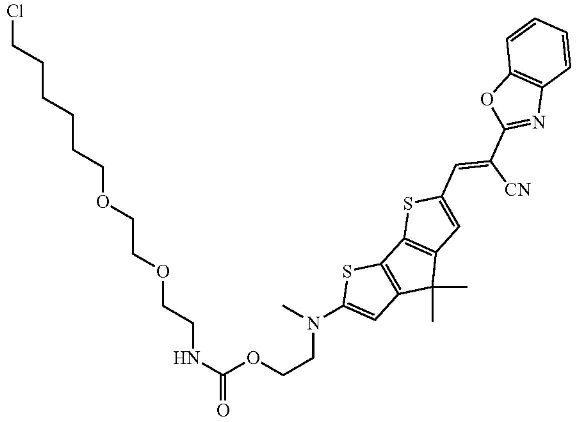

Probe49

Refer to the method of probe 48 for synthesis. $^1$H-NMR (400 MHz, DMSO-$d_6$): δ=8.18 (t, 1H), 7.89 (s, 1H), 7.74 (d, 1H, 3=4.0 Hz), 7.55 (d, 1H, J=4.0 Hz), 7.36-7.42 (m, 2H), 7.18 (s, 1H), 6.96 (d, 1H), 4.12 (s, 2H), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.50 (s, 6H), 1.46-1.39 (m, 2H), 1.36-1.28 (m, 2H)

Example 50

Molecular rotors were used as viscosity responsive fluorescent dyes to construct a fluorescent-activated covalently labeled fluorescent probe 50 for HaloTag:

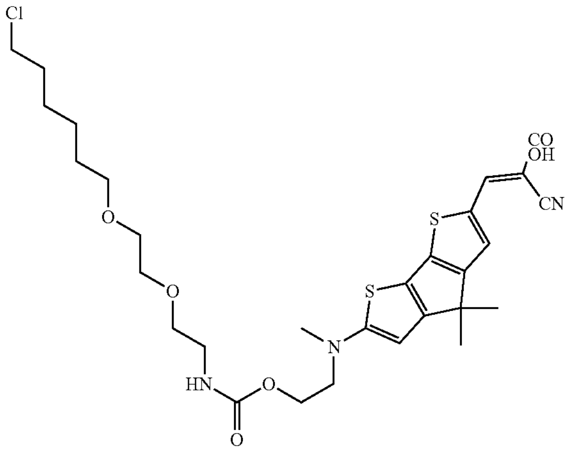
Probe50
Refer to the method of probe 48 for synthesis. H-NMR (400 MHz, DMSO-$d_6$): δ=8.18 (t, 1H), 7.89 (s, 1H), 7.18 (s, 1H), 6.96 (d, 1H), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.46-1.39 (m, 2H), 1.36-1.28 (m, 2H)
Example 51
Molecular rotors were used as viscosity responsive fluorescent dyes to construct a fluorescent-activated covalently labeled fluorescent probe 51 for HaloTag:
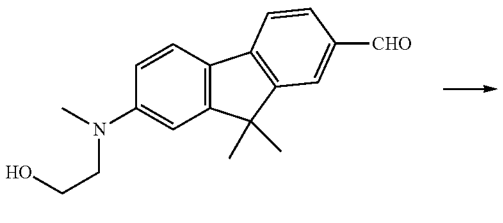
Compound 44
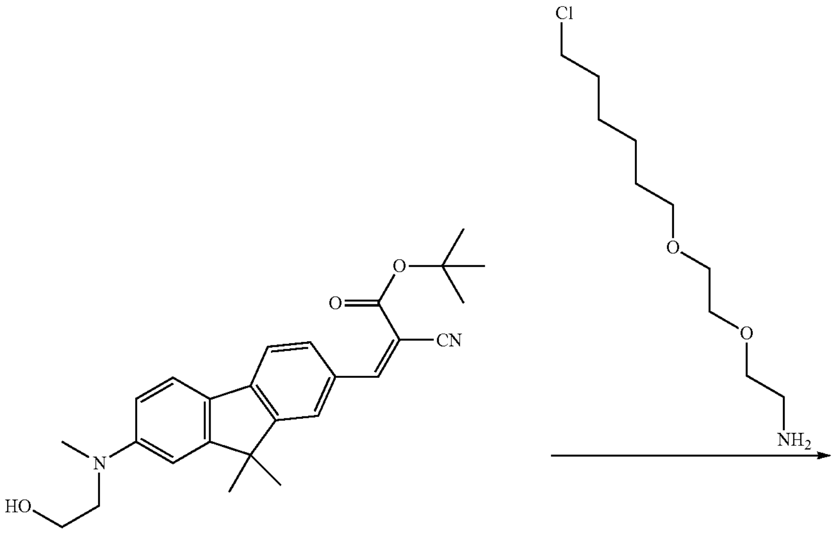
Compound 45

-continued

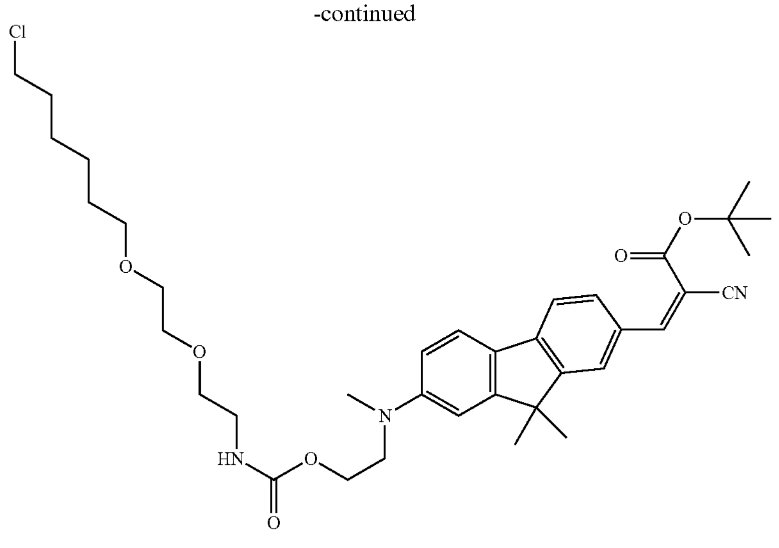

Probe 51

Compound 44:

Refer to the method of literature (Gen-ichi Konishi. et. al. Tetrahedron. 2014, 70. 7551-7559) for synthesis. $^{1}$H-NMR (400 MHz, $CDCl_3$): δ=9.92 (s, 1H), 7.82 (s, 1H), 7.71 (m, 1H), 7.60 (m, 2H), 6.78 (s, 2H), 3.82 (t, 2H, J=5.6 Hz), 3.54 (t, 2H, J=5.6 Hz), 3.10 (s, 3H), 1.42 (s, 6H)

Compound 45:

Refer to the method of compound 1 for synthesis, the yield of 96%. $^{1}$H-NMR (400 MHz, $CDCl_3$): δ=8.07 (s, 1H), 7.82 (s, 1H), 7.71 (m, 1H), 7.60 (m, 2H), 6.78 (s, 2H), 3.82 (t, 2H, J=5.6 Hz), 3.54 (t, 2H, J=5.6 Hz), 3.10 (s, 3H), 1.50 (s, 9H), 1.42 (s, 6H)

Probe 51

According to the synthesis method of probe 1, the yield was 85%. $^{1}$H-NMR (400 MHz, DMSO-$d_6$): δ=8.18 (t, 1H), 8.07 (s, 1H), 7.82 (s, 1H), 7.71 (m, 1H), 7.60 (m, 2H), 6.78 (s, 2H), 3.82 (t, 2H, J=5.6 Hz), 3.69 (t, J=4.9 Hz, 2H), 3.63-3.60 (m, 2H), 3.56-3.53 (m, 2H), 3.54 (t, 2H, J=5.6 Hz), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.50 (s, 9H), 1.46-1.39 (m, 2H), 1.42 (s, 6H), 1.36-1.28 (m, 2H)

Example 52

Molecular rotors were used as viscosity responsive fluorescent dyes to construct a fluorescent-activated covalently labeled fluorescent probe 52 for HaloTag:

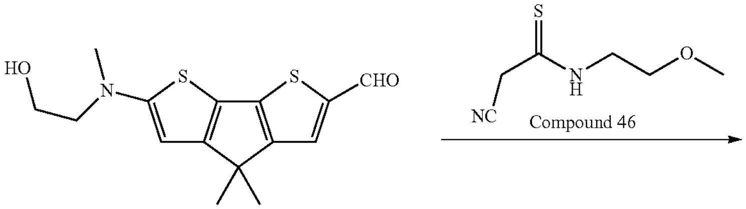

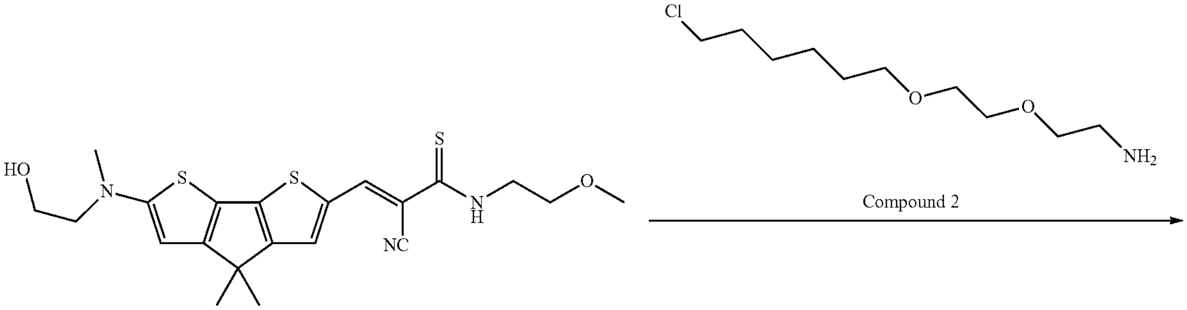

compound 47

-continued

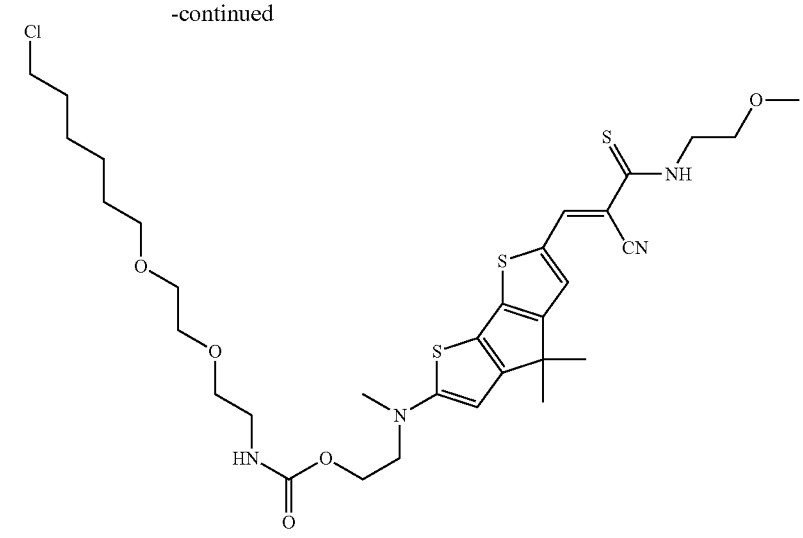

Probe 52

Compound 46:

Refer to the method of literature (Gamba-Sánchez. et. al. Tetrahedron Lett. 2015, 56, 4308-4311) for synthesis. $^1$H-NMR (400 MHz, $CDCl_3$): δ=6.52 (s, 2H), 3.48-3.52 (m, 4H), 3.38 (s, 3H)

Compound 47:

Refer to the method of compound 1 for synthesis, the yield of 96%. $^1$H-NMR (400 MHz, $CDCl_3$): δ=7.89 (s, 1H), 7.18 (s, 1H), 6.96 (d, 1H), 3.85 (t, 2H, J=5.6 Hz), 3.60 (t, 2H, J=5.6 Hz), 3.52-3.48 (m, 4H), 3.38 (s, 3H), 3.10 (s, 3H), 1.50 (s, 6H)

Probe 52:

According to the synthesis method of probe 1, the yield was 85%. $^1$H-NMR (400 MHz, DMSO-$d_6$): δ=8.18 (t, 1H), 7.89 (s, 1H), 7.18 (s, 1H), 6.96 (d, 1H), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.52-3.48 (m, 4H), 3.44 (t, J=6.8 Hz, 2H), 3.38 (s, 3H), 3.12 (t, J=4.9 Hz, 2H), 3.10 (s, 3H), 1.79-1.71 (m, 2H), 1.60-1.53 (m, 2H), 1.50 (s, 6H), 1.46-1.39 (m, 2H), 1.36-1.28 (m, 2H)

Example 53

Molecular rotors were used as viscosity responsive fluorescent dyes to construct a fluorescent-activated covalently labeled fluorescent probe 53 for HaloTag:

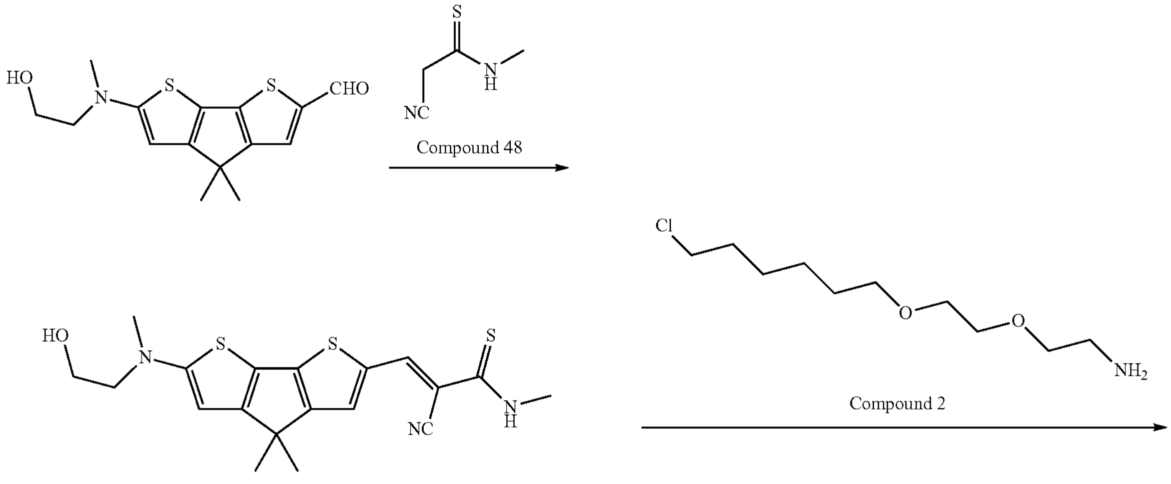

Compound 48

Compound 2

Compound 49

-continued

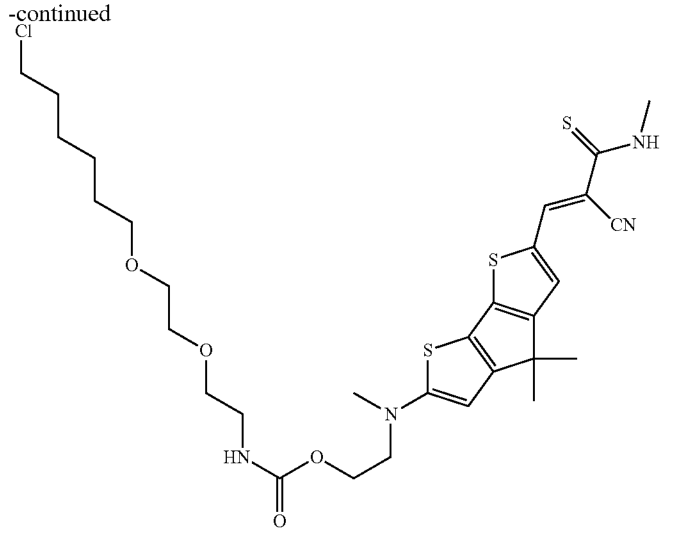

Probe 53

Compound 48:

Refer to the method of literature (Gamba-Sánchez. et. al. Tetrahedron Lett. 2015. 56, 4308-4311) for synthesis. $^1$H-NMR (400 MHz, $CDCl_3$): δ=6.56 (s, 2H), 3.42 (s, 3H)

Compound 49:

Refer to the method of compound 1 for synthesis, the yield of 96%. $^1$H-NMR (400 MHz, $CDCl_3$): δ=7.92 (s, 1H), 7.18 (s, 1H), 6.96 (d, 1H), 3.85 (t, 2H, J=5.6 Hz), 3.60 (t, 2H J=5.6 Hz), 3.42 (s, 3H), 3.10 (s, 3H), 1.50 (s, 6H)

Probe 53:

According to the synthesis method of probe 1, the yield was 85%. $^1$H-NMR (400 MHz, DMSO-$d_6$): δ=8.18 (t, 1H), 7.92 (s, 1H), 7.18 (s, 1H), 6.96 (d, 1H), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.44 (t, J=6.8 Hz, 2H), 3.42 (s, 3H), 3.12 (t, J=4.9 Hz, 2H), 3.10 (s, 3H), 1.79-1.71 (m, 2H), 1.60-1.53 (m, 2H), 1.50 (s, 6H), 1.46-1.39 (m, 2H), 1.36-1.28 (m, 2H)

Example 54

Molecular rotors were used as viscosity responsive fluorescent dyes to construct a fluorescent-activated covalently labeled fluorescent probe 54 for HaloTag:

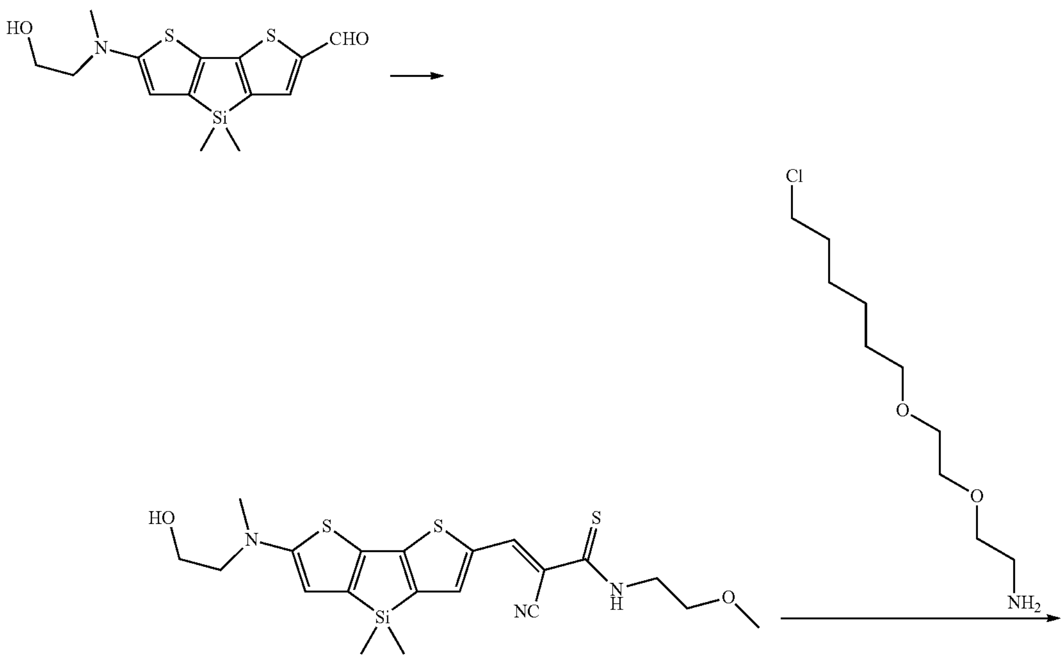

Compound 50

-continued

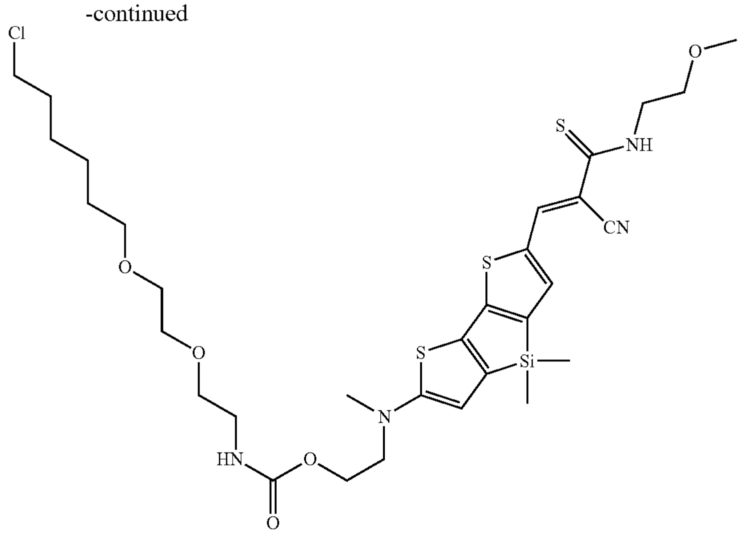

Probe 54

Compound 50:

Refer to the method of compound 47 for synthesis, the yield of 86%. $^1$H-NMR (400 MHz, $CDCl_3$): δ=7.83 (s, 1H), 7.11 (s, 1H), 3.52-3.48 (m, 4H), 3.85 (t, 2H, J=4.80 Hz), 3.46 (t, 2H, J=4.80 Hz), 3.38 (s, 3H), 3.06 (s, 3H), 0.46 (s, 6H)

Probe 54:

According to the synthesis method of probe 1, the yield was 85%. $^1$H-NMR (400 MHz, DMSO-$d_6$): δ=8.18 (t, 1H), 7.83 (s, 1H), 7.11 (s, 1H), 3.52-3.48 (m, 4H), 3.85 (t, 2H, J=4.80 Hz), 3.69 (t, J=4.9 Hz, 2H), 3.63-3.60 (m, 2H), 3.56-3.53 (m, 2H), 3.52 (t, J=6.6 Hz, 2H), 3.46 (t, 2H, J=4.80 Hz), 3.44 (t, J=6.8 Hz, 2H), 3.38 (s, 3H), 3.12 (t, J=4.9 Hz, 2H), 3.06 (s, 3H), 1.79-1.71 (m, 2H), 1.60-1.53 (m, 2H), 1.46-1.39 (m, 2H), 1.36-1.28 (m, 2H) 0.46 (s, 6H)

Example 55

Molecular rotors were used as viscosity responsive fluorescent dyes to construct a fluorescent-activated covalently labeled fluorescent probe 55 for HaloTag:

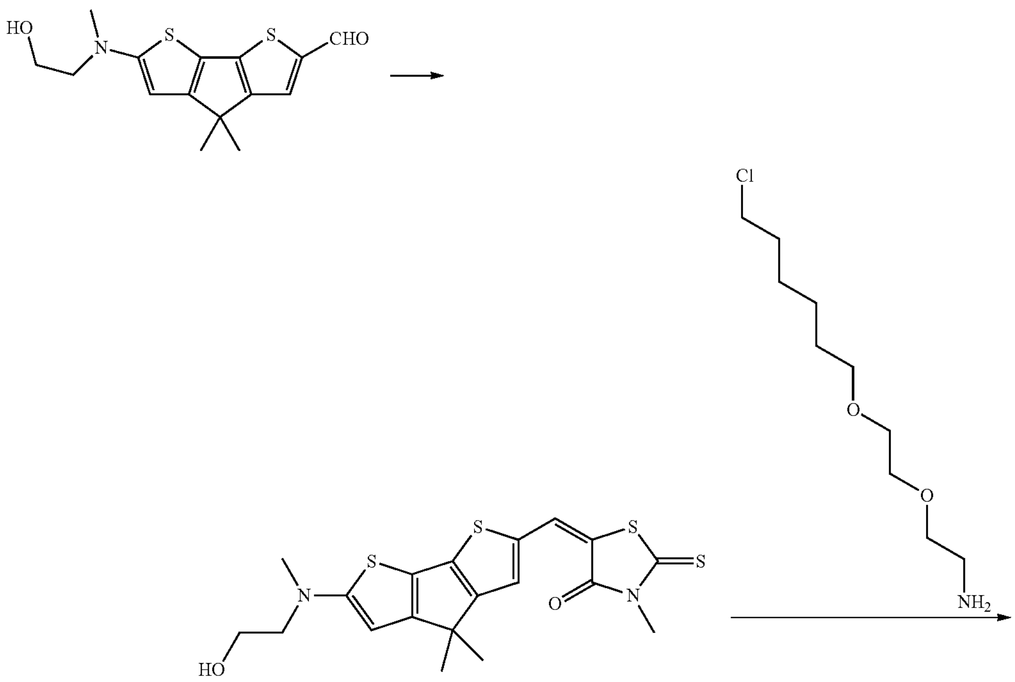

Compound 51

-continued

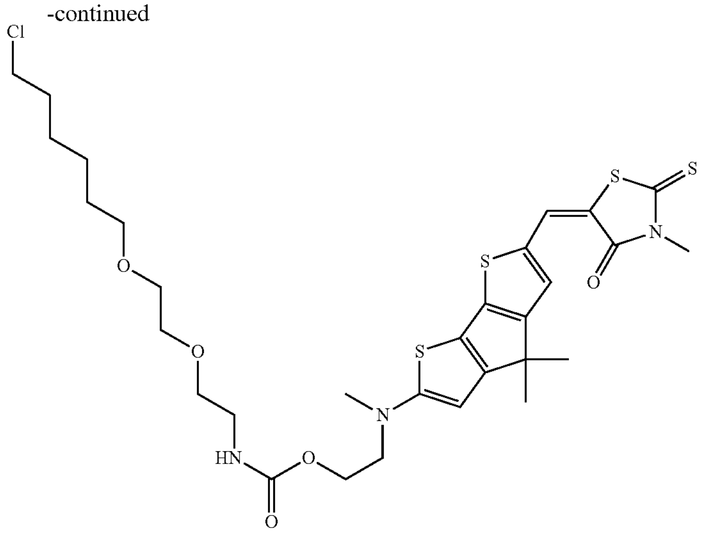

Probe 55

Compound 51:

Refer to the method of compound 1 for synthesis, the yield of 77%. $^1$H-NMR (400 MHz, $CDCl_3$): δ=7.89 (s, 1H), 7.18 (s, 1H), 6.96 (d, 1H), 3.85 (t, 2H, J=5.6 Hz), 3.60 (t, 2H, J=5.6 Hz), 3.48 (s, 3H), 3.10 (s, 3H), 1.50 (s, 6H)

Probe 55:

According to the synthesis method of probe 1, the yield was 82%. $^1$H-NMR (400 MHz, DMSO-$d_6$): δ=8.18 (t, 1H), 7.89 (s, 1H), 7.18 (s, 1H), 6.96 (d, 1H), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.52 (t, J=6.6 Hz, 2H), 3.48 (s, 3H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.50 (s, 6H), 1.46-1.39 (m, 2H), 1.36-1.28 (m, 2H)

Example 56

Molecular rotors were used as viscosity responsive fluorescent dyes to construct a fluorescent-activated covalently labeled fluorescent probe 56 for HaloTag:

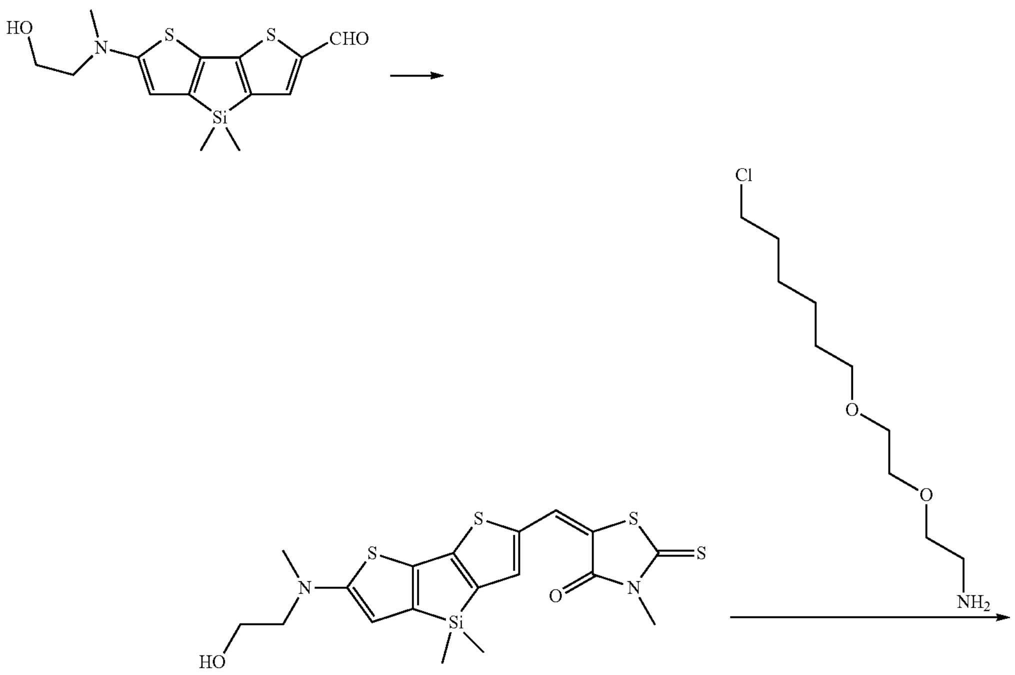

Compound 52

-continued

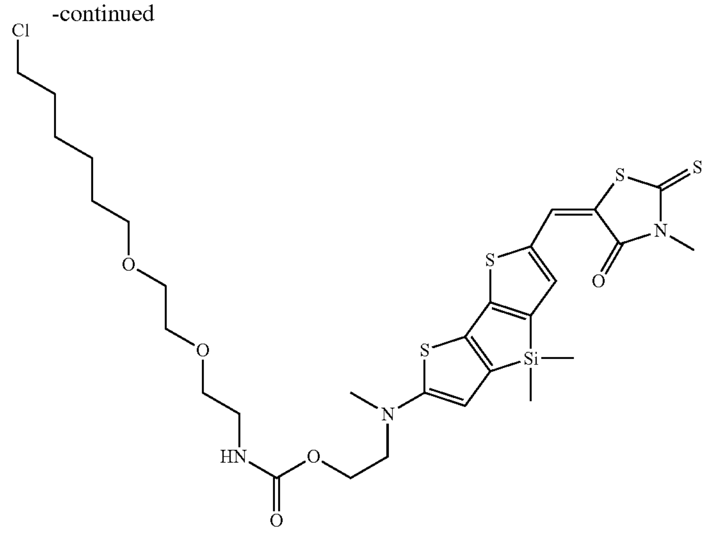

Probe 56

Compound 52:

Refer to the method of compound 1 for synthesis, the yield of 77%. $^1$H-NMR (400 MHz, $CDCl_3$): δ=7.93 (s, 1H), 7.11 (s, 1H), 6.42 (s, 1H), 3.85 (t, 2H, J=4.80 Hz), 3.46 (t, 2H, J=4.80 Hz), 3.32 (s, 3H), 3.06 (s, 3H), 0.42 (s, 6H)

Probe 56:

According to the synthesis method of probe 1, the yield was 82%. $^1$H-NMR (400 MHz, DMSO-$d_6$): δ=8.18 (t, 1H), 7.93 (s, 1H), 7.11 (s, 1H), 6.42 (s, 1H), 3.85 (t, 2H, J=4.80 Hz), 3.69 (t, J=4.9 Hz, 2H), 3.63-3.60 (m, 2H), 3.56-3.53 (m, 2H), 3.52 (t, J=6.6 Hz, 2H), 3.46 (t, 2H, J=4.80 Hz), 3.44 (t, J=6.8 Hz, 2H), 3.32 (s, 3H), 3.12 (t, J=4.9 Hz, 2H), 3.06 (s, 3H), 1.79-1.71 (m, 2H), 1.60-1.53 (m, 2H), 1.46-1.39 (m, 2H), 1.36-1.28 (m, 2H), 0.42 (s, 6H)

Example 57

Molecular rotors were used as viscosity responsive fluorescent dyes to construct a fluorescent-activated covalently labeled fluorescent probe 57 for HaloTag:

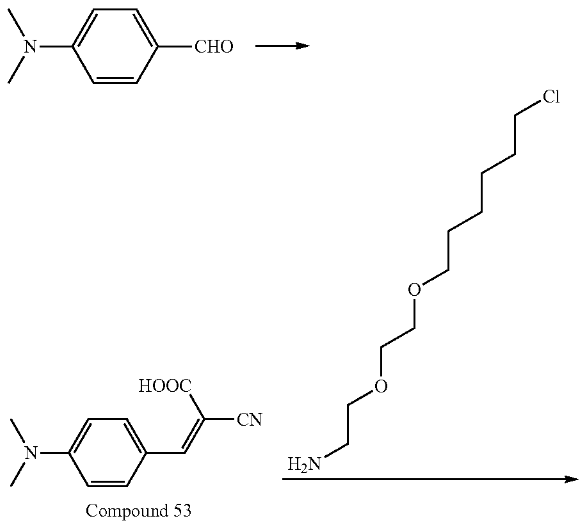

Compound 53

-continued

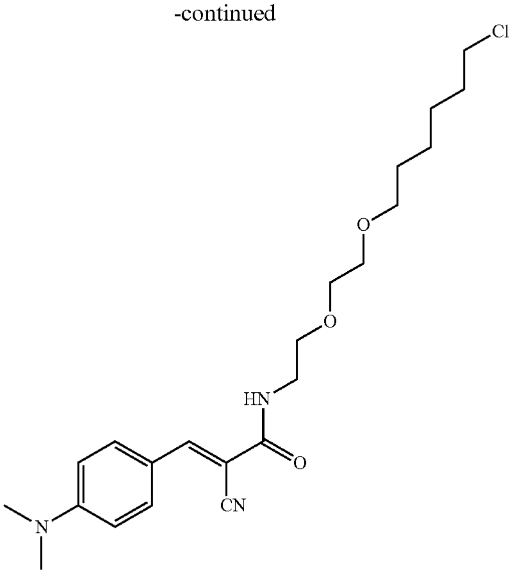

Probe 57

Compound 53:

Refer to the method of compound 1 for synthesis, the yield of 65%. $^1$H-NMR (400 MHz, $CDCl_3$): δ=8.11 (s, 1H), 7.97 (d, J=9.0 Hz, 2H), 6.69 (d, J=9.5 Hz, 2H), 3.38 (s, 6H)

Probe 57:

Compound (0.216 g, 1 tendency for 53) and compound 2 (0.223 g, 1 tendency) dissolved in 150 mL water DMF, join six fluoride phosphate benzotriazole 3-1-base-oxygen radicals pyrrole alkyl phosphate (0.512 g, 1 tendency) and 0.1 mL triethylamine, Ar protection under the condition of reaction and a half hours, spin dry solvents, residue column chromatography separation yellow solid 0.156 g, yield was 72%. $^1$H-NMR (400 MHz, DMSO-$d_6$): δ=8.18 (t, 1H), 8.11 (s, 1H), 7.97 (d, J=9.0 Hz, 2H), 6.69 (d, J=9.5 Hz, 2H), 3.69 (t, J=4.9 Hz, 2H), 3.63-3.60 (in 2H), 3.56-3.53 (m, 2H), 3.52 (t, J=6.6 Hz, 2H), 3.44 (t, J=6.8 Hz, 2H), 3.38 (s, 6H), 3.12 (t, J=4.9 Hz, 2H), 1.79-1.71 (m, 2H), 1.60-1.53 (m, 2H), 1.46-1.39 (m, 2H), 1.36-1.28 (n, 2H)

Example 58

Molecular rotors were used as viscosity responsive fluorescent dyes to construct a fluorescent-activated covalently labeled fluorescent probe 58 for HaloTag:

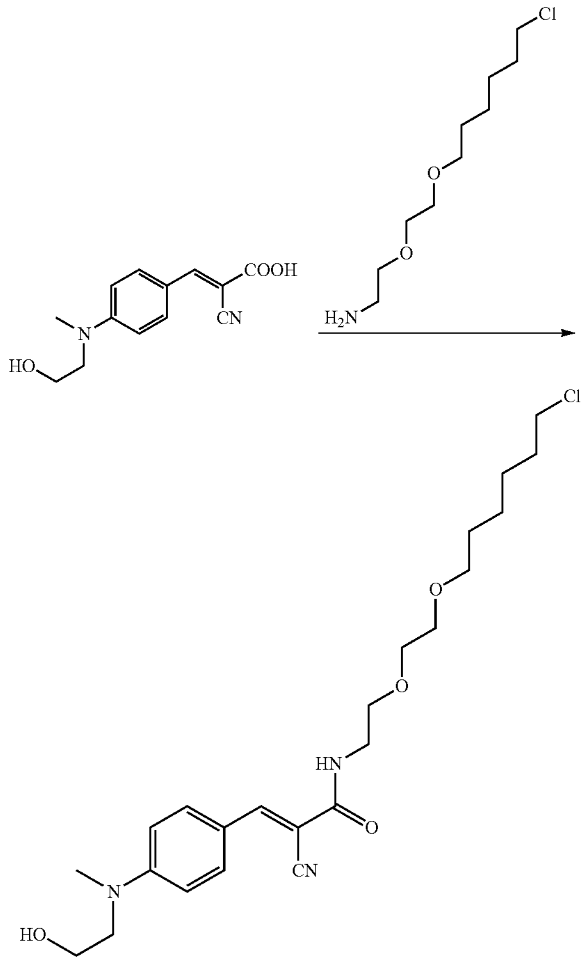

Probe 58

Refer to the method of probe 57 for synthesis. $^1$H-NMR (400 MHz, DMSO-$d_6$): δ=8.18 (t, 1H), 8.07 (s, 1H), 7.93 (d, 2H, J=9.2 Hz), 6.85 (d, 211. J=9.2 Hz), 3.69 (t, J=4.9 Hz, 2H), 3.63-3.60 (m, 2H), 3.56-3.53 (m, 6H), 3.52 (t, J=6.6 Hz, 2H), 3.44 (t, J=6.8 Hz, 2H), 3.12 (t, J=4.9 Hz, 2H), 3.08 (s, 3H), 1.79-1.71 (m, 2H), 1.60-1.53 (m, 2H), 1.46-1.39 (m, 2H), 1.36-1.28 (m, 2H)

Example 59

Molecular rotors were used as viscosity responsive fluorescent dyes to construct a fluorescent-activated covalently labeled fluorescent probe 59 for HaloTag:

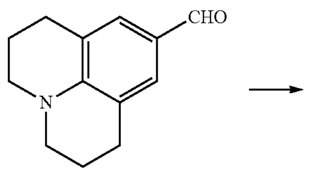

-continued

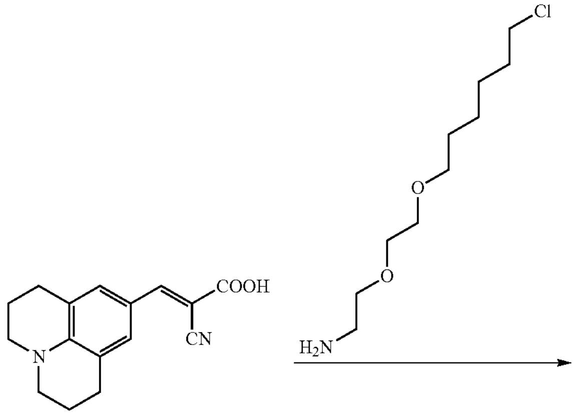

Compound 54

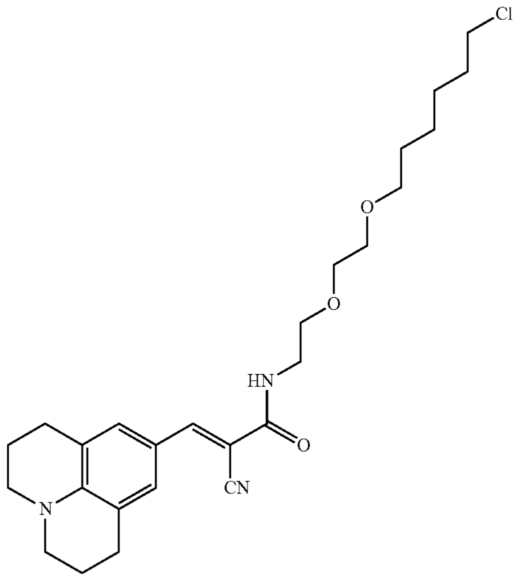

Probe 59

Compound 54:

Refer to the method of compound 1 for synthesis, the yield of 65%. $^1$H-NMR (400 MHz, $CDCl_3$): δ=7.92 (s, 1H), 7.49 (s, 2H), 3.37-3.26 (m, 4H), 2.80-2.67 (m, 4H), 2.07-1.85 (m, 4H)

Probe 59:

Refer to the method of probe 57 for synthesis. $^1$H-NMR (400 MHz, DMSO-$d_6$) δ=8.18 (t, 1H), 7.92 (s, 1H), 7.49 (s, 2H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.37-3.26 (m, 4H), 3.12 (t, J=4.9 Hz, 2H), 2.80-2.67 (m, 4H), 2.07-1.85 (m, 4H), 1.79-1.71 (m, 2H), 1.60-1.53 (m, 2H), 1.46-1.39 (m, 2H), 1.36-1.28 (m, 2H)

Example 60

Molecular rotors were used as viscosity responsive fluorescent dyes to construct a fluorescent-activated covalently labeled fluorescent probe 60 for HaloTag:

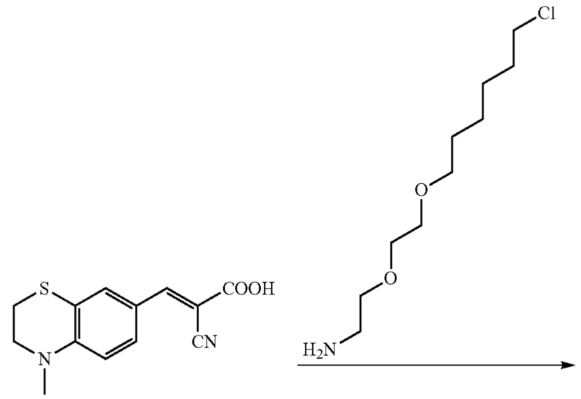

Compound 55

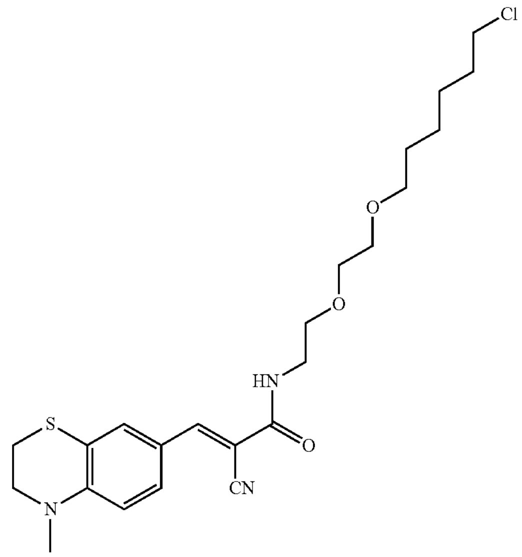

Probe 60

Compound 55:

Refer to the method of probe 44 for synthesis. $^1$H-NMR (400 MHz, $CDCl_3$): δ=7.84 (s, 1H), 7.71 (m, 1H), 7.55 (d, 1H), 6.73 (d, 1H), 3.90-3.86 (m, 4H), 3.61 (s, 3H)

Probe 60:

Refer to the method of probe 57 for synthesis. $^1$H-NMR (400 MHz, DMSO-$d_6$) δ=8.18 (t, 1H), δ=7.84 (s, 1H), 7.71 (m, 1H), 7.55 (d, 1H), 6.73 (d, 1H), 3.90-3.86 (m, 4H), 3.69 (t, J=4.9 Hz, 2H), 3.63-3.60 (m, 2H), 3.61 (s, 3H), 3.56-3.53 (m, 2H), 3.52 (t, J=6.6 Hz, 2H), 3.44 (t, J=6.8 Hz, 2H), 3.12 (t, J=4.9 Hz, 2H), 1.79-1.71 (m, 2H), 1.60-1.53 (m, 2H), 1.46-1.39 (m, 2H), 1.36-1.28 (m, 2H)

Example 61

Molecular rotors were used as viscosity responsive fluorescent dyes to construct a fluorescent-activated covalently labeled fluorescent probe 61 for HaloTag:

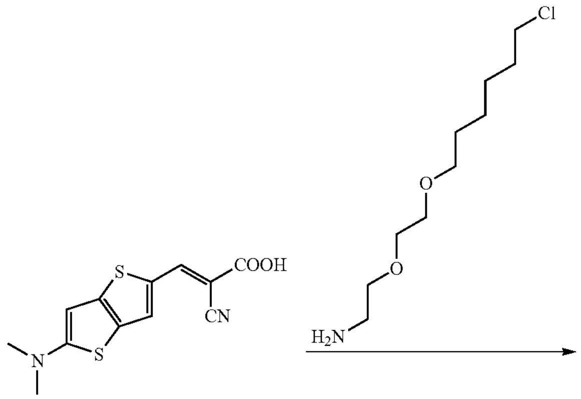

Compound 56

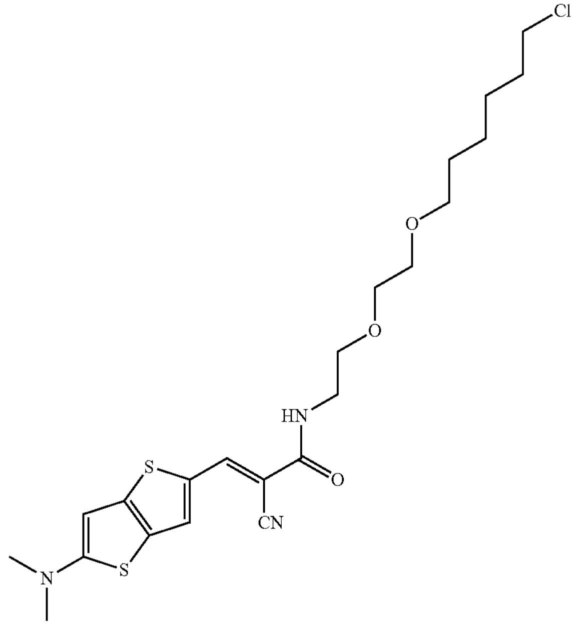

Probe 61

Compound 56:

Refer to the method of probe 10 for synthesis. $^1$H-NMR (400 MHz, $CDCl_3$): δ=8.22 (s, 1H), 8.02 (s, 1H), 6.43 (s, 1H), 3.10 (s, 6H)

Probe 61:

Refer to the method of probe 57 for synthesis. $^1$H-NMR (400 MHz, DMSO-$d_6$) δ=8.22 (s, 1H), 8.18 (t, 1H), 8.02 (s, 1H), 6.43 (s, 1H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 6H), 1.79-1.71 (m, 2H), 1.60-1.53 (m, 2H), 1.46-1.39 (m, 2H), 1.36-1.28 (m, 2H)

Example 62

Molecular rotors were used as viscosity responsive fluorescent dyes to construct a fluorescent-activated covalently labeled fluorescent probe 62 for HaloTag:

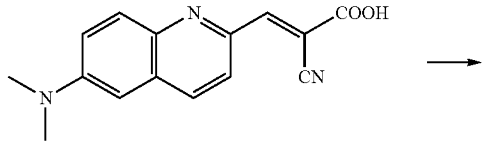

Compound57

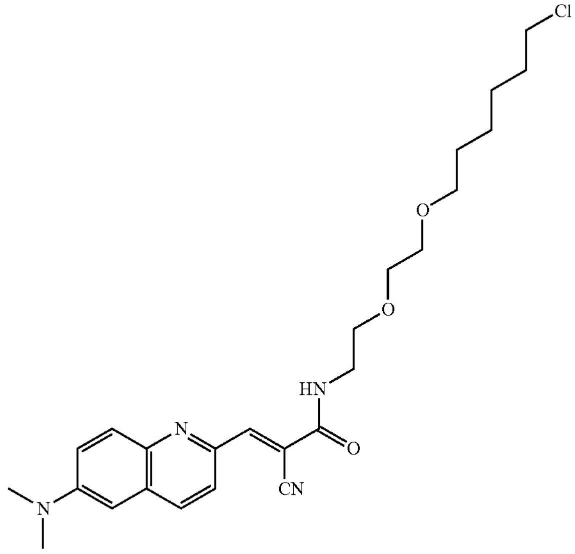

Probe62

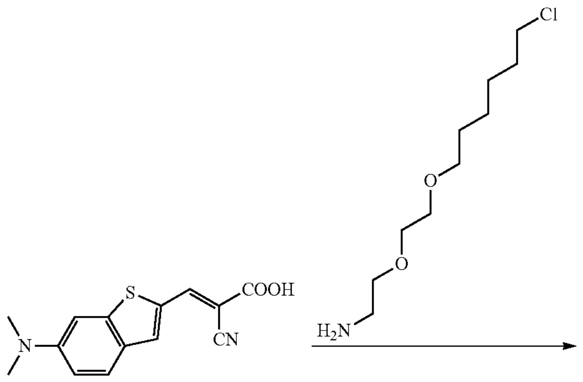

Compound 58

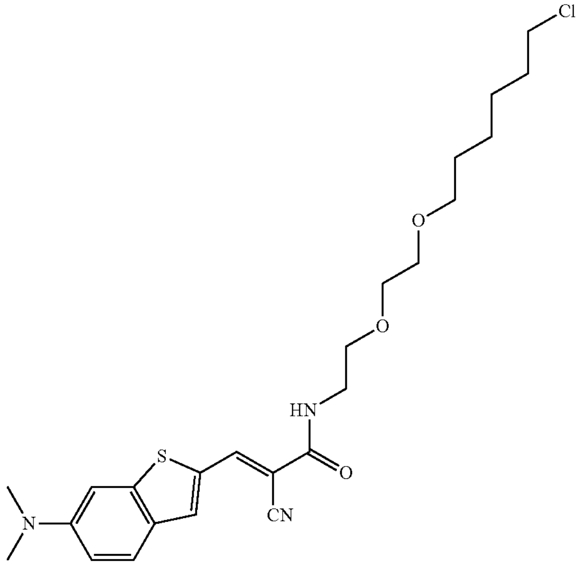

Probe 63

Compound 57:

Refer to the method of compound 42 for synthesis, $^1$H-NMR (400 MHz, $CDCl_3$): δ=8.07 (s, 1H), 7.83-7.89 (m, 2H), 7.25-7.34 (m, 1H), 7.13 (d, 1H), 6.73 (d, 1H), 3.08 (s, 6H)

Probe 62:

Refer to the method of probe 57 for synthesis. $^1$H-NMR (400 MHz, DMSO-$d_6$): δ=8.18 (t, 1H), 8.07 (s, 1H), 7.83-7.89 (m, 2H), 7.25-7.34 (m, 1H) 7.13 (d, 1H), 6.73 (d, 1H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.08 (s, 6H), 1.79-1.71 (m, 2H), 1.60-1.53 (m, 2H), 1.46-1.39 (m, 2H), 1.36-1.28 (m, 2H)

Example 63

Molecular rotors were used as viscosity responsive fluorescent dyes to construct a fluorescent-activated covalently labeled fluorescent probe 63 for HaloTag:

Compound 58:

Refer to the method of compound 23 for synthesis, $^1$H-NMR (400 MHz, $CDCl_3$): δ=7.95 (s, 1H), 7.81 (s, 1H), 7.68 (d, 1H, J=9.0 Hz), 6.92 (d, 1H, J=2.0), 6.82 (d, 1H, J=9.2 Hz), 3.10 (s, 6H)

Probe 63:

Refer to the method of probe 57 for synthesis. $^1$H-NMR (400 MHz, DMSO-$d_6$): δ=8.18 (t, 1H), 7.95 (s, 1H), 7.81 (s, 1H), 7.68 (d, 1H, J=9.0 Hz), 6.92 (d, 1H, J=2.0), 6.82 (d, 1H, J=9.2 Hz), 3.69 (t, J=4.9 Hz, 2H), 3.63-3.60 (nm, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 6H), 1.79-1.71 (m, 2H), 1.60-1.53 (m, 2H), 1.46-1.39 (m, 2H), 1.36-1.28 (m, 2H)

Example 64

Molecular rotors were used as viscosity responsive fluorescent dyes to construct a fluorescent-activated covalently labeled fluorescent probe 64 for HaloTag:

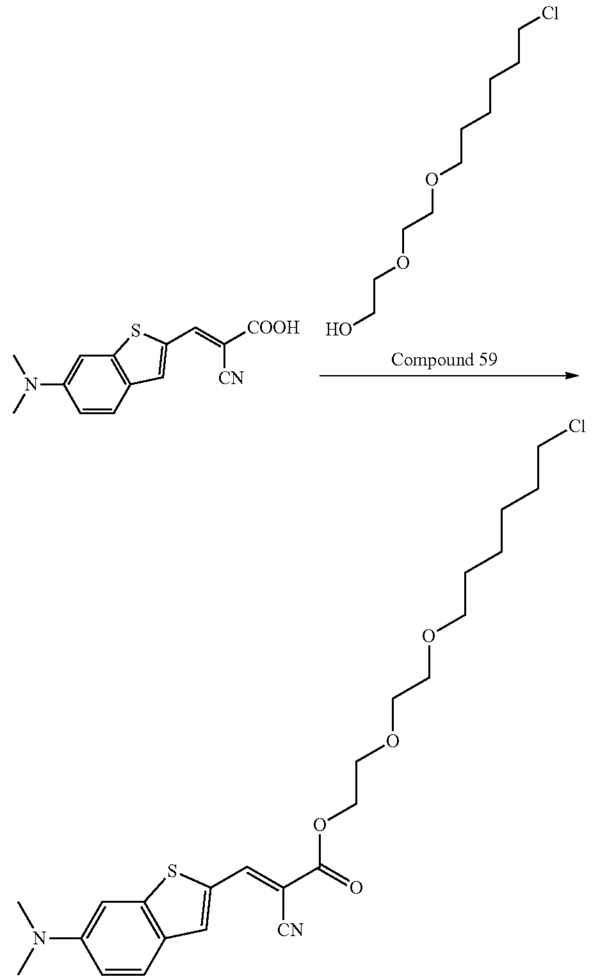

Probe 64

Compound 59:

Refer to the method of literature (Eric T. Kool et. al. Bioconjug Chem. 2016. 27. 2839-2843) for synthesis. $^{1}$H-NMR (400 MHz, $CDCl_3$): δ=3.74-3.70 (m, 2H), 3.69-3.65 (m, 2H), 3.63-3.56 (m, 4H), 3.53 (t, J=6.7 Hz, 2H), 3.47 (t, J=6.7 Hz, 2H), 2.42 (s, 1H), 1.82-1.72 (m, 2H), 1.66-1.55 (m, 2H), 1.50-1.31 (m, 4H)

Probe 64:

Refer to the method of probe 57 for synthesis. $^{1}$H-NMR (400 MHz, DMSO-$d_6$): δ=7.95 (s, 1H), 7.81 (s, 1H), 7.68 (d, 1H, J=9.0 Hz), 6.92 (d, 1H, J=2.0), 6.82 (d, 1H, J=9.2 Hz), 3.74-3.70 (m, 2H), 3.69-3.65 (m, 2H), 3.63-3.56 (m, 4H), 3.53 (t, J=6.7 Hz, 2H), 3.47 (t, J=6.7 Hz, 2H), 3.10 (s, 6H), 2.42 (s, 1H), 1.82-1.72 (m, 2H), 1.66-1.55 (m, 2H), 1.50-1.31 (m, 4H)

Example 65

Molecular rotors were used as viscosity responsive fluorescent dyes to construct a fluorescent-activated covalently labeled fluorescent probe 65 for HaloTag:

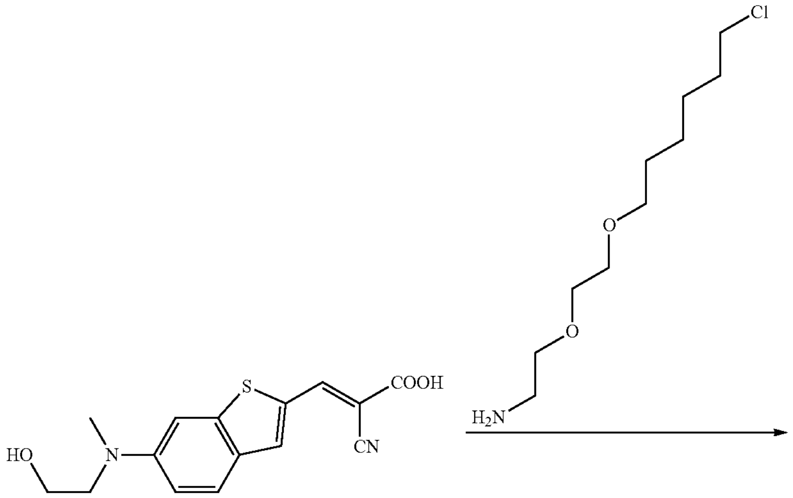

-continued

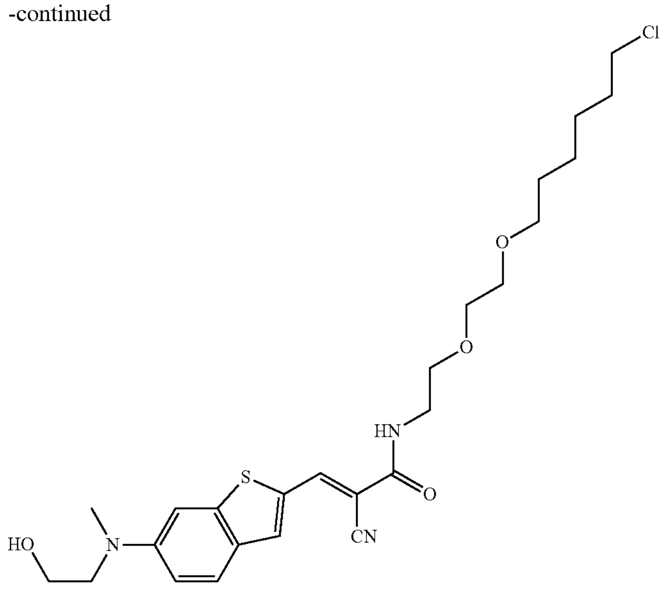

Probe 65

Refer to the method of probe 57 for synthesis. $^1$H-NMR (400 MHz, DMSO-$d_6$): δ=8.18 (t, 1H), 7.95 (s, 1H), 7.81 (s, 1H), 7.68 (d, 1H, J=9.0 Hz), 6.92 (d, 1H, J=2.0), 6.82 (d, 1H, J=9.2 Hz), 3.85 (t, 2H, J=5.6 Hz), 3.69 (t, J=4.9 Hz, 2H), 3.63-3.60 (m, 2H), 3.60 (t, 2H, J=5.6 Hz), 3.56-3.53 (m, 2H), 3.10 (s, 3H) 3.52 (t, J=6.6 Hz, 2H), 3.44 (t, J=6.8 Hz, 2H), 3.12 (t, J=4.9 Hz, 2H), 1.79-1.71 (m, 2H), 1.60-1.53 (m, 2H), 1.46-1.39 (m, 2H), 1.36-1.28 (m, 2H)

Example 66

Molecular rotors were used as viscosity responsive fluorescent dyes to construct a fluorescent-activated covalently labeled fluorescent probe 66 for HaloTag:

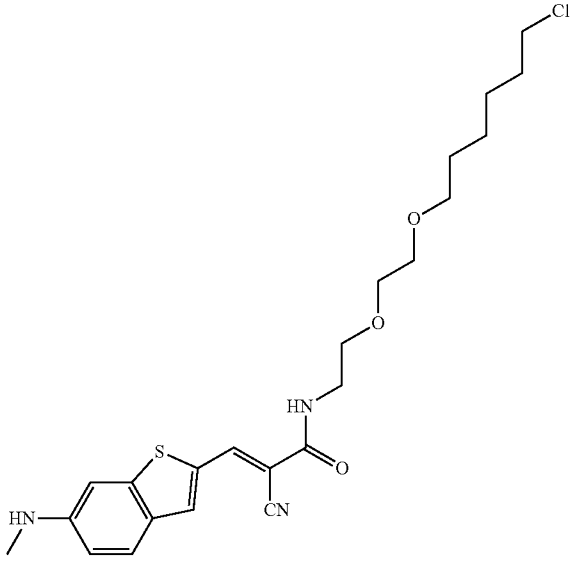

Probe66

Refer to the method of probe 63 for synthesis. $^1$H-NMR (400 MHz, DMSO-$d_6$): δ=8.18 (t, 1H), 7.95 (s, 1H), 7.81 (s, 1H), 7.68 (d, 1H, J=9.0 Hz), 6.92 (d, 1H, J=2.0), 6.82 (d, 1H, J=9.2 Hz), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 3H), 1.79-1.71 (m, 2H), 1.60-1.53 (m, 2H), 1.46-1.39 (m, 2H), 1.36-1.28 (m, 2H)

Example 67

Molecular rotors were used as viscosity responsive fluorescent dyes to construct a fluorescent-activated covalently labeled fluorescent probe 67 for HaloTag:

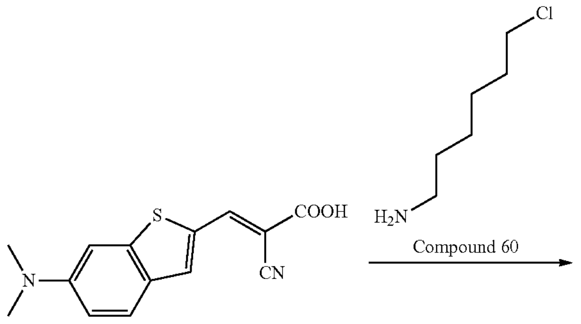

-continued

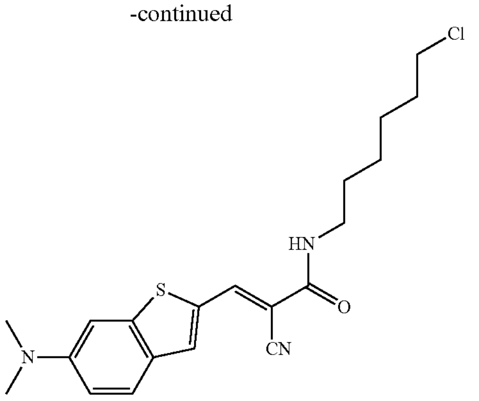

Probe 67

Compound 60:

Refer to the method of literature (Simon J. A. Pope. et. al. Chem. Commun. 2009. 4278-4280) for synthesis. $^1$H-NMR (400 MHz, $CDCl_3$): δ=3.61 (t, 2H), 3.08 (t, 2H), 2.07-1.82 (m, 8H)

Probe 67:

Refer to the method of probe 57 for synthesis. $^1$H-NMR (400 MHz, DMSO-$d_6$): δ=8.16 (t, 1H), 7.95 (s, 1H), 7.81 (s, 1H), 7.68 (d, 1H, J=9.0 Hz) 6.92 (d, 1H, J=2.0), 6.82 (d, 1H, J=9.2 Hz), 3.61 (t, 2H), 3.10 (s, 6H), 3.08 (t, 2H), 2.07-1.82 (m, 8H)

Example 68

Molecular rotors were used as viscosity responsive fluorescent dyes to construct a fluorescent-activated covalently labeled fluorescent probe 68 for HaloTag:

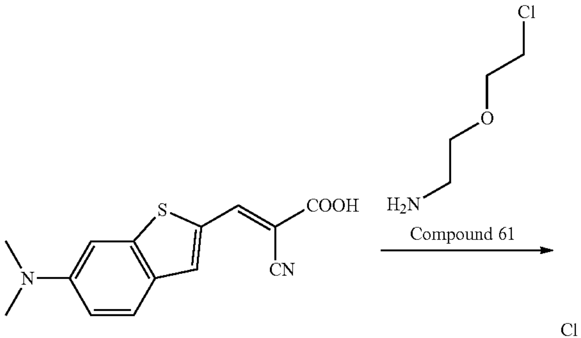

Compound 61

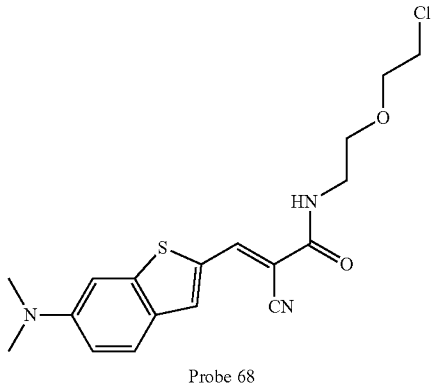

Probe 68

Compound 61:

Refer to the method of literature (Simon J. A. Pope. et. al. Chem. Commun. 2009. 4278-4280) for synthesis. $^1$H-NMR (400 MHz. $CDCl_3$): δ=3.85 (t, J=5.2 Hz, 2H), 3.81 (t, J=5.7 Hz, 2H), 3.72 (t, J=5.7 Hz, 2H), 3.27 (sext, J=5.2 Hz, 2H)

Probe 68:

Refer to the method of probe 57 for synthesis. $^1$H-NMR (400 MHz, DMSO-$d_6$): δ=8.19 (t, 1H), 7.95 (s, 1H), 7.81 (s, 1H), 7.68 (d, 1H, J=9.0 Hz), 6.92 (d, 1H, J=2.0), 6.82 (d, 1H, J=9.2 Hz), 3.85 (t, J=5.2 Hz, 2H), 3.81 (t, J=5.7 Hz, 2H), 3.72 (t, J=5.7 Hz, 2H), 3.27 (sext, J=5.2 Hz, 2H), 3.10 (s, 6H)

Example 69

Molecular rotors were used as viscosity responsive fluorescent dyes to construct a fluorescent-activated covalently labeled fluorescent probe 69 for HaloTag:

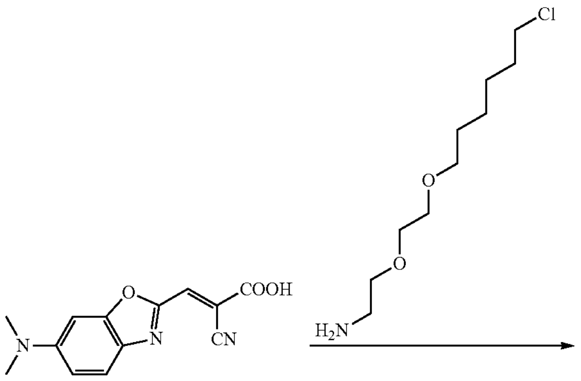

Compound 62

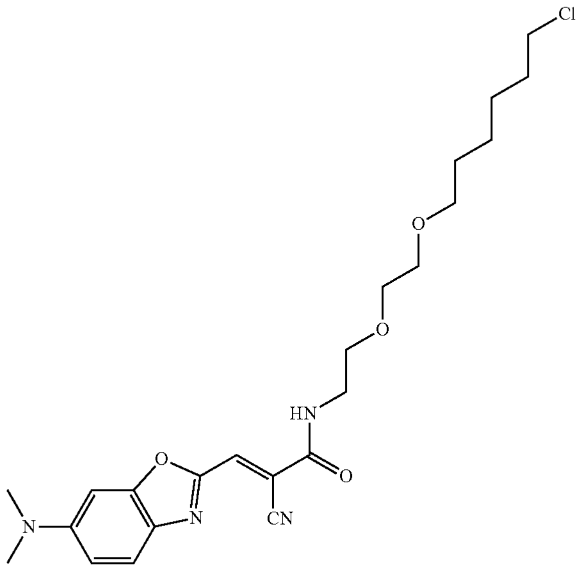

Probe 69

Compound 62:

Refer to the method of compound 34 for synthesis, H-NMR (400 MHz, $CDCl_3$): δ=7.99 (s, 1H), 7.61 (d, 1H, J=1.6 Hz), 7.49 (d, 1H, J=8.4 Hz), 7.40 (dd, 1H, $J_1$=8.4 Hz, $J_2$=1.6 Hz), 3.11 (s, 6H)

Probe 69:

Refer to the method of probe 57 for synthesis. H-NMR (400 MHz, DMSO-$d_6$): δ=8.18 (t, 1H), 7.99 (s, 1H), 7.61 (d, 1H, J=1.6 Hz), 7.49 (d, 1H, J=8.4 Hz), 7.40 (dd, 1H, $J_1$=8.4 Hz, $J_2$=1.6 Hz), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.11 (s, 6H), 1.79-1.71 (m, 2H), 1.60-1.53 (m, 2H), 1.46-1.39 (m, 2H), 1.36-1.28 (m, 2H)

Example 70

Molecular rotors were used as viscosity responsive fluorescent dyes to construct a fluorescent-activated covalently labeled fluorescent probe 70 for HaloTag:

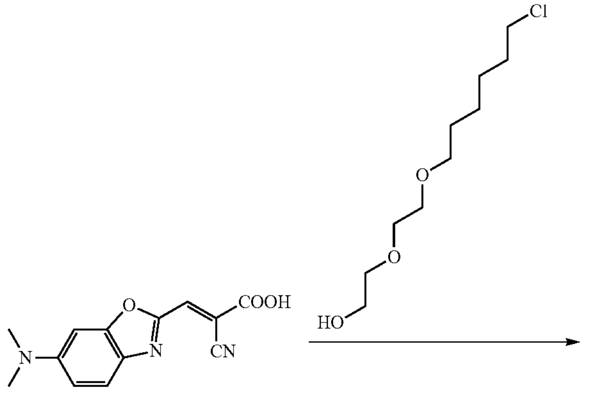

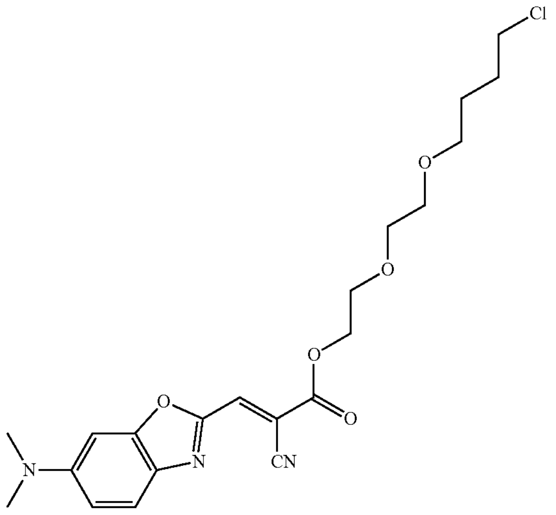

Probe 70

Refer to the method of probe 64 for synthesis. $^1$H-NMR (400 MHz, DMSO-$d_6$): δ=7.99 (s, 1H), 7.61 (d, 1H, J=1.6 Hz), 7.49 (d, 1H, J=8.4 Hz), 7.40 (dd, 1H, $J_1$=8.4 Hz, $J_2$=1.6 Hz), 3.74-3.70 (m, 2H), 3.69-3.65 (m, 2H), 3.63-3.56 (m, 4H), 3.53 (t, J=6.7 Hz, 2H), 3.47 (t, J=6.7 Hz, 2H), 3.11 (s, 3H), 2.42 (s, 1H), 1.82-1.72 (m, 2H), 1.66-1.55 (m, 2H), 1.50-1.31 (m, 4H)

Example 71

Molecular rotors were used as viscosity responsive fluorescent dyes to construct a fluorescent-activated covalently labeled fluorescent probe 71 for HaloTag:

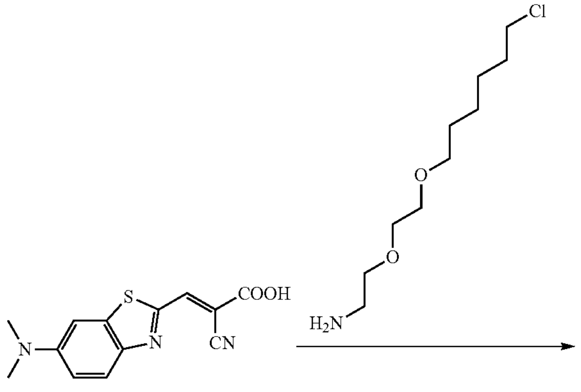

Compound 63

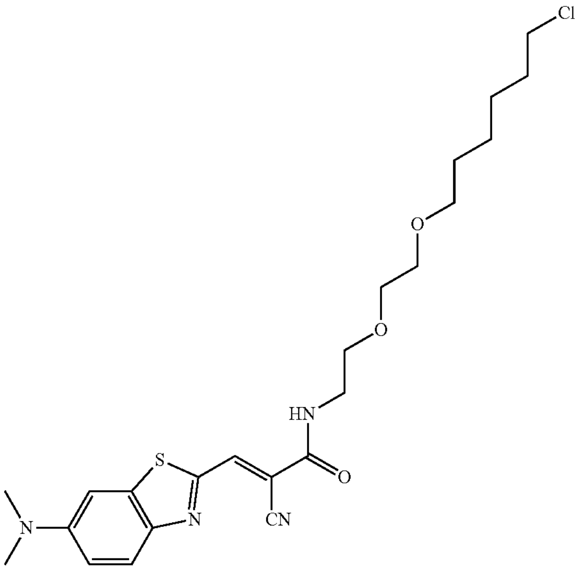

Probe 71

Compound 63:

Refer to the method of compound 34 for synthesis, $^1$H-NMR (400 MHz. $CDCl_3$): δ=8.06 (s, 1H), 8.03 (d, 1H), 7.07-7.04 (m, 2H), 3.10 (s, 6H)

Probe 71:

Refer to the method of probe 57 for synthesis. $^1$H-NMR (400 MHz, DMSO-$d_6$): δ=8.18 (t, 1H), 8.06 (s, 1H), 8.03 (d, 1H), 7.07-7.04 (m, 2H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 6H), 1.79-1.71 (nm, 2H), 1.60-1.53 (m, 2H), 1.46-1.39 (m, 2H), 1.36-1.28 (m, 2H)

Example 72

Molecular rotors were used as viscosity responsive fluorescent dyes to construct a fluorescent-activated covalently labeled fluorescent probe 72 for HaloTag:

Probe 72

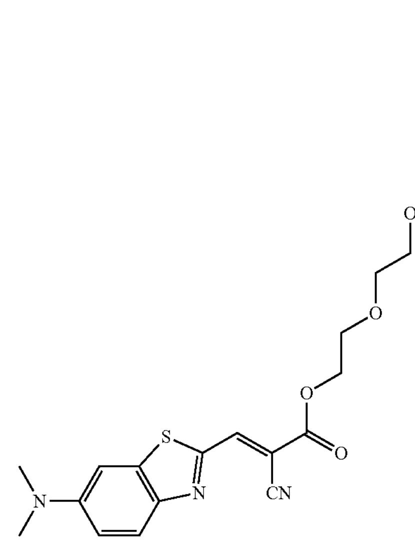

Refer to the method of probe 70 for synthesis. $^1$H-NMR (400 MHz, DMSO-$d_6$): δ=8.06 (s, 1H), 8.03 (d, 1H), 7.07-7.04 (m, 2H), 3.74-3.70 (m, 2H), 3.69-3.65 (m, 2H), 3.63-3.56 (m, 4H), 3.53 (t, J=6.7 Hz, 2H), 3.47 (t, J=6.7 Hz, 2H), 3.10 (s, 6H), 2.42 (s, 1H), 1.82-1.72 (m, 2H), 1.66-1.55 (m, 2H), 1.50-1.31 (m, 4H)

Example 73

Molecular rotors were used as viscosity responsive fluorescent dyes to construct a fluorescent-activated covalently labeled fluorescent probe 73 for HaloTag

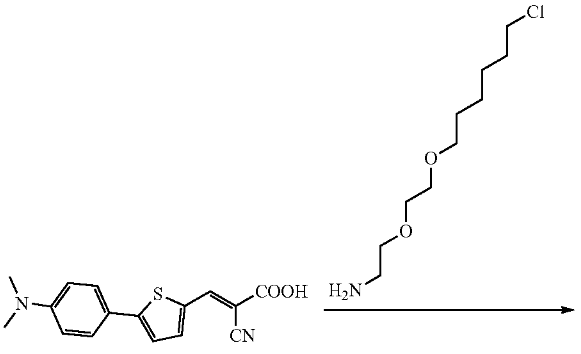

Compound 64

-continued

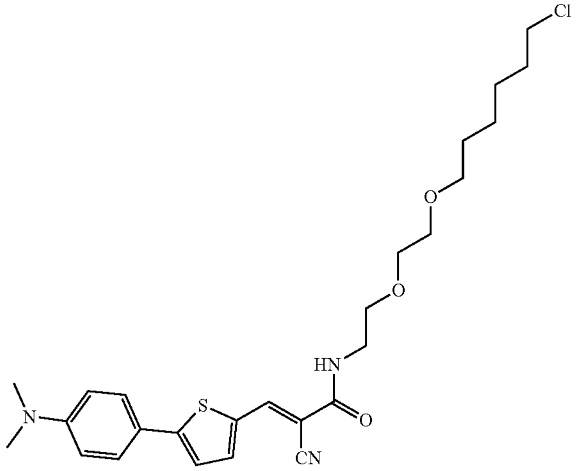

Probe 73

Compound 64:

Refer to the method of compound 33 for synthesis, $^1$H-NMR (400 MHz, $CDCl_3$): δ=8.00 (s, 1H), 7.68 (d, 1H, J=4.0 Hz), 7.56 (d, 2H, J=9.0 Hz), 7.24 (d, 1H, J=4.0 Hz), 6.72 (d, 2H J=9.0 Hz), 3.10 (s, 6H)

Probe 73:

Refer to the method of probe 57 for synthesis. $^1$H-NMR (400 MHz, DMSO-$d_6$): δ=8.18 (t, 1H), 8.00 (s, 1H), 7.68 (d, 1H, J=4.0 Hz), 7.56 (d, 2H, J=9.0 Hz), 7.24 (d, 1H, J=4.0 Hz), 6.72 (d, 2H, J=9.0 Hz), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 6H), 1.79-1.71 (m, 2H), 1.60-1.53 (m, 2H), 1.46-1.39 (m, 2H), 1.36-1.28 (m, 2H)

Example 74

Molecular rotors were used as viscosity responsive fluorescent dyes to construct a fluorescent-activated covalently labeled fluorescent probe 74 for HaloTag:

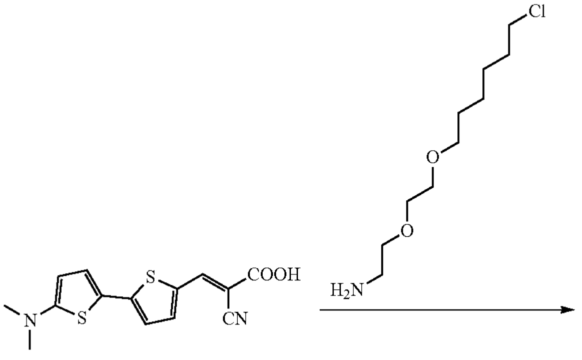

Compound 65

-continued

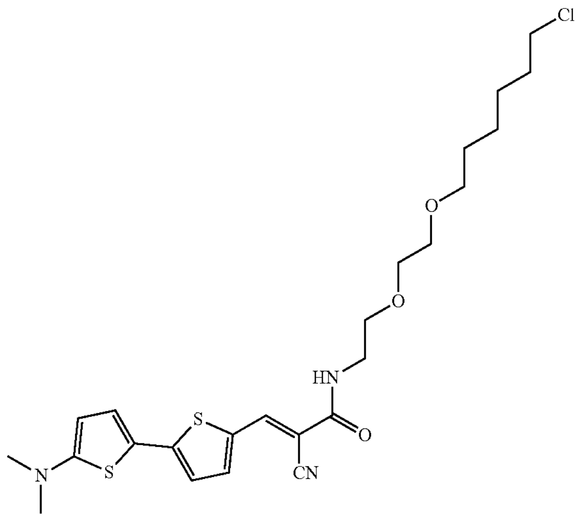

Probe 74

-continued

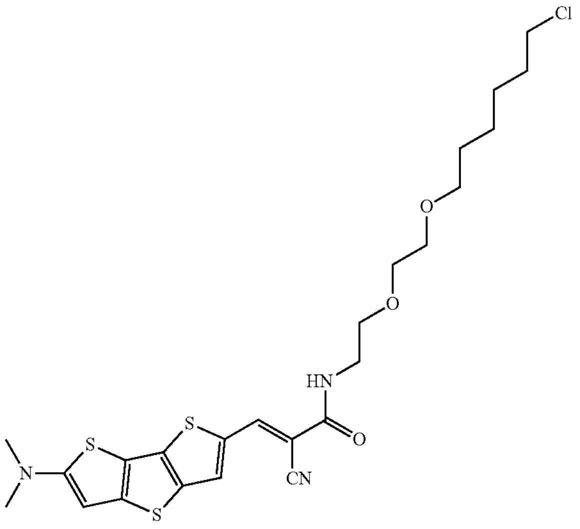

Probe 75

Compound 65:

Refer to the method of probe 40 for synthesis. $^1$H-NMR (400 MHz, $CDCl_3$): δ=7.99 (s, 1H), 7.57 (d, 1H, J=4.0 Hz), 7.13 (d, 1H, J=4.0 Hz), 6.95 (d, 1H, J=4.0 Hz), 5.81 (d, 1H, J=4.0 Hz), 3.00 (s, 6H)

Probe 74:

Refer to the method of probe 57 for synthesis. $^1$H-NMR (400 MHz, DMSO-$d_6$): δ=8.18 (t, 1H), δ=7.99 (s, 1H), 7.57 (d, 1H, J=4.0 Hz), 7.13 (d, 1H, J=4.0 Hz), 6.95 (d, 1H, J=4.0 Hz), 5.81 (d, 1H, J=4.0 Hz), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.00 (s, 6H), 1.79-1.71 (m, 2H), 1.60-1.53 (m, 2H), 1.46-1.39 (m, 2H), 1.36-1.28 (in, 2H)

Example 75

Molecular rotors were used as viscosity responsive fluorescent dyes to construct a fluorescent-activated covalently labeled fluorescent probe 75 for HaloTag:

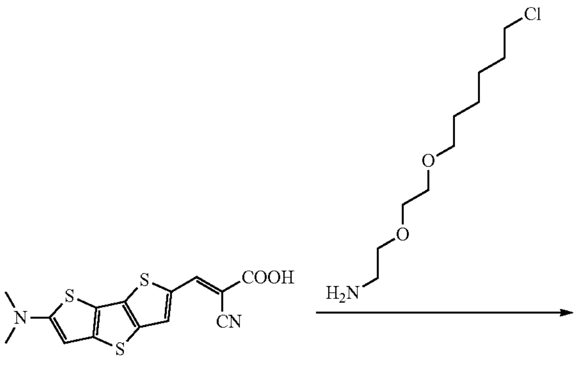

Compound 66

Compound 66:

Refer to the method of probe 29 for synthesis. $^1$H-NMR (400 MHz, $CDCl_3$): δ=8.01 (s, 1H), 7.84 (s, 1H), 7.24 (s, 1H), 3.02 (s, 6H)

Probe 75:

Refer to the method of probe 57 for synthesis. $^1$H-NMR (400 MHz, DMSO-$d_6$): 8.18 (t, 1H), 8.01 (s, 1H), 7.84 (s, 1H), 7.24 (s, 1H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.02 (s, 6H), 1.79-1.71 (m, 2H), 1.60-1.53 (m, 2H), 1.46-1.39 (m, 2H), 1.36-1.28 (m, 2H)

Example 76

Molecular rotors were used as viscosity responsive fluorescent dyes to construct a fluorescent-activated covalently labeled fluorescent probe 76 for HaloTag

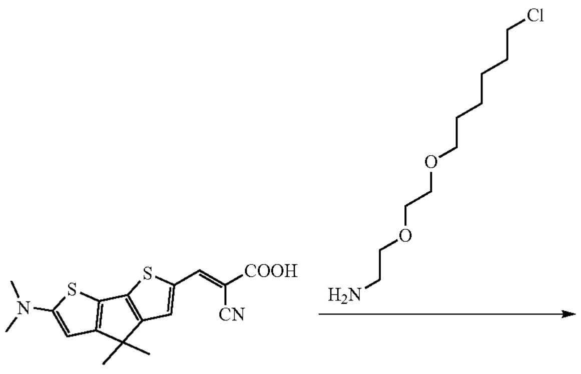

Compound 67

-continued

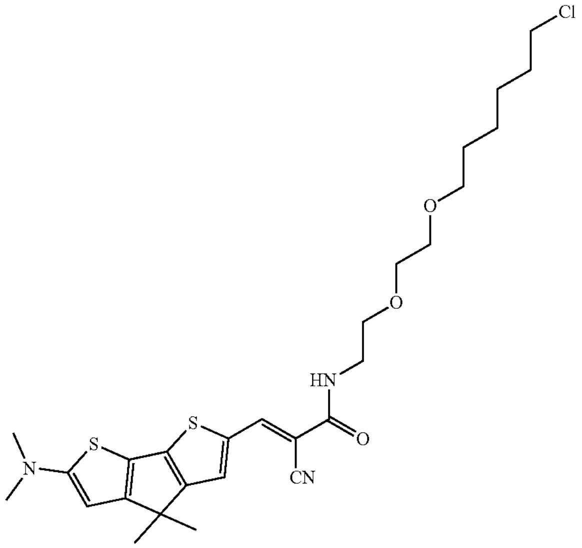

Probe 76

Compound 67:

Refer to the method of probe 48 for synthesis. $^1$H-NMR (400 MHz, $CDCl_3$): δ=7.89 (s, 1H), 7.18 (s, 1H), 6.96 (s, 1H), 3.10 (s, 6H), 1.50 (m, 6H)

Probe 76:

Refer to the method of probe 57 for synthesis. H-NMR (400 MHz, DMSO-$d_6$): δ=8.18 (t, 1H), 7.89 (s, 1H), 7.18 (s, 1H), 6.96 (s, 1H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 6H), 1.79-1.71 (m, 2H), 1.60-1.53 (m, 2H), 1.50 (m, 6H), 1.46-1.39 (m, 2H), 1.36-1.28 (m, 2H)

Example 77

Molecular rotors were used as viscosity responsive fluorescent dyes to construct a fluorescent-activated covalently labeled fluorescent probe 77 for HaloTag:

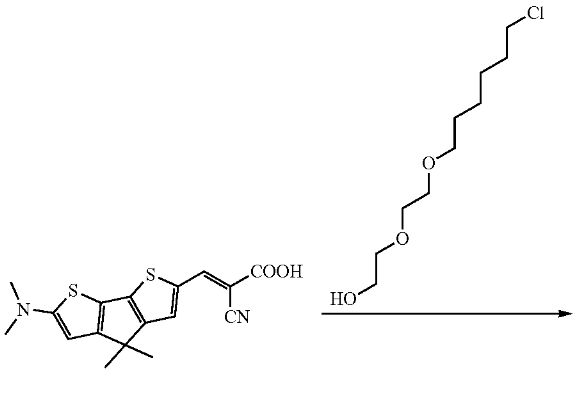

-continued

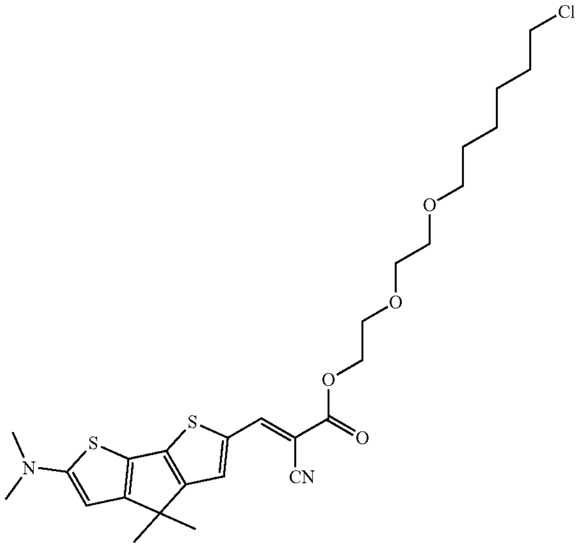

Probe 77

Refer to the method of probe 64 for synthesis. $^1$H-NMR (400 MHz, DMSO-$d_6$): δ=7.89 (s, 1H), 7.18 (s, 1H), 6.96 (s, 1H), 3.74-3.70 (m, 2H), 3.69-3.65 (m, 2H), 3.63-3.56 (m, 4H), 3.53 (t, J=6.7 Hz, 2H), 3.47 (t, J=6.7 Hz, 2H), 3.10 (s, 6H), 2.42 (s, 1H), 1.82-1.72 (m, 2H), 1.66-1.55 (m, 2H), 1.50 (m, 6H), 1.50-1.31 (m, 4H)

Example 78

Molecular rotors were used as viscosity responsive fluorescent dyes to construct a fluorescent-activated covalently labeled fluorescent probe 78 for HaloTag:

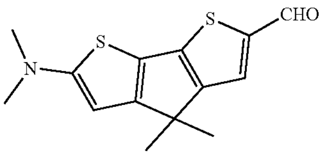

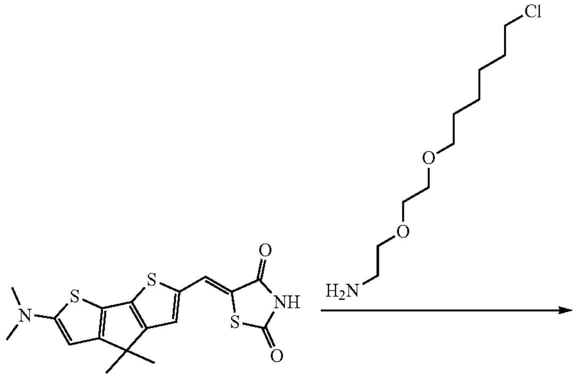

Compound 68

-continued

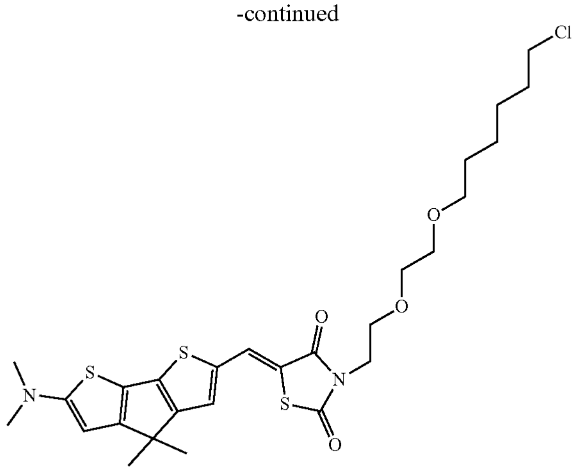

Probe 78

Compound 68:

Refer to the method of compound 1 for synthesis, $^1$H-NMR (400 MHz, $CDCl_3$): δ=8.01 (s, 1H), 7.18 (s, 1H), 6.96 (s, 1H), 3.10 (s, 6H), 1.50 (m, 6H)

Probe 78:

Compound 68 (0.376 g, 1.0 mmol) and compound 2 (0.446 g, 2 mmol) were mixed in 10 mL DMF with 0.1 ml triethylamine and stirred at room temperature for two days. $^1$H-NMR (400 MHz, DMSO-d): δ=8.01 (s, 1H), 7.18 (s, 1H), 6.96 (s, 1H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 6H), 1.79-1.71 (m, 2H), 1.60-1.53 (m, 2H), 1.50 (m, 6H), 1.46-1.39 (m, 2H), 1.36-1.28 (m, 2H)

Example 79

Molecular rotors were used as viscosity responsive fluorescent dyes to construct a fluorescent-activated covalently labeled fluorescent probe 79 for HaloTag:

Probe 79

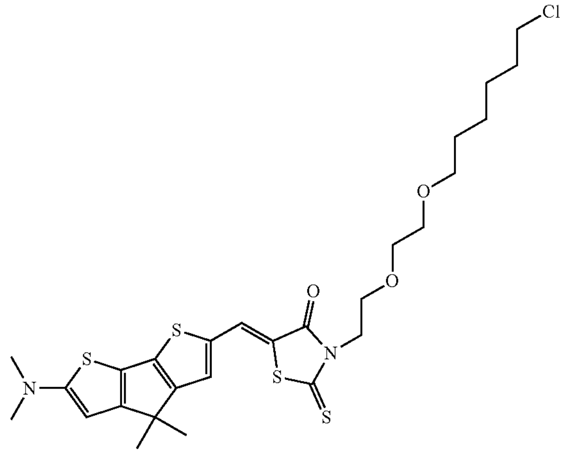

Refer to the method of probe 78 for synthesis. $^1$H-NMR (400 MHz, DMSO-$d_6$): δ=7.88 (s, 1H), 7.18 (s, 1H), 6.96 (s, 1H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 6H), 1.79-1.71 (m, 2H), 1.60-1.53 (m, 2H), 1.50 (m, 6H), 1.46-1.39 (m, 2H), 1.36-1.28 (m, 2H)

Example 80

Molecular rotors were used as viscosity responsive fluorescent dyes to construct a fluorescent-activated covalently labeled fluorescent probe 80 for HaloTag:

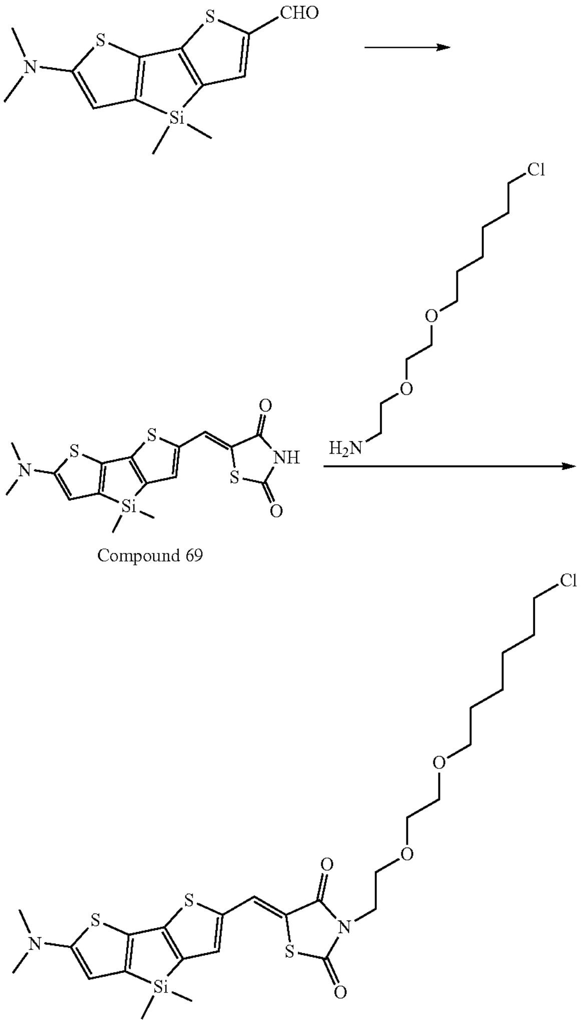

Compound 69

Probe 80

Compound 69:

Refer to the method of compound 1 for synthesis, $^1$H-NMR (400 MHz, $CDCl_3$): δ=8.01 (s, 1H), 7.18 (s, 1H), 6.96 (s, 1H), 3.10 (s, 6H), 0.41 (m, 6H)

Probe 80:

Refer to the method of probe 78 for synthesis. $^1$H-NMR (400 MHz, DMSO-$d_6$): δ=8.01 (s, 1H), 7.18 (s, 1H), 6.96 (s, 1H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 6H), 1.79-1.71 (m, 2H), 1.60-1.53 (m, 2H), 1.46-1.39 (m, 2H), 1.36-1.28 (m, 2H), 0.42 (m, 6H)

Example 81

Molecular rotors were used as viscosity responsive fluorescent dyes to construct a fluorescent-activated covalently labeled fluorescent probe 81 for HaloTag:

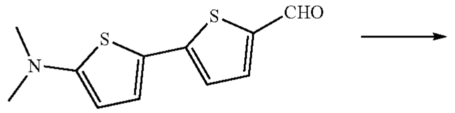

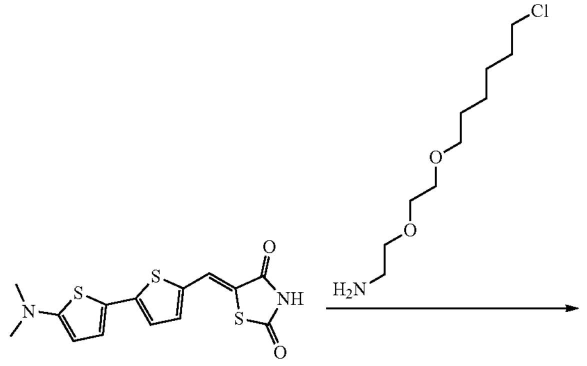

Compound 70

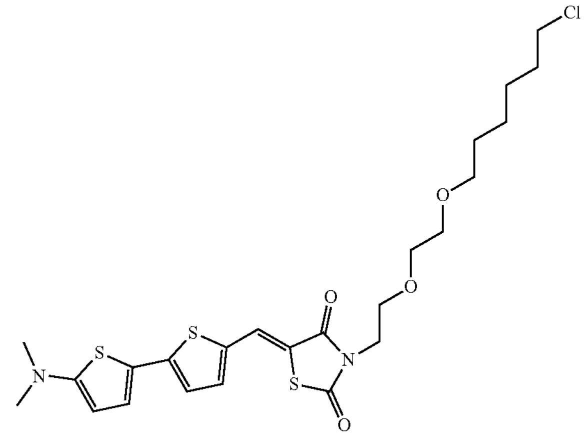

Probe 81

Compound 70:

Refer to the method of compound 1 for synthesis, $^{1}$H-NMR (400 MHz, $CDCl_3$): δ=8.00 (s, 1H), 7.57 (d, 1H, J=4.00 Hz), 7.13 (d, 1H, J=4.00 Hz), 6.95 (d, 1H, J=4.00 Hz), 5.81 (d, 1H, J=4.00 Hz), 3.13 (s, 6H)

Probe 81:

Refer to the method of probe 78 for synthesis. $^{1}$H-NMR (400 MHz, DMSO-$d_6$): δ=8.00 (s, 1H), 7.57 (d, 1H, J=4.00 Hz), 7.13 (d, 1H, J=4.00 Hz), 6.95 (d, 1H, J=4.00 Hz), 5.81 (d, 1H, J=4.00 Hz), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.13 (s, 6H), 3.12 (t, J=4.9 Hz, 2H), 1.79-1.71 (m, 2H), 1.60-1.53 (m, 2H), 1.46-1.39 (m, 2H), 1.36-1.28 (m, 2H)

Example 82

Molecular rotors were used as viscosity responsive fluorescent dyes to construct a fluorescent-activated covalently labeled fluorescent probe 82 for HaloTag:

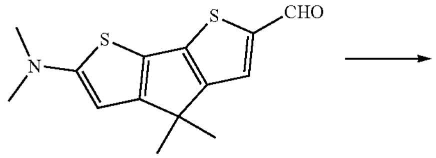

-continued

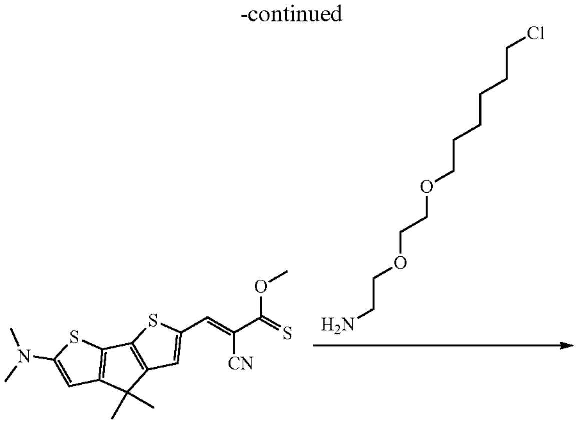

Compound 71

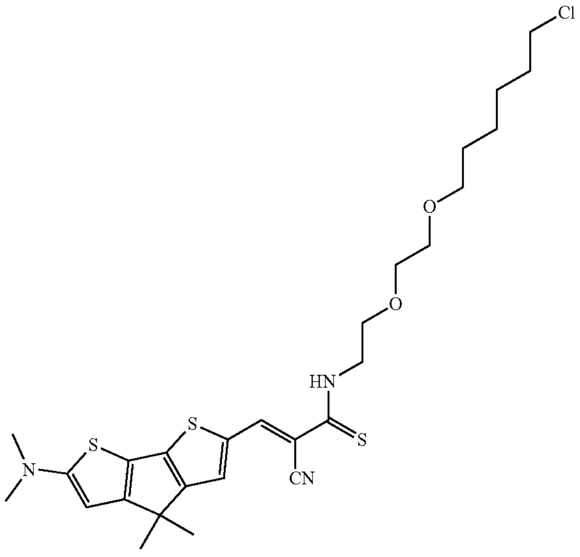

Probe 82

Compound 71:

Refer to the method of compound 49 for synthesis, $^{1}$H-NMR (400 MHz, $CDCl_3$): δ=7.89 (s, 1H), 7.18 (s, 1H), 6.96 (s, 1H), 3.47 (s, 3H), 3.10 (s, 6H), 1.50 (m, 6H)

Probe 82:

Refer to the method of probe 78 for synthesis. $^{1}$H-NMR (400 MHz, DMSO-$d_6$): δ=8.18 (t, 1H), 7.89 (s, 1H), 7.18 (s, 1H), 6.96 (s, 1H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 6H), 1.79-1.71 (m, 2H), 1.60-1.53 (m, 2H), 1.50 (m, 6H), 1.46-1.39 (m, 2H), 1.36-1.28 (m, 2H)

Example 83

Molecular rotors were used as viscosity responsive fluorescent dyes to construct a fluorescent-activated covalently labeled fluorescent probe 83 for HaloTag:

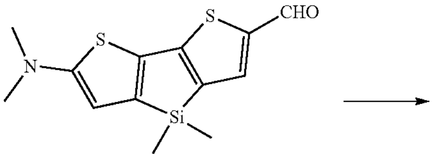

-continued

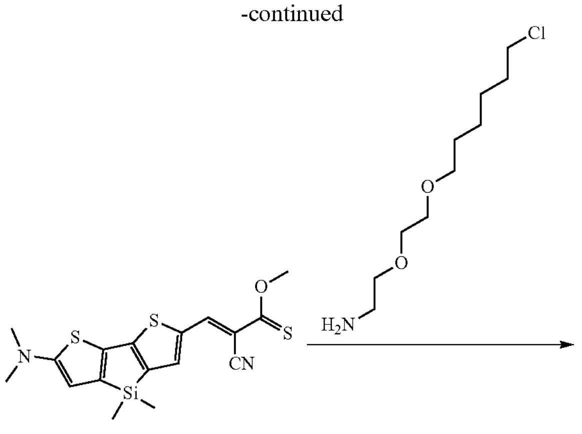

Compound 72

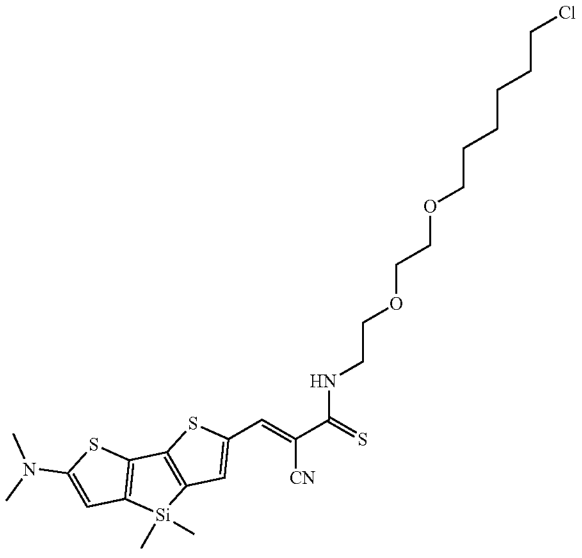

Probe 83

Compound 72:

Refer to the method of compound 50 for synthesis, $^1$H-NMR (400 MHz, $CDCl_3$): δ=7.89 (s, 1H), 7.18 (s, 1H), 6.96 (s, 1H), 3.47 (s, 3H), 3.10 (s, 6H), 0.42 (m, 6H)

Probe 83:

Refer to the method of probe 78 for synthesis. $^1$H-NMR (400 MHz, DMSO-$d_6$): δ=8.18 (t, 1H), 7.89 (s, 1H), 7.18 (s, 1H), 6.96 (s, 1H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.12 (t, J=4.9 Hz, 2H), 3.10 (s, 6H), 1.79-1.71 (m, 2H), 1.60-1.53 (m, 2H), 1.46-1.39 (m, 2H), 1.36-1.28 (m, 2H), 0.41 (m, 6H)

Example 84

Molecular rotors were used as viscosity responsive fluorescent dyes to construct a fluorescent-activated covalently labeled fluorescent probe 84 for HaloTag:

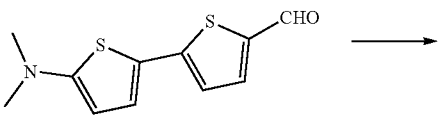

-continued

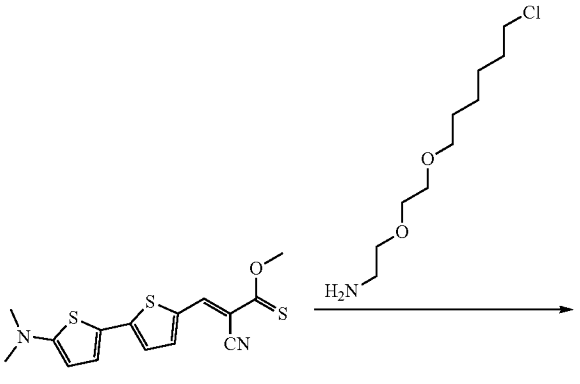

Compound 73

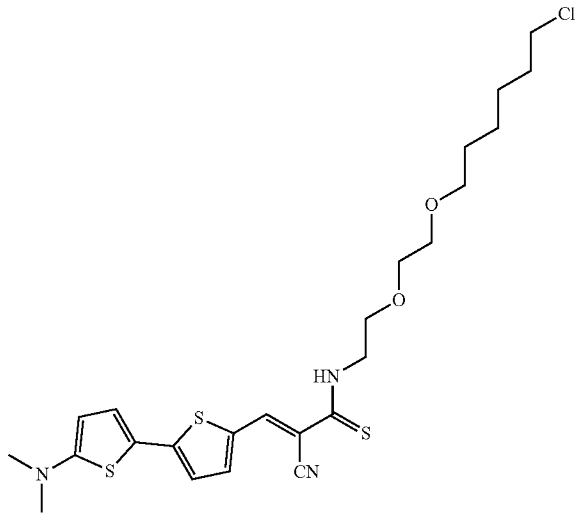

Probe 84

Compound 73:

Refer to the method of compound 49 for synthesis. $^1$H-NMR (400 MHz, $CDCl_3$): δ=8.00 (s, 1H), 7.57 (d, 1H, J=4.00 Hz), 7.13 (d, 1H, J=4.00 Hz), 6.95 (d, 1H, J=4.00 Hz), 5.81 (d, 1H, J=4.00 Hz), 3.47 (s, 3H), 3.13 (s, 6H)

Probe 84:

Refer to the method of probe 78 for synthesis. $^1$H-NMR (400 MHz, DMSO-$d_6$): δ=8.18 (t, 1H), 8.00 (s, 1H), 7.57 (d, 1H, J=4.00 Hz), 7.13 (d, 1H, J=4.00 Hz), 6.95 (d, 1H, J=4.00 Hz), 5.81 (d, 1H, J=4.00 Hz), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.13 (s, 6H), 3.12 (t, J=4.9 Hz, 2H), 1.79-1.71 (m, 2H), 1.60-1.53 (m, 2H), 1.46-1.39 (m, 2H), 1.36-1.28 (m, 2H)

Contrast Example 1

Molecular rotors were used as viscosity responsive fluorescent dyes to construct a fluorescent-activated covalently labeled fluorescent probe 85 for SNAP:

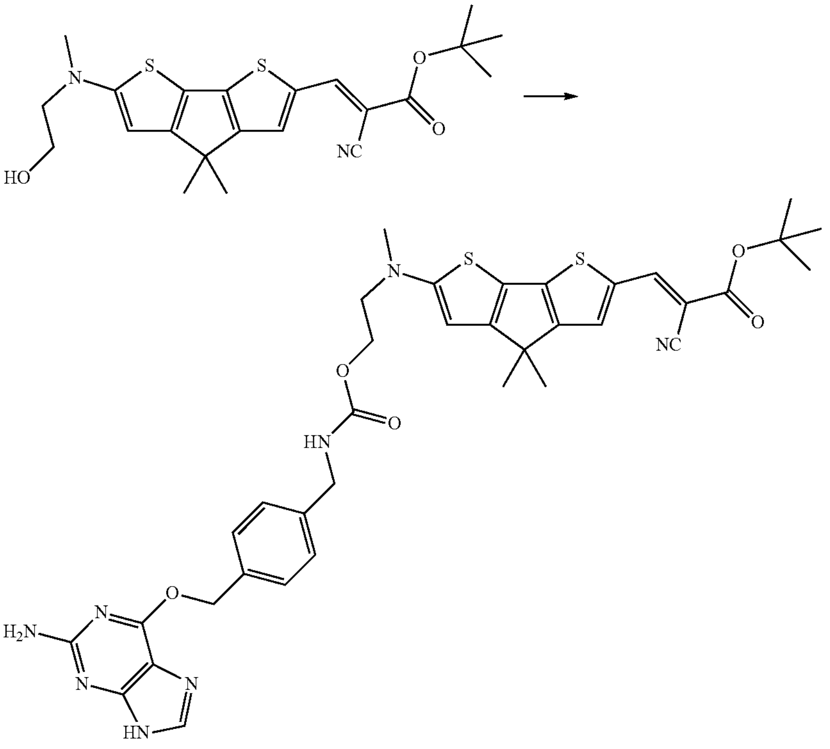

Reference probe85

Refer to the method of compound 49 for synthesis, the yield of 45%. 1H-NMR (400 MHz, DMSO-$d_6$): δ=12.42 (s, 1H), 10.01 (s, 1H), 7.89 (s, 1H), 7.18 (s, 1H), 7.81 (s, 1H), 7.4 (m, 4H), 6.96 (d, 2H, J=5.6 Hz), 6.29 (s, 2H), 5.46 (s, 2H), 4.40 (d, 2H, J=4.8 Hz), 3.85 (t, 2H, J=5.6 Hz), 3.60 (t, 2H, J=5.6 Hz), 3.10 (s, 3H), 1.50 (m, 15H)

Example 85

Molecular rotors were used as viscosity responsive fluorescent dyes to construct a fluorescent-activated covalently labeled fluorescent probe 86 for HaloTag:

Probe 86

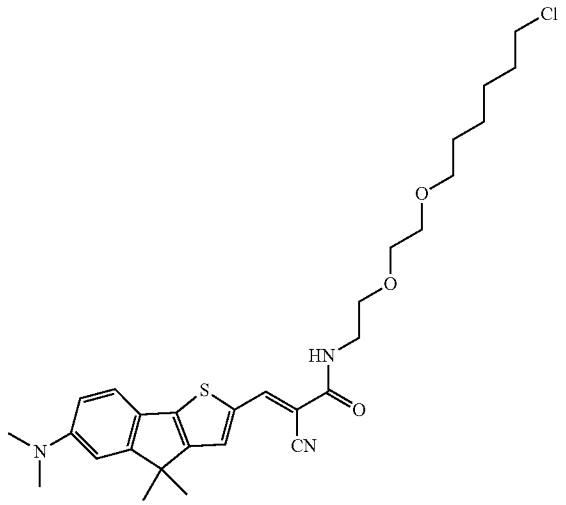

With reference to the literature (Kimin Lim et. al. 2011. 115. 22640-22646) and the method of probe 10 for synthesis. $^1$H-NMR (400 MHz, DMSO-d): δ=8.18 (t, 1H), 7.48 (s, 1H), 7.41 (s, 1H), 7.32 (m, 2H), 3.69 (t, J=4.9 Hz, 2H), 3.63-3.60 (m, 2H), 3.56-3.53 (m, 2H), 3.52 (t, J=6.6 Hz, 2H), 3.44 (t, J=6.8 Hz, 2H), 3.13 (s, 6H), 3.12 (t, J=4.9 Hz, 2H), 1.79-1.71 (m, 2H), 1.60-1.53 (m, 2H), 1.48 (s, 6H), 1.46-1.39 (m, 2H), 1.36-1.28 (m, 2H).

Example 86

A probe was mixed with a corresponding HaloTag protein tag to obtain a mixed sample. The final concentration of the probe in the mixed sample was 5 μM and the final concentration of the protein tag was 10 μM. The mixed sample was incubated at 37° C. for 1 hour, and the sample was detected using a fluorescence spectrophotometer. The fluorescence intensity was changed, and the results are shown in Table 1.

From the quantum yield of free probes in Table 1, it can be known that the fluorescence of the probes of the examples and the reference probes is extremely low when these probes do not react with the protein tag, which is close to the background fluorescence level of the PBS buffer solution, indicating that when the probes do not react with the protein tag, the fluorescence of the viscosity-responsive fluorescent probe is not activated, whereas from the quantum yield after the binding of the protein tag, it can be seen that after the probe of the example reacts with the protein tag, a significant fluorescence signal enhancement can be detected in the corresponding excitation emission channel, and the fluorescence activation multiple can reach several hundred times to more than one thousand times, and has high brightness, which indicates that the fluorescence can be activated after the probe of the example binds to the protein tag, and the probe has good fluorescent molecular switching properties. As can be seen from Table 1, the probes of the Examples have a wide range of fluorescence emission wavelengths, are greatly different in the fluorescence intensities in glycerol and methanol, and are sensitive to changes in viscosity and have viscosity responsiveness.

TABLE 1

Detection results of fluorescence emission spectra of different probes

| Name | The quantum yield of the free probe | The quantum yield after binding to Halo-tag | Emission/nm | Fluorescence enhancement | ratio |
|---|---|---|---|---|---|
| Probe 1 | <0.001 | 0.52 | 480 | 500 | 560 |
| Probe 2 | 0.001 | 0.48 | 510 | 410 | 410 |
| Probe 3 | 0.0011 | 0.45 | 515 | 512 | 399 |
| Probe 4 | <0.001 | 0.42 | 480 | 490 | 562 |
| Probe5 | <0.001 | 0.46 | 480 | 1174 | 790 |
| Probe 6 | <0.001 | 0.40 | 530 | 989 | 1183 |
| Probe 7 | <0.001 | 0.46 | 580 | 1502 | 1455 |
| Probe 8 | 0.0018 | 0.47 | 535 | 296 | 320 |
| Probe 9 | <0.001 | 0.50 | 480 | 745 | 851 |
| Probe 10 | <0.001 | 0.42 | 550 | 431 | 655 |
| Probe 11 | 0.0013 | 0.46 | 590 | 520 | 422 |
| Probe 12 | 0.0012 | 0.41 | 555 | 750 | 405 |
| Probe 13 | <0.001 | 0.56 | 570 | 816 | 391 |
| Probe 14 | <0.001 | 0.52 | 610 | 771 | 560 |
| Probe 15 | <0.001 | 0.53 | 570 | 379 | 320 |
| Probe 16 | <0.001 | 0.49 | 572 | 490 | 311 |
| Probe 17 | <0.001 | 0.56 | 575 | 498 | 402 |
| Probe 18 | 0.0017 | 0.51 | 568 | 444 | 301 |
| Probe 19 | 0.0012 | 0.53 | 625 | 561 | 299 |
| Probe 20 | <0.001 | 0.47 | 640 | 612 | 341 |
| Probe 21 | <0.001 | 0.48 | 628 | 560 | 1481 |
| Probe 22 | <0.001 | 0.36 | 632 | 610 | 1821 |
| Probe 23 | <0.001 | 0.52 | 637 | 712 | 1235 |
| Probe 24 | <0.001 | 0.52 | 622 | 590 | 1681 |
| Probe 25 | <0.001 | 0.51 | 620 | 670 | 1621 |
| Probe 26 | <0.001 | 0.56 | 590 | 910 | 1123 |
| Probe 27 | <0.001 | 0.43 | 620 | 665 | 1134 |
| Probe 28 | <0.001 | 0.41 | 566 | 551 | 1132 |
| Probe 29 | <0.001 | 0.53 | 640 | 621 | 998 |
| Probe 30 | <0.001 | 0.60 | 620 | 535 | 1125 |
| Probe 31 | <0.001 | 0.41 | 660 | 875 | 1135 |
| Probe 32 | <0.001 | 0.46 | 609 | 638 | 997 |
| Probe 33 | <0.001 | 0.47 | 620 | 957 | 1781 |
| Probe 34 | <0.001 | 0.32 | 615 | 857 | 1774 |
| Probe 35 | 0.0012 | 0.45 | 618 | 433 | 972 |
| Probe 36 | 0.001 | 0.58 | 630 | 488 | 1258 |
| Probe 37 | 0.0012 | 0.56 | 655 | 469 | 1135 |
| Probe 38 | 0.0011 | 0.56 | 650 | 503 | 1011 |
| Probe 39 | 0.0016 | 0.38 | 700 | 335 | 892 |
| Probe 40 | 0.001 | 0.47 | 657 | 421 | 759 |
| Probe 41 | 0.0015 | 0.44 | 700 | 418 | 101 |
| Probe 42 | 0.0013 | 0.39 | 702 | 375 | 178 |
| Probe 43 | <0.001 | 0.37 | 651 | 982 | 1028 |
| Probe 44 | <0.001 | 0.63 | 521 | 1586 | 1459 |
| Probe 45 | <0.001 | 0.54 | 545 | 958 | 752 |
| Probe 46 | <0.001 | 0.58 | 520 | 563 | 682 |
| Probe 47 | <0.001 | 0.45 | 523 | 358 | 235 |
| Probe 48 | <0.001 | 0.57 | 645 | 428 | 480 |
| Probe 49 | <0.001 | 0.54 | 680 | 541 | 334 |
| Probe 50 | <0.001 | 0.53 | 637 | 416 | 358 |
| Probe 51 | <0.001 | 0.48 | 625 | 392 | 359 |
| Probe 52 | <0.001 | 0.47 | 670 | 435 | 270 |
| Probe 53 | <0.001 | 0.48 | 690 | 579 | 401 |
| Probe 54 | <0.001 | 0.41 | 710 | 498 | 391 |
| Probe 55 | <0.001 | 0.39 | 660 | 382 | 211 |
| Probe 56 | <0.001 | 0.47 | 725 | 989 | 436 |
| Probe 57 | <0.001 | 0.56 | 480 | 1026 | 762 |
| Probe 58 | <0.001 | 0.58 | 480 | 519 | 419 |
| Probe 59 | <0.001 | 0.45 | 500 | 498 | 370 |
| Probe 60 | 0.0011 | 0.65 | 520 | 751 | 1199 |
| Probe 61 | 0.0012 | 0.59 | 552 | 668 | 817 |
| Probe 62 | <0.001 | 0.57 | 590 | 592 | 711 |
| Probe 63 | 0.0015 | 0.70 | 570 | 486 | 531 |
| Probe 64 | <0.001 | 0.60 | 585 | 519 | 632 |
| Probe 65 | <0.001 | 0.66 | 570 | 798 | 391 |
| Probe 66 | <0.001 | 0.53 | 550 | 512 | 386 |
| Probe 67 | <0.001 | 0.48 | 580 | 576 | 276 |
| Probe 68 | <0.001 | 0.50 | 580 | 681 | 381 |
| Probe 69 | <0.001 | 0.47 | 610 | 491 | 317 |
| Probe 70 | 0.0026 | 0.58 | 630 | 258 | 431 |
| Probe 71 | 0.0028 | 0.61 | 620 | 475 | 321 |
| Probe 72 | 0.001 | 0.47 | 640 | 486 | 268 |
| Probe 73 | 0.0031 | 0.55 | 620 | 561 | 325 |
| Probe 74 | 0.0025 | 0.42 | 630 | 611 | 297 |
| Probe 75 | 0.0021 | 0.56 | 620 | 589 | 500 |
| Probe 76 | 0.0011 | 0.58 | 640 | 666 | 386 |
| Probe 77 | 0.0014 | 0.53 | 652 | 721 | 479 |
| Probe 78 | <0.001 | 0.41 | 660 | 369 | 452 |
| Probe 79 | <0.001 | 0.51 | 725 | 419 | 498 |
| Probe 80 | 0.0011 | 0.44 | 740 | 641 | 712 |
| Probe 81 | <0.001 | 0.40 | 743 | 563 | 521 |
| Probe 82 | <0.001 | 0.51 | 660 | 781 | 475 |
| Probe 83 | <0.001 | 0.53 | 680 | 456 | 652 |
| Probe 84 | <0.001 | 0.47 | 680 | 431 | 522 |
| Reference Probe85 | <0.001 | 0.32 | 645 | 321 | 510 |
| Probe 86 | 0.0012 | 0.52 | 550 | 618 | 470 |

Example 87

5 μM HaloTag protein tag was added to 3 μM of solutions of probe 57, probe 60, probe 61, probe 63, probe 75, probe 76, and probe 79, respectively, to prepare HaloTag protein tag and probe mixed sample solutions. The mixed sample solutions were left to react at 37° C. for 1 hour, and the emission spectra of the samples were measured using a fluorescence spectrophotometer. The results are shown in FIG. 1 respectively. It can be seen from FIG. 1 that the above probes can achieve spectral coverage from an emission wavelength of 480 nm to 730 nm.

Example 88

A HaloTag protein tag was added to 30 μM of solutions of probe 57, probe 59, probe 60, probe 61, probe 62, probe 63, probe 69, probe 75, probe 76, and probe 82, respectively, to obtain mixed sample solutions with a final concentration of HaloTag protein tag of 0.1 μM, 0.5 μM, 0.7 μM, 1.2 μM, 4.5 μM, 8.1 μM, 13.1 μM, 14.8 μM. The mixed sample solutions were left to react at 37° C. for 1 hour. The fluorescence emission spectrophotometer was used to detect the change in excitation emission spectrum of the samples, and the relationship between HaloTag protein tag concentration and fluorescence intensity was plotted according to the emission spectrum intensity. The results are shown in FIG. 2 to FIG. 11 respectively.

Figure 2:
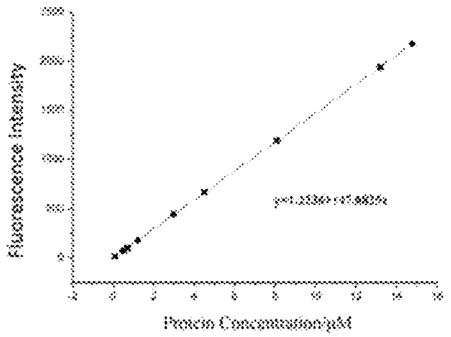
FIG. 2 to FIG. 11 are standard curves of corresponding fluorescence intensity versus different HaloTag protein tag concentrations for probe 57, probe 59, probe 60, probe 61, probe 62, probe 63, probe 75, probe 76, and probe 82, respectively.
Figure 3:
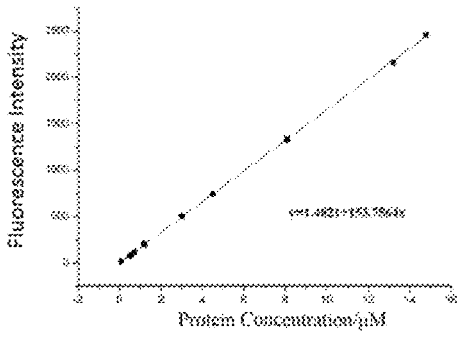
Figure 4:
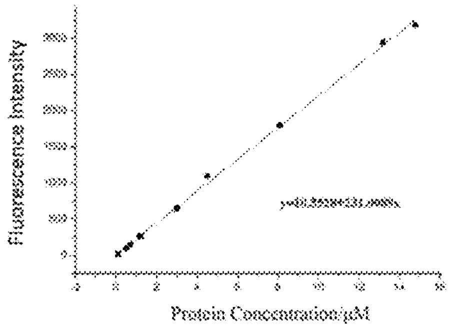
Figure 5:
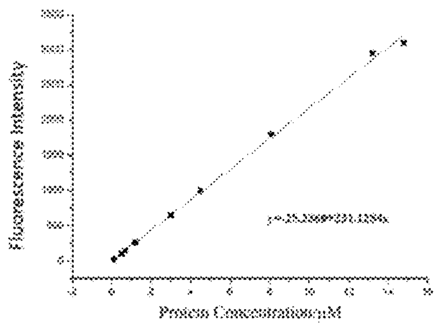
Figure 6:
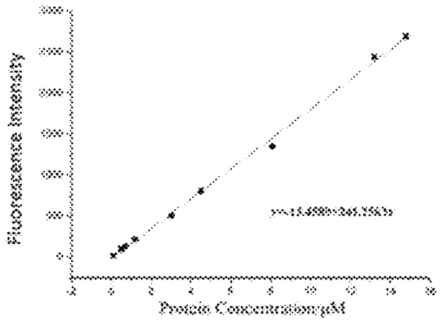
Figure 7:
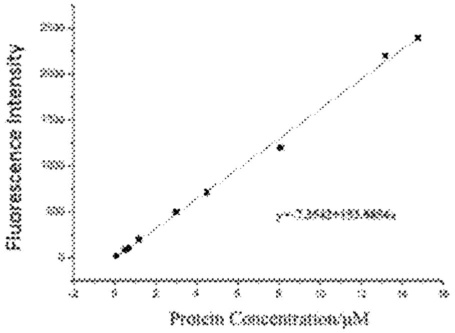
Figure 8:
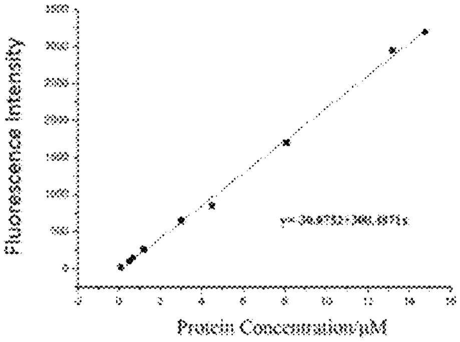
Figure 9:
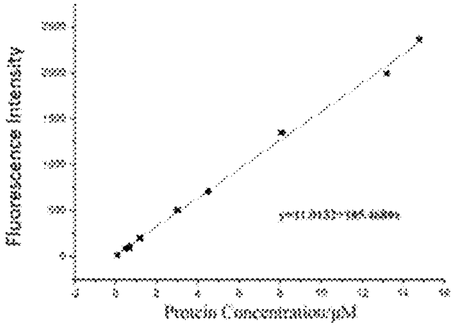
Figure 10:
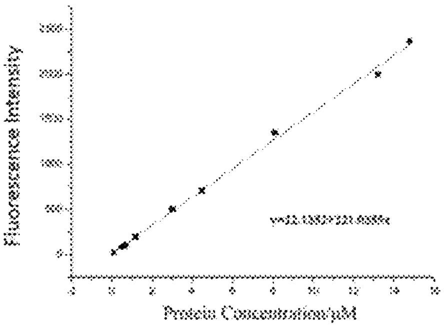
Figure 11:
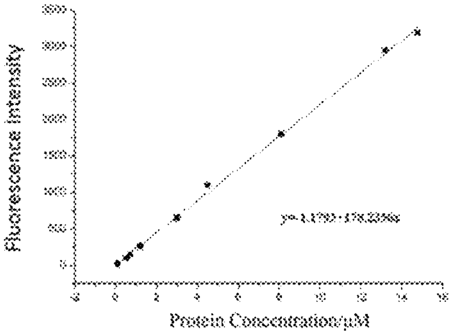
Figure 12:
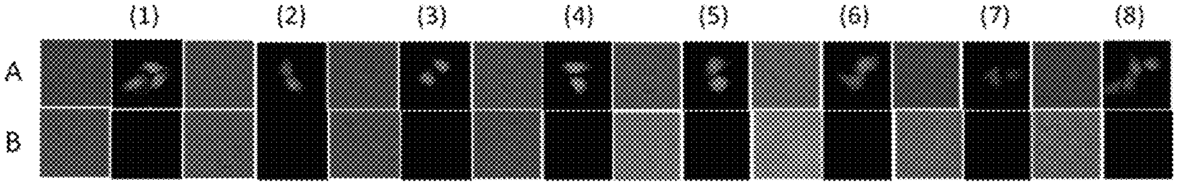
FIG. 12 is a fluorescence spectrum of cell labeled with different probes, wherein (1) to (8) are probe 57, probe 59, probe 60, probe 61, probe 69, probe 75, probe 76, probe 82, group A is a Hela cell with a protein tag expressed, and group B is a Hela-WT cell (Hela primitive cell, without a protein tag expressed)

It can be seen from FIG. 2 that the concentration of HaloTag protein in the range of 0.1 μM to 14.8 μM has a good linear relationship with the fluorescence intensity of the probes. Therefore, the protein tag can be quantitatively detected according to the standard curve.

Example 89

Hela cells are used as an example to test the labeling effect of compounds in mammalian cells. Hela cells and Hela-WT cells (Hela primitive cell, without a protein tag expressed) stably expressing HaloTag protein tags were planted in 14 mm 96-well glass bottom cell culture plates and stabilized for 10 hours. Probe 57, probe 59, probe 60, probe 61, probe 69, probe 75, probe 76, probe 82 were added to the culture medium and diluted to 5 μM, respectively. The cells were incubated in a 37° C. carbon dioxide incubator for 2 hours, and the fluorescence changes of the labeled cells were detected by imaging with a Leica TPS-8 confocal microscope. Results of group 12B show that no corresponding fluorescent signal could be detected in Hela-WT cells after the addition of the above probes, indicating that the probe fluorescence is not affected by the intracellular environment; while a strong fluorescence signal could be detected in Hela cells expressing the protein tag in group 12A, and the fluorescence signal is enhanced by nearly 200 times.

The above experiments show that the probe can achieve specific labeling of intracellular protein tags and achieve specific fluorescence lighting. At the same time, the probe fluorescence is not affected by the intracellular environment.

Example 90

Figure 13:
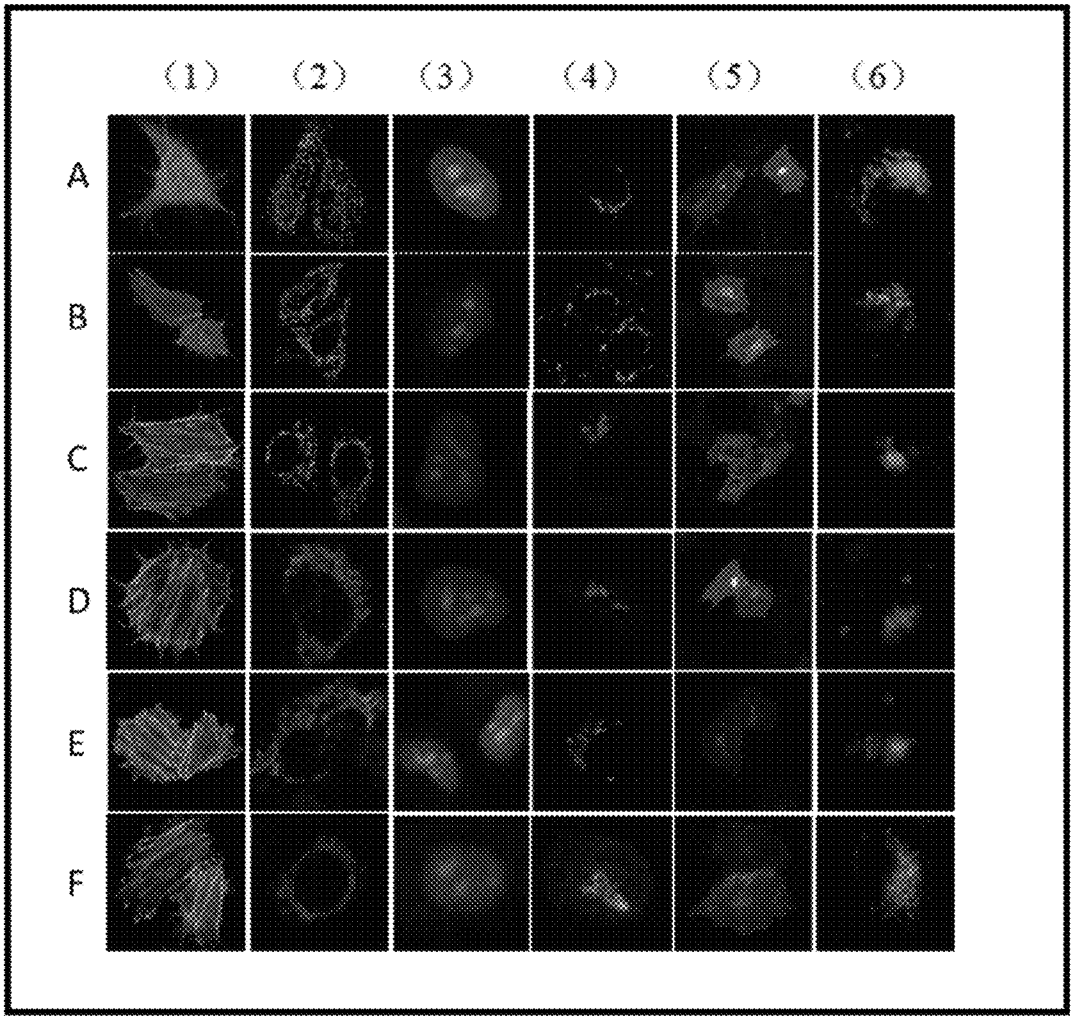
FIG. 13 shows organelles labeled with different probes, wherein groups A to F are probe 57, probe 59, probe 60, probe 61, probe 62, probe 63, respectively, and (1) to (6) are cytoskeleton, mitochondria, nucleus, Golgi apparatus, whole cell, lysosome, respectively.

In order to verify that probe 57, probe 59, probe 60, probe 61, probe 62, and probe 63 can be used to label target proteins located in different organelles. Hela cells were used as examples to detect the effect of probes on labeling HaloTag protein tags in different subcellular organelles. Hela cells were implanted 5000 cells per well in 96-well glass-bottom cell culture plates. After 14 hours, lipo2000 kit was used to transfect the plasmids localized by HaloTag protein tags in different organelles. The original culture medium was removed 24 hours after transfection, and the cells were washed twice with a phenol red-free DMEM medium, and incubated for 2 hours in a phenol red-free medium containing 0.2 μM probes, and the effect of cell labelling was detected by imaging using a Leica TCS-8 confocal microscope. The results are shown in FIG. 13. The probe can clearly display a variety of subcellular organelle structures without washing, such as cytoskeleton, mitochondria, nucleus, Golgi, whole cells, and lysosomes.

The above results demonstrate that the probe can be a powerful tool for labeling a variety of cellular subcellular organelles.

Example 91

Figure 14:
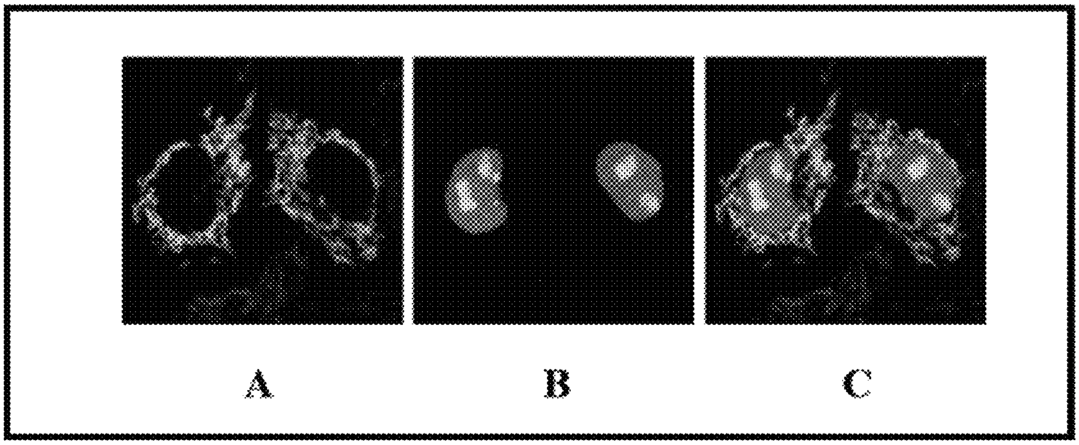
FIG. 14 is a two-color labeling of the same cell with different probes, wherein A is a mitochondria labeled with contrast probe 85, B is a nucleus labeled with probe 57, and C is an orthogonal imaging of A and B.

Hela cells were implanted 5000 cells per well in a 96-well glass-bottom cell culture plate, and after 14 hours, pcdna3.1-SNAP-NLS and pcdna3.1-mito-HaloTag (HaloTag protein-tagged mitochondrial localization plasmid) were co-transfected with a lipo2000 kit, 0.1 μg per well; the original medium was removed 24 hours after transfection, a phenol red-free DMEM medium was used twice, and the cells were incubated for 2 hours with phenol red-free medium containing 0.2 μM reference probe 85 and probe 57, respectively, and the effect of cell labeling was detected by imaging using a leica TCS-8 confocal microscope. The results are shown in FIG. 14. The reference probe 85 and probe 57 can clearly display the structures of the mitochondrial and the nucleus at the same time without washing, and the co-localization coefficient of the fluorescence channel of nucleus labeled by the reference probe 85 and the fluorescence channel of mitochondria labeled by probe 57 is less than 0.1, indicating that the two fluorescent channels will not interfere with each other.

The above experiments show that the spectra of fluorescence groups of different probes would not interfere with each other, and orthogonal label imaging can be performed at the same time.

Example 92

First, a plasmid pcdna3.1-HaloTag (sample group) expressing the HaloTag protein tag and a control plasmid pcdna3.1-CAT (control group) not expressing the HaloTag protein tag were introduced into mice. This method is to dissolve the plasmid in a large volume of solution and inject it into mice quickly through tail vein injection. The mouse liver absorbs DNA and then expresses the target protein. 20 hours after the plasmid injection, 0.4 μM probe 77 dissolved in 200 ul of PBS was injected into the mice via tail vein injection to label the HaloTag protein tag; 6 hours later, the mice were dissected out, and the fluorescence differences in the liver parts of different mouse samples were detected by KODAK multi-spectral in vivo imaging system.

Figure 15:
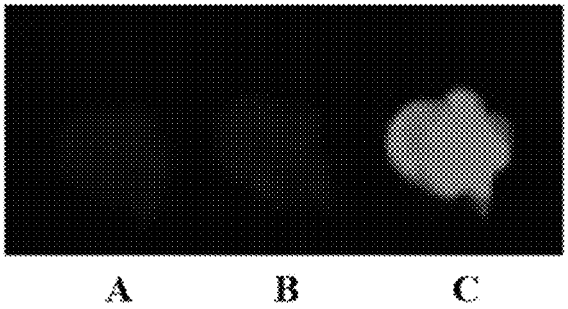
FIG. 15 shows the labeling of living mice with probe 77, wherein group A is a blank group, group B is a control group, and group C is a sample group.

The results are shown in FIG. 15. The fluorescence of the liver of the control plasmid pcdna3.1-CAT injected with the probe 77 was very low, which was close to the background fluorescence level of the blank liver without the probe injected, and the liver of the HaloTag plasmid pcdna3.1-HaloTag injected with the probe 77 had strong fluorescence, and the signal intensity was more than 20 times that of the control group.

The above experiments show that the fluorescence of the probe is not affected by the internal environment of the animal, and the probe can be applied to living animals and can specifically label the HaloTag protein tag expressed in the liver and generate a strong fluorescent signal.

Example 93

Figure 16:
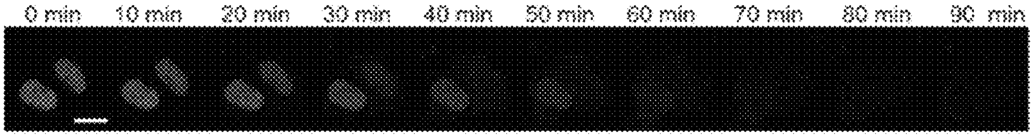
FIG. 16 shows the fluorescence changes of probe 61 in mammalian cells with the protein degradation.

In order to verify the correlation between the fluorescent activation of the probe and the presence of protein, the HaloTag protein in mammalian cells was taken as an example, and the AID degradation system in Hela cells was used as an example to detect the fluorescence changes of HaloTag protein binding probes after protein degradation. First, Hela cells were implanted 20,000/$cm^2$ in a 20 mm glass-bottomed cell culture dish. After 14 hours, pcdna3.1-TIR1 and pcdna3.1-HaloTag-IAA17-H2B plasmids were transfected with lipofectmain2000 transfection reagent from invirtogen. 24 hours after cell transfection, the original cell culture medium was replaced with a phenol red-free DMEM medium containing 1 μM probe 61 to label the cells, and the cell samples were incubated in a 37° C. carbon dioxide incubator for 1 hour. After the labeling was completed, the fluorescence signal of cell labels was detected by imaging using a Leica SP8 laser confocal microscope. Then, indole acetic acid (IAA) was added to induce the degradation of HaloTag-IAA17-H2B protein, and the changes in cell fluorescence during protein degradation were detected. The results are shown in FIG. 16. HaloTag-IAA17-H2B protein was localized in the nucleus (0 min), and protein degradation was induced by the addition of indole acetic acid. With the increase of time, the fluorescent signal of HaloTag-IAA17-H2B protein gradually decreased, and when indoleacetic acid was added for 90 min, the fluorescence signal was almost invisible, and the rate of protein degradation was consistent with the results reported in the literature. The above experiments show that the fluorescent properties of probes in mammalian cells also depend on the presence of proteins. When proteins are present, fluorescence is activated, and when proteins are degraded, fluorescence disappears, which can be used to track and monitor the degradation process of target proteins.

Example 94

Figure 17:
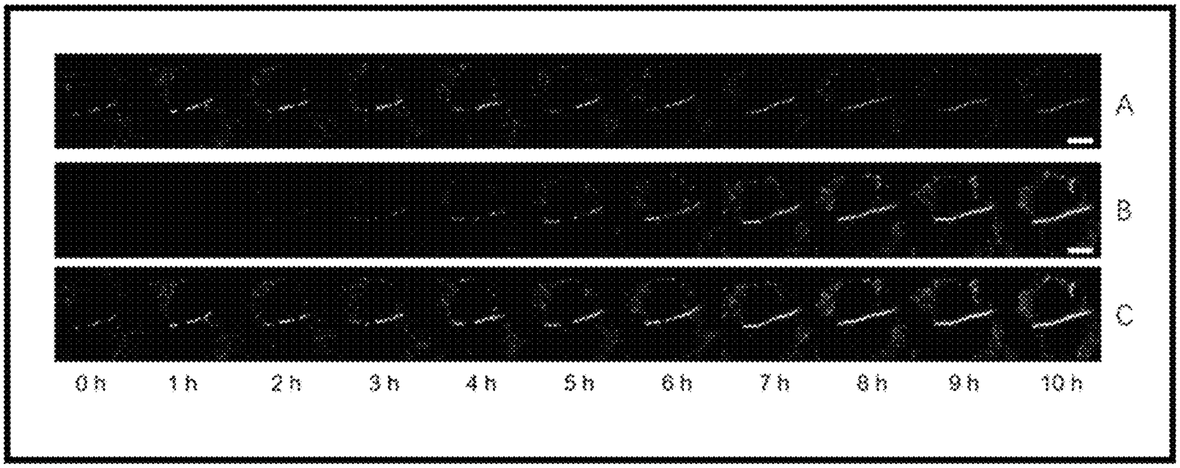
FIG. 17 shows tracing cell gap assembly process with different probes, wherein A represents the fluorescence channel of probe 61, B represents the fluorescence channel of probe 57, and C represents the superimposed fluorescent channel of probe 61 and probe 57.

To verify that the probe can be used to monitor the assembly and degradation of biomacromolecules in mammalian cells in real time, Hela cells were used as an example to detect the process of tracing, by a probe, the assembly of intercellular protein CX43 to form intercellular channels in mammalian cells. The C-terminus of CX43 gene was fused with HaloTag gene, and a Hela cell line stably expressing the fusion protein CX43-HaloTag was constructed and obtained by lentiviral infection technology. Hela-CX43-HaloTag cell lines were implanted in a 20 mm glass-bottom cell culture dish 10 hours before the probe labeling. When labeling, the probe 61 μM was first diluted to 2 μM with phenol red-free DMEM medium and replaced the original cell culture medium. The cells were incubated in a 37° C. carbon dioxide incubator for 1 hour. Thereafter, the cells were washed twice with fresh phenol red-free DMEM medium, and the unbound probe 61 was removed at intervals of 2 min. Then, a DMEM phenol-free medium containing 1 μM probe 57 was added to label the cells, and a Leica SP8 confocal microscope was used to monitor the fluorescence intensity and position changes of labeled cells at the corresponding fluorescence channels of probe 61 and probe 57 for a long time, which are shown in FIGS. 17A and 17B, respectively. A long column-shaped specific fluorescent signal between the two cells can be seen in the probe 61 fluorescence channel, as shown in FIG. 17A, consistent with the results reported in the literature (Guido Gaietta et al. Science 2002, 296, 503-507.). When the probe 57 was just added, the fluorescent signal could not be detected in its corresponding fluorescence channel. As shown in FIG. 17B, it shows that the probe 61 labeled all the CX43 proteins present in the cell. With the increase of culture time, new CX43-HaloTag protein was continuously synthesized and labeled with probe 57. After 1 hour of labeling, the fluorescence signal of probe 57 appeared on the edge of the original interstitial channel labeled with probe 61 and gradually increased, while the fluorescence signal of the old interstitial channel probe 61 gradually decreased, indicating that the CX43-HaloTag protein newly synthesized in the interstitial channel gradually replaces the original CX43-HaloTag protein from the periphery to the center. The superimposed channel is shown in FIG. 17C, which is consistent with the results reported in literatures. The above experimental results prove that HaloTag series of compounds can be used for real-time monitoring of the assembly and degradation of biological macromolecules in cells.

Example 95

To verify that the probe-labeled HaloTag protein tag has a faster labeling speed and higher fluorescence intensity than the probe-labeled SNAP protein tag, a probe 48-labeled HaloTag protein tag and a reference probe 85-labeled SNAP protein tag were taken as examples (probe 48 and reference probe 85 have the same fluorescent dye portion). When labeling, the purified HaloTag protein and SNAP protein were first diluted to 7.5 μM with PBS.

Probe 48 and reference probe 85 were diluted to 15 μM with PBS, and 20 μL of probe 48 was added to 80 μL of HaloTag protein and mixed, 20 μL of reference probe 85 was added to 80 μL of SNAP protein and mixed, and a microplate reader was used to monitor the changes in fluorescence intensity of the two solutions excited at 620 nm and emitted at 650 nm, which lasted for two hours.

Figure 18:
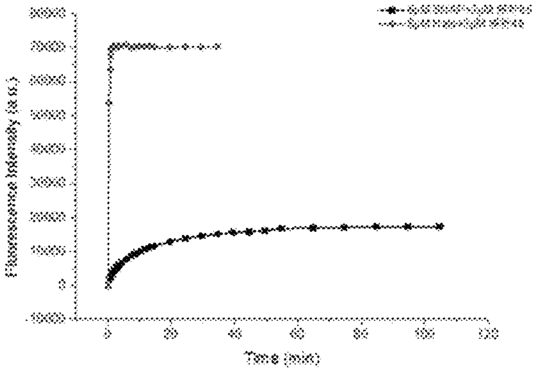
FIG. 18 shows comparison of the labeling speed and fluorescence intensity of a HaloTag protein tag labeled probe 48 and a SNAP protein tag labeled contrast probe 85 under the same conditions.

As shown in FIG. 18, $t_{1/2}$ of the HaloTag protein tag labeled by the probe 48 was less than 2 s, and the tin of the SNAP protein tag labeled by the reference probe 85 was about 7 min, and the fluorescence intensity is lower than the former by 1 time or more. The above experimental results prove that the probe-labeled HaloTag protein tag has a faster labeling speed and higher fluorescence intensity than the probe-labeled SNAP protein tag.

What is claimed is:

1. A fluorescent probe, the fluorescent probe is a compound having a structure represented by formula (I-a) or (I-b), or a salt thereof,

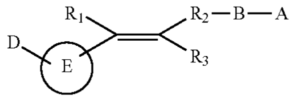

(I-a)

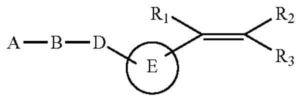

(I-b)

wherein,

A is a structure of the following formula:

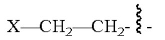

wherein, X is chlorine;

in formula (I-a), B is

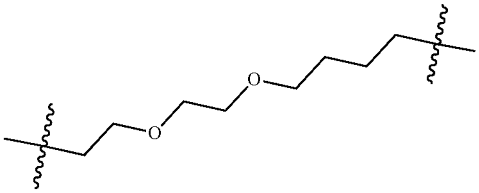

, or

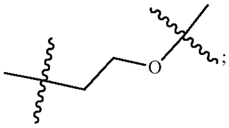

;

in formula (I-b), B is

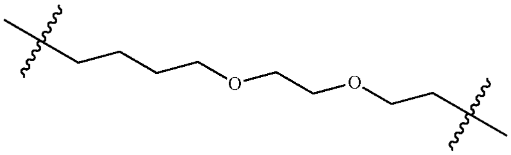

;

D is —$NX_1$—$X_2$, wherein in formula (I-a), D is —$NX_1$($X_2$), wherein, $X_1$ and $X_2$ is independently selected from hydrogen, an alkyl group, or

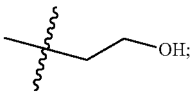

;

in formula (I-b), D is —$X_2$—$NX_1$, wherein, $X_1$ is selected from hydrogen, an alkyl group,

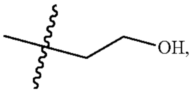
or
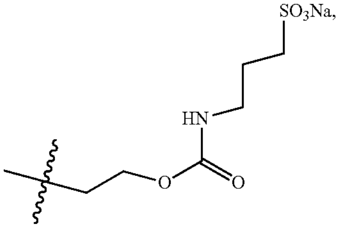
$X_2$ is
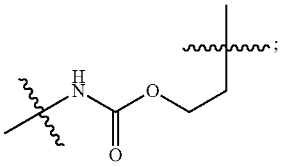 [SMILES: *CCOC(=O)N*]
E is selected from structures of the following:
(I-1-10)
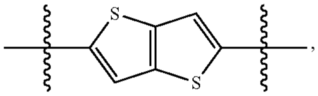
(I-1-14)
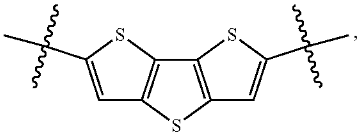
(I-1-17)
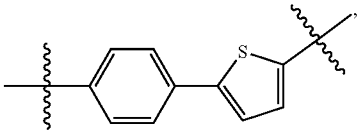
(I-1-19)
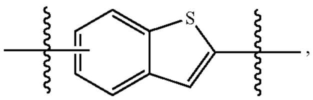
(I-1-23)
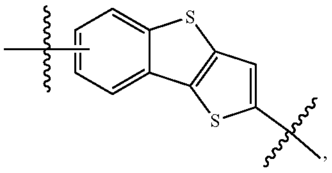
(I-1-24)
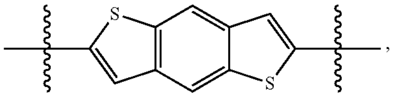
-continued
(I-1-27)
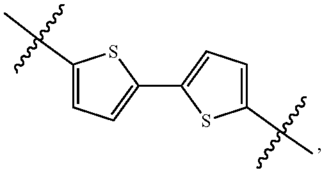
(I-1-29)
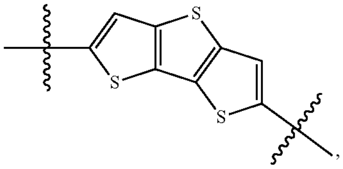
(I-1-33)
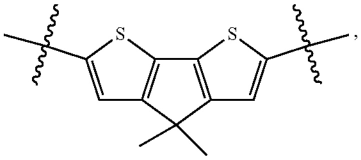
or
(I-1-39)
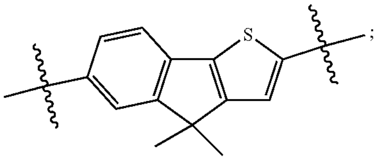
in formula (I-b),
(I-2)
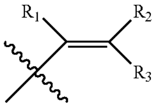
is one selected from the following formulae (I-2-1) to (I-2-28):
(I-2-1)
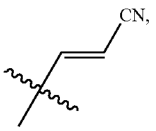
(I-2-2)
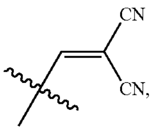
(I-2-3)
,
(I-2-4)
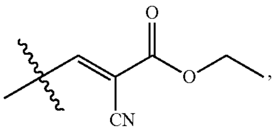

-continued
(I-2-5)
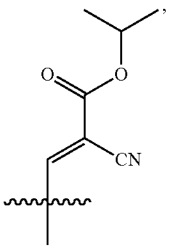
(I-2-6)
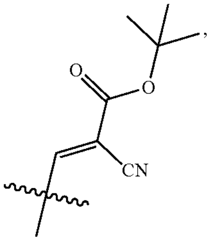
(I-2-7)
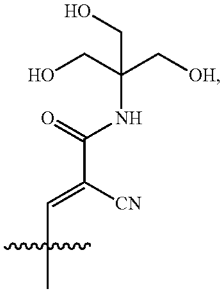
(I-2-8)
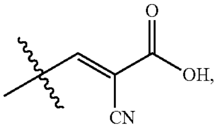
(I-2-9)
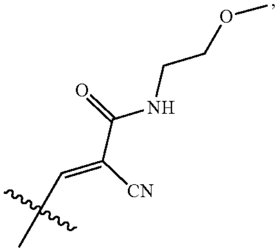
(I-2-10)
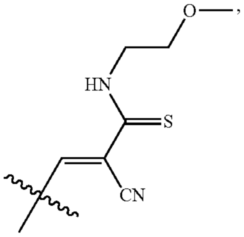
-continued
(I-2-11)
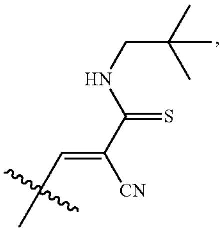
(I-2-12)
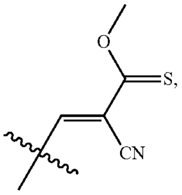
(I-2-13)
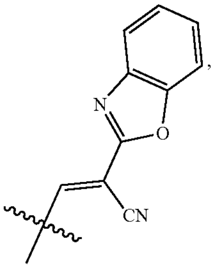
(I-2-14)
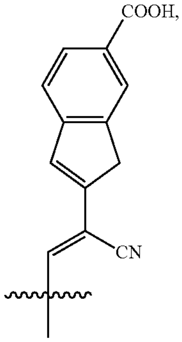
(I-2-15)
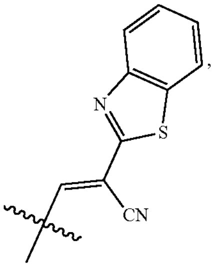

-continued
(I-2-16)
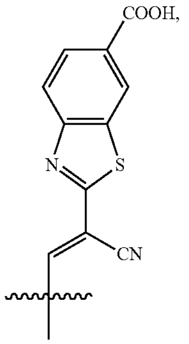
(I-2-17)
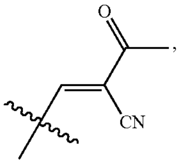
(I-2-18)
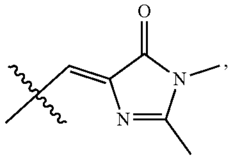
(I-2-19)
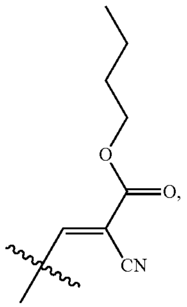
(I-2-20)
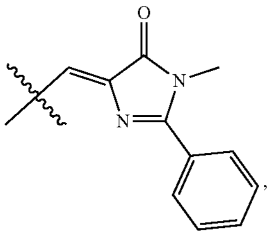
(I-2-21)
,
(I-2-22)
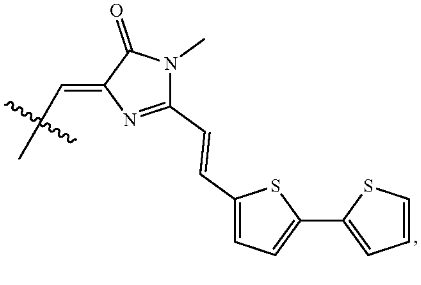
-continued
(I-2-23)
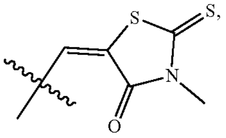
(I-2-24)
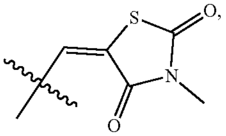
(I-2-25)
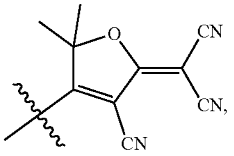
(I-2-26)
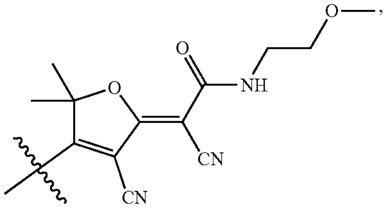
(I-2-27)
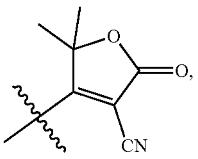
(I-2-28)
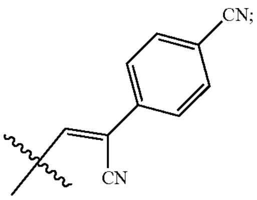
in formula (I-a),
(I-2-i)
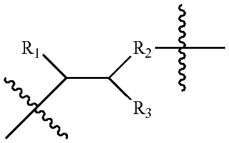
is one selected from the following formulae (I-2-29) to (I-2-38):

-continued
(I-2-29)
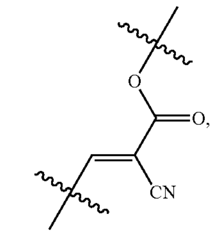
(I-2-30)
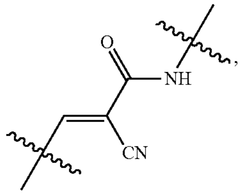
(I-2-31)
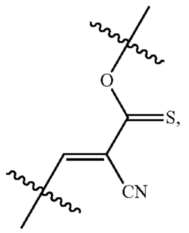
(I-2-32)
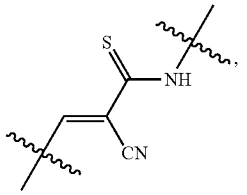
(I-2-33)
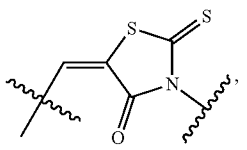
(I-2-34)
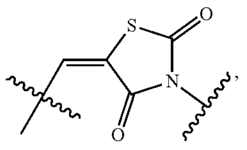
(I-2-35)
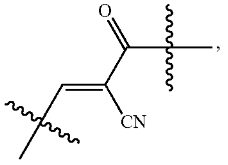
(I-2-36)
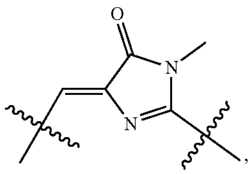
(I-2-37)
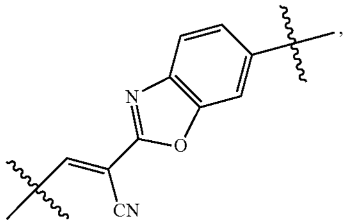
(I-2-38)
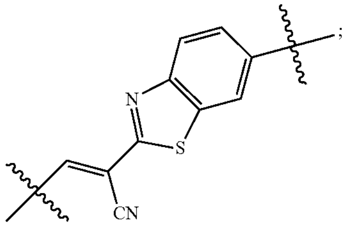
wherein the "alkyl" in formula (I-a) or formula (I-b) is a $C_1$-$C_{10}$ linear or branched alkyl.
2. A fluorescent probe selected from the following compounds or salts thereof:

Probe 10
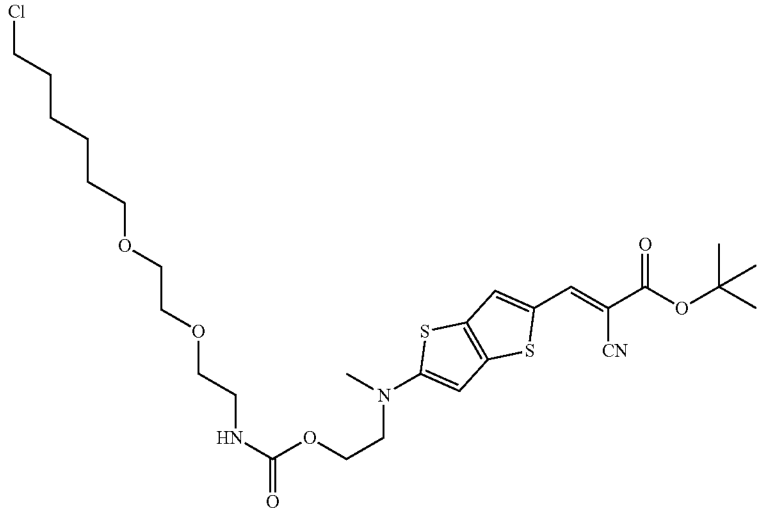
Probe 11
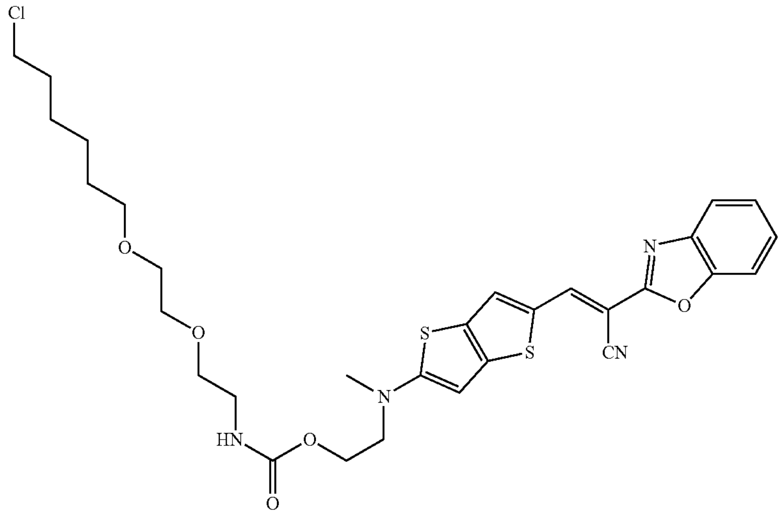
Probe 12
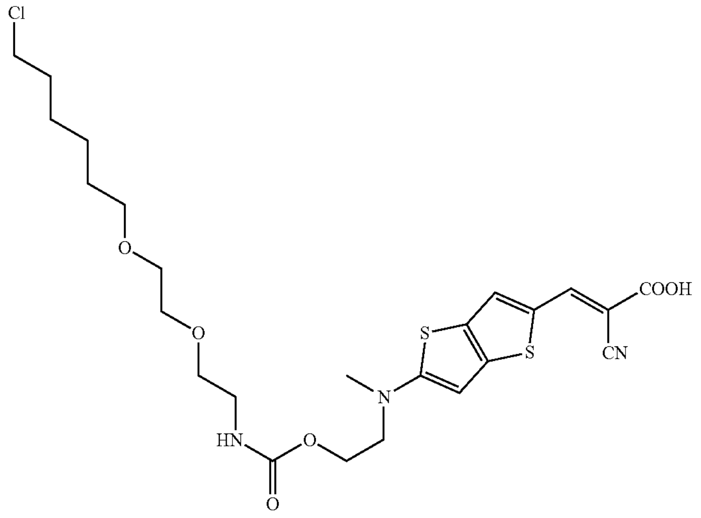

-continued
Probe 13
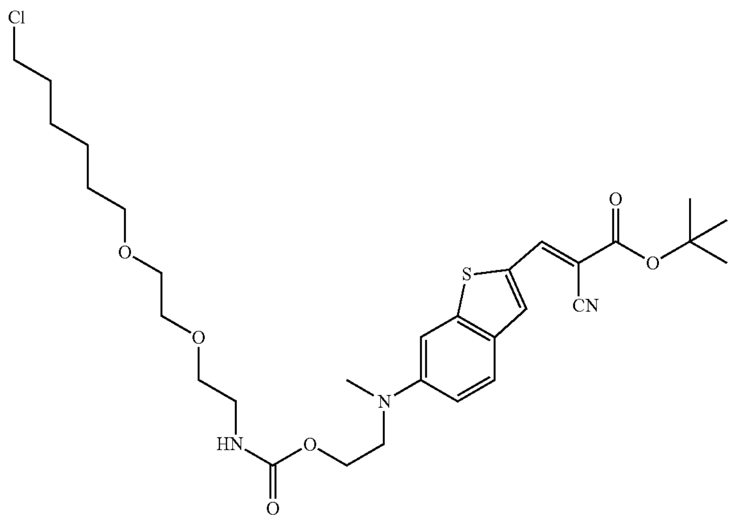
Probe 14
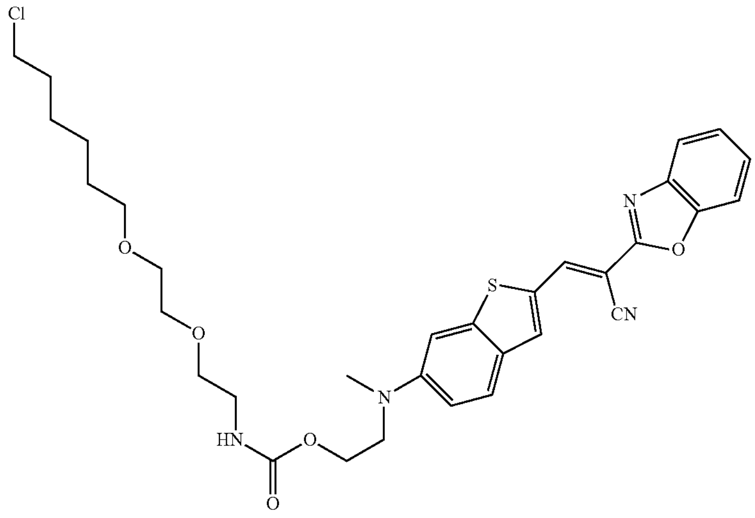
Probe 15
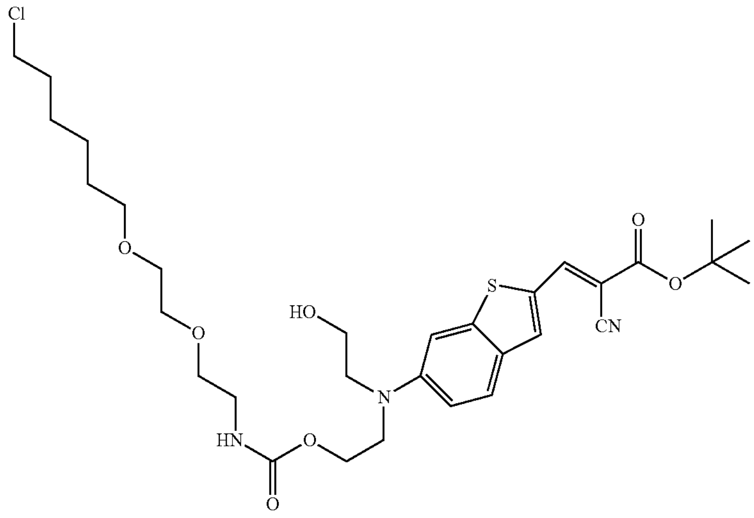

-continued
Probe 16
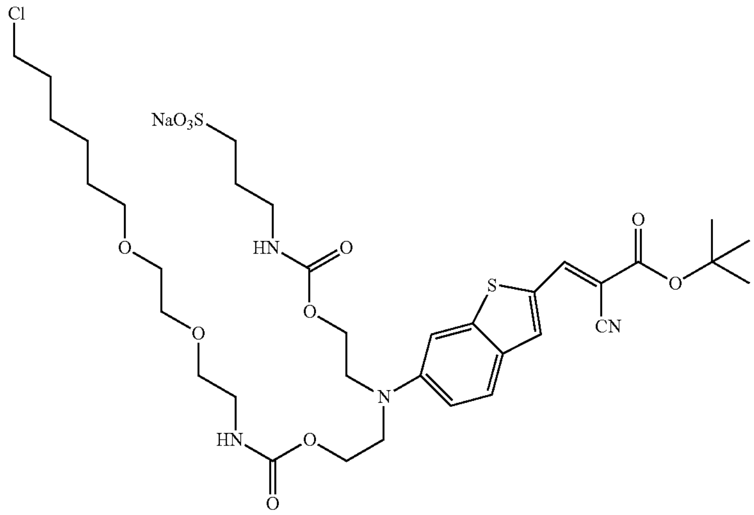
Probe 17
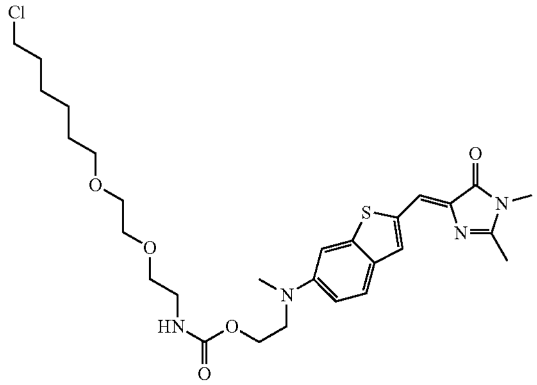
Probe 18
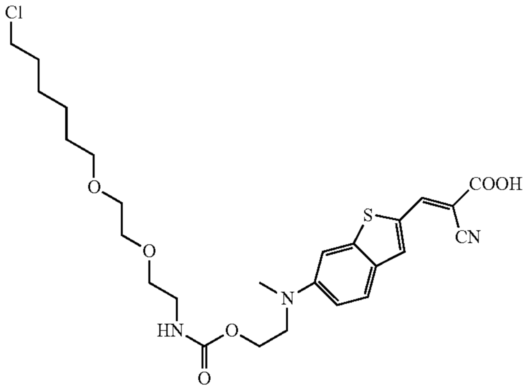
Probe 29
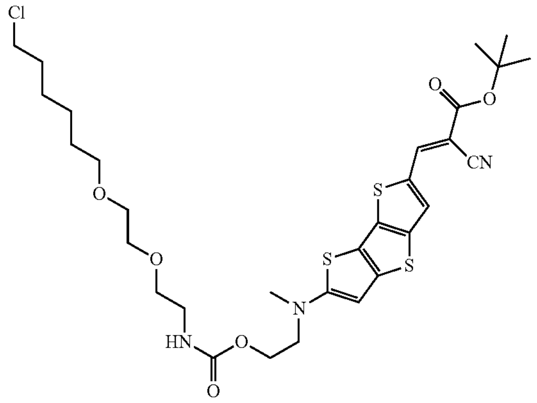
Probe 30
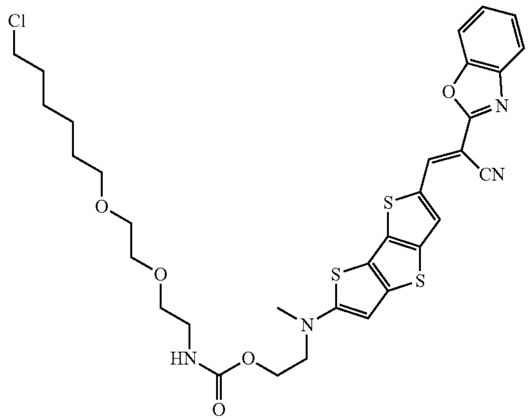

-continued
Probe 31
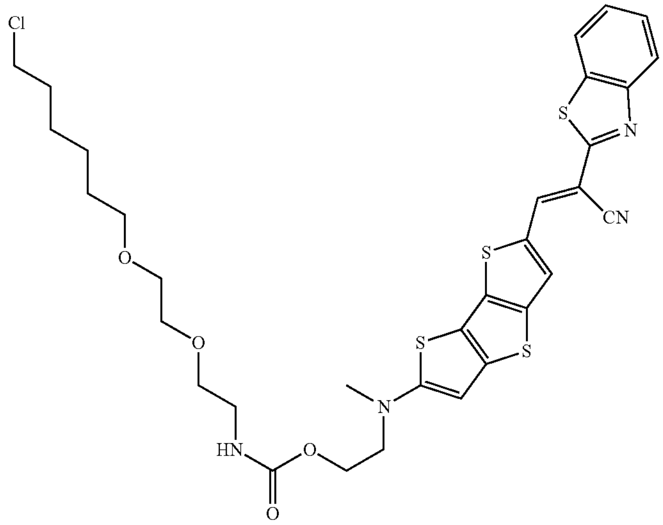
Probe 32
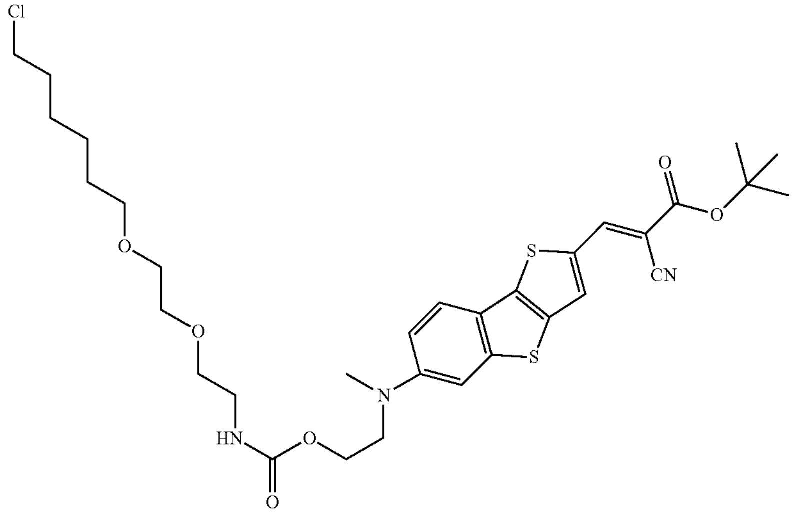
Probe 33
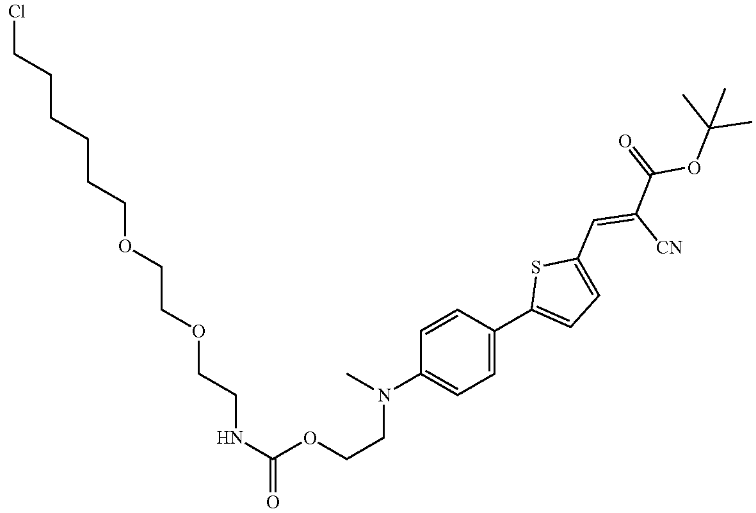

-continued
Probe 34
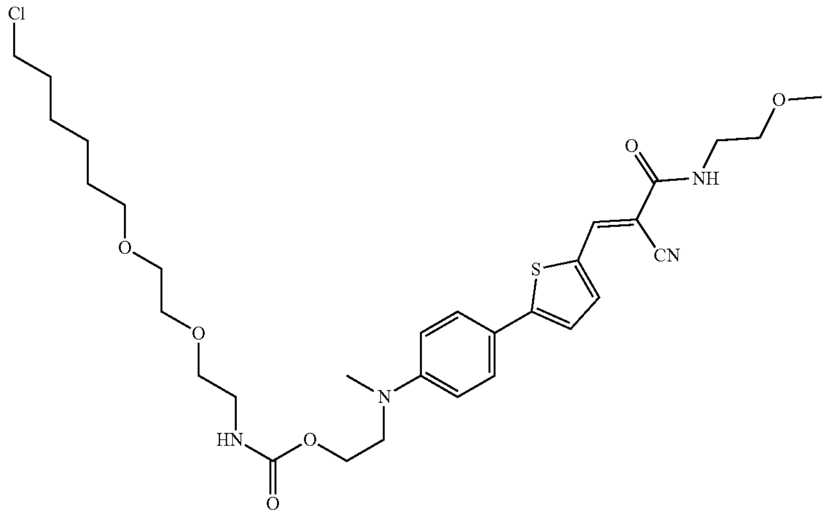
Probe 35
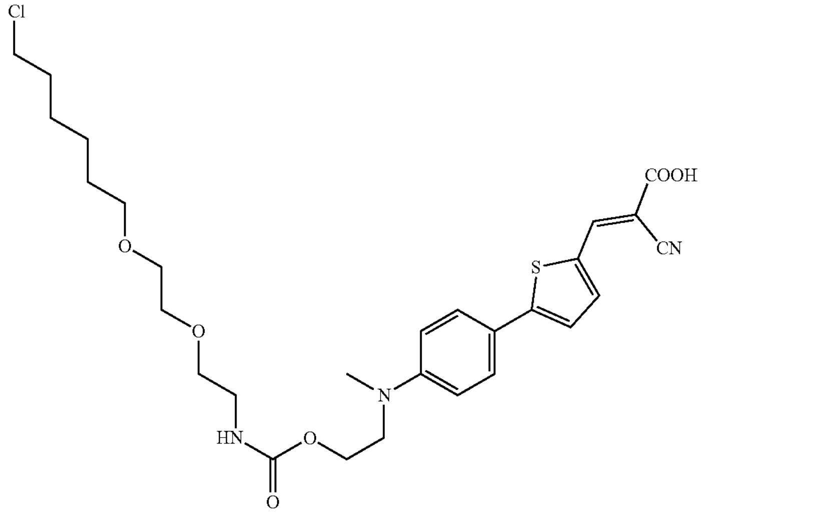
Probe 36
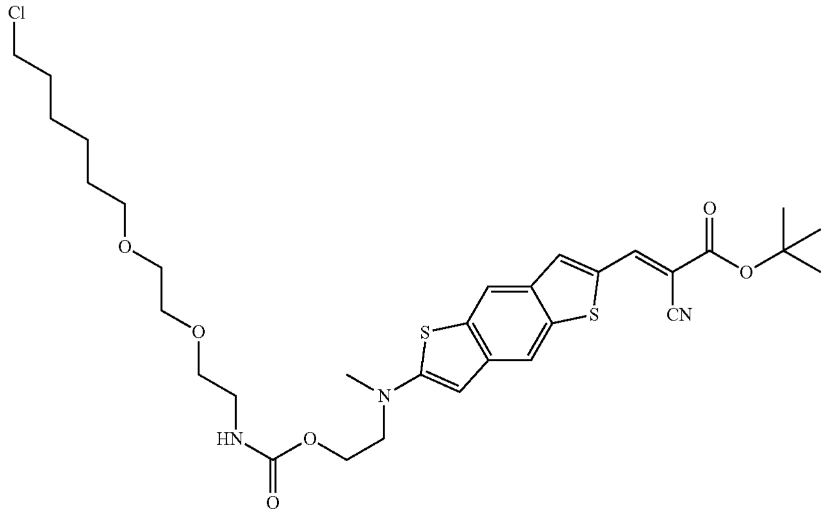

-continued
Probe 37
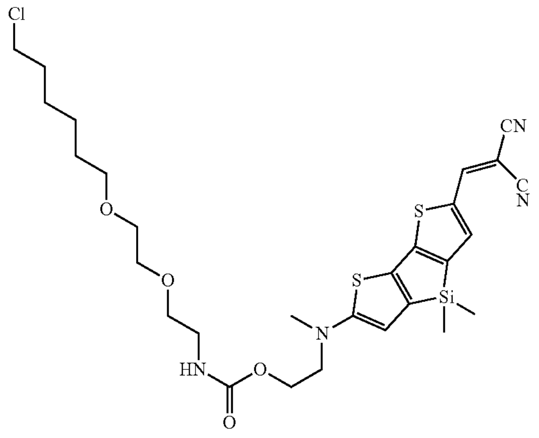
Probe 38
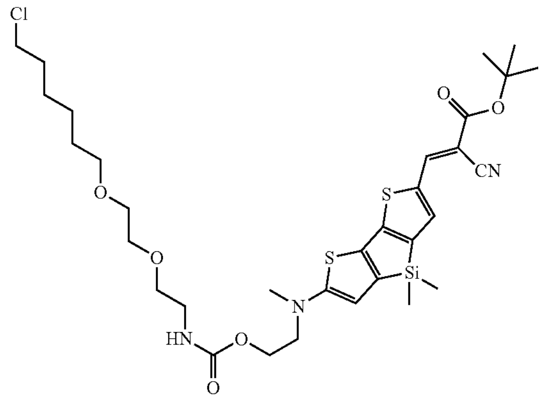
Probe 39
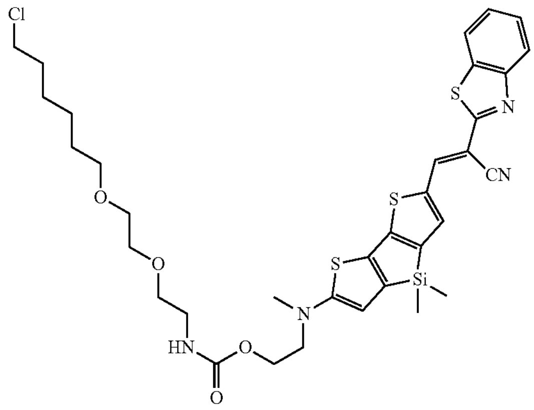
Probe 40
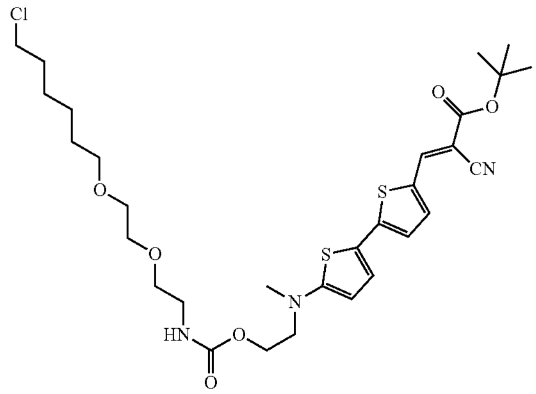
Probe 41
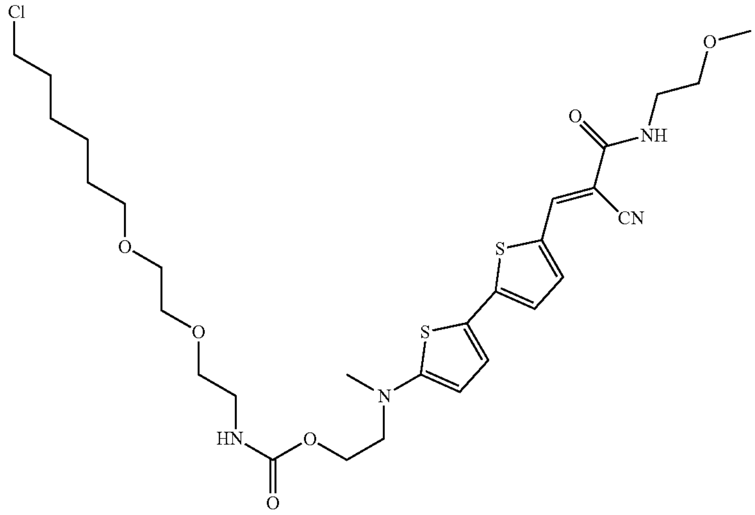

-continued
Probe 42
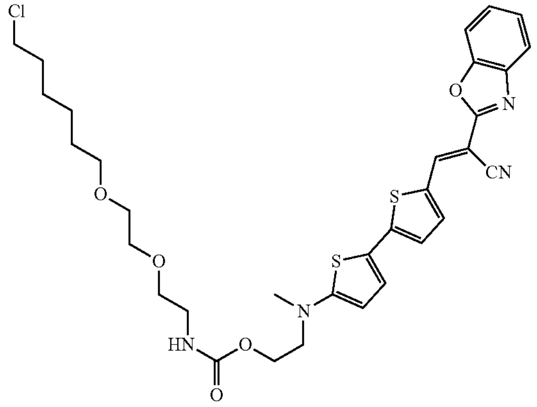
Probe 43
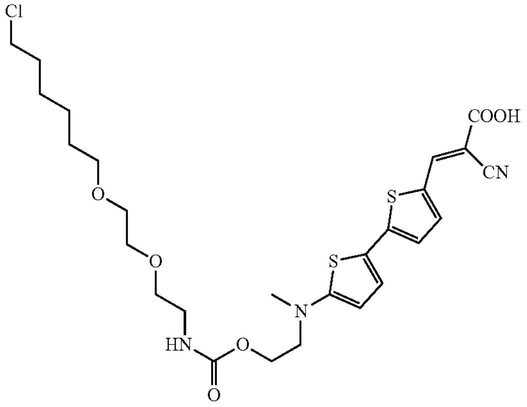
Probe 48
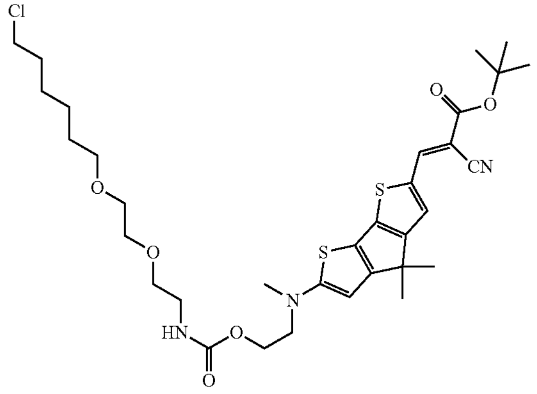
Probe 49
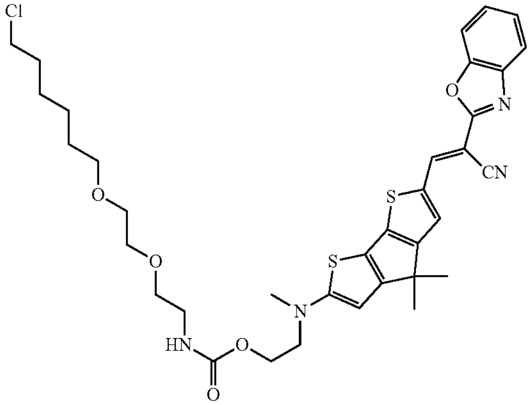
Probe 50
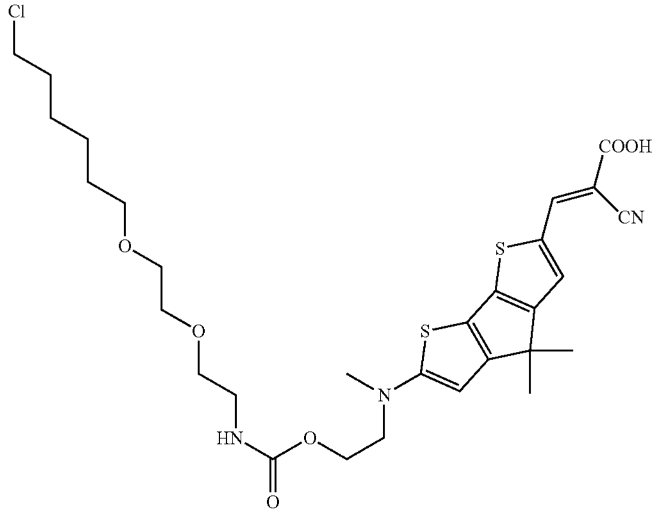

-continued
Probe 52
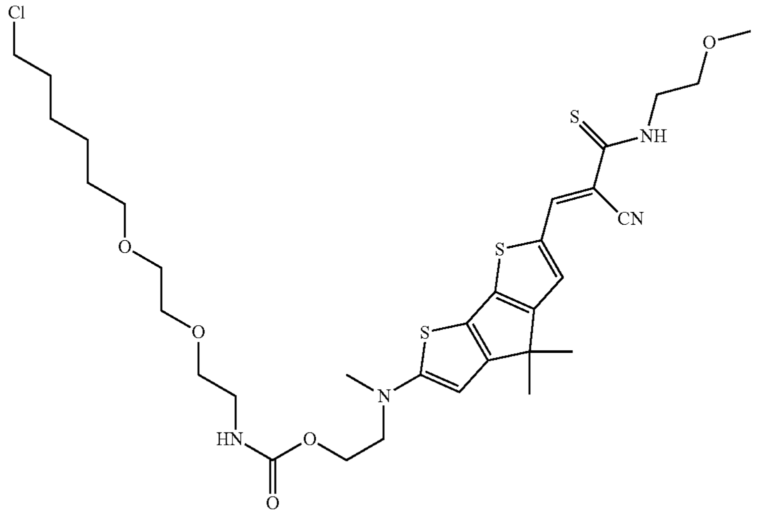
Probe 53
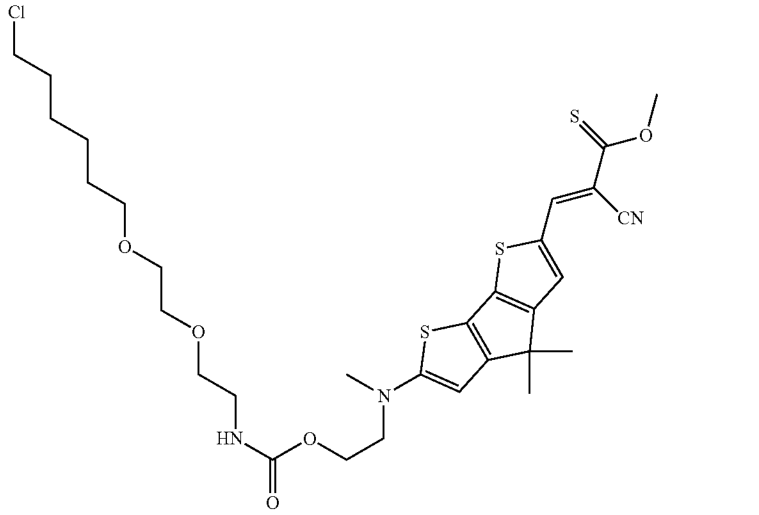
Probe 54
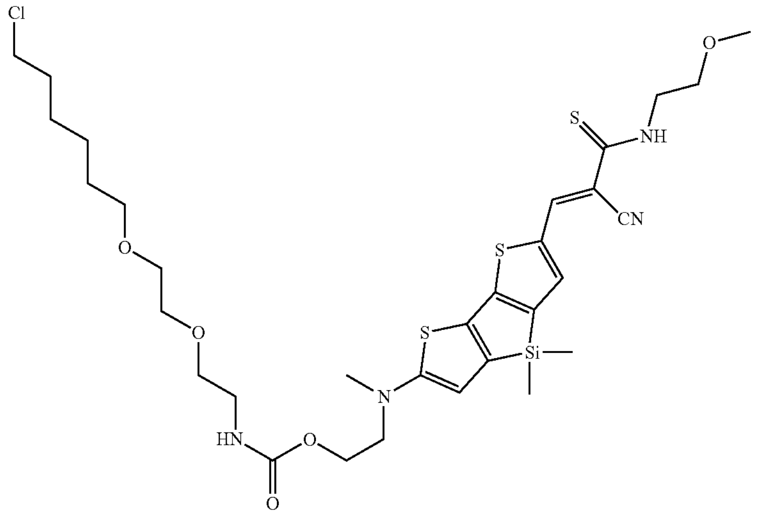

-continued
Probe 55
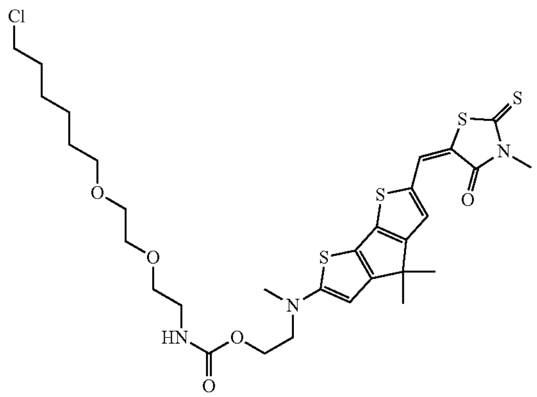
Probe 56
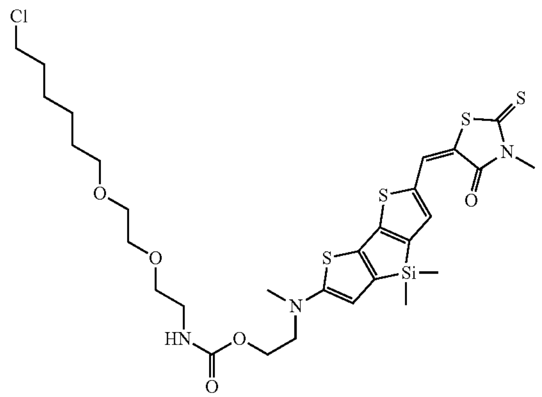
Probe 61
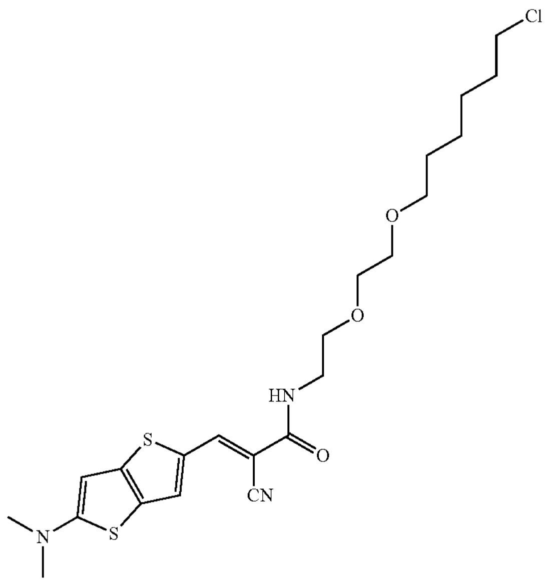
Probe 63
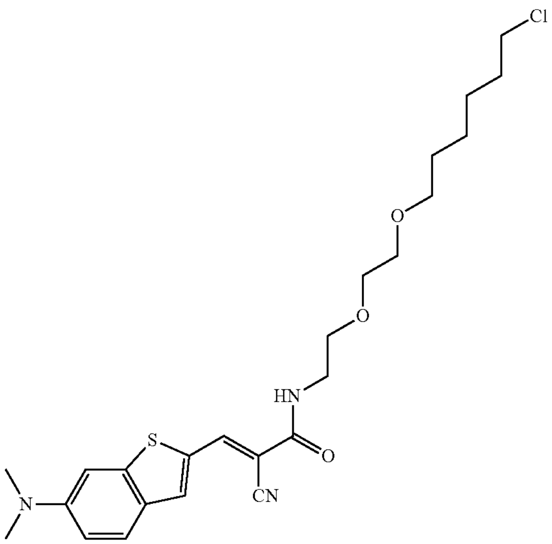
Probe 64
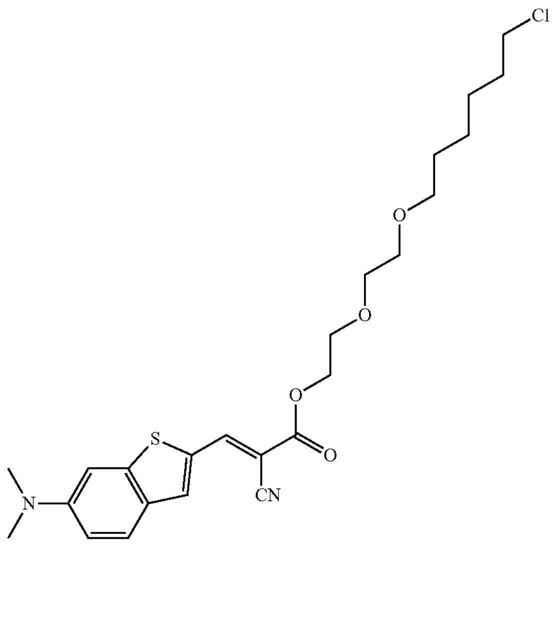
Probe 65
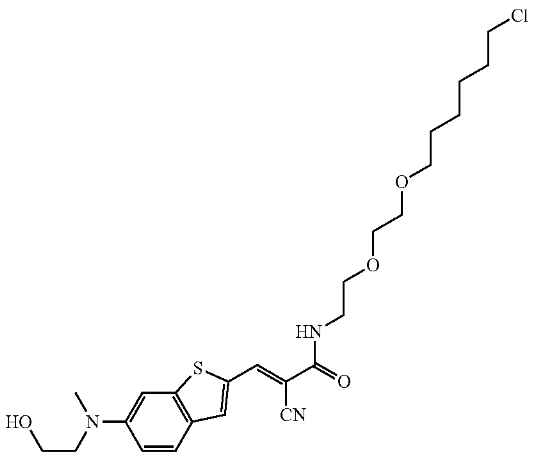

-continued
Probe 66
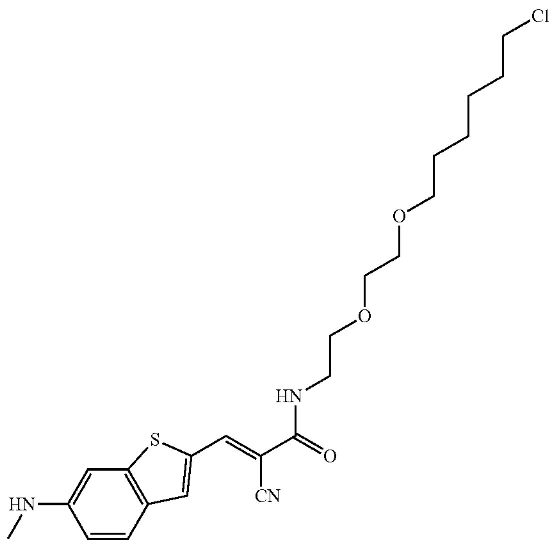
Probe 67
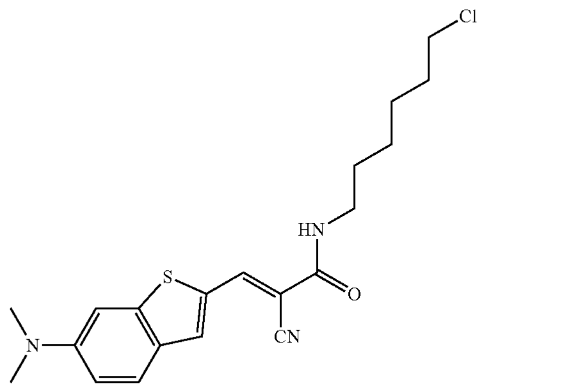
Probe 68
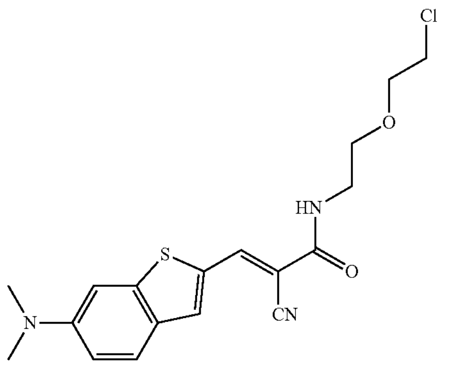
Probe 73
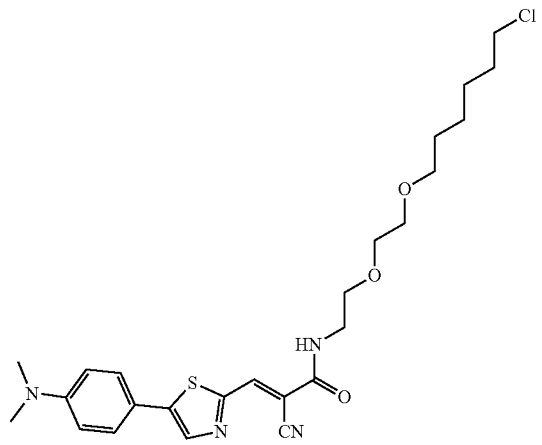
Probe 74
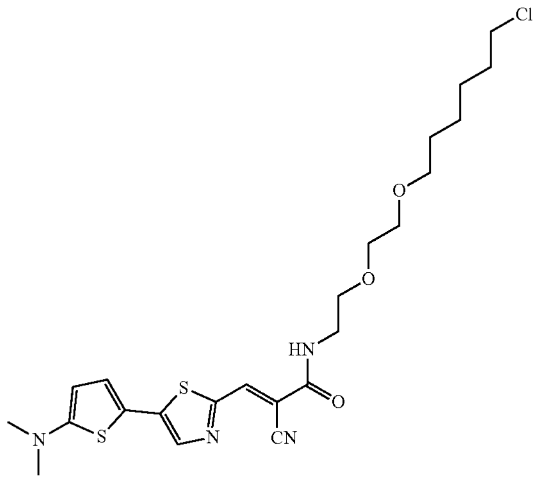
Probe 75
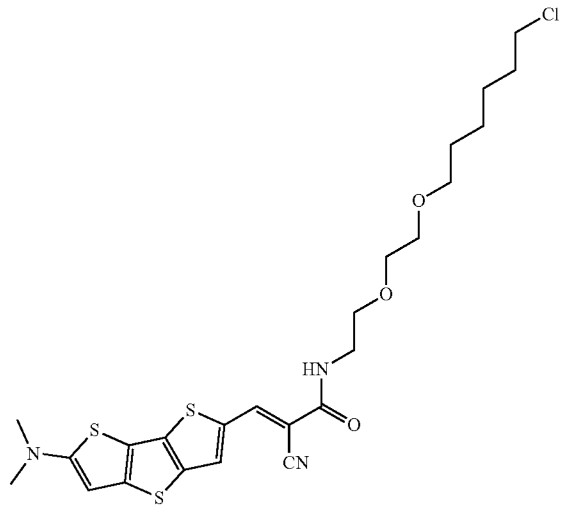

-continued
Probe 76
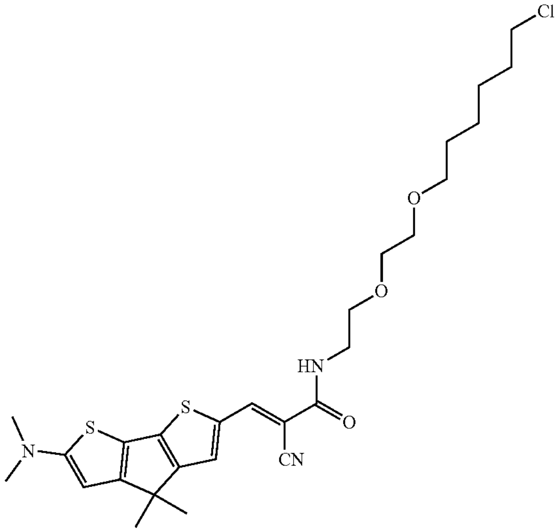
Probe 77
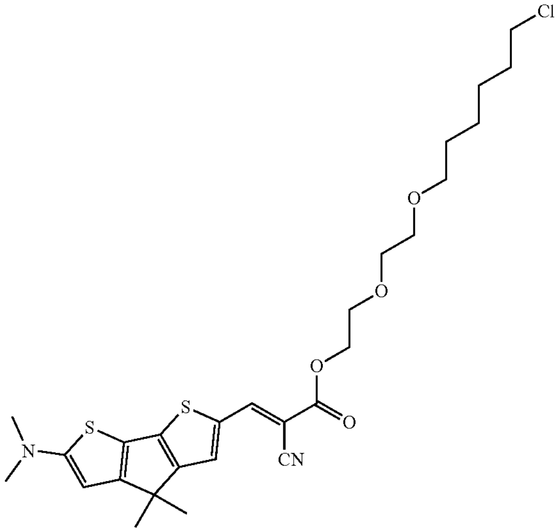
Probe 78
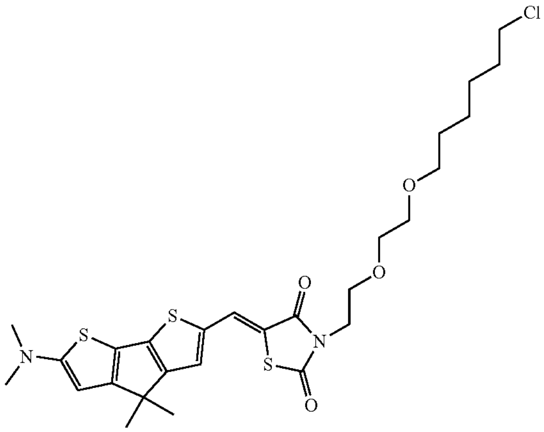
Probe 79
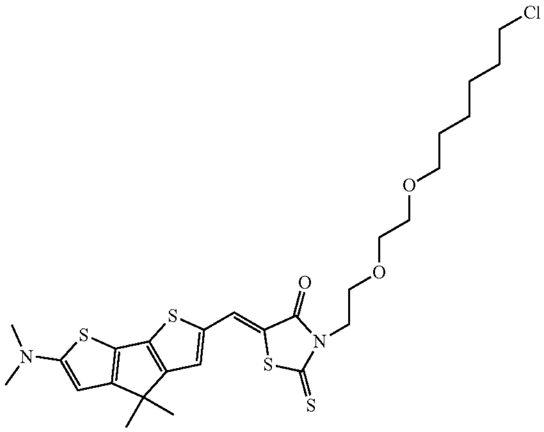
Probe 80
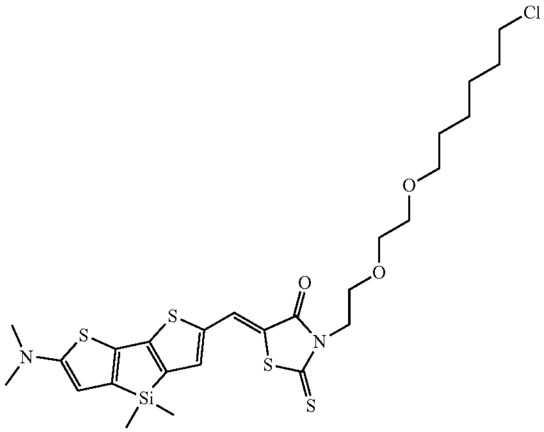
Probe 81
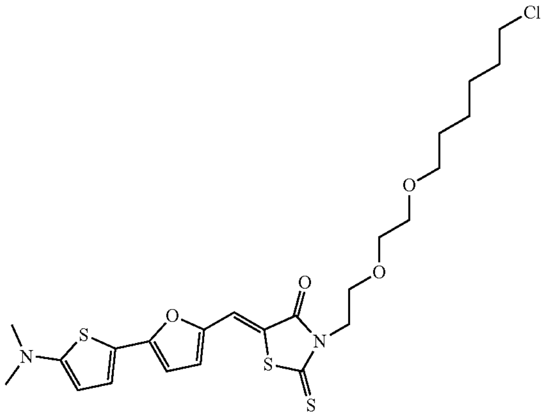

-continued

Probe 82

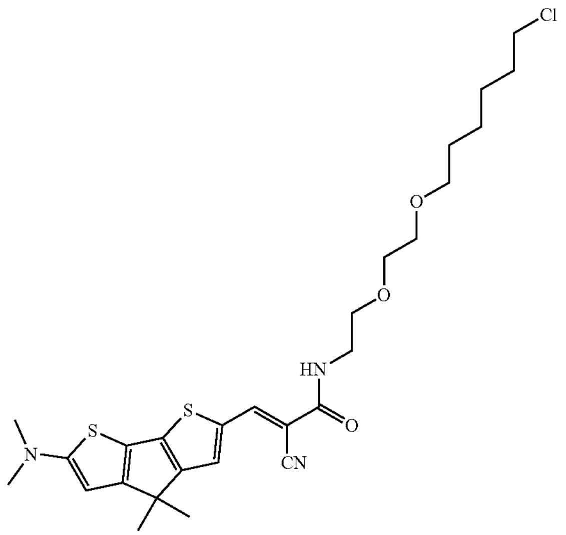

Probe 83

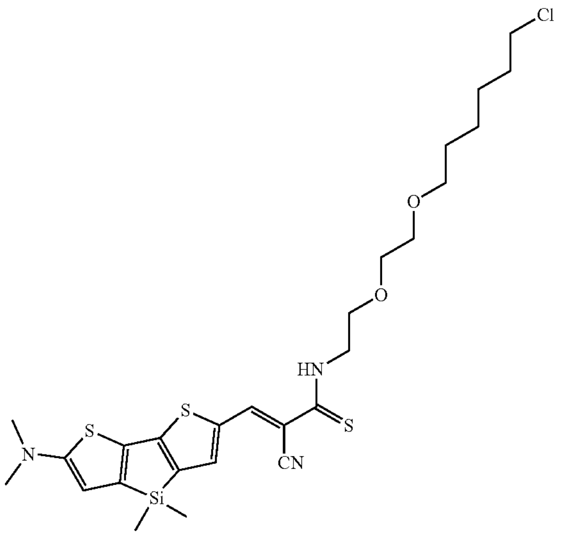

Probe 84

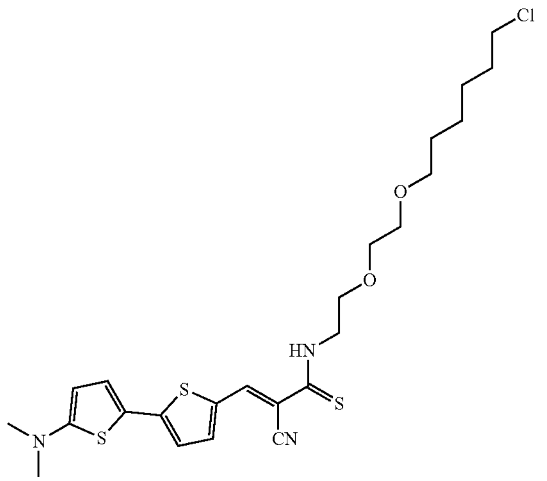

Probe 85

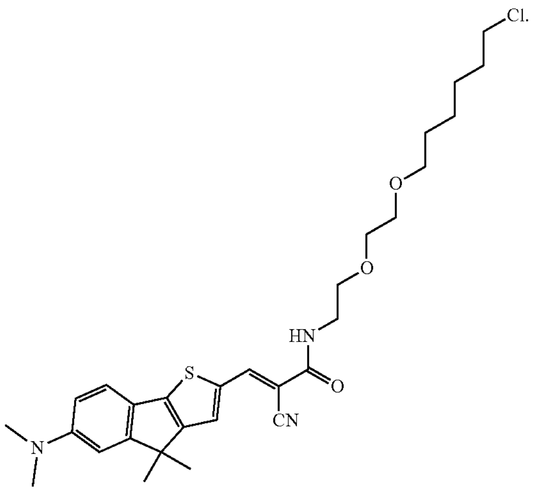

3. A fluorescent activated protein specific labeling method, comprising steps of contacting the fluorescent probe according to claim 1 with a target protein of a protein tag or a fusion protein tag; performing labeling reaction between the ligand moiety of the fluorescent probe and the protein tag to label the protein tag with the fluorescent probe; the labeling of the protein tag with the fluorescent probe is covalently labeling.

4. The fluorescent probe according to claim 1, wherein, the "alkyl" group in formula (I-a) or formula (I-b) is a $C_1$-$C_7$ linear or branched alkyl.

5. The fluorescent probe according to claim 1, wherein, the "alkyl" group in formula (I-a) or formula (I-b) is selected from methyl, ethyl, n-propyl, isopropyl, n-butyl, isobutyl, tert-butyl, sec-butyl, n-pentyl, 1-methylbutyl, 2-methylbutyl, 3-methylbutyl, isopentyl, 1-ethylpropyl, neopentyl, n-hexyl, 1-methylpentyl, 2-methylpentyl, 3-methylpentyl, isohexyl, 1,1-dimethylbutyl, 2,2-dimethylbutyl, 3,3-dimethylbutyl, 1,2-dimethylbutyl, 1,3-dimethylbutyl, 2,3-dimethylbutyl, 2-ethylbutyl, n-heptyl, 2-methylhexyl, 3-methylhexyl, 2,2-dimethylpentyl, 3,3-dimethylpentyl, 2,3-dimethylpentyl, 2,4-dimethylpentyl, 3-ethylpentyl or 2,2,3-trimethylbutyl.

6. The fluorescent activated protein specific labeling method according to claim 3, wherein, a reaction medium of the labeling reaction is selected from a pure protein solution, a cell lysate or an in situ medium in which the target protein of a protein tag or a fusion protein tag is located; the in situ medium is intracellular media, organelle media, living tissue media, blood or body fluids.

* * * * *